US010385101B2

(12) United States Patent
Akahata et al.

(10) Patent No.: US 10,385,101 B2
(45) **Date of Patent: *Aug. 20, 2019**

(54) VIRUS LIKE PARTICLE COMPRISING MODIFIED ENVELOPE PROTEIN E3

(71) Applicant: VLP Therapeutics, LLC, Wilmington, DE (US)

(72) Inventors: Wataru Akahata, Kensington, MD (US); Ryuji Ueno, Easton, MD (US)

(73) Assignee: VLP Therapeutics, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,502

(22) Filed: Jan. 7, 2016

(65) Prior Publication Data

US 2016/0200775 A1 Jul. 14, 2016

Related U.S. Application Data

(63) Continuation-in-part of application No. 14/820,785, filed on Aug. 7, 2015, now Pat. No. 9,969,986.

(60) Provisional application No. 62/198,949, filed on Jul. 30, 2015, provisional application No. 62/120,569, filed on Feb. 25, 2015, provisional application No. 62/101,514, filed on Jan. 9, 2015, provisional application No. 62/079,128, filed on Nov. 13, 2014, provisional application No. 62/035,037, filed on Aug. 8, 2014.

(51) Int. Cl.

| | |
|---|---|
| ***A61K 39/00*** | (2006.01) |
| ***C07K 14/005*** | (2006.01) |
| ***A61K 39/015*** | (2006.01) |
| ***A61K 39/12*** | (2006.01) |

(52) U.S. Cl.

CPC ........ *C07K 14/005* (2013.01); *A61K 39/0005* (2013.01); *A61K 39/0011* (2013.01); *A61K 39/015* (2013.01); *A61K 39/12* (2013.01); *A61K 2039/5258* (2013.01); *A61K 2039/58* (2013.01); *A61K 2039/585* (2013.01); *C07K 2319/40* (2013.01); *C12N 2770/36122* (2013.01); *C12N 2770/36123* (2013.01); *C12N 2770/36134* (2013.01); *C12N 2770/36142* (2013.01); *C12N 2770/36171* (2013.01)

(58) Field of Classification Search

CPC .... A61K 2039/5258; A61K 2039/5256; C12N 2770/36123; C12N 2760/18444

See application file for complete search history.

(56) References Cited

U.S. PATENT DOCUMENTS

| | | | |
|---|---|---|---|
| 5,439,809 A | 8/1995 | Haynes et al. | |
| 5,580,773 A | 12/1996 | Kang et al. | |
| 5,629,204 A | 5/1997 | Honjo et al. | |
| 5,698,520 A | 12/1997 | Honjo et al. | |
| 5,939,598 A | 8/1999 | Kucherlapati et al. | |
| 7,101,550 B2 | 9/2006 | Wood et al. | |
| 7,595,048 B2 | 9/2009 | Honjo et al. | |
| 7,790,181 B2 * | 9/2010 | Platteborze | A61K 39/193 424/204.1 |
| 9,249,191 B2 * | 2/2016 | Ueno | C07K 14/005 |
| 9,353,353 B2 | 5/2016 | Nabel et al. | |
| 9,363,353 B1 * | 6/2016 | Chik | H04M 1/72527 |
| 9,487,563 B2 | 11/2016 | Nabel et al. | |
| 9,512,190 B2 | 12/2016 | Ueno et al. | |
| 9,637,532 B2 | 5/2017 | Akahata et al. | |
| 9,969,986 B2 * | 5/2018 | Akahata | A61K 39/12 |
| 10,098,943 B2 | 10/2018 | Akahata et al. | |
| 2003/0108521 A1 | 6/2003 | Calatrava | |
| 2005/0214321 A1 | 9/2005 | Rasochova et al. | |
| 2007/0104689 A1 | 5/2007 | Gillies et al. | |
| 2007/0122378 A1 | 5/2007 | Freeman et al. | |
| 2008/0025067 A1 | 1/2008 | Scheuerlein et al. | |
| 2009/0079185 A1 | 3/2009 | Carbines-Evans et al. | |
| 2009/0298955 A1 | 12/2009 | Handa et al. | |
| 2009/0305950 A1 | 12/2009 | Minato et al. | |
| 2009/0312190 A1 | 12/2009 | Chinea Santiago et al. | |
| 2011/0027306 A1 | 2/2011 | Rayner et al. | |
| 2011/0035004 A1 | 2/2011 | Maxwell | |
| 2011/0081341 A1 | 4/2011 | Honjo et al. | |
| 2011/0207223 A1 | 8/2011 | Tang et al. | |
| 2011/0262389 A1 | 10/2011 | Mosca | |
| 2011/0318373 A1 | 12/2011 | Sasikumar et al. | |
| 2012/0003266 A1 * | 1/2012 | Nable | A61K 39/12 424/218.1 |
| 2013/0122262 A1 | 5/2013 | Nagakura et al. | |
| 2013/0251744 A1 | 9/2013 | Ueno et al. | |

(Continued)

FOREIGN PATENT DOCUMENTS

| | | |
|---|---|---|
| CN | 102321639 A | 1/2012 |
| CN | 106085974 A | 11/2016 |

(Continued)

OTHER PUBLICATIONS

Vitrop-Duits et al. Eur. J. Immunol. 2006, vol. 36, pp. 2410-2423.*
Communication, dated Feb. 10, 2017, issued by the United States Patent and Trademark Office in U.S. Appl. No. 14/820,785.
International Search Report, issued by International Searching Authority in corresponding International Application No. PCT/JP2015/003997, dated Oct. 27, 2015.
Rodion Gorchakov et al.,"Comparative analysis of the alphavirus-based vectors expressing Rift Valley fever virus glycoproteins", Virology, vol. 366, (2007), pp. 212-225.
António Roldao et al., "Virus-like particles in vaccine development", Expert Reviews Vaccines, vol. 9, No. 10, (2010), pp. 1149-1176.

(Continued)

*Primary Examiner* — Bao Q Li
(74) *Attorney, Agent, or Firm* — Sughrue Mion, PLLC

(57) ABSTRACT

A virus like particle comprising a viral structural protein which comprises modified envelope protein E3. The viral structural protein may be that derived from or alphavirus or flavivirus. Especially, the viral structural protein may be derived from Chikungunya virus or Venezuelan equine encephalitis virus.

20 Claims, 15 Drawing Sheets

Specification includes a Sequence Listing.

(56) References Cited

U.S. PATENT DOCUMENTS

| | | | |
|---|---|---|---|
| 2014/0120125 | A1 | 5/2014 | Ella et al. |
| 2014/0127247 | A1 | 5/2014 | Dubensky, Jr. et al. |
| 2014/0170186 | A1 | 6/2014 | Nabel et al. |
| 2014/0363458 | A1 | 12/2014 | Ueno et al. |
| 2015/0017194 | A1 | 1/2015 | Akahata et al. |
| 2016/0040134 | A1 | 2/2016 | Akahata et al. |
| 2016/0074501 | A1 | 3/2016 | Akahata et al. |
| 2016/0090403 | A1 | 3/2016 | Ueno et al. |
| 2016/0200775 | A1 | 7/2016 | Akahata et al. |
| 2016/0303221 | A1 | 10/2016 | Nabel et al. |
| 2017/0035871 | A1 | 2/2017 | Ueno et al. |
| 2017/0065703 | A1 | 3/2017 | Akahata et al. |
| 2017/0233450 | A1 | 8/2017 | Akahata et al. |
| 2017/0252425 | A1 | 9/2017 | Akahata et al. |

FOREIGN PATENT DOCUMENTS

| | | | |
|---|---|---|---|
| JP | 4-506301 | A | 11/1992 |
| JP | 2007-512842 | A | 5/2007 |
| JP | 2007-537761 | A | 12/2007 |
| JP | 2008-543774 | A | 12/2008 |
| RU | 2 411 040 | C2 | 2/2011 |
| WO | 93/10152 | A1 | 5/1993 |
| WO | 97/12048 | A1 | 4/1997 |
| WO | 99/41383 | A1 | 8/1999 |
| WO | 02/096939 | A2 | 12/2002 |
| WO | 03/102166 | A2 | 12/2003 |
| WO | 2004/043399 | A2 | 5/2004 |
| WO | 2006/040334 | A1 | 4/2006 |
| WO | 2006/088229 | A1 | 8/2006 |
| WO | 2007/003384 | A1 | 1/2007 |
| WO | 2007/059715 | A2 | 5/2007 |
| WO | 2007/100098 | A1 | 9/2007 |
| WO | 2008/025067 | A1 | 3/2008 |
| WO | 2009/079185 | A2 | 6/2009 |
| WO | 2010/062396 | A2 | 6/2010 |
| WO | 2011/035004 | A1 | 3/2011 |
| WO | 2012/006180 | A1 | 1/2012 |
| WO | 2012/023995 | A1 | 2/2012 |
| WO | 2012/106356 | A2 | 8/2012 |
| WO | 2012/123755 | A1 | 9/2012 |
| WO | 2012/172574 | A1 | 12/2012 |
| WO | 2013/009884 | A1 | 1/2013 |
| WO | 2013/063248 | A1 | 5/2013 |
| WO | 2013/122262 | A1 | 8/2013 |
| WO | 2013/151764 | A1 | 10/2013 |
| WO | 2015/005500 | A1 | 1/2015 |
| WO | 2015/139784 | A1 | 9/2015 |
| WO | 2016/021209 | A1 | 2/2016 |
| WO | 2016109792 | | 7/2016 |
| WO | 2016/199936 | A1 | 12/2016 |
| WO | 2016/210127 | A1 | 12/2016 |
| WO | 2017/009873 | A1 | 1/2017 |
| WO | 2017/015463 | A2 | 1/2017 |

OTHER PUBLICATIONS

Sigrid Elshuber et al., “Cleavage of protein prM is necessary for Infection of BHK-21 cells by tick-borne encephalitis virus”, Journal of General Virology, (2003), vol. 84, pp. 183-191.
Sigrid Elshuber et al., “Resuscitating Mutations in a Furin Cleavage-Deficient Mutant of the Flavivirus Tick-Borne Encephalitis Virus”, Journal Of Virology, vol. 79, No. 18, Sep. 2005, pp. 11813-11823.
Simona Ozden et al., “Inhibition of Chikungunya Virus Infection in Cultured Human Muscle Cells by Furin Inhibitors”, Journal of Biological Chemistry, vol. 283, No. 32, Aug. 8, 2008, pp. 21899-21908. (10 pages total).
Wataru Akahata et al., “A VLP vaccine for epidemic Chikungunya virus protects non-human primates against infection”, Nat Med., Mar. 2010, vol. 16, No. 3, pp. 334-338 (manuscript 12 pages total).
Written Opinion, issued by International Searching Authority in corresponding International Application No. PCT/JP2015/003997, dated Oct. 27, 2015.
Communication, dated Jun. 20, 2017, issued by the Japanese Patent Office in Japanese Patent Application No. 2014-557308.
Spohn et al., “A Virus-Like Particle-Based Vaccine Selectively Targeting Soluble TNF-α Protects from Arthritis without Inducing Reactivation of Latent Tuberculosis”, The Journal of Immunology, 2007, vol. 178, pp. 7450-7457. (8 pages total).
Grgacic et al., “Virus-Like Particles: Passport to Immune Recognition”, Methods, 2006, vol. 40, pp. 60-65. (6 pages total).
Jennings et al., “Immunodrugs: Therapeutic VLP-Based Vaccines for Chronic Diseases”, Annu. Rev. Pharmacol. Toxicol., 2009, vol. 49 pp. 303-326. (25 pages total).
Leibl et al., “Adjuvant/Carrier Activity of Inactivated Tick-Borne Encephalitis Virus”, Vaccine, vol. 16, No. 4, 1998, pp. 340-345. (6 pages total).
Chackerian et al., “Determinants of Autoantibody Induction by Conjugated Papillomavirus Virus-Like Particles”, The Journal of Immunology, vol. 169, No. 11, 2002, pp. 6120-6126. (7 pages total).
Palomba et al., “$CD8^+$ T-Cell-Dependent Immunity Following Xenogeneic DNA Immunization against CD20 in a Tumor Challenge Model of B-Cell Lymphoma”, Clinical Cancer Research, vol. 11, Jan. 1, 2005, pp. 370-379. (10 pages total).
Roberts et al., “Vaccination with CD20 Peptides Induces a Biologically Active, Specific Immune Response in Mice”, Blood, vol. 99, No. 10, May 15, 2002, pp. 3748-3755. (8 pages total).
McCoy et al., “Cytotoxic T Lymphocyte-associated Antigen 4 (CTLA-4) Can Regulate Dendritic Cell-induced Activation and Cytotoxicity of $CD8^+$ T Cells Independently of $CD4^+$ TCell Help”, J. Exp. Med., vol. 189, No. 7, Apr. 5, 1999, pp. 1157-1162. (6 pages total).
Atkins et al., “Therapeutic and Prophylactic Applications of Alphavirus Vectors”, Expert Reviews in Molecular Medicine, vol. 10, Ed. 33, Nov. 2008, pp. 1-17. (17 pages total).
Hevey et al., “Marburg Virus Vaccines Based upon Alphavirus Replicons Protect Guinea Pigs and Nonhuman Primates”, Virology, vol. 251, 1998, pp. 28-37. (11 pages total).
Communication, dated Jun. 6, 2017, issued by the United States Patent and Trademark Office in U.S. Appl. No. 15/299,859.
Bonaldo et al., “Surface Expression of an Immunodominant Malaria Protein B Cell Epitope by Yellow Fever Virus”, J. Mol. Biol., vol. 315, No. 4, Jan. 25, 2002, pp. 873-885. (13 pages total).
Vuola et al. “Differential Immunogenicity of Various Heterologous Prime-Boost Vaccine Regimens Using DNA and Viral Vectors in Healthy Volunteers”, The Journal of Immunology, vol. 174, No. 1, Jan. 1, 2005, pp. 449-455. (7 pages total).
Pushko et al., “Replicon-Helper Systems from Attenuated Venezuelan Equine Encephalitis Virus: Expression of Heterologous Genes in Vitro and Immunization against Heterologous Pathogens in Vivo”, Virology, 239:389-401 (1997).
Communication, dated Dec. 20, 2017, issued by the European Patent Office in counterpart European Patent Application No. 15829311.8.
Urakami et al., “Development of a Novel Virus-Like Particle Vaccine Platform That Mimics the Immature Form of Alphavirus,” Clinical and Vaccine Immunology, 24(7): e00090-17 (pp. 1-14).
Adams et al. The expression of hybrid H1V:Ty virus-like particles in yeast. Nature. Sep. 3-9, 1987;329(6134):68-70.
Agata Y et al., “Expression of the PD-1 antigen on the surface of stimulated mouse T and B lymphocytes”, International Immunology, 1996, vol. 8, No. 5, pp. 765-772.
Akahata W and G.J. Nabel, 2012, A specific domain of the Chikungunya virus E2 protein regulates particle formation in human cells: implications for alphavirus vaccine design, J. Virol. 86 (16) 8879-8883.
Allsopp CE et al., Comparison of numerous delivery systems for the induction of cytotoxic T lymphocytes by immunization, Eur. J. Immunol., 1996, vol. 26, No. 8, pp. 1951-1959.
Arora U et al., “Virus-like particles displaying envelope domain III of dengue virus type 2 induce virus-specific antibody response in mice”, Vaccine, Jan. 2013, vol. 31, No. 6, p. 873-878.
Birkett A et al. “A Modified Hepatitis B Virus Core Particle Containing Multiple Epitopes of the Plasmodium falciparum Circumsporozoite Protein Provides a Highly immunogenic Malaria Vaccine in Preclinical Analyses in Rodent and Primate Hosts”.

(56) References Cited

OTHER PUBLICATIONS

Infection and Immunity. American Society for Microbiology. US. vol. 70. No. 12: Dec. 1, 2002. pp. 6860-6870.
Calvo-Calle et al., A Linear Peptide Containing Minimal T- and B-Cell Epitopes of Plasmodium falciparum Circumsporozoite Protein Elicits Protection against Transgenic Sporozoite Challenge. Infection and 1mmunity. qec. 2006. p. 6929-6939. vol. 74, No. 12.
Carvalho et al., "Malaria Vaccine: Candidate Antigens, Mechanisms, Constraints and Prospects", Scand. J. Immunol., Blackwell Science Ltd., Jul. 1, 2002, vol. 56, pp. 327-343.
Charoensri N et al. "An optimized expression vector for improving the yield of dengue virus-like particles from transfected insect cells" Journal of Virological Methods, vol. 205, 2014 (pp. 116-123).
Cox Brian et al. "Predicting Zika virus structural biology: Challenges and opportunities for intervention" Antiviral Chemistry and Chemotherapy, vol. 24 (3-4), 2015 (pp. 118-126).
Crompton et al, "Advances and challenges in malaria vaccine development", Science in medicine, The Journal of Clinical Investigation, Dec. 2010, vol. 120, No. 12, pp. 4168-4178.
De Wispelaere Melissanne, et al., J. Virol., 2012, vol. 86, No. 13, pp. 7072-7083, ISSN:0022-538X, Abstract, Fig.1, Fig.8-9, p. 7073.
Dobano C et al., Alphavirus replicon particles are highly immunogenic in the murine Malaria model by homologous or heterologous immunization, Open Vaccine Journal, vol. 1, 2008, pp. 27-37.
Expert Rev. Vaccines 9(10), 1149-1176, 2010.
Federico M., Virus-like particles show promise as candidates for new vaccine strategies. Future Vito/. (2010) 5(4), 371-374.
GenBank: AAB02517.1, "Structural polyprotein precursor, Venezuelan equine encephalitis virus," dated Nov. 17, 2004, retrieved from https ://s6,6,6; rcbi,r1r1:.r.i1-1,qt)wpioeir./AAB0251 7.1.
GenBank: ADG95942.1 structural polyprotein [Chikungunya virus] http://www.ncbi.nlm.nih.gov/protein/296124572?report=genbank &log$=protalign&blast_rank=2&FilD=PBR7NTOU015. Dec. 28, 2010.
"GenBank: AAW78190.1. circumsporozoite protein, partial [Plasmodium falciparum]. Dec. 29, 2006. http://www.ncbi.nlm.nih.gov/brotein/58429573?report=genbank&log$=protalig n&biast_rank=18 &RID=P92DMO5R01R".
GenBank "Zika virus strain MR 766, complete genome" AY632535. 2, Nov. 23, 2010 (6 pages total) [Retrieved on May 16, 2017] Retrieved from the Internet, URL:<https://www.ncbi.nlm.nih.gov/nuccore/AY632535>.
Ghasparian A et al., Engineered synthetic virus-like particles and their use in vaccine delivery, Chembiochem, 2011, vol. 12, No. 1, pp. 100-109.
Gilbert SC et al., A protein particle vaccine containing multiple Malaria epitopes, Nat. Biotechnol., 1997, vol. 15, No. 12, pp. 1280-1284.
Gregson et al. Phase 1 Trial of an Alhydrogel Adjuvanted Hepatitis B Core Virus-Like Particle Containing Epitopes of Plasmodium falciparum Circumsperozoite Protein. PLoS ONE. Feb. 2008 | vol. 3 | issue 2 | e1556.
Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).
Hsieh Szu-Chia, et al., Virology, 2008, vol. 374, No. 2, pp. 338-350, ISSN: 0042-6822.
Hsieh Szu-Chia, et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).
http://wmv.whaintlimmunizalion/researchldevela_pmentldengue vaccines/en/ (3 pages).
Huang Claire Y.H., et al., Virology, 2010, vol. 396, No. 2, pp. 305-315, ISSN:0042-6822, Tablel, Fig.5, pp. 310-313.
Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi:10.1371/journal.pone.0079538.
Khetarpal Niyati, et al., J. Nanobiotechnology, 2013, vol. 11, No. 15, 8 pages, ISSN: 1477-3155.
Zika virus fact sheet, updated Sep. 6, 2016; URL:http://www.who.int/mediacentre/factsheets/zika/en/ ( 5 pages total).
Kostyuchenko V et al., Structure of the thermally stable Zika virus, Nature, May 9, 2016, vol. 533, pp. 425-428.
Kuo S.C., et al., 2012, Cell-based analysis of Chikungunya virus E1 protein in membrane fusion , J. Biomed. Sci 19 (44):1-12.
Larocca RA, et al., "Vaccine Protection Against Zika Virus from Brazil", Nature, Aug. 25, 2016, 536(7617), 474-478, doi:10.1038/nature18952 (24 pages total).
Lechner F et al., Virus-like particles as a modular system for novel vaccines, Intervirology, 2002, vol. 45, No. 4-6, pp. 212-217.
Lin et al., PLOS, 2012, 6(1):e1337, 12 pages.
"Malaria Vaccine Program, http://www.globalvaccines.org/content/malaria+vaccine+program/19614, 4 pages total (2012)".
Mellman I et al., "Cancer immunotherapy comes of age", Nature, 2011, 480: 480-489.
Milich D R et al. "Conversion of poorly immunogenic malaria repeat sequences into a highly immunogenic vaccine candidate". Vaccine. Elsevier Ltd. GB: vol. 20. No. 5-6: Dec. 12, 2001: pp. 771-788.
Notka F et al., "Accelerated clearance of SHIV in rhesus monkeys by virus-like particle vaccines is dependent on induction of neutralizing antibodies", Vaccine, 2000, vol. 18, No. 3-4, p. 291-301.
Oliveira G et al., Safety and enhanced immunogenicity of a Hepatitis B core practical Plasmodium falciparum Malaria vaccine formulated in adjuvant montanide ISA 720 in a Phase I Trial, Infect. Immun., 2005, vol. 73, No. 6, pp. 3587-3597.
Oliveira-Ferreira et al. Immunogenicity of Ty-VLP bearing a CD8 (+) T cell epitope of the CS protein of P. yoelii: enhanced memory response by boosting with recombinant vaccinia virus. Vaccine. Mar. 6, 2000;18(17):1863-9.
Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371.
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig.1-4. Table 1, pp. 240, 247-248.
Richner Justin et al. "Modified mRNA vaccines protect against Zika Virus infection" Cell, vol. 168., Mar. 9, 2017 , pp. 1114-1125, (23 pages total).
Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648.
Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445.
Seligman S, "Constancy and diversity in the flavivirus fusion peptide", http://www.virologyj.com/content/5/1/27.
Shiratsuchi T. et al. "Replacing adenoviral vector HVR1 with a malaria B cell epitope improves immunogenicity and circumvents preexisting immunity to adenovirus in mice". Journal of Clinical Investigation: vol. 120. No. 10: Oct. 2010: pp. 3688-3701.
Sun S et al: "Structural analyses at pseudo atomic resolution of Chikungunya virus and antibodies show mechanisms of neutralization", eLIFE, Apr. 2, 2013, vol. 2, pp. 1-27.
Taylor TJ et al. "Production of immunogenic West Nile virus-like particles using a herpes simplex virus 1 recombinant vector" Virology, vol. 496, 2016 (pp. 186-193).
Tsai et al., Journal of Virology, 2015 89: 7348-7362.
Vaccine 30 (2012) 4301-4306.
Yamaji H et al. "Efficient production of Japanese encephalitis virus-like particles by recombinant lepidopteran insect cells" Appl. Microbiol Biotechnol, vol. 97, 2013 (pp. 1071-1079).
Zhang et al., Virology Journal, 2011, 8:333, 9 pages.

(56) References Cited

OTHER PUBLICATIONS

Veltrop-Duits et al., "Human CD4$^+$ T cells stimulated by conserved adenovirus 5 hexon peptides recognize cells infected with different species of human adenovirus", Eur. J. Immunol., 2006, vol. 36, pp. 2410-2423 (14 pages total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha et al., "Virus-Like Particles: Models for Assembly Studies and Foreign Epitope Carriers," Progress in Nucleic Acid Research and Molecular Biology, 2005, vol. 30, pp. 135-168.
Metz et al., PLoS ONE, 2011, vol. 6, Issue 10, pp. 1-10.
Liu et al., "Recombinant dengue virus-like particles from Pichia pastoris: efficient production and immunological properties," Vir. Genes, 2010: 40:53-59.
Berthet et al., GenBank Accession No: AHF49783.1, 2015, retrieved from https://www.ncbi.nlm.nih.gov/protein/AHF49783.
Enfissi et al., GenBank: ALX35659.1, 2016, retrieved from https://www.ncbi.nlm.nih.gov/protein/ALX35659.1.
Chhabra, et al., "Chikungunya fever: a re-emerging viral infection", Indian J Med Microbiol., 2008, vol. 26, No. 1, pp. 5-12 (10 pages total).
Lamballerie, et al., "Chikungunya virus adapts to tiger mosquito via evolutionary convergence: a sign of things to come?", Virology Journal, 2008, vol. 5, No. 33, pp. 1-4 (4 pages total).

* cited by examiner

CHIKV- Xa : Replace furin recognition site to Factor Xa recognition motive (IDGR)

CHIKV- En ; Replace furin recognition site to Enterokinase recognition motif (DDDDK)

VEEV- IDGR ; Replace furin recognition site to Factor Xa recognition motif (IDGR)

VEEV- IEGR ; Replace furin recognition site to Factor Xa recognition motif (IEGR)

human IL-2 wild type and mutant i-αVLP marker | Wild Type | FDVVF mutant

Blotting; anti-CHIKV mouse serum 1;1000

Mouse IL-2 wild type and the mutants i-αVLP

Wild Type | F54A | D34K

Control CHIKV VLP          261.261 VLP
 1   2   3   4   5   Marker   1   2   3   4   5   6   7   8   9   10

Control CHIKV VLP          264.264 VLP
 6   7   8   9   10  Marker   1   2   3   4   5   6   7   8   9   10

- ● 74 i-αVLP (E2 insert)
- ■ 74 i-αVLP (E3 insert)
- ▲ 74.74 i-αVLP Dual (E2 and E3 insert)

Anti-CHIKV mouse serum blotting (1:1000)

SEQUENCE LISTING

<160> NUMBER OF SEQ ID NOS: 154

<210> SEQ ID NO 1
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K

<400> SEQUENCE: 1

```
Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350
```

```
Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765
```

-continued

```
Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Val  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Met  Pro Ile Ser Ile Asp  Ile Pro Glu Ala Ala  Phe Thr Arg
    1085                 1090                 1095

Val Val  Asp Ala Pro Ser Leu  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Ala  Ala Ser Lys Lys Gly  Lys Cys Ala Val His  Ser Met Thr
    1130                 1135                 1140

Asn Ala  Val Thr Ile Arg Glu  Ala Glu Ile Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Glu
```

```
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp
    1205                1210                1215

Val Gln  Lys Ile Thr Gly Gly  Val Gly Leu Val Val  Ala Val Ala
    1220                1225                1230

Ala Leu  Ile Leu Ile Val Val  Leu Cys Val Ser Phe  Ser Arg His
    1235                1240                1245


<210> SEQ ID NO 2
<211> LENGTH: 1248
<212> TYPE: PRT
<213> ORGANISM: Chikungunya virus
<220> FEATURE:
<221> NAME/KEY: misc_feature
<222> LOCATION: (749)..(809)
<223> OTHER INFORMATION: 6K

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285
```

-continued

```
Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700
```

-continued

```
Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Ala  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Ile  Pro Ile Ser Ile Asp  Ile Pro Asp Ala Ala  Phe Thr Arg
    1085                1090                1095

Val Val  Asp Ala Pro Ser Val  Thr Asp Met Ser Cys  Glu Val Pro
    1100                1105                1110

Ala Cys  Thr His Ser Ser Asp  Phe Gly Gly Val Ala  Ile Ile Lys
```

```
    1115                1120                1125

Tyr Thr  Ala Ser Lys Lys Gly  Lys Cys Ala Val His  Ser Met Thr
    1130                1135                1140

Asn Ala  Val Thr Ile Arg Glu  Ala Asp Val Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Ala
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Thr Thr Ala  Met Ser Trp
    1205                1210                1215

Val Gln  Lys Ile Thr Gly Gly  Val Gly Leu Ile Val  Ala Val Ala
    1220                1225                1230

Ala Leu  Ile Leu Ile Val Val  Leu Cys Val Ser Phe  Ser Arg His
    1235                1240                1245


<210> SEQ ID NO 3
<211> LENGTH: 1255
<212> TYPE: PRT
<213> ORGANISM: Venezuelan equine encephalitis virus
<220> FEATURE:
<221> NAME/KEY: misc_feature
<222> LOCATION: (758)..(813)
<223> OTHER INFORMATION: 6K

<400> SEQUENCE: 3

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220
```

```
Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
        595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640
```

-continued

```
Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
        675                 680                 685

Val Ile Thr His Tyr Tyr His Arg Tyr Pro Met Ser Thr Ile Leu Gly
    690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
        755                 760                 765

Asn Asn Asn Gln Gln Met Phe Trp Ile Gln Leu Leu Ile Pro Leu Ala
    770                 775                 780

Ala Leu Ile Val Val Thr Arg Leu Leu Arg Cys Val Cys Cys Val Val
785                 790                 795                 800

Pro Phe Leu Val Met Ala Gly Ala Ala Gly Ala Gly Ala Tyr Glu His
                805                 810                 815

Ala Thr Thr Met Pro Ser Gln Ala Gly Ile Ser Tyr Asn Thr Ile Val
            820                 825                 830

Asn Arg Ala Gly Tyr Ala Pro Leu Pro Ile Ser Ile Thr Pro Thr Lys
        835                 840                 845

Ile Lys Leu Ile Pro Thr Val Asn Leu Glu Tyr Val Thr Cys His Tyr
    850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
        915                 920                 925

Ala Asp His Ala Glu Ala Tyr Lys Ala His Thr Ala Ser Val Gln Ala
    930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr  Asp Phe Pro Glu Tyr  Gly Ala Gly
        995                 1000                1005

Gln Pro  Gly Ala Phe Gly Asp  Ile Gln Ser Arg Thr  Val Ser Ser
    1010                1015                1020

Ser Asp  Leu Tyr Ala Asn Thr  Asn Leu Val Leu Gln  Arg Pro Lys
    1025                1030                1035

Ala Gly  Ala Ile His Val Pro  Tyr Thr Gln Ala Pro  Ser Gly Phe
    1040                1045                1050

Glu Gln  Trp Lys Lys Asp Lys  Ala Pro Ser Leu Lys  Phe Thr Ala
```

```
    1055                1060                1065

Pro Phe  Gly Cys Glu Ile Tyr  Thr Asn Pro Ile Arg  Ala Glu Asn
    1070                1075                1080

Cys Ala  Val Gly Ser Ile Pro  Leu Ala Phe Asp Ile  Pro Asp Ala
    1085                1090                1095

Leu Phe  Thr Arg Val Ser Glu  Thr Pro Thr Leu Ser  Ala Ala Glu
    1100                1105                1110

Cys Thr  Leu Asn Glu Cys Val  Tyr Ser Ser Asp Phe  Gly Gly Ile
    1115                1120                1125

Ala Thr  Val Lys Tyr Ser Ala  Ser Lys Ser Gly Lys  Cys Ala Val
    1130                1135                1140

His Val  Pro Ser Gly Thr Ala  Thr Leu Lys Glu Ala  Ala Val Glu
    1145                1150                1155

Leu Thr  Glu Gln Gly Ser Ala  Thr Ile His Phe Ser  Thr Ala Asn
    1160                1165                1170

Ile His  Pro Glu Phe Arg Leu  Gln Ile Cys Thr Ser  Tyr Val Thr
    1175                1180                1185

Cys Lys  Gly Asp Cys His Pro  Pro Lys Asp His Ile  Val Thr His
    1190                1195                1200

Pro Gln  Tyr His Ala Gln Thr  Phe Thr Ala Ala Val  Ser Lys Thr
    1205                1210                1215

Ala Trp  Thr Trp Leu Thr Ser  Leu Leu Gly Gly Ser  Ala Val Ile
    1220                1225                1230

Ile Ile  Ile Gly Leu Val Leu  Ala Thr Ile Val Ala  Met Tyr Val
    1235                1240                1245

Leu Thr  Asn Gln Lys His Asn
    1250                1255


<210> SEQ ID NO 4
<211> LENGTH: 20
<212> TYPE: PRT
<213> ORGANISM: Artificial Sequence
<220> FEATURE:
<223> OTHER INFORMATION: Synthetic CSP antigen

<400> SEQUENCE: 4

Glu Tyr Leu Asn Lys Ile Gln Asn Ser Leu Ser Thr Glu Trp Ser Pro
1               5                   10                  15

Cys Ser Val Thr
            20


<210> SEQ ID NO 5
<211> LENGTH: 20
<212> TYPE: PRT
<213> ORGANISM: Artificial Sequence
<220> FEATURE:
<223> OTHER INFORMATION: Synthetic CSP antigen

<400> SEQUENCE: 5

Tyr Asn Arg Asn Ile Val Asn Arg Leu Leu Gly Asp Ala Leu Asn Gly
1               5                   10                  15

Pro Glu Glu Lys
            20


<210> SEQ ID NO 6
<211> LENGTH: 18
<212> TYPE: PRT
<213> ORGANISM: Artificial Sequence
<220> FEATURE:
```

-continued

<223> OTHER INFORMATION: Synthetic PD-1 antigen

<400> SEQUENCE: 6

Leu Asn Trp Tyr Arg Met Ser Pro Ser Asn Gln Thr Asp Lys Leu Ala
1 5 10 15

Ala Phe

<210> SEQ ID NO 7
<211> LENGTH: 20
<212> TYPE: PRT
<213> ORGANISM: Artificial Sequence
<220> FEATURE:
<223> OTHER INFORMATION: Synthetic PD-1 antigen

<400> SEQUENCE: 7

Met Leu Asn Trp Tyr Arg Met Ser Pro Ser Asn Gln Thr Asp Lys Leu
1 5 10 15

Ala Ala Phe Ser
20

<210> SEQ ID NO 8
<211> LENGTH: 20
<212> TYPE: PRT
<213> ORGANISM: Artificial Sequence
<220> FEATURE:
<223> OTHER INFORMATION: Synthetic PD-1 antigen

<400> SEQUENCE: 8

Val Leu Asn Trp Tyr Arg Met Ser Pro Ser Asn Gln Thr Asp Lys Leu
1 5 10 15

Ala Ala Phe Pro
20

<210> SEQ ID NO 9
<211> LENGTH: 14
<212> TYPE: PRT
<213> ORGANISM: Artificial Sequence
<220> FEATURE:
<223> OTHER INFORMATION: Synthetic PD-1 antigen

<400> SEQUENCE: 9

Gly Ala Ile Ser Leu His Pro Lys Ala Lys Ile Glu Glu Ser
1 5 10

<210> SEQ ID NO 10
<211> LENGTH: 15
<212> TYPE: PRT
<213> ORGANISM: Artificial Sequence
<220> FEATURE:
<223> OTHER INFORMATION: Synthetic PD-1 antigen

<400> SEQUENCE: 10

Cys Gly Ala Ile Ser Leu His Pro Lys Ala Lys Ile Glu Glu Cys
1 5 10 15

<210> SEQ ID NO 11
<211> LENGTH: 19
<212> TYPE: PRT
<213> ORGANISM: Artificial Sequence
<220> FEATURE:
<223> OTHER INFORMATION: Synthetic PD-1 antigen

<400> SEQUENCE: 11

Val Leu Asn Trp Tyr Arg Met Ser Pro Ser Asn Gln Thr Asp Lys Leu
1 5 10 15

Ala Ala Phe

<210> SEQ ID NO 12
<211> LENGTH: 14
<212> TYPE: PRT
<213> ORGANISM: Artificial Sequence
<220> FEATURE:
<223> OTHER INFORMATION: Synthetic PD-1 antigen

<400> SEQUENCE: 12

```
Gly Ala Ile Ser Leu Ala Pro Lys Ala Gln Ile Lys Glu Ser
1               5                   10
```

<210> SEQ ID NO 13
<211> LENGTH: 31
<212> TYPE: PRT
<213> ORGANISM: Artificial Sequence
<220> FEATURE:
<223> OTHER INFORMATION: Synthetic PD-1 antigen

<400> SEQUENCE: 13

```
Arg Asn Asp Ser Gly Thr Tyr Leu Cys Gly Ala Ile Ser Leu Ala Pro
1               5                   10                  15

Lys Ala Gln Ile Lys Glu Ser Leu Arg Ala Glu Leu Arg Val Thr
            20                  25                  30
```

<210> SEQ ID NO 14
<211> LENGTH: 31
<212> TYPE: PRT
<213> ORGANISM: Artificial Sequence
<220> FEATURE:
<223> OTHER INFORMATION: Synthetic PD-1 antigen

<400> SEQUENCE: 14

```
Arg Asn Asp Ser Gly Ile Tyr Leu Cys Gly Ala Ile Ser Leu His Pro
1               5                   10                  15

Lys Ala Lys Ile Glu Glu Ser Pro Gly Ala Glu Leu Val Val Thr
            20                  25                  30
```

<210> SEQ ID NO 15
<211> LENGTH: 11
<212> TYPE: PRT
<213> ORGANISM: Artificial Sequence
<220> FEATURE:
<223> OTHER INFORMATION: Synthetic PD-L1 antigen

<400> SEQUENCE: 15

```
Cys Ile Ile Ser Tyr Gly Gly Ala Asp Tyr Cys
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: Synthetic PD-L1 antigen

<400> SEQUENCE: 16

```
Cys Met Ile Ser Tyr Gly Gly Ala Asp Tyr Cys
1               5                   10
```

<210> SEQ ID NO 17
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 17

Leu Gln Asp Ala Gly Val Tyr Arg Cys Met Ile Ser Tyr Gly Gly Ala
1               5                   10                  15

Asp Tyr Lys Arg Ile Thr Val Lys Val Asn
            20                  25

<210> SEQ ID NO 18
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 18

Leu Gln Asp Ala Gly Val Tyr Arg Ala Met Ile Ser Tyr Gly Gly Ala
1               5                   10                  15

Asp Tyr Lys Arg Ile Thr Val Lys Val Asn
            20                  25

<210> SEQ ID NO 19
<211> LENGTH: 21
<212> TYPE: PRT
<213> ORGANISM: Artificial Sequence
<220> FEATURE:
<223> OTHER INFORMATION: Synthetic PD-L1 antigen

<400> SEQUENCE: 19

Asp Leu Ala Ala Leu Ile Val Tyr Trp Glu Met Glu Asp Lys Asn Ile
1               5                   10                  15

Ile Gln Phe Val His
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic PD-L1 antigen

<400> SEQUENCE: 20

Asp Leu Ala Ala Leu Ile Val Tyr Trp Glu Met Glu Asp Lys Asn Ile
1               5                   10                  15

Ile Gln Phe Val His Gly Gly
            20

<210> SEQ ID NO 21
<211> LENGTH: 27
<212> TYPE: PRT
<213> ORGANISM: Artificial Sequence
<220> FEATURE:
<223> OTHER INFORMATION: Synthetic PD-L1 antigen

<400> SEQUENCE: 21

Phe Thr Val Thr Val Pro Lys Asp Leu Tyr Val Val Glu Tyr Gly Ser
1               5                   10                  15

Asn Met Thr Ile Glu Cys Lys Phe Pro Val Glu
            20                  25

<210> SEQ ID NO 22
<211> LENGTH: 26
<212> TYPE: PRT

<213> ORGANISM: Artificial Sequence
<220> FEATURE:
<223> OTHER INFORMATION: Synthetic PD-L1 antigen

<400> SEQUENCE: 22

Leu Gln Asp Ala Gly Val Tyr Cys Cys Ile Ile Ser Tyr Gly Gly Ala
1 5 10 15

Asp Tyr Lys Arg Ile Thr Leu Lys Val Asn
20 25

<210> SEQ ID NO 23
<211> LENGTH: 26
<212> TYPE: PRT
<213> ORGANISM: Artificial Sequence
<220> FEATURE:
<223> OTHER INFORMATION: Synthetic PD-L1 antigen

<400> SEQUENCE: 23

Leu Gln Asp Ala Gly Val Tyr Ala Ala Ile Ile Ser Tyr Gly Gly Ala
1 5 10 15

Asp Tyr Lys Arg Ile Thr Leu Lys Val Asn
20 25

<210> SEQ ID NO 24
<211> LENGTH: 21
<212> TYPE: PRT
<213> ORGANISM: Artificial Sequence
<220> FEATURE:
<223> OTHER INFORMATION: Synthetic PD-L1 antigen

<400> SEQUENCE: 24

Asp Leu Leu Ala Leu Val Val Tyr Trp Glu Lys Glu Asp Glu Gln Val
1 5 10 15

Ile Gln Phe Val Ala
20

<210> SEQ ID NO 25
<211> LENGTH: 23
<212> TYPE: PRT
<213> ORGANISM: Artificial Sequence
<220> FEATURE:
<223> OTHER INFORMATION: Synthetic PD-L1 antigen

<400> SEQUENCE: 25

Asp Leu Leu Ala Leu Val Val Tyr Trp Glu Lys Glu Asp Glu Gln Val
1 5 10 15

Ile Gln Phe Val Ala Gly Gly
20

<210> SEQ ID NO 26
<211> LENGTH: 27
<212> TYPE: PRT
<213> ORGANISM: Artificial Sequence
<220> FEATURE:
<223> OTHER INFORMATION: Synthetic PD-L1 antigen

<400> SEQUENCE: 26

Phe Thr Ile Thr Ala Pro Lys Asp Leu Tyr Val Val Glu Tyr Gly Ser
1 5 10 15

Asn Val Thr Met Glu Cys Arg Phe Pro Val Glu
20 25

<210> SEQ ID NO 27
<211> LENGTH: 18

-continued

<212> TYPE: PRT
<213> ORGANISM: Artificial Sequence
<220> FEATURE:
<223> OTHER INFORMATION: Synthetic CTLA-4 antigen

<400> SEQUENCE: 27

Gly Gly Lys Val Glu Leu Met Tyr Pro Pro Pro Tyr Phe Val Gly Met
1               5                   10                  15

Gly Gly

<210> SEQ ID NO 28
<211> LENGTH: 19
<212> TYPE: PRT
<213> ORGANISM: Artificial Sequence
<220> FEATURE:
<223> OTHER INFORMATION: Synthetic CTLA-4 antigen

<400> SEQUENCE: 28

Cys Ala Thr Thr Phe Thr Glu Lys Asn Thr Val Gly Phe Leu Asp Tyr
1               5                   10                  15

Pro Phe Cys

<210> SEQ ID NO 29
<211> LENGTH: 17
<212> TYPE: PRT
<213> ORGANISM: Artificial Sequence
<220> FEATURE:
<223> OTHER INFORMATION: Synthetic CTLA-4 antigen

<400> SEQUENCE: 29

Ala Thr Thr Phe Thr Glu Lys Asn Thr Val Gly Phe Leu Asp Tyr Pro
1               5                   10                  15

Phe

<210> SEQ ID NO 30
<211> LENGTH: 8401
<212> TYPE: DNA
<213> ORGANISM: Artificial Sequence
<220> FEATURE:
<223> OTHER INFORMATION: Synthetic _CHI 0 antigen (E3) vector

<400> SEQUENCE: 30
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttccatggg tcttttctgc agtcaccgtc gtcgacacgt gtgatcagat atcgcggccg 900
ccaccatgga gttcatcccg acgcaaactt tctataacag aaggtaccaa ccccgaccct 960
gggccccacg ccctacaatt caagtaatta gacctagacc acgtccacag aggcaggctg 1020
ggcaactcgc ccagctgatc tccgcagtca acaaattgac catgcgcgcg gtacctcaac 1080
agaagcctcg cagaaatcgg aaaaacaaga agcaaaggca gaagaagcag gcgccgcaaa 1140
acgacccaaa gcaaaagaag caaccaccac aaaagaagcc ggctcaaaag aagaagaaac 1200
caggccgtag ggagagaatg tgcatgaaaa ttgaaaatga ttgcatcttc gaagtcaagc 1260
atgaaggcaa agtgatgggc tacgcatgcc tggtggggga taaagtaatg aaaccagcac 1320
atgtgaaggg aactatcgac aatgccgatc tggctaaact ggcctttaag cggtcgtcta 1380
aatacgatct tgaatgtgca cagataccgg tgcacatgaa gtctgatgcc tcgaagttta 1440
cccacgagaa acccgagggg tactataact ggcatcacgg agcagtgcag tattcaggag 1500
gccggttcac tatcccgacg ggtgcaggca agccgggaga cagcggcaga ccgatcttcg 1560
acaacaaagg acgggtggtg gccatcgtcc taggaggggc caacgaaggt gcccgcacgg 1620
ccctctccgt ggtgacgtgg aacaaagaca tcgtcacaaa aattacccct gagggagccg 1680
aagagtggag cctcgccctc ccggtcttgt gcctgttggc aaacactaca ttcccctgct 1740
ctcagccgcc ttgcacaccc tgctgctacg aaaaggaacc ggaaagcacc ttgcgcatgc 1800
ttgaggacaa cgtgatgaga cccggatact accagctact aaaagcatcg ctgacttgct 1860
ctccccactc cggaggagga tccagtacta aggacaattt taatgtctat aaagccacaa 1920
gaccatatct agctcattgt cctgactgcg gagaagggca ttcgtgccac agccctatcg 1980
cattggagcg catcagaaat gaagcaacgg acggaacgct gaaaatccag gtctctttgc 2040
agatcgggat aaagacagat gacagccacg attggaccaa gctgcgctat atggatagcc 2100
atacgcccgc ggacgcggag cgagccggat tgcttgtaag gacttcagca ccgtgcacga 2160
tcaccgggac catgggacac tttattctcg cccgatgccc gaaaggagag acgctgacag 2220
tgggatttac ggacagcaga aagatcagcc acacatgcac acacccgttc catcatgaac 2280
cacctgtgat aggtagggag aggttccact ctcgaccaca acatggtaaa gagttacctt 2340
gcagcacgta cgtgcagagc accgctgcca ctgctgagga gatagaggtg catatgcccc 2400
cagatactcc tgaccgcacg ctgatgacgc agcagtctgg caacgtgaag atcacagtta 2460
atgggcagac ggtgcggtac aagtgcaact gcggtggctc aaacgaggga ctgacaacca 2520
cagacaaagt gatcaataac tgcaaaattg atcagtgcca tgctgcagtc actaatcaca 2580
agaattggca atacaactcc cctttagtcc cgcgcaacgc tgaactcggg gaccgtaaag 2640
gaaagatcca catcccattc ccattggcaa acgtgacttg cagagtgcca aaagcaagaa 2700
accctacagt aacttacgga aaaaaccaag tcaccatgct gctgtatcct gaccatccga 2760
cactcttgtc ttaccgtaac atgggacagg aaccaaatta ccacgaggag tgggtgacac 2820
acaagaagga ggttaccttg accgtgccta ctgagggtct ggaggtcact tggggcaaca 2880
acgaaccata caagtactgg ccgcagatgt ctacgaacgg tactgctcat ggtcacccac 2940
atgagataat cttgtactat tatgagctgt accccactat gactgtagtc attgtgtcgg 3000
tggcctcgtt cgtgcttctg tcgatggtgg gcacagcagt gggaatgtgt gtgtgcgcac 3060
ggcgcagatg cattacacca tatgaattaa caccaggagc cactgttccc ttcctgctca 3120
gcctgctatg ctgcgtcaga acgaccaagg cggccacata ttacgaggct gcggcatatc 3180

-continued tatggaacga acagcagccc ctgttctggt tgcaggctct tatcccgctg gccgccttga 3240
tcgtcctgtg caactgtctg aaactcttgc catgctgctg taagaccctg gctttttag 3300 ccgtaatgag catcggtgcc cacactgtga gcgcgtacga acacgtaaca gtgatcccga 3360
acacggtggg agtaccgtat aagactcttg tcaacagacc gggttacagc cccatggtgt 3420
tggagatgga gctacaatca gtcaccttgg aaccaacact gtcacttgac tacatcacgt 3480
gcgagtacaa aactgtcatc ccctccccgt acgtgaagtg ctgtggtaca gcagagtgca 3540
aggacaagag cctaccagac tacagctgca aggtctttac tggagtctac ccatttatgt 3600
ggggcggcgc ctactgcttt tgcgacgccg aaaatacgca attgagcgag gcacatgtag 3660
agaaatctga atcttgcaaa acagagtttg catcggccta cagagcccac accgcatcgg 3720
cgtcggcgaa gctccgcgtc ctttaccaag gaaacaacat taccgtagct gcctacgcta 3780
acggtgacca tgccgtcaca gtaaaggacg ccaagtttgt cgtgggccca atgtcctccg 3840
cctggacacc ttttgacaac aaaatcgtgg tgtacaaagg cgacgtctac aacatggact 3900
acccaccttt tggcgcagga agaccaggac aatttggtga cattcaaagt cgtacaccgg 3960
aaagtaaaga cgtttatgcc aacactcagt tggtactaca gaggccagca gcaggcacgg 4020
tacatgtacc atactctcag gcaccatctg gcttcaagta ttggctgaag gaacgaggag 4080
catcgctaca gcacacggca ccgttcggtt gccagattgc gacaaacccg gtaagagctg 4140
taaattgcgc tgtggggaac ataccaattt ccatcgacat accggatgcg gcctttacta 4200
gggttgtcga tgcaccctct gtaacggaca tgtcatgcga agtaccagcc tgcactcact 4260
cctccgactt tgggggcgtc gccatcatca aatacacagc tagcaagaaa ggtaaatgtg 4320
cagtacattc gatgaccaac gccgttacca ttcgagaagc cgacgtagaa gtagagggga 4380
actcccagct gcaaatatcc ttctcaacag ccctggcaag cgccgagttt cgcgtgcaag 4440
tgtgctccac acaagtacac tgcgcagccg catgccaccc tccaaaggac cacatagtca 4500
attacccagc atcacacacc acccttgggg tccaggatat atccacaacg gcaatgtctt 4560
gggtgcagaa gattacggga ggagtaggat taattgttgc tgttgctgcc ttaattttaa 4620
ttgtggtgct atgcgtgtcg tttagcaggc actaaggatc tagatctgct gtgccttcta 4680
gttgccagcc atctgttgtt tgcccctccc ccgtgccttc cttgaccctg gaaggtgcca 4740
ctcccactgt cctttcctaa taaaatgagg aaattgcatc gcattgtctg agtaggtgtc 4800
attctattct ggggggtggg gtggggcagg acagcaaggg ggaggattgg gaagacaata 4860
gcaggcatgc tggggatgcg gtgggctcta tgggtaccca ggtgctgaag aattgacccg 4920
gttcctcctg ggccagaaag aagcaggcac atccccttct ctgtgacaca ccctgtccac 4980
gcccctggtt cttagttcca gccccactca taggacactc atagctcagg agggctccgc 5040
cttcaatccc acccgctaaa gtacttggag cggtctctcc ctccctcatc agcccaccaa 5100
accaaaccta gcctccaaga gtgggaagaa attaaagcaa gataggctat taagtgcaga 5160
gggagagaaa atgcctccaa catgtgagga agtaatgaga gaaatcatag aattttaagg 5220
ccatgattta aggccatcat ggcctaagct tgaaaggaga taggatcaaa gcttggcgta 5280
atcatggtca tagctgtttc ctgtgtgaaa ttgttatccg ctcacaattc cacacaacat 5340
acgagccgga agcataaagt gtaaagcctg gggtgcctaa tgagtgagct aactcacatt 5400
aattgcgttg cgctcactgc ccgctttcca gtcgggaaac ctgtcgtgcc agctgcatta 5460
atgaatcggc caacgcgcgg ggagaggcgg tttgcgtatt gggcgctctt ccgcttcctc 5520
gctcactgac tcgctgcgct cggtcgttcg gctgcggcga gcggtatcag ctcactcaaa 5580

-continued

```
ggcggtaata cggttatcca cagaatcagg ggataacgca ggaaagaaca tgtgagcaaa   5640
aggccagcaa aaggccagga accgtaaaaa ggccgcgttg ctggcgtttt tccataggct   5700
ccgcccccct gacgagcatc acaaaaatcg acgctcaagt cagaggtggc gaaacccgac   5760
aggactataa agataccagg cgtttccccc tggaagctcc ctcgtgcgct ctcctgttcc   5820
gaccctgccg cttaccggat acctgtccgc ctttctccct tcgggaagcg tggcgctttc   5880
tcatagctca cgctgtaggt atctcagttc ggtgtaggtc gttcgctcca agctgggctg   5940
tgtgcacgaa ccccccgttc agcccgaccg ctgcgcctta tccggtaact atcgtcttga   6000
gtccaacccg gtaagacacg acttatcgcc actggcagca gccactggta acaggattag   6060
cagagcgagg tatgtaggcg gtgctacaga gttcttgaag tggtggccta actacggcta   6120
cactagaaga acagtatttg gtatctgcgc tctgctgaag ccagttacct tcggaaaaag   6180
agttggtagc tcttgatccg gcaaacaaac caccgctggt agcggtggtt tttttgtttg   6240
caagcagcag attacgcgca gaaaaaaagg atctcaagaa gatcctttga tcttttctac   6300
ggggtctgac gctcagtgga acgaaaactc acgttaaggg attttggtca tgagattatc   6360
aaaaaggatc ttcacctaga tccttttaaa ttaaaaatga agttttaaat caatctaaag   6420
tatatatgag taaacttggt ctgacagtta ccaatgctta atcagtgagg cacctatctc   6480
agcgatctgt ctatttcgtt catccatagt tgcctgactc cccgtcgtgt agataactac   6540
gatacgggag ggcttaccat ctggccccag tgctgcaatg ataccgcgag aaccacgctc   6600
accggctcca gatttatcag caataaacca gccagccgga agggccgagc gcagaagtgg   6660
tcctgcaact ttatccgcct ccatccagtc tattaattgt tgccgggaag ctagagtaag   6720
tagttcgcca gttaatagtt tgcgcaacgt tgttgccatt gctacaggca tcgtggtgtc   6780
acgctcgtcg tttggtatgg cttcattcag ctccggttcc caacgatcaa ggcgagttac   6840
atgatccccc atgttgtgca aaaaagcggt tagctccttc ggtcctccga tcgttgtcag   6900
aagtaagttg gccgcagtgt tatcactcat ggttatggca gcactgcata attctcttac   6960
tgtcatgcca tccgtaagat gcttttctgt gactggtgag tactcaacca agtcattctg   7020
agaatagtgt atgcggcgac cgagttgctc ttgcccggcg tcaatacggg ataataccgc   7080
gccacatagc agaactttaa aagtgctcat cattggaaaa cgttcttcgg ggcgaaaact   7140
ctcaaggatc ttaccgctgt tgagatccag ttcgatgtaa cccactcgtg cacccaactg   7200
atcttcagca tcttttactt tcaccagcgt ttctgggtga gcaaaaacag gaaggcaaaa   7260
tgccgcaaaa aagggaataa gggcgacacg gaaatgttga atactcatac tcttcctttt   7320
tcaatattat tgaagcattt atcagggtta ttgtctcatg agcggataca tatttgaatg   7380
tatttagaaa aataaacaaa taggggttcc gcgcacattt ccccgaaaag tgccacctga   7440
cgtctaagaa accattatta tcatgacatt aacctataaa aataggcgta tcacgaggcc   7500
ctttcgggtc gcgcgtttcg gtgatgacgg tgaaaacctc tgacacatgc agctcccgtt   7560
gacggtcaca gcttgtctgt aagcggatgc cgggagcaga caagcccgtc agggcgcgtc   7620
agcgggtgtt ggcgggtgtc ggggctggct taactatgcg gcatcagagc agattgtact   7680
gagagtgcac cataaaattg taaacgttaa tattttgtta aaattcgcgt taaatttttg   7740
ttaaatcagc tcatttttta accaataggc cgaaatcggc aaaatccctt ataaatcaaa   7800
agaatagccc gagatagggt tgagtgttgt tccagtttgg aacaagagtc cactattaaa   7860
gaacgtggac tccaacgtca aagggcgaaa aaccgtctat cagggcgatg gcccactacg   7920
```

-continued

```
tgaaccatca cccaaatcaa gttttttggg gtcgaggtgc cgtaaagcac taaatcggaa   7980

ccctaaaggg agcccccgat ttagagcttg acggggaaag ccggcgaacg tggcgagaaa   8040

ggaagggaag aaagcgaaag gagcgggcgc tagggcgctg gcaagtgtag cggtcacgct   8100

gcgcgtaacc accacacccg ccgcgcttaa tgcgccgcta cagggcgcgt actatggttg   8160

ctttgacgta tgcggtgtga aataccgcac agatgcgtaa ggagaaaata ccgcatcagg   8220

cgccattcgc cattcaggct gcgcaactgt tgggaagggc gatcggtgcg ggcctcttcg   8280

ctattacgcc agctggcgaa aggggggatgt gctgcaaggc gattaagttg ggtaacgcca   8340

gggttttccc agtcacgacg ttgtaaaacg acggccagtg aattccatgg tctcaacttt   8400

c                                                                   8401
```

```
<210> SEQ ID NO 31
<211> LENGTH: 261
<212> TYPE: PRT
<213> ORGANISM: Artificial Sequence
<220> FEATURE:
<223> OTHER INFORMATION: Synthetic CHIKV Capsid (37997 strain)

<400> SEQUENCE: 31

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260
```

<210> SEQ ID NO 32
<211> LENGTH: 439
<212> TYPE: PRT
<213> ORGANISM: Artificial Sequence
<220> FEATURE:
<223> OTHER INFORMATION: Synthetic CHIKV E1 (37997 strain)

<400> SEQUENCE: 32

```
Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

Gln Ile Ser Phe Ser Thr Ala Leu Ala Ser Ala Glu Phe Arg Val Gln
        355                 360                 365
```

```
Val Cys Ser Thr Gln Val His Cys Ala Ala Ala Cys His Pro Pro Lys
    370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
                405                 410                 415

Val Gly Leu Ile Val Ala Val Ala Ala Leu Ile Leu Ile Val Val Leu
            420                 425                 430

Cys Val Ser Phe Ser Arg His
        435


<210> SEQ ID NO 33
<211> LENGTH: 483
<212> TYPE: PRT
<213> ORGANISM: Artificial Sequence
<220> FEATURE:
<223> OTHER INFORMATION: Synthetic CHIKV E3-insert-E2 (37997 strain)
<220> FEATURE:
<221> NAME/KEY: NON_CONS
<222> LOCATION: (60)..(61)
<223> OTHER INFORMATION: antigen will be inserted

<400> SEQUENCE: 33

Ser Leu Ala Leu Pro Val Leu Cys Leu Leu Ala Asn Thr Thr Phe Pro
1               5                   10                  15

Cys Ser Gln Pro Pro Cys Thr Pro Cys Cys Tyr Glu Lys Glu Pro Glu
            20                  25                  30

Ser Thr Leu Arg Met Leu Glu Asp Asn Val Met Arg Pro Gly Tyr Tyr
        35                  40                  45

Gln Leu Leu Lys Ala Ser Leu Thr Cys Ser Pro His Ser Thr Lys Asp
    50                  55                  60

Asn Phe Asn Val Tyr Lys Ala Thr Arg Pro Tyr Leu Ala His Cys Pro
65                  70                  75                  80

Asp Cys Gly Glu Gly His Ser Cys His Ser Pro Ile Ala Leu Glu Arg
                85                  90                  95

Ile Arg Asn Glu Ala Thr Asp Gly Thr Leu Lys Ile Gln Val Ser Leu
            100                 105                 110

Gln Ile Gly Ile Lys Thr Asp Asp Ser His Asp Trp Thr Lys Leu Arg
        115                 120                 125

Tyr Met Asp Ser His Thr Pro Ala Asp Ala Glu Arg Ala Gly Leu Leu
    130                 135                 140

Val Arg Thr Ser Ala Pro Cys Thr Ile Thr Gly Thr Met Gly His Phe
145                 150                 155                 160

Ile Leu Ala Arg Cys Pro Lys Gly Glu Thr Leu Thr Val Gly Phe Thr
                165                 170                 175

Asp Ser Arg Lys Ile Ser His Thr Cys Thr His Pro Phe His His Glu
            180                 185                 190

Pro Pro Val Ile Gly Arg Glu Arg Phe His Ser Arg Pro Gln His Gly
        195                 200                 205

Lys Glu Leu Pro Cys Ser Thr Tyr Val Gln Ser Thr Ala Ala Thr Ala
    210                 215                 220

Glu Glu Ile Glu Val His Met Pro Pro Asp Thr Pro Asp Arg Thr Leu
225                 230                 235                 240

Met Thr Gln Gln Ser Gly Asn Val Lys Ile Thr Val Asn Gly Gln Thr
                245                 250                 255

Val Arg Tyr Lys Cys Asn Cys Gly Gly Ser Asn Glu Gly Leu Thr Thr
            260                 265                 270
```

Thr Asp Lys Val Ile Asn Asn Cys Lys Ile Asp Gln Cys His Ala Ala
275 280 285

Val Thr Asn His Lys Asn Trp Gln Tyr Asn Ser Pro Leu Val Pro Arg
290 295 300

Asn Ala Glu Leu Gly Asp Arg Lys Gly Lys Ile His Ile Pro Phe Pro
305 310 315 320

Leu Ala Asn Val Thr Cys Arg Val Pro Lys Ala Arg Asn Pro Thr Val
325 330 335

Thr Tyr Gly Lys Asn Gln Val Thr Met Leu Leu Tyr Pro Asp His Pro
340 345 350

Thr Leu Leu Ser Tyr Arg Asn Met Gly Gln Glu Pro Asn Tyr His Glu
355 360 365

Glu Trp Val Thr His Lys Lys Glu Val Thr Leu Thr Val Pro Thr Glu
370 375 380

Gly Leu Glu Val Thr Trp Gly Asn Asn Glu Pro Tyr Lys Tyr Trp Pro
385 390 395 400

Gln Met Ser Thr Asn Gly Thr Ala His Gly His Pro His Glu Ile Ile
405 410 415

Leu Tyr Tyr Tyr Glu Leu Tyr Pro Thr Met Thr Val Val Ile Val Ser
420 425 430

Val Ala Ser Phe Val Leu Leu Ser Met Val Gly Thr Ala Val Gly Met
435 440 445

Cys Val Cys Ala Arg Arg Arg Cys Ile Thr Pro Tyr Glu Leu Thr Pro
450 455 460

Gly Ala Thr Val Pro Phe Leu Leu Ser Leu Leu Cys Cys Val Arg Thr
465 470 475 480

Thr Lys Ala

<210> SEQ ID NO 34
<211> LENGTH: 8422
<212> TYPE: DNA
<213> ORGANISM: Artificial Sequence
<220> FEATURE:
<223> OTHER INFORMATION: Synthetic _VEEV 0.66 vector

<400> SEQUENCE: 34
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840

-continued

```
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa gggggaggcc   1140
aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccgggtccgg aggtggatcc tccaccgagg   1920
agctgtttaa tgagtataag ctaacgcgcc cttacatggc cagatgcatc agatgtgcag   1980
ttgggagctg ccatagtcca atagcaatcg aggcagtaaa gagcgacggg cacgacggtt   2040
atgttagact tcagacttcc tcgcagtatg gcctggattc ctccggcaac ttaaagggca   2100
ggaccatgcg gtatgacatg cacgggacca ttaaagagat accactacat caagtgtcac   2160
tctatacatc tcgcccgtgt cacattgtgg atgggcacgg ttatttcctg ctagccaggt   2220
gcccggcagg ggactccatc accatggaat ttaagaaaga ttccgtcaga cactcctgct   2280
cggtgccgta tgaagtgaaa tttaatcctg taggcagaga actctatact catcccccag   2340
aacacggagt agagcaagcg tgccaagtct acgcacatga tgcacagaac agaggagctt   2400
atgtcgagat gcacctcccg ggctcagaag tggacagcag tttggtttcc ttgagcggca   2460
gttcagtcac cgtgacacct cctgatggga ctagcgccct ggtggaatgc gagtgtggcg   2520
gcacaaagat ctccgagacc atcaacaaga caaaacagtt cagccagtgc acaaagaagg   2580
agcagtgcag agcatatcgg ctgcagaacg ataagtgggt gtataattct gacaaactgc   2640
ccaaagcagc gggagccacc ttaaaaggaa aactgcatgt cccattcttg ctggcagacg   2700
gcaaatgcac cgtgcctcta gcaccagaac ctatgataac cttcggtttc agatcagtgt   2760
cactgaaact gcaccctaag aatcccacat atctaatcac ccgccaactt gctgatgagc   2820
ctcactacac gcacgagctc atatctgaac cagctgttag gaattttacc gtcaccgaaa   2880
aagggtggga gtttgtatgg ggaaaccacc cgccgaaaag gttttgggca caggaaacag   2940
cacccggaaa tccacatggg ctaccgcacg aggtgataac tcattattac cacagatacc   3000
ctatgtccac catcctgggt ttgtcaattt gtgccgccat tgcaaccgtt tccgttgcag   3060
cgtctacctg gctgttttgc agatcaagag ttgcgtgcct aactccttac cggctaacac   3120
ctaacgctag gataccattt tgtctggctg tgctttgctg cgcccgcact gcccgggccg   3180
```

-continued agaccacctg ggagtccttg gatcacctat ggaacaataa ccaacagatg ttctggattc 3240
aattgctgat ccctctggcc gccttgatcg tagtgactcg cctgctcagg tgcgtgtgct 3300
gtgtcgtgcc tttttagtc atggccggcg ccgcaggcgc cggcgcctac gagcacgcga 3360
ccacgatgcc gagccaagcg ggaatctcgt ataacactat agtcaacaga gcaggctacg 3420
caccactccc tatcagcata acaccaacaa agatcaagct gatacctaca gtgaacttgg 3480
agtacgtcac ctgccactac aaaacaggaa tggattcacc agccatcaaa tgctgcggat 3540
ctcaggaatg cactccaact tacaggcctg atgaacagtg caaagtcttc acaggggttt 3600
acccgttcat gtggggtggt gcatattgct tttgcgacac tgagaacacc caagtcagca 3660
aggcctacgt aatgaaatct gacgactgcc ttgcggatca tgctgaagca tataaagcgc 3720
acacagcctc agtgcaggcg ttcctcaaca tcacagtggg agaacactct attgtgacta 3780
ccgtgtatgt gaatggagaa actcctgtga atttcaatgg ggtcaaaata actgcaggtc 3840
cgctttccac agcttggaca ccctttgatc gcaaaatcgt gcagtatgcc ggggagatct 3900
ataattatga ttttcctgag tatggggcag gacaaccagg agcatttgga gatatacaat 3960
ccagaacagt ctcaagctct gatctgtatg ccaataccaa cctagtgctg cagagaccca 4020
aagcaggagc gatccacgtg ccatacactc aggcaccttc gggttttgag caatggaaga 4080
aagataaagc tccatcattg aaatttaccg cccctttcgg atgcgaaata tatacaaacc 4140
ccattcgcgc cgaaaactgt gctgtagggt caattccatt agcctttgac attcccgacg 4200
ccttgttcac cagggtgtca gaaacaccga cactttcagc ggccgaatgc actcttaacg 4260
agtgcgtgta ttcttccgac tttggtggga tcgccacggt caagtactcg gccagcaagt 4320
caggcaagtg cgcagtccat gtgccatcag ggactgctac cctaaaagaa gcagcagtcg 4380
agctaaccga gcaagggtcg gcgactatcc atttctcgac cgcaaatatc cacccggagt 4440
tcaggctcca aatatgcaca tcatatgtta cgtgcaaagg tgattgtcac cccccgaaag 4500
accatattgt gacacaccct cagtatcacg cccaaacatt tacagccgcg gtgtcaaaaa 4560
ccgcgtggac gtggttaaca tccctgctgg gaggatcagc cgtaattatt ataattggct 4620
tggtgctggc tactattgtg gccatgtacg tgctgaccaa ccagaaacat aattaaggat 4680
ctagatctgc tgtgccttct agttgccagc catctgttgt ttgcccctcc cccgtgcctt 4740
ccttgaccct ggaaggtgcc actcccactg tcctttccta ataaaatgag gaaattgcat 4800
cgcattgtct gagtaggtgt cattctattc tggggggtgg ggtggggcag gacagcaagg 4860
gggaggattg ggaagacaat agcaggcatg ctggggatgc ggtgggctct atgggtaccc 4920
aggtgctgaa gaattgaccc ggttcctcct gggccagaaa gaagcaggca catccccttc 4980
tctgtgacac accctgtcca cgcccctggt tcttagttcc agccccactc ataggacact 5040
catagctcag gagggctccg ccttcaatcc cacccgctaa agtacttgga gcggtctctc 5100
cctccctcat cagcccacca aaccaaacct agcctccaag agtgggaaga aattaaagca 5160
agataggcta ttaagtgcag agggagagaa aatgcctcca acatgtgagg aagtaatgag 5220
agaaatcata gaattttaag gccatgattt aaggccatca tggcctaagc ttgaaaggag 5280
ataggatcaa agcttggcgt aatcatggtc atagctgttt cctgtgtgaa attgttatcc 5340
gctcacaatt ccacacaaca tacgagccgg aagcataaag tgtaaagcct ggggtgccta 5400
atgagtgagc taactcacat taattgcgtt gcgctcactg cccgctttcc agtcgggaaa 5460
cctgtcgtgc cagctgcatt aatgaatcgg ccaacgcgcg gggagaggcg gtttgcgtat 5520
tgggcgctct tccgcttcct cgctcactga ctcgctgcgc tcggtcgttc ggctgcggcg 5580
agcggtatca gctcactcaa aggcggtaat acggttatcc acagaatcag gggataacgc 5640
aggaaagaac atgtgagcaa aaggccagca aaaggccagg aaccgtaaaa aggccgcgtt 5700
gctggcgttt ttccataggc tccgcccccc tgacgagcat cacaaaaatc gacgctcaag 5760
tcagaggtgg cgaaacccga caggactata aagataccag gcgtttcccc ctggaagctc 5820
cctcgtgcgc tctcctgttc cgaccctgcc gcttaccgga tacctgtccg cctttctccc 5880
ttcgggaagc gtggcgcttt ctcatagctc acgctgtagg tatctcagtt cggtgtaggt 5940
cgttcgctcc aagctgggct gtgtgcacga accccccgtt cagcccgacc gctgcgcctt 6000
atccggtaac tatcgtcttg agtccaaccc ggtaagacac gacttatcgc cactggcagc 6060
agccactggt aacaggatta gcagagcgag gtatgtaggc ggtgctacag agttcttgaa 6120
gtggtggcct aactacggct acactagaag aacagtattt ggtatctgcg ctctgctgaa 6180
gccagttacc ttcggaaaaa gagttggtag ctcttgatcc ggcaaacaaa ccaccgctgg 6240
tagcggtggt ttttttgttt gcaagcagca gattacgcgc agaaaaaaag gatctcaaga 6300
agatcctttg atcttttcta cggggtctga cgctcagtgg aacgaaaact cacgttaagg 6360
gattttggtc atgagattat caaaaaggat cttcacctag atccttttaa attaaaaatg 6420
aagttttaaa tcaatctaaa gtatatatga gtaaacttgg tctgacagtt accaatgctt 6480
aatcagtgag gcacctatct cagcgatctg tctatttcgt tcatccatag ttgcctgact 6540
ccccgtcgtg tagataacta cgatacggga gggcttacca tctggcccca gtgctgcaat 6600
gataccgcga gaaccacgct caccggctcc agatttatca gcaataaacc agccagccgg 6660
aagggccgag cgcagaagtg gtcctgcaac tttatccgcc tccatccagt ctattaattg 6720
ttgccgggaa gctagagtaa gtagttcgcc agttaatagt ttgcgcaacg ttgttgccat 6780
tgctacaggc atcgtggtgt cacgctcgtc gtttggtatg gcttcattca gctccggttc 6840
ccaacgatca aggcgagtta catgatcccc catgttgtgc aaaaaagcgg ttagctcctt 6900
cggtcctccg atcgttgtca gaagtaagtt ggccgcagtg ttatcactca tggttatggc 6960
agcactgcat aattctctta ctgtcatgcc atccgtaaga tgcttttctg tgactggtga 7020
gtactcaacc aagtcattct gagaatagtg tatgcggcga ccgagttgct cttgcccggc 7080
gtcaatacgg gataataccg cgccacatag cagaacttta aaagtgctca tcattggaaa 7140
acgttcttcg gggcgaaaac tctcaaggat cttaccgctg ttgagatcca gttcgatgta 7200
acccactcgt gcacccaact gatcttcagc atcttttact ttcaccagcg tttctgggtg 7260
agcaaaaaca ggaaggcaaa atgccgcaaa aaagggaata agggcgacac ggaaatgttg 7320
aatactcata ctcttccttt ttcaatatta ttgaagcatt tatcagggtt attgtctcat 7380
gagcggatac atatttgaat gtatttagaa aaataaacaa ataggggttc cgcgcacatt 7440
tccccgaaaa gtgccacctg acgtctaaga aaccattatt atcatgacat taacctataa 7500
aaataggcgt atcacgaggc cctttcgggt cgcgcgtttc ggtgatgacg gtgaaaacct 7560
ctgacacatg cagctcccgt tgacggtcac agcttgtctg taagcggatg ccgggagcag 7620
acaagcccgt cagggcgcgt cagcgggtgt tggcgggtgt cggggctggc ttaactatgc 7680
ggcatcagag cagattgtac tgagagtgca ccataaaatt gtaaacgtta atattttgtt 7740
aaaattcgcg ttaaattttt gttaaatcag ctcatttttt aaccaatagg ccgaaatcgg 7800
caaaatccct tataaatcaa aagaatagcc cgagataggg ttgagtgttg ttccagtttg 7860
gaacaagagt ccactattaa agaacgtgga ctccaacgtc aaagggcgaa aaaccgtcta 7920

```
tcagggcgat ggcccactac gtgaaccatc acccaaatca agttttttgg ggtcgaggtg   7980

ccgtaaagca ctaaatcgga accctaaagg gagcccccga tttagagctt gacggggaaa   8040

gccggcgaac gtggcgagaa aggaagggaa gaaagcgaaa ggagcgggcg ctagggcgct   8100

ggcaagtgta gcggtcacgc tgcgcgtaac caccacaccc gccgcgctta atgcgccgct   8160

acagggcgcg tactatggtt gctttgacgt atgcggtgtg aaataccgca cagatgcgta   8220

aggagaaaat accgcatcag gcgccattcg ccattcaggc tgcgcaactg ttgggaaggg   8280

cgatcggtgc gggcctcttc gctattacgc cagctggcga aagggggatg tgctgcaagg   8340

cgattaagtt gggtaacgcc agggttttcc cagtcacgac gttgtaaaac gacggccagt   8400

gaattccatg gtctcaactt tc                                            8422
```

<210> SEQ ID NO 35
<211> LENGTH: 275
<212> TYPE: PRT
<213> ORGANISM: Artificial Sequence
<220> FEATURE:
<223> OTHER INFORMATION: Synthetic VEEV Capsid

<400> SEQUENCE: 35

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Asn
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270
```

Glu Gln Trp
        275

<210> SEQ ID NO 36
<211> LENGTH: 442
<212> TYPE: PRT
<213> ORGANISM: Artificial Sequence
<220> FEATURE:
<223> OTHER INFORMATION: Synthetic VEEV E1

<400> SEQUENCE: 36

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Val Tyr Val Asn Gly Glu Thr Pro Val Asn Phe Asn Gly Val Lys
145                 150                 155                 160

Ile Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
            180                 185                 190

Gly Ala Gly Gln Pro Gly Ala Phe Gly Asp Ile Gln Ser Arg Thr Val
        195                 200                 205

Ser Ser Ser Asp Leu Tyr Ala Asn Thr Asn Leu Val Leu Gln Arg Pro
    210                 215                 220

Lys Ala Gly Ala Ile His Val Pro Tyr Thr Gln Ala Pro Ser Gly Phe
225                 230                 235                 240

Glu Gln Trp Lys Lys Asp Lys Ala Pro Ser Leu Lys Phe Thr Ala Pro
                245                 250                 255

Phe Gly Cys Glu Ile Tyr Thr Asn Pro Ile Arg Ala Glu Asn Cys Ala
            260                 265                 270

Val Gly Ser Ile Pro Leu Ala Phe Asp Ile Pro Asp Ala Leu Phe Thr
        275                 280                 285

Arg Val Ser Glu Thr Pro Thr Leu Ser Ala Ala Glu Cys Thr Leu Asn
    290                 295                 300

Glu Cys Val Tyr Ser Ser Asp Phe Gly Gly Ile Ala Thr Val Lys Tyr
305                 310                 315                 320

Ser Ala Ser Lys Ser Gly Lys Cys Ala Val His Val Pro Ser Gly Thr
                325                 330                 335

Ala Thr Leu Lys Glu Ala Ala Val Glu Leu Thr Glu Gln Gly Ser Ala
            340                 345                 350

```
Thr Ile His Phe Ser Thr Ala Asn Ile His Pro Glu Phe Arg Leu Gln
        355                 360                 365

Ile Cys Thr Ser Tyr Val Thr Cys Lys Gly Asp Cys His Pro Pro Lys
    370                 375                 380

Asp His Ile Val Thr His Pro Gln Tyr His Ala Gln Thr Phe Thr Ala
385                 390                 395                 400

Ala Val Ser Lys Thr Ala Trp Thr Trp Leu Thr Ser Leu Leu Gly Gly
                405                 410                 415

Ser Ala Val Ile Ile Ile Ile Gly Leu Val Leu Ala Thr Ile Val Ala
            420                 425                 430

Met Tyr Val Leu Thr Asn Gln Lys His Asn
        435                 440


<210> SEQ ID NO 37
<211> LENGTH: 478
<212> TYPE: PRT
<213> ORGANISM: Artificial Sequence
<220> FEATURE:
<223> OTHER INFORMATION: Synthetic VEEV E3-insert-E2
<220> FEATURE:
<221> NAME/KEY: NON_CONS
<222> LOCATION: (61)..(62)
<223> OTHER INFORMATION: antigen will be inserted

<400> SEQUENCE: 37

Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Thr Glu Glu Leu Phe Asn Glu Tyr
    50                  55                  60

Lys Leu Thr Arg Pro Tyr Met Ala Arg Cys Ile Arg Cys Ala Val Gly
65                  70                  75                  80

Ser Cys His Ser Pro Ile Ala Ile Glu Ala Val Lys Ser Asp Gly His
                85                  90                  95

Asp Gly Tyr Val Arg Leu Gln Thr Ser Ser Gln Tyr Gly Leu Asp Ser
            100                 105                 110

Ser Gly Asn Leu Lys Gly Arg Thr Met Arg Tyr Asp Met His Gly Thr
        115                 120                 125

Ile Lys Glu Ile Pro Leu His Gln Val Ser Leu Tyr Thr Ser Arg Pro
    130                 135                 140

Cys His Ile Val Asp Gly His Gly Tyr Phe Leu Leu Ala Arg Cys Pro
145                 150                 155                 160

Ala Gly Asp Ser Ile Thr Met Glu Phe Lys Lys Asp Ser Val Arg His
                165                 170                 175

Ser Cys Ser Val Pro Tyr Glu Val Lys Phe Asn Pro Val Gly Arg Glu
            180                 185                 190

Leu Tyr Thr His Pro Pro Glu His Gly Val Glu Gln Ala Cys Gln Val
        195                 200                 205

Tyr Ala His Asp Ala Gln Asn Arg Gly Ala Tyr Val Glu Met His Leu
    210                 215                 220

Pro Gly Ser Glu Val Asp Ser Ser Leu Val Ser Leu Ser Gly Ser Ser
225                 230                 235                 240

Val Thr Val Thr Pro Pro Asp Gly Thr Ser Ala Leu Val Glu Cys Glu
                245                 250                 255
```

```
Cys Gly Gly Thr Lys Ile Ser Glu Thr Ile Asn Lys Thr Lys Gln Phe
            260                 265                 270

Ser Gln Cys Thr Lys Lys Glu Gln Cys Arg Ala Tyr Arg Leu Gln Asn
        275                 280                 285

Asp Lys Trp Val Tyr Asn Ser Asp Lys Leu Pro Lys Ala Ala Gly Ala
    290                 295                 300

Thr Leu Lys Gly Lys Leu His Val Pro Phe Leu Leu Ala Asp Gly Lys
305                 310                 315                 320

Cys Thr Val Pro Leu Ala Pro Glu Pro Met Ile Thr Phe Gly Phe Arg
                325                 330                 335

Ser Val Ser Leu Lys Leu His Pro Lys Asn Pro Thr Tyr Leu Ile Thr
            340                 345                 350

Arg Gln Leu Ala Asp Glu Pro His Tyr Thr His Glu Leu Ile Ser Glu
        355                 360                 365

Pro Ala Val Arg Asn Phe Thr Val Thr Glu Lys Gly Trp Glu Phe Val
    370                 375                 380

Trp Gly Asn His Pro Pro Lys Arg Phe Trp Ala Gln Glu Thr Ala Pro
385                 390                 395                 400

Gly Asn Pro His Gly Leu Pro His Glu Val Ile Thr His Tyr Tyr His
                405                 410                 415

Arg Tyr Pro Met Ser Thr Ile Leu Gly Leu Ser Ile Cys Ala Ala Ile
            420                 425                 430

Ala Thr Val Ser Val Ala Ala Ser Thr Trp Leu Phe Cys Arg Ser Arg
        435                 440                 445

Val Ala Cys Leu Thr Pro Tyr Arg Leu Thr Pro Asn Ala Arg Ile Pro
    450                 455                 460

Phe Cys Leu Ala Val Leu Cys Cys Ala Arg Thr Ala Arg Ala
465                 470                 475
```

```
<210> SEQ ID NO 38
<211> LENGTH: 3822
<212> TYPE: DNA
<213> ORGANISM: Artificial Sequence
<220> FEATURE:
<223> OTHER INFORMATION: Synthetic Expression vector for CHIKV viral
      structural protein containing CSP repeat antigen 74 in E3

<400> SEQUENCE: 38

atggagttca tcccgacgca aactttctat aacagaaggt accaaccccg accctgggcc      60

ccacgcccta caattcaagt aattagacct agaccacgtc cacagaggca ggctgggcaa     120

ctcgcccagc tgatctccgc agtcaacaaa ttgaccatgc gcgcggtacc tcaacagaag     180

cctcgcagaa atcggaaaaa caagaagcaa aggcagaaga agcaggcgcc gcaaaacgac     240

ccaaagcaaa agaagcaacc accacaaaag aagccggctc aaaagaagaa gaaaccaggc     300

cgtagggaga gaatgtgcat gaaaattgaa aatgattgca tcttcgaagt caagcatgaa     360

ggcaaagtga tgggctacgc atgcctggtg ggggataaag taatgaaacc agcacatgtg     420

aagggaacta tcgacaatgc cgatctggct aaactggcct ttaagcggtc gtctaaatac     480

gatcttgaat gtgcacagat accggtgcac atgaagtctg atgcctcgaa gtttacccac     540

gagaaacccg aggggtacta taactggcat cacggagcag tgcagtattc aggaggccgg     600

ttcactatcc cgacgggtgc aggcaagccg ggagacagcg gcagaccgat cttcgacaac     660

aaaggacggg tggtggccat cgtcctagga ggggccaacg aaggtgcccg cacggccctc     720

tccgtggtga cgtggaacaa agacatcgtc acaaaaatta cccctgaggg agccgaagag     780
```

-continued

```
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
cactccggag gaaacccgaa tgccaatccc aacgcgaacc ccaatgctaa cccaaatgcc   1020
aacccaaacg ccaaccccaa cgctggtgga tccagtacta aggacaattt taatgtctat   1080
aaagccacaa gaccatatct agctcattgt cctgactgcg gagaagggca ttcgtgccac   1140
agccctatcg cattggagcg catcagaaat gaagcaacgg acggaacgct gaaaatccag   1200
gtctctttgc agatcgggat aaagacagat gacagccacg attggaccaa gctgcgctat   1260
atggatagcc atacgcccgc ggacgcggag cgagccggat tgcttgtaag gacttcagca   1320
ccgtgcacga tcaccgggac catgggacac tttattctcg cccgatgccc gaaaggagag   1380
acgctgacag tgggatttac ggacagcaga aagatcagcc acacatgcac acacccgttc   1440
catcatgaac cacctgtgat aggtagggag aggttccact ctcgaccaca acatggtaaa   1500
gagttacctt gcagcacgta cgtgcagagc accgctgcca ctgctgagga gatagaggtg   1560
catatgcccc cagatactcc tgaccgcacg ctgatgacgc agcagtctgg caacgtgaag   1620
atcacagtta atgggcagac ggtgcggtac aagtgcaact gcggtggctc aaacgaggga   1680
ctgacaacca cagacaaagt gatcaataac tgcaaaattg atcagtgcca tgctgcagtc   1740
actaatcaca agaattggca atacaactcc cctttagtcc cgcgcaacgc tgaactcggg   1800
gaccgtaaag gaaagatcca catcccattc ccattggcaa acgtgacttg cagagtgcca   1860
aaagcaagaa accctacagt aacttacgga aaaaaccaag tcaccatgct gctgtatcct   1920
gaccatccga cactcttgtc ttaccgtaac atgggacagg aaccaaatta ccacgaggag   1980
tgggtgacac acaagaagga ggttaccttg accgtgccta ctgagggtct ggaggtcact   2040
tggggcaaca acgaaccata caagtactgg ccgcagatgt ctacgaacgg tactgctcat   2100
ggtcacccac atgagataat cttgtactat tatgagctgt accccactat gactgtagtc   2160
attgtgtcgg tggcctcgtt cgtgcttctg tcgatggtgg gcacagcagt gggaatgtgt   2220
gtgtgcgcac ggcgcagatg cattacacca tatgaattaa caccaggagc cactgttccc   2280
ttcctgctca gcctgctatg ctgcgtcaga acgaccaagg cggccacata ttacgaggct   2340
gcggcatatc tatggaacga acagcagccc ctgttctggt tgcaggctct tatcccgctg   2400
gccgccttga tcgtcctgtg caactgtctg aaactcttgc catgctgctg taagaccctg   2460
gctttttttag ccgtaatgag catcggtgcc cacactgtga gcgcgtacga acacgtaaca   2520
gtgatcccga acacggtggg agtaccgtat aagactcttg tcaacagacc gggttacagc   2580
cccatggtgt tggagatgga gctacaatca gtcaccttgg aaccaacact gtcacttgac   2640
tacatcacgt gcgagtacaa aactgtcatc ccctccccgt acgtgaagtg ctgtggtaca   2700
gcagagtgca aggacaagag cctaccagac tacagctgca aggtctttac tggagtctac   2760
ccatttatgt ggggcggcgc ctactgcttt tgcgacgccg aaaatacgca attgagcgag   2820
gcacatgtag agaaatctga atcttgcaaa acagagtttg catcggccta cagagcccac   2880
accgcatcgg cgtcggcgaa gctccgcgtc ctttaccaag gaaacaacat taccgtagct   2940
gcctacgcta acggtgacca tgccgtcaca gtaaaggacg ccaagtttgt cgtgggccca   3000
atgtcctccg cctggacacc ttttgacaac aaaatcgtgg tgtacaaagg cgacgtctac   3060
aacatggact acccaccttt tggcgcagga agaccaggac aatttggtga cattcaaagt   3120
```

```
cgtacaccgg aaagtaaaga cgtttatgcc aacactcagt tggtactaca gaggccagca   3180

gcaggcacgg tacatgtacc atactctcag gcaccatctg gcttcaagta ttggctgaag   3240

gaacgaggag catcgctaca gcacacggca ccgttcggtt gccagattgc gacaaacccg   3300

gtaagagctg taaattgcgc tgtggggaac ataccaattt ccatcgacat accggatgcg   3360

gcctttacta gggttgtcga tgcaccctct gtaacggaca tgtcatgcga agtaccagcc   3420

tgcactcact cctccgactt tgggggcgtc gccatcatca aatacacagc tagcaagaaa   3480

ggtaaatgtg cagtacattc gatgaccaac gccgttacca ttcgagaagc cgacgtagaa   3540

gtagagggga actcccagct gcaaatatcc ttctcaacag ccctggcaag cgccgagttt   3600

cgcgtgcaag tgtgctccac acaagtacac tgcgcagccg catgccaccc tccaaaggac   3660

cacatagtca attacccagc atcacacacc acccttgggg tccaggatat atccacaacg   3720

gcaatgtctt gggtgcagaa gattacggga ggagtaggat taattgttgc tgttgctgcc   3780

ttaattttaa ttgtggtgct atgcgtgtcg tttagcaggc ac                      3822
```

<210> SEQ ID NO 39
<211> LENGTH: 3843
<212> TYPE: DNA
<213> ORGANISM: Artificial Sequence
<220> FEATURE:
<223> OTHER INFORMATION: Synthetic Expression vector for VEEV viral structural protein containing CSP repeat antigen 74 in E3 (74.66)

<400> SEQUENCE: 39

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaaccccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccggg tccggaggaa acccgaatgc caatcccaac   1020

gcgaacccca atgctaaccc aaatgccaac ccaaacgcca accccaacgc tggtggatcc   1080

tccaccgagg agctgtttaa tgagtataag ctaacgcgcc cttacatggc cagatgcatc   1140

agatgtgcag ttgggagctg ccatagtcca atagcaatcg aggcagtaaa gagcgacggg   1200

cacgacggtt atgttagact tcagacttcc tcgcagtatg gcctggattc ctccggcaac   1260

ttaaagggca ggaccatgcg gtatgacatg cacgggacca ttaaagagat accactacat   1320
```

-continued caagtgtcac tctatacatc tcgcccgtgt cacattgtgg atgggcacgg ttatttcctg 1380
ctagccaggt gcccggcagg ggactccatc accatggaat ttaagaaaga ttccgtcaga 1440
cactcctgct cggtgccgta tgaagtgaaa tttaatcctg taggcagaga actctatact 1500
catcccccag aacacggagt agagcaagcg tgccaagtct acgcacatga tgcacagaac 1560
agaggagctt atgtcgagat gcacctcccg ggctcagaag tggacagcag tttggtttcc 1620
ttgagcggca gttcagtcac cgtgacacct cctgatggga ctagcgccct ggtggaatgc 1680
gagtgtggcg gcacaaagat ctccgagacc atcaacaaga caaaacagtt cagccagtgc 1740
acaaagaagg agcagtgcag agcatatcgg ctgcagaacg ataagtgggt gtataattct 1800
gacaaactgc ccaaagcagc gggagccacc ttaaaaggaa aactgcatgt cccattcttg 1860
ctggcagacg gcaaatgcac cgtgcctcta gcaccagaac ctatgataac cttcggtttc 1920
agatcagtgt cactgaaact gcaccctaag aatcccacat atctaatcac ccgccaactt 1980
gctgatgagc ctcactacac gcacgagctc atatctgaac cagctgttag gaattttacc 2040
gtcaccgaaa aagggtggga gtttgtatgg ggaaaccacc cgccgaaaag gttttgggca 2100
caggaaacag cacccggaaa tccacatggg ctaccgcacg aggtgataac tcattattac 2160
cacagatacc ctatgtccac catcctgggt ttgtcaattt gtgccgccat tgcaaccgtt 2220
tccgttgcag cgtctacctg gctgttttgc agatcaagag ttgcgtgcct aactccttac 2280
cggctaacac ctaacgctag gataccattt tgtctggctg tgctttgctg cgcccgcact 2340
gcccgggccg agaccacctg ggagtccttg gatcacctat ggaacaataa ccaacagatg 2400
ttctggattc aattgctgat ccctctggcc gccttgatcg tagtgactcg cctgctcagg 2460
tgcgtgtgct gtgtcgtgcc ttttttagtc atggccggcg ccgcaggcgc cggcgcctac 2520
gagcacgcga ccacgatgcc gagccaagcg ggaatctcgt ataacactat agtcaacaga 2580
gcaggctacg caccactccc tatcagcata acaccaacaa agatcaagct gatacctaca 2640
gtgaacttgg agtacgtcac ctgccactac aaaacaggaa tggattcacc agccatcaaa 2700
tgctgcggat ctcaggaatg cactccaact tacaggcctg atgaacagtg caaagtcttc 2760
acaggggttt acccgttcat gtggggtggt gcatattgct tttgcgacac tgagaacacc 2820
caagtcagca aggcctacgt aatgaaatct gacgactgcc ttgcggatca tgctgaagca 2880
tataaagcgc acacagcctc agtgcaggcg ttcctcaaca tcacagtggg agaacactct 2940
attgtgacta ccgtgtatgt gaatggagaa actcctgtga atttcaatgg ggtcaaaata 3000
actgcaggtc cgctttccac agcttggaca ccctttgatc gcaaaatcgt gcagtatgcc 3060
ggggagatct ataattatga ttttcctgag tatggggcag gacaaccagg agcatttgga 3120
gatatacaat ccagaacagt ctcaagctct gatctgtatg ccaataccaa cctagtgctg 3180
cagagaccca aagcaggagc gatccacgtg ccatacactc aggcaccttc gggttttgag 3240
caatggaaga aagataaagc tccatcattg aaatttaccg ccccttttcgg atgcgaaata 3300 tatacaaacc ccattcgcgc cgaaaactgt gctgtagggt caattccatt agcctttgac 3360
attcccgacg ccttgttcac cagggtgtca gaaacaccga cactttcagc ggccgaatgc 3420
actcttaacg agtgcgtgta ttcttccgac tttggtggga tcgccacggt caagtactcg 3480
gccagcaagt caggcaagtg cgcagtccat gtgccatcag ggactgctac cctaaaagaa 3540
gcagcagtcg agctaaccga gcaagggtcg gcgactatcc atttctcgac cgcaaatatc 3600
cacccggagt tcaggctcca aatatgcaca tcatatgtta cgtgcaaagg tgattgtcac 3660
cccccgaaag accatattgt gacacaccct cagtatcacg cccaaacatt tacagccgcg 3720
gtgtcaaaaa ccgcgtggac gtggttaaca tccctgctgg gaggatcagc cgtaattatt 3780
ataattggct tggtgctggc tactattgtg gccatgtacg tgctgaccaa ccagaaacat 3840
aat 3843

<210> SEQ ID NO 40
<211> LENGTH: 3789
<212> TYPE: DNA
<213> ORGANISM: Artificial Sequence
<220> FEATURE:
<223> OTHER INFORMATION: Synthetic Expression vector for CHIKV viral structural protein containing mouse PD-1 antigen “274” in E3

<400> SEQUENCE: 40
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
cactccggag gcggcgccat cagcctgcac cccaaggcca agatcgagga atctggatcc 1020
agtactaagg acaattttaa tgtctataaa gccacaagac catatctagc tcattgtcct 1080
gactgcggag aagggcattc gtgccacagc cctatcgcat tggagcgcat cagaaatgaa 1140
gcaacggacg gaacgctgaa aatccaggtc tctttgcaga tcgggataaa gacagatgac 1200
agccacgatt ggaccaagct gcgctatatg gatagccata cgcccgcgga cgcggagcga 1260
gccggattgc ttgtaaggac ttcagcaccg tgcacgatca ccgggaccat gggacacttt 1320
attctcgccc gatgcccgaa aggagagacg ctgacagtgg gatttacgga cagcagaaag 1380
atcagccaca catgcacaca cccgttccat catgaaccac ctgtgatagg tagggagagg 1440
ttccactctc gaccacaaca tggtaaagag ttaccttgca gcacgtacgt gcagagcacc 1500
gctgccactg ctgaggagat agaggtgcat atgcccccag atactcctga ccgcacgctg 1560
atgacgcagc agtctggcaa cgtgaagatc acagttaatg ggcagacggt gcggtacaag 1620
tgcaactgcg gtggctcaaa cgagggactg acaaccacag acaaagtgat caataactgc 1680
aaaattgatc agtgccatgc tgcagtcact aatcacaaga attggcaata caactcccct 1740
ttagtcccgc gcaacgctga actcggggac cgtaaaggaa agatccacat cccattccca 1800
ttggcaaacg tgacttgcag agtgccaaaa gcaagaaacc ctacagtaac ttacggaaaa 1860

```
aaccaagtca ccatgctgct gtatcctgac catccgacac tcttgtctta ccgtaacatg   1920

ggacaggaac caaattacca cgaggagtgg gtgacacaca agaaggaggt taccttgacc   1980

gtgcctactg agggtctgga ggtcacttgg ggcaacaacg aaccatacaa gtactggccg   2040

cagatgtcta cgaacggtac tgctcatggt cacccacatg agataatctt gtactattat   2100

gagctgtacc ccactatgac tgtagtcatt gtgtcggtgg cctcgttcgt gcttctgtcg   2160

atggtgggca cagcagtggg aatgtgtgtg tgcgcacggc gcagatgcat tacaccatat   2220

gaattaacac caggagccac tgttcccttc ctgctcagcc tgctatgctg cgtcagaacg   2280

accaaggcgg ccacatatta cgaggctgcg gcatatctat ggaacgaaca gcagcccctg   2340

ttctggttgc aggctcttat cccgctggcc gccttgatcg tcctgtgcaa ctgtctgaaa   2400

ctcttgccat gctgctgtaa gaccctggct tttttagccg taatgagcat cggtgcccac   2460

actgtgagcg cgtacgaaca cgtaacagtg atcccgaaca cggtgggagt accgtataag   2520

actcttgtca acagaccggg ttacagcccc atggtgttgg agatggagct acaatcagtc   2580

accttggaac caacactgtc acttgactac atcacgtgcg agtacaaaac tgtcatcccc   2640

tccccgtacg tgaagtgctg tggtacagca gagtgcaagg acaagagcct accagactac   2700

agctgcaagg tctttactgg agtctaccca tttatgtggg gcggcgccta ctgcttttgc   2760

gacgccgaaa atacgcaatt gagcgaggca catgtagaga aatctgaatc ttgcaaaaca   2820

gagtttgcat cggcctacag agcccacacc gcatcggcgt cggcgaagct ccgcgtcctt   2880

taccaaggaa acaacattac cgtagctgcc tacgctaacg gtgaccatgc cgtcacagta   2940

aaggacgcca agtttgtcgt gggcccaatg tcctccgcct ggacaccttt tgacaacaaa   3000

atcgtggtgt acaaaggcga cgtctacaac atggactacc caccttttgg cgcaggaaga   3060

ccaggacaat ttggtgacat tcaaagtcgt acaccggaaa gtaaagacgt ttatgccaac   3120

actcagttgg tactacagag gccagcagca ggcacggtac atgtaccata ctctcaggca   3180

ccatctggct tcaagtattg gctgaaggaa cgaggagcat cgctacagca cacggcaccg   3240

ttcggttgcc agattgcgac aaacccggta agagctgtaa attgcgctgt ggggaacata   3300

ccaatttcca tcgacatacc ggatgcggcc tttactaggg ttgtcgatgc accctctgta   3360

acggacatgt catgcgaagt accagcctgc actcactcct ccgactttgg gggcgtcgcc   3420

atcatcaaat acacagctag caagaaaggt aaatgtgcag tacattcgat gaccaacgcc   3480

gttaccattc gagaagccga cgtagaagta gaggggaact cccagctgca aatatccttc   3540

tcaacagccc tggcaagcgc cgagtttcgc gtgcaagtgt gctccacaca agtacactgc   3600

gcagccgcat gccaccctcc aaaggaccac atagtcaatt acccagcatc acacaccacc   3660

cttggggtcc aggatatatc cacaacggca atgtcttggg tgcagaagat tacgggagga   3720

gtaggattaa ttgttgctgt tgctgcctta attttaattg tggtgctatg cgtgtcgttt   3780

agcaggcac                                                           3789
```

<210> SEQ ID NO 41
<211> LENGTH: 3810
<212> TYPE: DNA
<213> ORGANISM: Artificial Sequence
<220> FEATURE:
<223> OTHER INFORMATION: Synthetic Expression vector for VEEV viral structural protein comprising mouse PD-1 antigen "274" in E3 (274.66)

<400> SEQUENCE: 41

-continued

```
atgttcccgt tccagccaat gtatccgatg cagccaatgc cctatcgcaa cccgttcgcg     60
gccccgcgca ggccctggtt ccccagaacc gacccttttc tggcgatgca ggtgcaggaa    120
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga agaaccaagg gaagaagaag gctaagacag ggccgcctaa tccgaaggca    300
cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccggg tccggaggcg gcgccatcag cctgcacccc   1020
aaggccaaga tcgaggaatc tggatcctcc accgaggagc tgtttaatga gtataagcta   1080
acgcgccctt acatggccag atgcatcaga tgtgcagttg ggagctgcca tagtccaata   1140
gcaatcgagg cagtaaagag cgacgggcac gacggttatg ttagacttca gacttcctcg   1200
cagtatggcc tggattcctc cggcaactta aagggcagga ccatgcggta tgacatgcac   1260
gggaccatta aagagatacc actacatcaa gtgtcactct atacatctcg cccgtgtcac   1320
attgtggatg ggcacggtta tttcctgcta gccaggtgcc cggcagggga ctccatcacc   1380
atggaattta agaaagattc cgtcagacac tcctgctcgg tgccgtatga agtgaaattt   1440
aatcctgtag gcagagaact ctatactcat cccccagaac acggagtaga gcaagcgtgc   1500
caagtctacg cacatgatgc acagaacaga ggagcttatg tcgagatgca cctcccgggc   1560
tcagaagtgg acagcagttt ggtttccttg agcggcagtt cagtcaccgt gacacctcct   1620
gatgggacta gcgccctggt ggaatgcgag tgtggcggca caaagatctc cgagaccatc   1680
aacaagacaa aacagttcag ccagtgcaca aagaaggagc agtgcagagc atatcggctg   1740
cagaacgata agtgggtgta taattctgac aaactgccca aagcagcggg agccacctta   1800
aaaggaaaac tgcatgtccc attcttgctg gcagacggca aatgcaccgt gcctctagca   1860
ccagaaccta tgataacctt cggtttcaga tcagtgtcac tgaaactgca ccctaagaat   1920
cccacatatc taatcacccg ccaacttgct gatgagcctc actacacgca cgagctcata   1980
tctgaaccag ctgttaggaa ttttaccgtc accgaaaaag ggtgggagtt tgtatgggga   2040
aaccacccgc cgaaaaggtt ttgggcacag gaaacagcac ccggaaatcc acatgggcta   2100
ccgcacgagg tgataactca ttattaccac agatacccta tgtccaccat cctgggtttg   2160
tcaatttgtg ccgccattgc aaccgtttcc gttgcagcgt ctacctggct gttttgcaga   2220
tcaagagttg cgtgcctaac tccttaccgg ctaacaccta acgctaggat accattttgt   2280
ctggctgtgc tttgctgcgc ccgcactgcc cgggccgaga ccacctggga gtccttggat   2340
cacctatgga acaataacca acagatgttc tggattcaat tgctgatccc tctggccgcc   2400
```

-continued ttgatcgtag tgactcgcct gctcaggtgc gtgtgctgtg tcgtgccttt tttagtcatg 2460
gccggcgccg caggcgccgg cgcctacgag cacgcgacca cgatgccgag ccaagcggga 2520
atctcgtata acactatagt caacagagca ggctacgcac cactccctat cagcataaca 2580
ccaacaaaga tcaagctgat acctacagtg aacttggagt acgtcacctg ccactacaaa 2640
acaggaatgg attcaccagc catcaaatgc tgcggatctc aggaatgcac tccaacttac 2700
aggcctgatg aacagtgcaa agtcttcaca ggggtttacc cgttcatgtg gggtggtgca 2760
tattgctttt gcgacactga gaacacccaa gtcagcaagg cctacgtaat gaaatctgac 2820
gactgccttg cggatcatgc tgaagcatat aaagcgcaca cagcctcagt gcaggcgttc 2880
ctcaacatca cagtgggaga acactctatt gtgactaccg tgtatgtgaa tggagaaact 2940
cctgtgaatt tcaatggggt caaaataact gcaggtccgc tttccacagc ttggacaccc 3000
tttgatcgca aaatcgtgca gtatgccggg gagatctata attatgattt tcctgagtat 3060
ggggcaggac aaccaggagc atttggagat atacaatcca gaacagtctc aagctctgat 3120
ctgtatgcca ataccaacct agtgctgcag agacccaaag caggagcgat ccacgtgcca 3180
tacactcagg caccttcggg ttttgagcaa tggaagaaag ataaagctcc atcattgaaa 3240
tttaccgccc ctttcggatg cgaaatatat acaaacccca ttcgcgccga aaactgtgct 3300
gtagggtcaa ttccattagc ctttgacatt cccgacgcct tgttcaccag ggtgtcagaa 3360
acaccgacac tttcagcggc cgaatgcact cttaacgagt gcgtgtattc ttccgacttt 3420
ggtgggatcg ccacggtcaa gtactcggcc agcaagtcag gcaagtgcgc agtccatgtg 3480
ccatcaggga ctgctaccct aaaagaagca gcagtcgagc taaccgagca agggtcggcg 3540
actatccatt tctcgaccgc aaatatccac ccggagttca ggctccaaat atgcacatca 3600
tatgttacgt gcaaaggtga ttgtcacccc ccgaaagacc atattgtgac acaccctcag 3660
tatcacgccc aaacatttac agccgcggtg tcaaaaaccg cgtggacgtg gttaacatcc 3720
ctgctgggag gatcagccgt aattattata attggcttgg tgctggctac tattgtggcc 3780
atgtacgtgc tgaccaacca gaaacataat 3810

<210> SEQ ID NO 42
<211> LENGTH: 3783
<212> TYPE: DNA
<213> ORGANISM: Artificial Sequence
<220> FEATURE:
<223> OTHER INFORMATION: Synthetic Expression vector for CHIKV viral structural protein containing mouse PDL1 antigen “299” in E3

<400> SEQUENCE: 42
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600

-continued

```
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
cactccggag gctgcatcat cagctacggc ggagccgact actgcggcgg atccagtact   1020
aaggacaatt ttaatgtcta taaagccaca agaccatatc tagctcattg tcctgactgc   1080
ggagaagggc attcgtgcca cagccctatc gcattggagc gcatcagaaa tgaagcaacg   1140
gacggaacgc tgaaaatcca ggtctctttg cagatcggga taaagacaga tgacagccac   1200
gattggacca agctgcgcta tatggatagc catacgcccg cggacgcgga gcgagccgga   1260
ttgcttgtaa ggacttcagc accgtgcacg atcaccggga ccatgggaca ctttattctc   1320
gcccgatgcc cgaaaggaga gacgctgaca gtgggattta cggacagcag aaagatcagc   1380
cacacatgca cacacccgtt ccatcatgaa ccacctgtga taggtaggga gaggttccac   1440
tctcgaccac aacatggtaa agagttacct tgcagcacgt acgtgcagag caccgctgcc   1500
actgctgagg agatagaggt gcatatgccc ccagatactc ctgaccgcac gctgatgacg   1560
cagcagtctg gcaacgtgaa gatcacagtt aatgggcaga cggtgcggta caagtgcaac   1620
tgcggtggct caaacgaggg actgacaacc acagacaaag tgatcaataa ctgcaaaatt   1680
gatcagtgcc atgctgcagt cactaatcac aagaattggc aatacaactc ccctttagtc   1740
ccgcgcaacg ctgaactcgg ggaccgtaaa ggaaagatcc acatcccatt cccattggca   1800
aacgtgactt gcagagtgcc aaaagcaaga aaccctacag taacttacgg aaaaaaccaa   1860
gtcaccatgc tgctgtatcc tgaccatccg acactcttgt cttaccgtaa catgggacag   1920
gaaccaaatt accacgagga gtgggtgaca cacaagaagg aggttacctt gaccgtgcct   1980
actgagggtc tggaggtcac ttggggcaac aacgaaccat acaagtactg gccgcagatg   2040
tctacgaacg gtactgctca tggtcaccca catgagataa tcttgtacta ttatgagctg   2100
taccccacta tgactgtagt cattgtgtcg gtggcctcgt tcgtgcttct gtcgatggtg   2160
ggcacagcag tgggaatgtg tgtgtgcgca cggcgcagat gcattacacc atatgaatta   2220
acaccaggag ccactgttcc cttcctgctc agcctgctat gctgcgtcag aacgaccaag   2280
gcggccacat attacgaggc tgcggcatat ctatggaacg aacagcagcc cctgttctgg   2340
ttgcaggctc ttatcccgct ggccgccttg atcgtcctgt gcaactgtct gaaactcttg   2400
ccatgctgct gtaagaccct ggcttttta gccgtaatga gcatcggtgc ccacactgtg   2460
agcgcgtacg aacacgtaac agtgatcccg aacacggtgg gagtaccgta taagactctt   2520
gtcaacagac cgggttacag ccccatggtg ttggagatgg agctacaatc agtcaccttg   2580
gaaccaacac tgtcacttga ctacatcacg tgcgagtaca aaactgtcat cccctccccg   2640
tacgtgaagt gctgtggtac agcagagtgc aaggacaaga gcctaccaga ctacagctgc   2700
aaggtcttta ctggagtcta cccatttatg tggggcggcg cctactgctt ttgcgacgcc   2760
gaaaatacgc aattgagcga ggcacatgta gagaaatctg aatcttgcaa aacagagttt   2820
gcatcggcct acagagccca caccgcatcg gcgtcggcga agctccgcgt cctttaccaa   2880
ggaaacaaca ttaccgtagc tgcctacgct aacggtgacc atgccgtcac agtaaaggac   2940
```

```
gccaagtttg tcgtgggccc aatgtcctcc gcctggacac cttttgacaa caaaatcgtg   3000

gtgtacaaag gcgacgtcta caacatggac tacccacctt ttggcgcagg aagaccagga   3060

caatttggtg acattcaaag tcgtacaccg gaaagtaaag acgtttatgc caacactcag   3120

ttggtactac agaggccagc agcaggcacg gtacatgtac catactctca ggcaccatct   3180

ggcttcaagt attggctgaa ggaacgagga gcatcgctac agcacacggc accgttcggt   3240

tgccagattg cgacaaaccc ggtaagagct gtaaattgcg ctgtggggaa cataccaatt   3300

tccatcgaca taccggatgc ggcctttact agggttgtcg atgcaccctc tgtaacggac   3360

atgtcatgcg aagtaccagc ctgcactcac tcctccgact ttgggggcgt cgccatcatc   3420

aaatacacag ctagcaagaa aggtaaatgt gcagtacatt cgatgaccaa cgccgttacc   3480

attcgagaag ccgacgtaga agtagagggg aactcccagc tgcaaatatc cttctcaaca   3540

gccctggcaa gcgccgagtt tcgcgtgcaa gtgtgctcca cacaagtaca ctgcgcagcc   3600

gcatgccacc ctccaaagga ccacatagtc aattacccag catcacacac caccccttggg   3660

gtccaggata tatccacaac ggcaatgtct tgggtgcaga agattacggg aggagtagga   3720

ttaattgttg ctgttgctgc cttaatttta attgtggtgc tatgcgtgtc gtttagcagg   3780

cac                                                                 3783
```

<210> SEQ ID NO 43
<211> LENGTH: 3804
<212> TYPE: DNA
<213> ORGANISM: Artificial Sequence
<220> FEATURE:
<223> OTHER INFORMATION: Synthetic Expression vector for VEEV viral structural protein containing mouse PDL1 antigen in E3 (299.66)

<400> SEQUENCE: 43

```
atgttcccgt tccagccaat gtatccgatg cagccaatgc cctatcgcaa cccgttcgcg     60

gccccgcgca ggccctggtt ccccagaacc gacccttttc tggcgatgca ggtgcaggaa    120

ttaacccgct cgatggctaa cctgacgttc aagcaacgcc gggacgcgcc acctgagggg    180

ccatccgcta ataaaccgaa gaaggaggcc tcgcaaaaac agaaaggggg aggccaaggg    240

aagaagaaga agaaccaagg gaagaagaag gctaagacag ggccgcctaa tccgaaggca    300

cagaatggaa acaagaagaa gaccaacaag aaaccaggca agagacagcg catggtcatg    360

aaattggaat ctgacaagac gttcccaatc atgttggaag ggaagataaa cggctacgct    420

tgtgtggtcg gagggaagtt attcaggccg atgcatgtgg aaggcaagat cgacaacgac    480

gttctggccg cgcttaagac gaagaaagca tccaaatacg atcttgagta tgcagatgtg    540

ccacagaaca tgcgggccga tacattcaaa tacacccatg agaaacccca aggctattac    600

agctggcatc atggagcagt ccaatatgaa aatgggcgtt tcacggtgcc gaaaggagtt    660

ggggccaagg gagacagcgg acgacccatt ctggataacc agggacgggt ggtcgctatt    720

gtgctgggag gtgtgaatga aggatctagg acagcccttt cagtcgtcat gtggaacgag    780

aagggagtta ccgtgaagta tactccagag aactgcgagc aatggtcact agtgaccacc    840

atgtgtctgc tcgccaatgt gacgttccca tgtgctcaac caccaatttg ctacgacaga    900

aaaccagcag agactttggc catgctcagc gttaacgttg acaacccggg ctacgatgag    960

ctgctggaag cagctgttaa gtgccccggg tccggaggct gcatcatcag ctacggcgga   1020

gccgactact gcggcggatc ctccaccgag gagctgttta atgagtataa gctaacgcgc   1080

ccttacatgg ccagatgcat cagatgtgca gttgggagct gccatagtcc aatagcaatc   1140
```

-continued

```
gaggcagtaa agagcgacgg gcacgacggt tatgttagac ttcagacttc ctcgcagtat   1200
ggcctggatt cctccggcaa cttaaagggc aggaccatgc ggtatgacat gcacgggacc   1260
attaaagaga taccactaca tcaagtgtca ctctatacat ctcgcccgtg tcacattgtg   1320
gatgggcacg gttatttcct gctagccagg tgcccggcag gggactccat caccatggaa   1380
tttaagaaag attccgtcag acactcctgc tcggtgccgt atgaagtgaa atttaatcct   1440
gtaggcagag aactctatac tcatcccccca gaacacggag tagagcaagc gtgccaagtc   1500
tacgcacatg atgcacagaa cagaggagct tatgtcgaga tgcacctccc gggctcagaa   1560
gtggacagca gtttggtttc cttgagcggc agttcagtca ccgtgacacc tcctgatggg   1620
actagcgccc tggtggaatg cgagtgtggc ggcacaaaga tctccgagac catcaacaag   1680
acaaaacagt tcagccagtg cacaaagaag gagcagtgca gagcatatcg gctgcagaac   1740
gataagtggg tgtataattc tgacaaactg cccaaagcag cgggagccac cttaaaagga   1800
aaactgcatg tcccattctt gctggcagac ggcaaatgca ccgtgcctct agcaccagaa   1860
cctatgataa ccttcggttt cagatcagtg tcactgaaac tgcaccctaa gaatcccaca   1920
tatctaatca cccgccaact tgctgatgag cctcactaca cgcacgagct catatctgaa   1980
ccagctgtta ggaattttac cgtcaccgaa aaagggtggg agtttgtatg ggaaaccac    2040
ccgccgaaaa ggttttgggc acaggaaaca gcacccggaa atccacatgg gctaccgcac   2100
gaggtgataa ctcattatta ccacagatac cctatgtcca ccatcctggg tttgtcaatt   2160
tgtgccgcca ttgcaaccgt ttccgttgca gcgtctacct ggctgttttg cagatcaaga   2220
gttgcgtgcc taactcctta ccggctaaca cctaacgcta ggataccatt ttgtctggct   2280
gtgctttgct gcgcccgcac tgcccgggcc gagaccacct gggagtcctt ggatcaccta   2340
tggaacaata accaacagat gttctggatt caattgctga tccctctggc cgccttgatc   2400
gtagtgactc gcctgctcag gtgcgtgtgc tgtgtcgtgc ctttttttagt catggccggc   2460
gccgcaggcg ccggcgccta cgagcacgcg accacgatgc cgagccaagc gggaatctcg   2520
tataacacta tagtcaacag agcaggctac gcaccactcc ctatcagcat aacaccaaca   2580
aagatcaagc tgatacctac agtgaacttg gagtacgtca cctgccacta caaaacagga   2640
atggattcac cagccatcaa atgctgcgga tctcaggaat gcactccaac ttacaggcct   2700
gatgaacagt gcaaagtctt cacaggggtt tacccgttca tgtggggtgg tgcatattgc   2760
ttttgcgaca ctgagaacac ccaagtcagc aaggcctacg taatgaaatc tgacgactgc   2820
cttgcggatc atgctgaagc atataaagcg cacacagcct cagtgcaggc gttcctcaac   2880
atcacagtgg gagaacactc tattgtgact accgtgtatg tgaatggaga aactcctgtg   2940
aatttcaatg ggtcaaaat aactgcaggt ccgctttcca cagcttggac accctttgat    3000
cgcaaaatcg tgcagtatgc cggggagatc tataattatg attttcctga gtatggggca   3060
ggacaaccag gagcatttgg agatatacaa tccagaacag tctcaagctc tgatctgtat   3120
gccaatacca acctagtgct gcagagaccc aaagcaggag cgatccacgt gccatacact   3180
caggcacctt cgggttttga gcaatggaag aaagataaag ctccatcatt gaaatttacc   3240
gccccttcg gatgcgaaat atatacaaac cccattcgcg ccgaaaactg tgctgtaggg    3300
tcaattccat tagcctttga cattcccgac gccttgttca ccagggtgtc agaaacaccg   3360
acactttcag cggccgaatg cactcttaac gagtgcgtgt attcttccga ctttggtggg   3420
atcgccacgg tcaagtactc ggccagcaag tcaggcaagt gcgcagtcca tgtgccatca   3480
gggactgcta ccctaaaaga agcagcagtc gagctaaccg agcaagggtc ggcgactatc   3540
```

-continued

```
catttctcga ccgcaaatat ccacccggag ttcaggctcc aaatatgcac atcatatgtt   3600

acgtgcaaag gtgattgtca ccccccgaaa gaccatattg tgacacaccc tcagtatcac   3660

gcccaaacat ttacagccgc ggtgtcaaaa accgcgtgga cgtggttaac atccctgctg   3720

ggaggatcag ccgtaattat tataattggc ttggtgctgg ctactattgt ggccatgtac   3780

gtgctgacca accagaaaca taat                                          3804
```

<210> SEQ ID NO 44
<211> LENGTH: 3804
<212> TYPE: DNA
<213> ORGANISM: Artificial Sequence
<220> FEATURE:
<223> OTHER INFORMATION: Synthetic Expression vector for CHIKV viral structural protein comprising mouse CTLA4_Ver2 antigen in E3

<400> SEQUENCE: 44

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

cactccggag gcggcggcaa ggtggaactc atgtacccac cgccatactt tgtgggcatg   1020

ggcggcggcg gatccagtac taaggacaat tttaatgtct ataaagccac aagaccatat   1080

ctagctcatt gtcctgactg cggagaaggg cattcgtgcc acagccctat cgcattggag   1140

cgcatcagaa atgaagcaac ggacggaacg ctgaaaatcc aggtctcttt gcagatcggg   1200

ataaagacag atgacagcca cgattggacc aagctgcgct atatggatag ccatacgccc   1260

gcggacgcgg agcgagccgg attgcttgta aggacttcag caccgtgcac gatcaccggg   1320

accatgggac actttattct cgcccgatgc ccgaaaggag agacgctgac agtgggattt   1380

acggacagca gaaagatcag ccacacatgc acacacccgt tccatcatga accacctgtg   1440

ataggtaggg agaggttcca ctctcgacca caacatggta aagagttacc ttgcagcacg   1500

tacgtgcaga gcaccgctgc cactgctgag gagatagagg tgcatatgcc cccagatact   1560

cctgaccgca cgctgatgac gcagcagtct ggcaacgtga agatcacagt taatgggcag   1620

acggtgcggt acaagtgcaa ctgcggtggc tcaaacgagg gactgacaac cacagacaaa   1680

gtgatcaata actgcaaaat tgatcagtgc catgctgcag tcactaatca caagaattgg   1740
```

-continued caatacaact ccccttagt cccgcgcaac gctgaactcg gggaccgtaa aggaaagatc 1800
cacatcccat tcccattggc aaacgtgact tgcagagtgc caaaagcaag aaaccctaca 1860
gtaacttacg gaaaaaacca agtcaccatg ctgctgtatc ctgaccatcc gacactcttg 1920
tcttaccgta acatgggaca ggaaccaaat taccacgagg agtgggtgac acacaagaag 1980
gaggttacct tgaccgtgcc tactgagggt ctggaggtca cttggggcaa caacgaacca 2040
tacaagtact ggccgcagat gtctacgaac ggtactgctc atggtcaccc acatgagata 2100
atcttgtact attatgagct gtaccccact atgactgtag tcattgtgtc ggtggcctcg 2160
ttcgtgcttc tgtcgatggt gggcacagca gtgggaatgt gtgtgtgcgc acggcgcaga 2220
tgcattacac catatgaatt aacaccagga gccactgttc ccttcctgct cagcctgcta 2280
tgctgcgtca gaacgaccaa ggcggccaca tattacgagg ctgcggcata tctatggaac 2340
gaacagcagc ccctgttctg gttgcaggct cttatcccgc tggccgcctt gatcgtcctg 2400
tgcaactgtc tgaaactctt gccatgctgc tgtaagaccc tggctttttt agccgtaatg 2460
agcatcggtg cccacactgt gagcgcgtac gaacacgtaa cagtgatccc gaacacggtg 2520
ggagtaccgt ataagactct tgtcaacaga ccgggttaca gccccatggt gttggagatg 2580
gagctacaat cagtcacctt ggaaccaaca ctgtcacttg actacatcac gtgcgagtac 2640
aaaactgtca tcccctcccc gtacgtgaag tgctgtggta cagcagagtg caaggacaag 2700
agcctaccag actacagctg caaggtcttt actggagtct acccatttat gtggggcggc 2760
gcctactgct tttgcgacgc cgaaaatacg caattgagcg aggcacatgt agagaaatct 2820
gaatcttgca aaacagagtt tgcatcggcc tacagagccc acaccgcatc ggcgtcggcg 2880
aagctccgcg tcctttacca aggaaacaac attaccgtag ctgcctacgc taacggtgac 2940
catgccgtca cagtaaagga cgccaagttt gtcgtgggcc caatgtcctc cgcctggaca 3000
ccttttgaca acaaaatcgt ggtgtacaaa ggcgacgtct acaacatgga ctacccacct 3060
tttggcgcag gaagaccagg acaatttggt gacattcaaa gtcgtacacc ggaaagtaaa 3120
gacgtttatg ccaacactca gttggtacta cagaggccag cagcaggcac ggtacatgta 3180
ccatactctc aggcaccatc tggcttcaag tattggctga aggaacgagg agcatcgcta 3240
cagcacacgg caccgttcgg ttgccagatt gcgacaaacc cggtaagagc tgtaaattgc 3300
gctgtgggga acataccaat ttccatcgac ataccggatg cggcctttac tagggttgtc 3360
gatgcaccct ctgtaacgga catgtcatgc gaagtaccag cctgcactca ctcctccgac 3420
tttgggggcg tcgccatcat caaatacaca gctagcaaga aaggtaaatg tgcagtacat 3480
tcgatgacca acgccgttac cattcgagaa gccgacgtag aagtagaggg gaactcccag 3540
ctgcaaatat ccttctcaac agccctggca agcgccgagt ttcgcgtgca agtgtgctcc 3600
acacaagtac actgcgcagc cgcatgccac cctccaaagg accacatagt caattaccca 3660
gcatcacaca ccacccttgg ggtccaggat atatccacaa cggcaatgtc ttgggtgcag 3720
aagattacgg gaggagtagg attaattgtt gctgttgctg ccttaatttt aattgtggtg 3780
ctatgcgtgt cgtttagcag gcac 3804

<210> SEQ ID NO 45
<211> LENGTH: 3825
<212> TYPE: DNA
<213> ORGANISM: Artificial Sequence
<220> FEATURE:
<223> OTHER INFORMATION: Synthetic Expression vector for VEEV viral
structural protein comprising mouse CTLA4ver2 antigen in E3

<400> SEQUENCE: 45
atgttcccgt tccagccaat gtatccgatg cagccaatgc cctatcgcaa cccgttcgcg 60
gccccgcgca ggccctggtt ccccagaacc gacccttttc tggcgatgca ggtgcaggaa 120
ttaacccgct cgatggctaa cctgacgttc aagcaacgcc gggacgcgcc acctgagggg 180
ccatccgcta ataaaccgaa gaaggaggcc tcgcaaaaac agaaaggggg aggccaaggg 240
aagaagaaga agaaccaagg gaagaagaag gctaagacag ggccgcctaa tccgaaggca 300
cagaatggaa acaagaagaa gaccaacaag aaaccaggca agagacagcg catggtcatg 360
aaattggaat ctgacaagac gttcccaatc atgttggaag ggaagataaa cggctacgct 420
tgtgtggtcg gagggaagtt attcaggccg atgcatgtgg aaggcaagat cgacaacgac 480
gttctggccg cgcttaagac gaagaaagca tccaaatacg atcttgagta tgcagatgtg 540
ccacagaaca tgcgggccga tacattcaaa tacacccatg agaaaccccca aggctattac 600
agctggcatc atggagcagt ccaatatgaa aatgggcgtt tcacggtgcc gaaaggagtt 660
ggggccaagg gagacagcgg acgacccatt ctggataacc agggacgggt ggtcgctatt 720
gtgctgggag gtgtgaatga aggatctagg acagcccttt cagtcgtcat gtggaacgag 780
aagggagtta ccgtgaagta tactccagag aactgcgagc aatggtcact agtgaccacc 840
atgtgtctgc tcgccaatgt gacgttccca tgtgctcaac caccaatttg ctacgacaga 900
aaaccagcag agactttggc catgctcagc gttaacgttg acaacccggg ctacgatgag 960
ctgctggaag cagctgttaa gtgccccggg tccggaggcg gcggcaaggt ggaactcatg 1020
tacccaccgc catactttgt gggcatgggc ggcggcggat cctccaccga ggagctgttt 1080
aatgagtata agctaacgcg cccttacatg gccagatgca tcagatgtgc agttgggagc 1140
tgccatagtc caatagcaat cgaggcagta aagagcgacg ggcacgacgg ttatgttaga 1200
cttcagactt cctcgcagta tggcctggat tcctccggca acttaaaggg caggaccatg 1260
cggtatgaca tgcacgggac cattaaagag ataccactac atcaagtgtc actctataca 1320
tctcgcccgt gtcacattgt ggatgggcac ggttatttcc tgctagccag gtgcccggca 1380
ggggactcca tcaccatgga atttaagaaa gattccgtca gacactcctg ctcggtgccg 1440
tatgaagtga aatttaatcc tgtaggcaga gaactctata ctcatccccc agaacacgga 1500
gtagagcaag cgtgccaagt ctacgcacat gatgcacaga acagaggagc ttatgtcgag 1560
atgcacctcc cgggctcaga agtggacagc agtttggttt ccttgagcgg cagttcagtc 1620
accgtgacac ctcctgatgg gactagcgcc ctggtggaat gcgagtgtgg cggcacaaag 1680
atctccgaga ccatcaacaa gacaaaacag ttcagccagt gcacaaagaa ggagcagtgc 1740
agagcatatc ggctgcagaa cgataagtgg gtgtataatt ctgacaaact gcccaaagca 1800
gcgggagcca ccttaaaagg aaaactgcat gtcccattct tgctggcaga cggcaaatgc 1860
accgtgcctc tagcaccaga acctatgata accttcggtt tcagatcagt gtcactgaaa 1920
ctgcacccta agaatcccac atatctaatc acccgccaac ttgctgatga gcctcactac 1980
acgcacgagc tcatatctga accagctgtt aggaatttta ccgtcaccga aaaagggtgg 2040
gagtttgtat ggggaaacca cccgccgaaa aggttttggg cacaggaaac agcacccgga 2100
aatccacatg ggctaccgca cgaggtgata actcattatt accacagata ccctatgtcc 2160
accatcctgg gtttgtcaat ttgtgccgcc attgcaaccg tttccgttgc agcgtctacc 2220
tggctgtttt gcagatcaag agttgcgtgc ctaactcctt accggctaac acctaacgct 2280

-continued

```
aggataccat tttgtctggc tgtgctttgc tgcgcccgca ctgcccgggc cgagaccacc   2340

tgggagtcct tggatcacct atggaacaat aaccaacaga tgttctggat tcaattgctg   2400

atccctctgg ccgccttgat cgtagtgact cgcctgctca ggtgcgtgtg ctgtgtcgtg   2460

cctttttag tcatggccgg cgccgcaggc gccggcgcct acgagcacgc gaccacgatg    2520

ccgagccaag cgggaatctc gtataacact atagtcaaca gagcaggcta cgcaccactc   2580

cctatcagca taacaccaac aaagatcaag ctgataccta cagtgaactt ggagtacgtc   2640

acctgccact acaaaacagg aatggattca ccagccatca aatgctgcgg atctcaggaa   2700

tgcactccaa cttacaggcc tgatgaacag tgcaaagtct tcacaggggt ttacccgttc   2760

atgtggggtg gtgcatattg cttttgcgac actgagaaca cccaagtcag caaggcctac   2820

gtaatgaaat ctgacgactg ccttgcggat catgctgaag catataaagc gcacacagcc   2880

tcagtgcagg cgttcctcaa catcacagtg ggagaacact ctattgtgac taccgtgtat   2940

gtgaatggag aaactcctgt gaatttcaat ggggtcaaaa taactgcagg tccgctttcc   3000

acagcttgga caccctttga tcgcaaaatc gtgcagtatg ccggggagat ctataattat   3060

gattttcctg agtatggggc aggacaacca ggagcatttg gagatataca atccagaaca   3120

gtctcaagct ctgatctgta tgccaatacc aacctagtgc tgcagagacc caaagcagga   3180

gcgatccacg tgccatacac tcaggcacct tcgggttttg agcaatggaa gaaagataaa   3240

gctccatcat tgaaatttac cgcccctttc ggatgcgaaa tatatacaaa ccccattcgc   3300

gccgaaaact gtgctgtagg gtcaattcca ttagcctttg acattcccga cgccttgttc   3360

accagggtgt cagaaacacc gacactttca gcggccgaat gcactcttaa cgagtgcgtg   3420

tattcttccg actttggtgg gatcgccacg gtcaagtact cggccagcaa gtcaggcaag   3480

tgcgcagtcc atgtgccatc agggactgct accctaaaag aagcagcagt cgagctaacc   3540

gagcaagggt cggcgactat ccatttctcg accgcaaata tccacccgga gttcaggctc   3600

caaatatgca catcatatgt tacgtgcaaa ggtgattgtc accccccgaa agaccatatt   3660

gtgacacacc ctcagtatca cgcccaaaca tttacagccg cggtgtcaaa aaccgcgtgg   3720

acgtggttaa catccctgct gggaggatca gccgtaatta ttataattgg cttggtgctg   3780

gctactattg tggccatgta cgtgctgacc aaccagaaac ataat                  3825
```

<210> SEQ ID NO 46
<211> LENGTH: 351
<212> TYPE: PRT
<213> ORGANISM: Artificial Sequence
<220> FEATURE:
<223> OTHER INFORMATION: Synthetic CHIKV E3-Malaria-E2

<400> SEQUENCE: 46

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95
```

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Leu Pro Val Leu Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Ser Thr Leu Arg Met Leu Glu Asp Asn Val Met
290 295 300

Arg Pro Gly Tyr Tyr Gln Leu Leu Lys Ala Ser Leu Thr Cys Ser Pro
305 310 315 320

His Ser Gly Gly Asn Pro Asn Ala Asn Pro Asn Ala Asn Pro Asn Ala
325 330 335

Asn Pro Asn Ala Asn Pro Asn Ala Asn Pro Asn Ala Gly Gly Ser
340 345 350

<210> SEQ ID NO 47
<211> LENGTH: 502
<212> TYPE: PRT
<213> ORGANISM: Artificial Sequence
<220> FEATURE:
<223> OTHER INFORMATION: Synthetic CHIKV E3-PD-1-E2

<400> SEQUENCE: 47

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Ser Thr Leu Arg Met Leu Glu Asp Asn Val Met Arg Pro Gly Tyr Tyr
35 40 45

Gln Leu Leu Lys Ala Ser Leu Thr Cys Ser Pro His Ser Gly Gly Gly
50 55 60

Ala Ile Ser Leu His Pro Lys Ala Lys Ile Glu Glu Ser Gly Ser Ser
65 70 75 80

Thr Lys Asp Asn Phe Asn Val Tyr Lys Ala Thr Arg Pro Tyr Leu Ala
85 90 95

His Cys Pro Asp Cys Gly Glu Gly His Ser Cys His Ser Pro Ile Ala
100 105 110

-continued

```
Leu Glu Arg Ile Arg Asn Glu Ala Thr Asp Gly Thr Leu Lys Ile Gln
        115                 120                 125

Val Ser Leu Gln Ile Gly Ile Lys Thr Asp Asp Ser His Asp Trp Thr
    130                 135                 140

Lys Leu Arg Tyr Met Asp Ser His Thr Pro Ala Asp Ala Glu Arg Ala
145                 150                 155                 160

Gly Leu Leu Val Arg Thr Ser Ala Pro Cys Thr Ile Thr Gly Thr Met
                165                 170                 175

Gly His Phe Ile Leu Ala Arg Cys Pro Lys Gly Glu Thr Leu Thr Val
            180                 185                 190

Gly Phe Thr Asp Ser Arg Lys Ile Ser His Thr Cys Thr His Pro Phe
        195                 200                 205

His His Glu Pro Pro Val Ile Gly Arg Glu Arg Phe His Ser Arg Pro
    210                 215                 220

Gln His Gly Lys Glu Leu Pro Cys Ser Thr Tyr Val Gln Ser Thr Ala
225                 230                 235                 240

Ala Thr Ala Glu Glu Ile Glu Val His Met Pro Pro Asp Thr Pro Asp
                245                 250                 255

Arg Thr Leu Met Thr Gln Gln Ser Gly Asn Val Lys Ile Thr Val Asn
            260                 265                 270

Gly Gln Thr Val Arg Tyr Lys Cys Asn Cys Gly Gly Ser Asn Glu Gly
        275                 280                 285

Leu Thr Thr Thr Asp Lys Val Ile Asn Asn Cys Lys Ile Asp Gln Cys
    290                 295                 300

His Ala Ala Val Thr Asn His Lys Asn Trp Gln Tyr Asn Ser Pro Leu
305                 310                 315                 320

Val Pro Arg Asn Ala Glu Leu Gly Asp Arg Lys Gly Lys Ile His Ile
                325                 330                 335

Pro Phe Pro Leu Ala Asn Val Thr Cys Arg Val Pro Lys Ala Arg Asn
            340                 345                 350

Pro Thr Val Thr Tyr Gly Lys Asn Gln Val Thr Met Leu Leu Tyr Pro
        355                 360                 365

Asp His Pro Thr Leu Leu Ser Tyr Arg Asn Met Gly Gln Glu Pro Asn
    370                 375                 380

Tyr His Glu Glu Trp Val Thr His Lys Lys Glu Val Thr Leu Thr Val
385                 390                 395                 400

Pro Thr Glu Gly Leu Glu Val Thr Trp Gly Asn Asn Glu Pro Tyr Lys
                405                 410                 415

Tyr Trp Pro Gln Met Ser Thr Asn Gly Thr Ala His Gly His Pro His
            420                 425                 430

Glu Ile Ile Leu Tyr Tyr Tyr Glu Leu Tyr Pro Thr Met Thr Val Val
        435                 440                 445

Ile Val Ser Val Ala Ser Phe Val Leu Leu Ser Met Val Gly Thr Ala
    450                 455                 460

Val Gly Met Cys Val Cys Ala Arg Arg Arg Cys Ile Thr Pro Tyr Glu
465                 470                 475                 480

Leu Thr Pro Gly Ala Thr Val Pro Phe Leu Leu Ser Leu Leu Cys Cys
                485                 490                 495

Val Arg Thr Thr Lys Ala
            500
```

<210> SEQ ID NO 48
<211> LENGTH: 500

<212> TYPE: PRT
<213> ORGANISM: Artificial Sequence
<220> FEATURE:
<223> OTHER INFORMATION: Synthetic CHIKV E3-PD-L1-E2

<400> SEQUENCE: 48

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Ser Thr Leu Arg Met Leu Glu Asp Asn Val Met Arg Pro Gly Tyr Tyr
35 40 45

Gln Leu Leu Lys Ala Ser Leu Thr Cys Ser Pro His Ser Gly Gly Cys
50 55 60

Ile Ile Ser Tyr Gly Gly Ala Asp Tyr Cys Gly Gly Ser Ser Thr Lys
65 70 75 80

Asp Asn Phe Asn Val Tyr Lys Ala Thr Arg Pro Tyr Leu Ala His Cys
85 90 95

Pro Asp Cys Gly Glu Gly His Ser Cys His Ser Pro Ile Ala Leu Glu
100 105 110

Arg Ile Arg Asn Glu Ala Thr Asp Gly Thr Leu Lys Ile Gln Val Ser
115 120 125

Leu Gln Ile Gly Ile Lys Thr Asp Asp Ser His Asp Trp Thr Lys Leu
130 135 140

Arg Tyr Met Asp Ser His Thr Pro Ala Asp Ala Glu Arg Ala Gly Leu
145 150 155 160

Leu Val Arg Thr Ser Ala Pro Cys Thr Ile Thr Gly Thr Met Gly His
165 170 175

Phe Ile Leu Ala Arg Cys Pro Lys Gly Glu Thr Leu Thr Val Gly Phe
180 185 190

Thr Asp Ser Arg Lys Ile Ser His Thr Cys Thr His Pro Phe His His
195 200 205

Glu Pro Pro Val Ile Gly Arg Glu Arg Phe His Ser Arg Pro Gln His
210 215 220

Gly Lys Glu Leu Pro Cys Ser Thr Tyr Val Gln Ser Thr Ala Ala Thr
225 230 235 240

Ala Glu Glu Ile Glu Val His Met Pro Pro Asp Thr Pro Asp Arg Thr
245 250 255

Leu Met Thr Gln Gln Ser Gly Asn Val Lys Ile Thr Val Asn Gly Gln
260 265 270

Thr Val Arg Tyr Lys Cys Asn Cys Gly Gly Ser Asn Glu Gly Leu Thr
275 280 285

Thr Thr Asp Lys Val Ile Asn Asn Cys Lys Ile Asp Gln Cys His Ala
290 295 300

Ala Val Thr Asn His Lys Asn Trp Gln Tyr Asn Ser Pro Leu Val Pro
305 310 315 320

Arg Asn Ala Glu Leu Gly Asp Arg Lys Gly Lys Ile His Ile Pro Phe
325 330 335

Pro Leu Ala Asn Val Thr Cys Arg Val Pro Lys Ala Arg Asn Pro Thr
340 345 350

Val Thr Tyr Gly Lys Asn Gln Val Thr Met Leu Leu Tyr Pro Asp His
355 360 365

Pro Thr Leu Leu Ser Tyr Arg Asn Met Gly Gln Glu Pro Asn Tyr His
370 375 380

-continued

Glu Glu Trp Val Thr His Lys Lys Glu Val Thr Leu Thr Val Pro Thr
385 390 395 400

Glu Gly Leu Glu Val Thr Trp Gly Asn Asn Glu Pro Tyr Lys Tyr Trp
405 410 415

Pro Gln Met Ser Thr Asn Gly Thr Ala His Gly His Pro His Glu Ile
420 425 430

Ile Leu Tyr Tyr Tyr Glu Leu Tyr Pro Thr Met Thr Val Val Ile Val
435 440 445

Ser Val Ala Ser Phe Val Leu Leu Ser Met Val Gly Thr Ala Val Gly
450 455 460

Met Cys Val Cys Ala Arg Arg Arg Cys Ile Thr Pro Tyr Glu Leu Thr
465 470 475 480

Pro Gly Ala Thr Val Pro Phe Leu Leu Ser Leu Leu Cys Cys Val Arg
485 490 495

Thr Thr Lys Ala
500

<210> SEQ ID NO 49
<211> LENGTH: 507
<212> TYPE: PRT
<213> ORGANISM: Artificial Sequence
<220> FEATURE:
<223> OTHER INFORMATION: Synthetic CHIKV E3-CTLA-4-E2

<400> SEQUENCE: 49

Ser Leu Ala Leu Pro Val Leu Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Ser Thr Leu Arg Met Leu Glu Asp Asn Val Met Arg Pro Gly Tyr Tyr
35 40 45

Gln Leu Leu Lys Ala Ser Leu Thr Cys Ser Pro His Ser Gly Gly Gly
50 55 60

Gly Lys Val Glu Leu Met Tyr Pro Pro Pro Tyr Phe Val Gly Met Gly
65 70 75 80

Gly Gly Gly Ser Ser Thr Lys Asp Asn Phe Asn Val Tyr Lys Ala Thr
85 90 95

Arg Pro Tyr Leu Ala His Cys Pro Asp Cys Gly Glu Gly His Ser Cys
100 105 110

His Ser Pro Ile Ala Leu Glu Arg Ile Arg Asn Glu Ala Thr Asp Gly
115 120 125

Thr Leu Lys Ile Gln Val Ser Leu Gln Ile Gly Ile Lys Thr Asp Asp
130 135 140

Ser His Asp Trp Thr Lys Leu Arg Tyr Met Asp Ser His Thr Pro Ala
145 150 155 160

Asp Ala Glu Arg Ala Gly Leu Leu Val Arg Thr Ser Ala Pro Cys Thr
165 170 175

Ile Thr Gly Thr Met Gly His Phe Ile Leu Ala Arg Cys Pro Lys Gly
180 185 190

Glu Thr Leu Thr Val Gly Phe Thr Asp Ser Arg Lys Ile Ser His Thr
195 200 205

Cys Thr His Pro Phe His His Glu Pro Pro Val Ile Gly Arg Glu Arg
210 215 220

Phe His Ser Arg Pro Gln His Gly Lys Glu Leu Pro Cys Ser Thr Tyr
225 230 235 240

-continued

```
Val Gln Ser Thr Ala Ala Thr Ala Glu Glu Ile Glu Val His Met Pro
                245                 250                 255

Pro Asp Thr Pro Asp Arg Thr Leu Met Thr Gln Gln Ser Gly Asn Val
            260                 265                 270

Lys Ile Thr Val Asn Gly Gln Thr Val Arg Tyr Lys Cys Asn Cys Gly
        275                 280                 285

Gly Ser Asn Glu Gly Leu Thr Thr Thr Asp Lys Val Ile Asn Asn Cys
    290                 295                 300

Lys Ile Asp Gln Cys His Ala Ala Val Thr Asn His Lys Asn Trp Gln
305                 310                 315                 320

Tyr Asn Ser Pro Leu Val Pro Arg Asn Ala Glu Leu Gly Asp Arg Lys
                325                 330                 335

Gly Lys Ile His Ile Pro Phe Pro Leu Ala Asn Val Thr Cys Arg Val
            340                 345                 350

Pro Lys Ala Arg Asn Pro Thr Val Thr Tyr Gly Lys Asn Gln Val Thr
        355                 360                 365

Met Leu Leu Tyr Pro Asp His Pro Thr Leu Leu Ser Tyr Arg Asn Met
    370                 375                 380

Gly Gln Glu Pro Asn Tyr His Glu Glu Trp Val Thr His Lys Lys Glu
385                 390                 395                 400

Val Thr Leu Thr Val Pro Thr Glu Gly Leu Glu Val Thr Trp Gly Asn
                405                 410                 415

Asn Glu Pro Tyr Lys Tyr Trp Pro Gln Met Ser Thr Asn Gly Thr Ala
            420                 425                 430

His Gly His Pro His Glu Ile Ile Leu Tyr Tyr Tyr Glu Leu Tyr Pro
        435                 440                 445

Thr Met Thr Val Val Ile Val Ser Val Ala Ser Phe Val Leu Leu Ser
    450                 455                 460

Met Val Gly Thr Ala Val Gly Met Cys Val Cys Ala Arg Arg Arg Cys
465                 470                 475                 480

Ile Thr Pro Tyr Glu Leu Thr Pro Gly Ala Thr Val Pro Phe Leu Leu
                485                 490                 495

Ser Leu Leu Cys Cys Val Arg Thr Thr Lys Ala
            500                 505
```

<210> SEQ ID NO 50
<211> LENGTH: 508
<212> TYPE: PRT
<213> ORGANISM: Artificial Sequence
<220> FEATURE:
<223> OTHER INFORMATION: Synthetic VEEV E3-malaria-E2(74.66)

<400> SEQUENCE: 50

```
Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Asn Pro Asn Ala Asn Pro
    50                  55                  60

Asn Ala Asn Pro Asn Ala Asn Pro Asn Ala Asn Pro Asn Ala Asn Pro
65                  70                  75                  80

Asn Ala Gly Gly Ser Ser Thr Glu Glu Leu Phe Asn Glu Tyr Lys Leu
                85                  90                  95
```

-continued

```
Thr Arg Pro Tyr Met Ala Arg Cys Ile Arg Cys Ala Val Gly Ser Cys
            100                 105                 110

His Ser Pro Ile Ala Ile Glu Ala Val Lys Ser Asp Gly His Asp Gly
        115                 120                 125

Tyr Val Arg Leu Gln Thr Ser Ser Gln Tyr Gly Leu Asp Ser Ser Gly
    130                 135                 140

Asn Leu Lys Gly Arg Thr Met Arg Tyr Asp Met His Gly Thr Ile Lys
145                 150                 155                 160

Glu Ile Pro Leu His Gln Val Ser Leu Tyr Thr Ser Arg Pro Cys His
                165                 170                 175

Ile Val Asp Gly His Gly Tyr Phe Leu Leu Ala Arg Cys Pro Ala Gly
            180                 185                 190

Asp Ser Ile Thr Met Glu Phe Lys Lys Asp Ser Val Arg His Ser Cys
        195                 200                 205

Ser Val Pro Tyr Glu Val Lys Phe Asn Pro Val Gly Arg Glu Leu Tyr
    210                 215                 220

Thr His Pro Pro Glu His Gly Val Glu Gln Ala Cys Gln Val Tyr Ala
225                 230                 235                 240

His Asp Ala Gln Asn Arg Gly Ala Tyr Val Glu Met His Leu Pro Gly
                245                 250                 255

Ser Glu Val Asp Ser Ser Leu Val Ser Leu Ser Gly Ser Ser Val Thr
            260                 265                 270

Val Thr Pro Pro Asp Gly Thr Ser Ala Leu Val Glu Cys Glu Cys Gly
        275                 280                 285

Gly Thr Lys Ile Ser Glu Thr Ile Asn Lys Thr Lys Gln Phe Ser Gln
    290                 295                 300

Cys Thr Lys Lys Glu Gln Cys Arg Ala Tyr Arg Leu Gln Asn Asp Lys
305                 310                 315                 320

Trp Val Tyr Asn Ser Asp Lys Leu Pro Lys Ala Ala Gly Ala Thr Leu
                325                 330                 335

Lys Gly Lys Leu His Val Pro Phe Leu Leu Ala Asp Gly Lys Cys Thr
            340                 345                 350

Val Pro Leu Ala Pro Glu Pro Met Ile Thr Phe Gly Phe Arg Ser Val
        355                 360                 365

Ser Leu Lys Leu His Pro Lys Asn Pro Thr Tyr Leu Ile Thr Arg Gln
    370                 375                 380

Leu Ala Asp Glu Pro His Tyr Thr His Glu Leu Ile Ser Glu Pro Ala
385                 390                 395                 400

Val Arg Asn Phe Thr Val Thr Glu Lys Gly Trp Glu Phe Val Trp Gly
                405                 410                 415

Asn His Pro Pro Lys Arg Phe Trp Ala Gln Glu Thr Ala Pro Gly Asn
            420                 425                 430

Pro His Gly Leu Pro His Glu Val Ile Thr His Tyr Tyr His Arg Tyr
        435                 440                 445

Pro Met Ser Thr Ile Leu Gly Leu Ser Ile Cys Ala Ala Ile Ala Thr
    450                 455                 460

Val Ser Val Ala Ala Ser Thr Trp Leu Phe Cys Arg Ser Arg Val Ala
465                 470                 475                 480

Cys Leu Thr Pro Tyr Arg Leu Thr Pro Asn Ala Arg Ile Pro Phe Cys
                485                 490                 495

Leu Ala Val Leu Cys Cys Ala Arg Thr Ala Arg Ala
            500                 505
```

<210> SEQ ID NO 51
<211> LENGTH: 497
<212> TYPE: PRT
<213> ORGANISM: Artificial Sequence
<220> FEATURE:
<223> OTHER INFORMATION: Synthetic VEEV E3-PD-1-E2

<400> SEQUENCE: 51

```
Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Gly Ala Ile Ser Leu His
    50                  55                  60

Pro Lys Ala Lys Ile Glu Glu Ser Gly Ser Ser Thr Glu Glu Leu Phe
65                  70                  75                  80

Asn Glu Tyr Lys Leu Thr Arg Pro Tyr Met Ala Arg Cys Ile Arg Cys
                85                  90                  95

Ala Val Gly Ser Cys His Ser Pro Ile Ala Ile Glu Ala Val Lys Ser
            100                 105                 110

Asp Gly His Asp Gly Tyr Val Arg Leu Gln Thr Ser Ser Gln Tyr Gly
        115                 120                 125

Leu Asp Ser Ser Gly Asn Leu Lys Gly Arg Thr Met Arg Tyr Asp Met
    130                 135                 140

His Gly Thr Ile Lys Glu Ile Pro Leu His Gln Val Ser Leu Tyr Thr
145                 150                 155                 160

Ser Arg Pro Cys His Ile Val Asp Gly His Gly Tyr Phe Leu Leu Ala
                165                 170                 175

Arg Cys Pro Ala Gly Asp Ser Ile Thr Met Glu Phe Lys Lys Asp Ser
            180                 185                 190

Val Arg His Ser Cys Ser Val Pro Tyr Glu Val Lys Phe Asn Pro Val
        195                 200                 205

Gly Arg Glu Leu Tyr Thr His Pro Pro Glu His Gly Val Glu Gln Ala
    210                 215                 220

Cys Gln Val Tyr Ala His Asp Ala Gln Asn Arg Gly Ala Tyr Val Glu
225                 230                 235                 240

Met His Leu Pro Gly Ser Glu Val Asp Ser Ser Leu Val Ser Leu Ser
                245                 250                 255

Gly Ser Ser Val Thr Val Thr Pro Pro Asp Gly Thr Ser Ala Leu Val
            260                 265                 270

Glu Cys Glu Cys Gly Gly Thr Lys Ile Ser Glu Thr Ile Asn Lys Thr
        275                 280                 285

Lys Gln Phe Ser Gln Cys Thr Lys Lys Glu Gln Cys Arg Ala Tyr Arg
    290                 295                 300

Leu Gln Asn Asp Lys Trp Val Tyr Asn Ser Asp Lys Leu Pro Lys Ala
305                 310                 315                 320

Ala Gly Ala Thr Leu Lys Gly Lys Leu His Val Pro Phe Leu Leu Ala
                325                 330                 335

Asp Gly Lys Cys Thr Val Pro Leu Ala Pro Glu Pro Met Ile Thr Phe
            340                 345                 350

Gly Phe Arg Ser Val Ser Leu Lys Leu His Pro Lys Asn Pro Thr Tyr
        355                 360                 365

Leu Ile Thr Arg Gln Leu Ala Asp Glu Pro His Tyr Thr His Glu Leu
```

```
    370                 375                 380

Ile Ser Glu Pro Ala Val Arg Asn Phe Thr Val Thr Glu Lys Gly Trp
385                 390                 395                 400

Glu Phe Val Trp Gly Asn His Pro Pro Lys Arg Phe Trp Ala Gln Glu
                405                 410                 415

Thr Ala Pro Gly Asn Pro His Gly Leu Pro His Glu Val Ile Thr His
            420                 425                 430

Tyr Tyr His Arg Tyr Pro Met Ser Thr Ile Leu Gly Leu Ser Ile Cys
        435                 440                 445

Ala Ala Ile Ala Thr Val Ser Val Ala Ala Ser Thr Trp Leu Phe Cys
    450                 455                 460

Arg Ser Arg Val Ala Cys Leu Thr Pro Tyr Arg Leu Thr Pro Asn Ala
465                 470                 475                 480

Arg Ile Pro Phe Cys Leu Ala Val Leu Cys Cys Ala Arg Thr Ala Arg
                485                 490                 495

Ala


<210> SEQ ID NO 52
<211> LENGTH: 495
<212> TYPE: PRT
<213> ORGANISM: Artificial Sequence
<220> FEATURE:
<223> OTHER INFORMATION: Synthetic VEEV E3-PD-L1-E2

<400> SEQUENCE: 52

Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Cys Ile Ile Ser Tyr Gly
    50                  55                  60

Gly Ala Asp Tyr Cys Gly Gly Ser Ser Thr Glu Glu Leu Phe Asn Glu
65                  70                  75                  80

Tyr Lys Leu Thr Arg Pro Tyr Met Ala Arg Cys Ile Arg Cys Ala Val
                85                  90                  95

Gly Ser Cys His Ser Pro Ile Ala Ile Glu Ala Val Lys Ser Asp Gly
            100                 105                 110

His Asp Gly Tyr Val Arg Leu Gln Thr Ser Ser Gln Tyr Gly Leu Asp
        115                 120                 125

Ser Ser Gly Asn Leu Lys Gly Arg Thr Met Arg Tyr Asp Met His Gly
    130                 135                 140

Thr Ile Lys Glu Ile Pro Leu His Gln Val Ser Leu Tyr Thr Ser Arg
145                 150                 155                 160

Pro Cys His Ile Val Asp Gly His Gly Tyr Phe Leu Leu Ala Arg Cys
                165                 170                 175

Pro Ala Gly Asp Ser Ile Thr Met Glu Phe Lys Lys Asp Ser Val Arg
            180                 185                 190

His Ser Cys Ser Val Pro Tyr Glu Val Lys Phe Asn Pro Val Gly Arg
        195                 200                 205

Glu Leu Tyr Thr His Pro Pro Glu His Gly Val Glu Gln Ala Cys Gln
    210                 215                 220

Val Tyr Ala His Asp Ala Gln Asn Arg Gly Ala Tyr Val Glu Met His
225                 230                 235                 240
```

Leu Pro Gly Ser Glu Val Asp Ser Ser Leu Val Ser Leu Ser Gly Ser
245 250 255

Ser Val Thr Val Thr Pro Pro Asp Gly Thr Ser Ala Leu Val Glu Cys
260 265 270

Glu Cys Gly Gly Thr Lys Ile Ser Glu Thr Ile Asn Lys Thr Lys Gln
275 280 285

Phe Ser Gln Cys Thr Lys Lys Glu Gln Cys Arg Ala Tyr Arg Leu Gln
290 295 300

Asn Asp Lys Trp Val Tyr Asn Ser Asp Lys Leu Pro Lys Ala Ala Gly
305 310 315 320

Ala Thr Leu Lys Gly Lys Leu His Val Pro Phe Leu Leu Ala Asp Gly
325 330 335

Lys Cys Thr Val Pro Leu Ala Pro Glu Pro Met Ile Thr Phe Gly Phe
340 345 350

Arg Ser Val Ser Leu Lys Leu His Pro Lys Asn Pro Thr Tyr Leu Ile
355 360 365

Thr Arg Gln Leu Ala Asp Glu Pro His Tyr Thr His Glu Leu Ile Ser
370 375 380

Glu Pro Ala Val Arg Asn Phe Thr Val Thr Glu Lys Gly Trp Glu Phe
385 390 395 400

Val Trp Gly Asn His Pro Pro Lys Arg Phe Trp Ala Gln Glu Thr Ala
405 410 415

Pro Gly Asn Pro His Gly Leu Pro His Glu Val Ile Thr His Tyr Tyr
420 425 430

His Arg Tyr Pro Met Ser Thr Ile Leu Gly Leu Ser Ile Cys Ala Ala
435 440 445

Ile Ala Thr Val Ser Val Ala Ala Ser Thr Trp Leu Phe Cys Arg Ser
450 455 460

Arg Val Ala Cys Leu Thr Pro Tyr Arg Leu Thr Pro Asn Ala Arg Ile
465 470 475 480

Pro Phe Cys Leu Ala Val Leu Cys Cys Ala Arg Thr Ala Arg Ala
485 490 495

<210> SEQ ID NO 53
<211> LENGTH: 502
<212> TYPE: PRT
<213> ORGANISM: Artificial Sequence
<220> FEATURE:
<223> OTHER INFORMATION: Synthetic VEEV E3-CTLA-4-E2

<400> SEQUENCE: 53

Ser Leu Val Thr Thr Met Cys Leu Leu Ala Asn Val Thr Phe Pro Cys
1 5 10 15

Ala Gln Pro Pro Ile Cys Tyr Asp Arg Lys Pro Ala Glu Thr Leu Ala
20 25 30

Met Leu Ser Val Asn Val Asp Asn Pro Gly Tyr Asp Glu Leu Leu Glu
35 40 45

Ala Ala Val Lys Cys Pro Gly Ser Gly Gly Gly Gly Lys Val Glu Leu
50 55 60

Met Tyr Pro Pro Pro Tyr Phe Val Gly Met Gly Gly Gly Gly Ser Ser
65 70 75 80

Thr Glu Glu Leu Phe Asn Glu Tyr Lys Leu Thr Arg Pro Tyr Met Ala
85 90 95

Arg Cys Ile Arg Cys Ala Val Gly Ser Cys His Ser Pro Ile Ala Ile
100 105 110

```
Glu Ala Val Lys Ser Asp Gly His Asp Gly Tyr Val Arg Leu Gln Thr
        115                 120                 125

Ser Ser Gln Tyr Gly Leu Asp Ser Ser Gly Asn Leu Lys Gly Arg Thr
    130                 135                 140

Met Arg Tyr Asp Met His Gly Thr Ile Lys Glu Ile Pro Leu His Gln
145                 150                 155                 160

Val Ser Leu Tyr Thr Ser Arg Pro Cys His Ile Val Asp Gly His Gly
                165                 170                 175

Tyr Phe Leu Leu Ala Arg Cys Pro Ala Gly Asp Ser Ile Thr Met Glu
            180                 185                 190

Phe Lys Lys Asp Ser Val Arg His Ser Cys Ser Val Pro Tyr Glu Val
        195                 200                 205

Lys Phe Asn Pro Val Gly Arg Glu Leu Tyr Thr His Pro Pro Glu His
    210                 215                 220

Gly Val Glu Gln Ala Cys Gln Val Tyr Ala His Asp Ala Gln Asn Arg
225                 230                 235                 240

Gly Ala Tyr Val Glu Met His Leu Pro Gly Ser Glu Val Asp Ser Ser
                245                 250                 255

Leu Val Ser Leu Ser Gly Ser Ser Val Thr Val Thr Pro Pro Asp Gly
            260                 265                 270

Thr Ser Ala Leu Val Glu Cys Glu Cys Gly Gly Thr Lys Ile Ser Glu
        275                 280                 285

Thr Ile Asn Lys Thr Lys Gln Phe Ser Gln Cys Thr Lys Lys Glu Gln
    290                 295                 300

Cys Arg Ala Tyr Arg Leu Gln Asn Asp Lys Trp Val Tyr Asn Ser Asp
305                 310                 315                 320

Lys Leu Pro Lys Ala Ala Gly Ala Thr Leu Lys Gly Lys Leu His Val
                325                 330                 335

Pro Phe Leu Leu Ala Asp Gly Lys Cys Thr Val Pro Leu Ala Pro Glu
            340                 345                 350

Pro Met Ile Thr Phe Gly Phe Arg Ser Val Ser Leu Lys Leu His Pro
        355                 360                 365

Lys Asn Pro Thr Tyr Leu Ile Thr Arg Gln Leu Ala Asp Glu Pro His
    370                 375                 380

Tyr Thr His Glu Leu Ile Ser Glu Pro Ala Val Arg Asn Phe Thr Val
385                 390                 395                 400

Thr Glu Lys Gly Trp Glu Phe Val Trp Gly Asn His Pro Pro Lys Arg
                405                 410                 415

Phe Trp Ala Gln Glu Thr Ala Pro Gly Asn Pro His Gly Leu Pro His
            420                 425                 430

Glu Val Ile Thr His Tyr Tyr His Arg Tyr Pro Met Ser Thr Ile Leu
        435                 440                 445

Gly Leu Ser Ile Cys Ala Ala Ile Ala Thr Val Ser Val Ala Ala Ser
    450                 455                 460

Thr Trp Leu Phe Cys Arg Ser Arg Val Ala Cys Leu Thr Pro Tyr Arg
465                 470                 475                 480

Leu Thr Pro Asn Ala Arg Ile Pro Phe Cys Leu Ala Val Leu Cys Cys
                485                 490                 495

Ala Arg Thr Ala Arg Ala
            500
```

<210> SEQ ID NO 54
<211> LENGTH: 3747

```
<212> TYPE: DNA
<213> ORGANISM: Artificial Sequence
<220> FEATURE:
<223> OTHER INFORMATION: Synthetic CHIKV

<400> SEQUENCE: 54

atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540

gagaaacccg aggggtacta taactggcat cacggagcag tgcagtattc aggaggccgg    600

ttcactatcc cgacgggtgc aggcaagccg ggagacagcg gcagaccgat cttcgacaac    660

aaaggacggg tggtggccat cgtcctagga ggggccaacg aaggtgcccg cacggccctc    720

tccgtggtga cgtggaacaa agacatcgtc acaaaaatta cccctgaggg agccgaagag    780

tggagcctcg ccctcccggt cttgtgcctg ttggcaaaca ctacattccc ctgctctcag    840

ccgccttgca caccctgctg ctacgaaaag gaaccggaaa gcaccttgcg catgcttgag    900

gacaacgtga tgagacccgg atactaccag ctactaaaag catcgctgac ttgctctccc    960

cactccggag gcggatccag tactaaggac aattttaatg tctataaagc cacaagacca   1020

tatctagctc attgtcctga ctgcggagaa gggcattcgt gccacagccc tatcgcattg   1080

gagcgcatca gaaatgaagc aacggacgga acgctgaaaa tccaggtctc tttgcagatc   1140

gggataaaga cagatgacag ccacgattgg accaagctgc gctatatgga tagccatacg   1200

cccgcggacg cggagcgagc cggattgctt gtaaggactt cagcaccgtg cacgatcacc   1260

gggaccatgg gacactttat tctcgcccga tgcccgaaag gagagacgct gacagtggga   1320

tttacggaca gcagaaagat cagccacaca tgcacacacc cgttccatca tgaaccacct   1380

gtgataggta gggagaggtt ccactctcga ccacaacatg gtaaagagtt accttgcagc   1440

acgtacgtgc agagcaccgc tgccactgct gaggagatag aggtgcatat gcccccagat   1500

actcctgacc gcacgctgat gacgcagcag tctggcaacg tgaagatcac agttaatggg   1560

cagacggtgc ggtacaagtg caactgcggt ggctcaaacg agggactgac aaccacagac   1620

aaagtgatca ataactgcaa aattgatcag tgccatgctg cagtcactaa tcacaagaat   1680

tggcaataca actccccttt agtcccgcgc aacgctgaac tcggggaccg taaaggaaag   1740

atccacatcc cattcccatt ggcaaacgtg acttgcagag tgccaaaagc aagaaaccct   1800

acagtaactt acggaaaaaa ccaagtcacc atgctgctgt atcctgacca tccgacactc   1860

ttgtcttacc gtaacatggg acaggaacca aattaccacg aggagtgggt gacacacaag   1920

aaggaggtta ccttgaccgt gcctactgag ggtctggagg tcacttgggg caacaacgaa   1980

ccatacaagt actggccgca gatgtctacg aacggtactg ctcatggtca cccacatgag   2040

ataatcttgt actattatga gctgtacccc actatgactg tagtcattgt gtcggtggcc   2100

tcgttcgtgc ttctgtcgat ggtgggcaca gcagtgggaa tgtgtgtgtg cgcacggcgc   2160
```

agatgcatta caccatatga attaacacca ggagccactg ttcccttcct gctcagcctg 2220
ctatgctgcg tcagaacgac caaggcggcc acatattacg aggctgcggc atatctatgg 2280
aacgaacagc agcccctgtt ctggttgcag gctcttatcc cgctggccgc cttgatcgtc 2340
ctgtgcaact gtctgaaact cttgccatgc tgctgtaaga ccctggcttt tttagccgta 2400
atgagcatcg gtgcccacac tgtgagcgcg tacgaacacg taacagtgat cccgaacacg 2460
gtgggagtac cgtataagac tcttgtcaac agaccgggtt acagccccat ggtgttggag 2520
atggagctac aatcagtcac cttggaacca acactgtcac ttgactacat cacgtgcgag 2580
tacaaaactg tcatcccctc cccgtacgtg aagtgctgtg gtacagcaga gtgcaaggac 2640
aagagcctac cagactacag ctgcaaggtc tttactggag tctacccatt tatgtggggc 2700
ggcgcctact gcttttgcga cgccgaaaat acgcaattga gcgaggcaca tgtagagaaa 2760
tctgaatctt gcaaaacaga gtttgcatcg gcctacagag cccacaccgc atcggcgtcg 2820
gcgaagctcc gcgtccttta ccaaggaaac aacattaccg tagctgccta cgctaacggt 2880
gaccatgccg tcacagtaaa ggacgccaag tttgtcgtgg gcccaatgtc ctccgcctgg 2940
acaccttttg acaacaaaat cgtggtgtac aaaggcgacg tctacaacat ggactaccca 3000
ccttttggcg caggaagacc aggacaattt ggtgacattc aaagtcgtac accggaaagt 3060
aaagacgttt atgccaacac tcagttggta ctacagaggc cagcagcagg cacggtacat 3120
gtaccatact ctcaggcacc atctggcttc aagtattggc tgaaggaacg aggagcatcg 3180
ctacagcaca cggcaccgtt cggttgccag attgcgacaa acccggtaag agctgtaaat 3240
tgcgctgtgg ggaacatacc aatttccatc gacataccgg atgcggcctt tactagggtt 3300
gtcgatgcac cctctgtaac ggacatgtca tgcgaagtac cagcctgcac tcactcctcc 3360
gactttgggg gcgtcgccat catcaaatac acagctagca agaaaggtaa atgtgcagta 3420
cattcgatga ccaacgccgt taccattcga gaagccgacg tagaagtaga ggggaactcc 3480
cagctgcaaa tatccttctc aacagccctg gcaagcgccg agtttcgcgt gcaagtgtgc 3540
tccacacaag tacactgcgc agccgcatgc caccctccaa aggaccacat agtcaattac 3600
ccagcatcac acaccaccct tggggtccag gatatatcca caacggcaat gtcttgggtg 3660
cagaagatta cgggaggagt aggattaatt gttgctgttg ctgccttaat tttaattgtg 3720
gtgctatgcg tgtcgtttag caggcac 3747

<210> SEQ ID NO 55
<211> LENGTH: 3768
<212> TYPE: DNA
<213> ORGANISM: Artificial Sequence
<220> FEATURE:
<223> OTHER INFORMATION: Synthetic VEEV

<400> SEQUENCE: 55
atgttcccgt tccagccaat gtatccgatg cagccaatgc cctatcgcaa cccgttcgcg 60
gccccgcgca ggccctggtt ccccagaacc gacccttttc tggcgatgca ggtgcaggaa 120
ttaacccgct cgatggctaa cctgacgttc aagcaacgcc gggacgcgcc acctgagggg 180
ccatccgcta ataaaccgaa gaaggaggcc tcgcaaaaac agaaaggggg aggccaaggg 240
aagaagaaga agaaccaagg gaagaagaag gctaagacag ggccgcctaa tccgaaggca 300
cagaatggaa acaagaagaa gaccaacaag aaaccaggca agagacagcg catggtcatg 360
aaattggaat ctgacaagac gttcccaatc atgttggaag ggaagataaa cggctacgct 420
tgtgtggtcg gagggaagtt attcaggccg atgcatgtgg aaggcaagat cgacaacgac 480

-continued

```
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccggg tccggaggtg gatcctccac cgaggagctg   1020
tttaatgagt ataagctaac gcgcccttac atggccagat gcatcagatg tgcagttggg   1080
agctgccata gtccaatagc aatcgaggca gtaaagagcg acgggcacga cggttatgtt   1140
agacttcaga cttcctcgca gtatggcctg gattcctccg gcaacttaaa gggcaggacc   1200
atgcggtatg acatgcacgg gaccattaaa gagataccac tacatcaagt gtcactctat   1260
acatctcgcc cgtgtcacat tgtggatggg cacggttatt tcctgctagc caggtgcccg   1320
gcaggggact ccatcaccat ggaatttaag aaagattccg tcagacactc ctgctcggtg   1380
ccgtatgaag tgaaatttaa tcctgtaggc agagaactct atactcatcc cccagaacac   1440
ggagtagagc aagcgtgcca agtctacgca catgatgcac agaacagagg agcttatgtc   1500
gagatgcacc tcccgggctc agaagtggac agcagtttgg tttccttgag cggcagttca   1560
gtcaccgtga cacctcctga tgggactagc gccctggtgg aatgcgagtg tggcggcaca   1620
aagatctccg agaccatcaa caagacaaaa cagttcagcc agtgcacaaa gaaggagcag   1680
tgcagagcat atcggctgca gaacgataag tgggtgtata attctgacaa actgcccaaa   1740
gcagcgggag ccaccttaaa aggaaaactg catgtcccat tcttgctggc agacggcaaa   1800
tgcaccgtgc ctctagcacc agaacctatg ataaccttcg gtttcagatc agtgtcactg   1860
aaactgcacc ctaagaatcc cacatatcta atcacccgcc aacttgctga tgagcctcac   1920
tacacgcacg agctcatatc tgaaccagct gttaggaatt ttaccgtcac cgaaaaaggg   1980
tgggagtttg tatggggaaa ccacccgccg aaaaggtttt gggcacagga aacagcaccc   2040
ggaaatccac atgggctacc gcacgaggtg ataactcatt attaccacag ataccctatg   2100
tccaccatcc tgggtttgtc aatttgtgcc gccattgcaa ccgtttccgt tgcagcgtct   2160
acctggctgt tttgcagatc aagagttgcg tgcctaactc cttaccggct aacacctaac   2220
gctaggatac cattttgtct ggctgtgctt tgctgcgccc gcactgcccg ggccgagacc   2280
acctgggagt ccttggatca cctatggaac aataaccaac agatgttctg gattcaattg   2340
ctgatccctc tggccgcctt gatcgtagtg actcgcctgc tcaggtgcgt gtgctgtgtc   2400
gtgccttttt tagtcatggc cggcgccgca ggcgccggcg cctacgagca cgcgaccacg   2460
atgccgagcc aagcgggaat ctcgtataac actatagtca acagagcagg ctacgcacca   2520
ctccctatca gcataacacc aacaaagatc aagctgatac ctacagtgaa cttggagtac   2580
gtcacctgcc actacaaaac aggaatggat tcaccagcca tcaaatgctg cggatctcag   2640
gaatgcactc caacttacag gcctgatgaa cagtgcaaag tcttcacagg ggtttacccg   2700
ttcatgtggg gtggtgcata ttgcttttgc gacactgaga acacccaagt cagcaaggcc   2760
tacgtaatga aatctgacga ctgccttgcg gatcatgctg aagcatataa agcgcacaca   2820
```

gcctcagtgc aggcgttcct caacatcaca gtgggagaac actctattgt gactaccgtg 2880
tatgtgaatg gagaaactcc tgtgaatttc aatggggtca aaataactgc aggtccgctt 2940
tccacagctt ggacaccctt tgatcgcaaa atcgtgcagt atgccgggga gatctataat 3000
tatgattttc ctgagtatgg ggcaggacaa ccaggagcat ttggagatat acaatccaga 3060
acagtctcaa gctctgatct gtatgccaat accaacctag tgctgcagag acccaaagca 3120
ggagcgatcc acgtgccata cactcaggca ccttcgggtt ttgagcaatg gaagaaagat 3180
aaagctccat cattgaaatt taccgcccct ttcggatgcg aaatatatac aaaccccatt 3240
cgcgccgaaa actgtgctgt agggtcaatt ccattagcct ttgacattcc cgacgccttg 3300
ttcaccaggg tgtcagaaac accgacactt tcagcggccg aatgcactct taacgagtgc 3360
gtgtattctt ccgactttgg tggatcgcc acggtcaagt actcggccag caagtcaggc 3420
aagtgcgcag tccatgtgcc atcagggact gctaccctaa aagaagcagc agtcgagcta 3480
accgagcaag ggtcggcgac tatccatttc tcgaccgcaa atatccaccc ggagttcagg 3540
ctccaaatat gcacatcata tgttacgtgc aaaggtgatt gtcacccccc gaaagaccat 3600
attgtgacac accctcagta tcacgcccaa acatttacag ccgcggtgtc aaaaaccgcg 3660
tggacgtggt taacatccct gctgggagga tcagccgtaa ttattataat tggcttggtg 3720
ctggctacta ttgtggccat gtacgtgctg accaaccaga aacataat 3768

<210> SEQ ID NO 56
<211> LENGTH: 30
<212> TYPE: PRT
<213> ORGANISM: Artificial Sequence
<220> FEATURE:
<223> OTHER INFORMATION: Synthetic malaria antigen with linker

<400> SEQUENCE: 56

Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Ala Gly Gly Ser
            20                  25                  30

<210> SEQ ID NO 57
<211> LENGTH: 8476
<212> TYPE: DNA
<213> ORGANISM: Artificial Sequence
<220> FEATURE:
<223> OTHER INFORMATION: Synthetic Expression vector for CHIKV viral
      structural protein containing CSP repeat antigen “74” in E3
      (74.16)

<400> SEQUENCE: 57
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600

-continued

```
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt tctataacag aaggtaccaa ccccgaccct    960
gggccccacg ccctacaatt caagtaatta gacctagacc acgtccacag aggcaggctg   1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtgggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca agccgggaga cagcggcaga ccgatcttcg   1560
acaacaaagg acgggtggtg gccatcgtcc taggaggggc caacgaaggt gcccgcacgg   1620
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccactc cggaggaaac ccgaatgcca atcccaacgc gaaccccaat gctaacccaa   1920
atgccaaccc aaacgccaac cccaacgctg gtggatccag tactaaggac aattttaatg   1980
tctataaagc cacaagacca tatctagctc attgtcctga ctgcggagaa gggcattcgt   2040
gccacagccc tatcgcattg gagcgcatca gaaatgaagc aacggacgga acgctgaaaa   2100
tccaggtctc tttgcagatc gggataaaga cagatgacag ccacgattgg accaagctgc   2160
gctatatgga tagccatacg cccgcggacg cggagcgagc cggattgctt gtaaggactt   2220
cagcaccgtg cacgatcacc gggaccatgg gacactttat tctcgcccga tgcccgaaag   2280
gagagacgct gacagtggga tttacggaca gcagaaagat cagccacaca tgcacacacc   2340
cgttccatca tgaaccacct gtgataggta gggagaggtt ccactctcga ccacaacatg   2400
gtaaagagtt accttgcagc acgtacgtgc agagcaccgc tgccactgct gaggagatag   2460
aggtgcatat gcccccagat actcctgacc gcacgctgat gacgcagcag tctggcaacg   2520
tgaagatcac agttaatggg cagacggtgc ggtacaagtg caactgcggt ggctcaaacg   2580
agggactgac aaccacagac aaagtgatca ataactgcaa aattgatcag tgccatgctg   2640
cagtcactaa tcacaagaat tggcaataca actccccttt agtcccgcgc aacgctgaac   2700
tcggggaccg taaaggaaag atccacatcc cattcccatt ggcaaacgtg acttgcagag   2760
tgccaaaagc aagaaaccct acagtaactt acggaaaaaa ccaagtcacc atgctgctgt   2820
atcctgacca tccgacactc ttgtcttacc gtaacatggg acaggaacca aattaccacg   2880
aggagtgggt gacacacaag aaggaggtta ccttgaccgt gcctactgag ggtctggagg   2940
```

-continued

```
tcacttgggg caacaacgaa ccatacaagt actggccgca gatgtctacg aacggtactg   3000
ctcatggtca cccacatgag ataatcttgt actattatga gctgtacccc actatgactg   3060
tagtcattgt gtcggtggcc tcgttcgtgc ttctgtcgat ggtgggcaca gcagtgggaa   3120
tgtgtgtgtg cgcacggcgc agatgcatta caccatatga attaacacca ggagccactg   3180
ttcccttcct gctcagcctg ctatgctgcg tcagaacgac caaggcggcc acatattacg   3240
aggctgcggc atatctatgg aacgaacagc agcccctgtt ctggttgcag gctcttatcc   3300
cgctggccgc cttgatcgtc ctgtgcaact gtctgaaact cttgccatgc tgctgtaaga   3360
ccctggcttt tttagccgta atgagcatcg gtgcccacac tgtgagcgcg tacgaacacg   3420
taacagtgat cccgaacacg gtgggagtac cgtataagac tcttgtcaac agaccgggtt   3480
acagccccat ggtgttggag atggagctac aatcagtcac cttggaacca acactgtcac   3540
ttgactacat cacgtgcgag tacaaaactg tcatcccctc cccgtacgtg aagtgctgtg   3600
gtacagcaga gtgcaaggac aagagcctac cagactacag ctgcaaggtc tttactggag   3660
tctacccatt tatgtggggc ggcgcctact gcttttgcga cgccgaaaat acgcaattga   3720
gcgaggcaca tgtagagaaa tctgaatctt gcaaaacaga gtttgcatcg gcctacagag   3780
cccacaccgc atcggcgtcg gcgaagctcc gcgtccttta ccaaggaaac aacattaccg   3840
tagctgccta cgctaacggt gaccatgccg tcacagtaaa ggacgccaag tttgtcgtgg   3900
gcccaatgtc ctccgcctgg acaccttttg acaacaaaat cgtggtgtac aaaggcgacg   3960
tctacaacat ggactaccca ccttttggcg caggaagacc aggacaattt ggtgacattc   4020
aaagtcgtac accggaaagt aaagacgttt atgccaacac tcagttggta ctacagaggc   4080
cagcagcagg cacggtacat gtaccatact ctcaggcacc atctggcttc aagtattggc   4140
tgaaggaacg aggagcatcg ctacagcaca cggcaccgtt cggttgccag attgcgacaa   4200
acccggtaag agctgtaaat tgcgctgtgg ggaacatacc aatttccatc gacataccgg   4260
atgcggcctt tactagggtt gtcgatgcac cctctgtaac ggacatgtca tgcgaagtac   4320
cagcctgcac tcactcctcc gactttgggg gcgtcgccat catcaaatac acagctagca   4380
agaaaggtaa atgtgcagta cattcgatga ccaacgccgt taccattcga gaagccgacg   4440
tagaagtaga ggggaactcc cagctgcaaa tatccttctc aacagccctg gcaagcgccg   4500
agtttcgcgt gcaagtgtgc tccacacaag tacactgcgc agccgcatgc caccctccaa   4560
aggaccacat agtcaattac ccagcatcac acaccaccct tggggtccag gatatatcca   4620
caacggcaat gtcttgggtg cagaagatta cgggaggagt aggattaatt gttgctgttg   4680
ctgccttaat tttaattgtg gtgctatgcg tgtcgtttag caggcactaa ggatctagat   4740
ctgctgtgcc ttctagttgc cagccatctg ttgtttgccc ctcccccgtg ccttccttga   4800
ccctggaagg tgccactccc actgtccttt cctaataaaa tgaggaaatt gcatcgcatt   4860
gtctgagtag gtgtcattct attctggggg gtggggtggg gcaggacagc aagggggagg   4920
attgggaaga caatagcagg catgctgggg atgcggtggg ctctatgggt acccaggtgc   4980
tgaagaattg acccggttcc tcctgggcca gaaagaagca ggcacatccc cttctctgtg   5040
acacaccctg tccacgcccc tggttcttag ttccagcccc actcatagga cactcatagc   5100
tcaggagggc tccgccttca atcccacccg ctaaagtact tggagcggtc tctccctccc   5160
tcatcagccc accaaaccaa acctagcctc caagagtggg aagaaattaa agcaagatag   5220
gctattaagt gcagagggag agaaaatgcc tccaacatgt gaggaagtaa tgagagaaat   5280
catagaattt taaggccatg atttaaggcc atcatggcct aagcttgaaa ggagatagga   5340
```

```
tcaaagcttg gcgtaatcat ggtcatagct gtttcctgtg tgaaattgtt atccgctcac   5400

aattccacac aacatacgag ccggaagcat aaagtgtaaa gcctggggtg cctaatgagt   5460

gagctaactc acattaattg cgttgcgctc actgcccgct ttccagtcgg gaaacctgtc   5520

gtgccagctg cattaatgaa tcggccaacg cgcggggaga ggcggtttgc gtattgggcg   5580

ctcttccgct tcctcgctca ctgactcgct gcgctcggtc gttcggctgc ggcgagcggt   5640

atcagctcac tcaaaggcgg taatacggtt atccacagaa tcaggggata acgcaggaaa   5700

gaacatgtga gcaaaaggcc agcaaaaggc caggaaccgt aaaaaggccg cgttgctggc   5760

gtttttccat aggctccgcc cccctgacga gcatcacaaa aatcgacgct caagtcagag   5820

gtggcgaaac ccgacaggac tataaagata ccaggcgttt ccccctggaa gctccctcgt   5880

gcgctctcct gttccgaccc tgccgcttac cggatacctg tccgcctttc tcccttcggg   5940

aagcgtggcg ctttctcata gctcacgctg taggtatctc agttcggtgt aggtcgttcg   6000

ctccaagctg ggctgtgtgc acgaaccccc cgttcagccc gaccgctgcg ccttatccgg   6060

taactatcgt cttgagtcca acccggtaag acacgactta tcgccactgg cagcagccac   6120

tggtaacagg attagcagag cgaggtatgt aggcggtgct acagagttct tgaagtggtg   6180

gcctaactac ggctacacta gaagaacagt atttggtatc tgcgctctgc tgaagccagt   6240

taccttcgga aaaagagttg gtagctcttg atccggcaaa caaaccaccg ctggtagcgg   6300

tggttttttt gtttgcaagc agcagattac gcgcagaaaa aaaggatctc aagaagatcc   6360

tttgatcttt tctacggggt ctgacgctca gtggaacgaa aactcacgtt aagggatttt   6420

ggtcatgaga ttatcaaaaa ggatcttcac ctagatcctt ttaaattaaa aatgaagttt   6480

taaatcaatc taaagtatat atgagtaaac ttggtctgac agttaccaat gcttaatcag   6540

tgaggcacct atctcagcga tctgtctatt tcgttcatcc atagttgcct gactccccgt   6600

cgtgtagata actacgatac gggagggctt accatctggc cccagtgctg caatgatacc   6660

gcgagaacca cgctcaccgg ctccagattt atcagcaata aaccagccag ccggaagggc   6720

cgagcgcaga agtggtcctg caactttatc cgcctccatc cagtctatta attgttgccg   6780

ggaagctaga gtaagtagtt cgccagttaa tagtttgcgc aacgttgttg ccattgctac   6840

aggcatcgtg gtgtcacgct cgtcgtttgg tatggcttca ttcagctccg gttcccaacg   6900

atcaaggcga gttacatgat cccccatgtt gtgcaaaaaa gcggttagct ccttcggtcc   6960

tccgatcgtt gtcagaagta agttggccgc agtgttatca ctcatggtta tggcagcact   7020

gcataattct cttactgtca tgccatccgt aagatgcttt tctgtgactg gtgagtactc   7080

aaccaagtca ttctgagaat agtgtatgcg gcgaccgagt tgctcttgcc cggcgtcaat   7140

acgggataat accgcgccac atagcagaac tttaaaagtg ctcatcattg gaaaacgttc   7200

ttcggggcga aaactctcaa ggatcttacc gctgttgaga tccagttcga tgtaacccac   7260

tcgtgcaccc aactgatctt cagcatcttt tactttcacc agcgtttctg ggtgagcaaa   7320

aacaggaagg caaaatgccg caaaaaaggg aataagggcg acacggaaat gttgaatact   7380

catactcttc ctttttcaat attattgaag catttatcag ggttattgtc tcatgagcgg   7440

atacatattt gaatgtattt agaaaaataa acaaataggg gttccgcgca catttccccg   7500

aaaagtgcca cctgacgtct aagaaaccat tattatcatg acattaacct ataaaaatag   7560

gcgtatcacg aggccctttc gggtcgcgcg tttcggtgat gacggtgaaa acctctgaca   7620

catgcagctc ccgttgacgg tcacagcttg tctgtaagcg gatgccggga gcagacaagc   7680
```

-continued ccgtcagggc gcgtcagcgg gtgttggcgg gtgtcggggc tggcttaact atgcggcatc 7740
agagcagatt gtactgagag tgcaccataa aattgtaaac gttaatattt tgttaaaatt 7800
cgcgttaaat ttttgttaaa tcagctcatt ttttaaccaa taggccgaaa tcggcaaaat 7860
cccttataaa tcaaaagaat agcccgagat agggttgagt gttgttccag tttggaacaa 7920
gagtccacta ttaaagaacg tggactccaa cgtcaaaggg cgaaaaaccg tctatcaggg 7980
cgatggccca ctacgtgaac catcacccaa atcaagtttt ttggggtcga ggtgccgtaa 8040
agcactaaat cggaacccta aagggagccc ccgatttaga gcttgacggg gaaagccggc 8100
gaacgtggcg agaaaggaag ggaagaaagc gaaaggagcg ggcgctaggg cgctggcaag 8160
tgtagcggtc acgctgcgcg taaccaccac acccgccgcg cttaatgcgc cgctacaggg 8220
cgcgtactat ggttgctttg acgtatgcgg tgtgaaatac cgcacagatg cgtaaggaga 8280
aaataccgca tcaggcgcca ttcgccattc aggctgcgca actgttggga agggcgatcg 8340
gtgcgggcct cttcgctatt acgccagctg gcgaaagggg gatgtgctgc aaggcgatta 8400
agttgggtaa cgccagggtt ttcccagtca cgacgttgta aaacgacggc cagtgaattc 8460
catggtctca actttc 8476

<210> SEQ ID NO 58
<211> LENGTH: 30
<212> TYPE: PRT
<213> ORGANISM: Artificial Sequence
<220> FEATURE:
<223> OTHER INFORMATION: Synthetic malaria antigen with linker

<400> SEQUENCE: 58

Ser Gly Gly Gln Gly Pro Gly Ala Pro Gln Gly Pro Gly Ala Pro Gln
1 5 10 15

Gly Pro Gly Ala Pro Gln Gly Pro Gly Ala Pro Gly Gly Ser
20 25 30

<210> SEQ ID NO 59
<211> LENGTH: 8497
<212> TYPE: DNA
<213> ORGANISM: Artificial Sequence
<220> FEATURE:
<223> OTHER INFORMATION: Synthetic Expression vector for VEEV viral structural protein containing an antigen "261" in E3 (261.66)

<400> SEQUENCE: 59
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720

-continued

```
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa gggggaggcc   1140
aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga aagcatccaa atacgatctt gagtatgcag   1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc caagggagac agcggacgac ccattctgga taaccaggga cgggtggtcg   1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccgggtccgg aggacaggga cctggcgctc   1920
ctcagggacc aggggcacca cagggcccag gcgccccaca ggggcctggg gcccctgggg   1980
gatcctccac cgaggagctg tttaatgagt ataagctaac gcgcccttac atggccagat   2040
gcatcagatg tgcagttggg agctgccata gtccaatagc aatcgaggca gtaaagagcg   2100
acgggcacga cggttatgtt agacttcaga cttcctcgca gtatggcctg gattcctccg   2160
gcaacttaaa gggcaggacc atgcggtatg acatgcacgg gaccattaaa gagataccac   2220
tacatcaagt gtcactctat acatctcgcc cgtgtcacat tgtggatggg cacggttatt   2280
tcctgcttgc caggtgcccg gcaggggact ccatcaccat ggaatttaag aaagattccg   2340
tcagacactc ctgctcggtg ccgtatgaag tgaaatttaa tcctgtaggc agagaactct   2400
atactcatcc cccagaacac ggagtagagc aagcgtgcca agtctacgca catgatgcac   2460
agaacagagg agcttatgtc gagatgcacc tcccgggctc agaagtggac agcagtttgg   2520
tttccttgag cggcagttca gtcaccgtga cacctcctga tgggactagc gccctggtgg   2580
aatgcgagtg tggcggcaca aagatctccg agaccatcaa caagacaaaa cagttcagcc   2640
agtgcacaaa gaaggagcag tgcagagcat atcggctgca gaacgataag tgggtgtata   2700
attctgacaa actgcccaaa gcagcgggag ccaccttaaa aggaaaactg catgtcccat   2760
tcttgctggc agacggcaaa tgcaccgtgc ctctagcacc agaacctatg ataaccttcg   2820
gtttcagatc agtgtcactg aaactgcacc ctaagaatcc cacatatcta atcacccgcc   2880
aacttgctga tgagcctcac tacacgcacg agctcatatc tgaaccagct gttaggaatt   2940
ttaccgtcac cgaaaaaggg tgggagtttg tatggggaaa ccacccgccg aaaaggtttt   3000
gggcacagga aacagcaccc ggaaatccac atgggctacc gcacgaggtg ataactcatt   3060
attaccacag ataccctatg tccaccatcc tgggtttgtc aatttgtgcc gccattgcaa   3120
```

ccgtttccgt tgcagcgtct acctggctgt tttgcagatc aagagttgcg tgcctaactc 3180
cttaccggct aacacctaac gctaggatac cattttgtct ggctgtgctt tgctgcgccc 3240
gcactgcccg ggccgagacc acctgggagt ccttggatca cctatggaac aataaccaac 3300
agatgttctg gattcaattg ctgatccctc tggccgcctt gatcgtagtg actcgcctgc 3360
tcaggtgcgt gtgctgtgtc gtgccttttt tagtcatggc cggcgccgca ggcgccggcg 3420
cctacgagca cgcgaccacg atgccgagcc aagcgggaat ctcgtataac actatagtca 3480
acagagcagg ctacgcacca ctccctatca gcataacacc aacaaagatc aagctgatac 3540
ctacagtgaa cttggagtac gtcacctgcc actacaaaac aggaatggat tcaccagcca 3600
tcaaatgctg cggatctcag gaatgcactc caacttacag gcctgatgaa cagtgcaaag 3660
tcttcacagg ggtttacccg ttcatgtggg gtggtgcata ttgcttttgc gacactgaga 3720
acacccaagt cagcaaggcc tacgtaatga aatctgacga ctgccttgcg gatcatgctg 3780
aagcatataa agcgcacaca gcctcagtgc aggcgttcct caacatcaca gtgggagaac 3840
actctattgt gactaccgtg tatgtgaatg gagaaactcc tgtgaatttc aatggggtca 3900
aaataactgc aggtccgctt tccacagctt ggacaccctt tgatcgcaaa atcgtgcagt 3960
atgccgggga gatctataat tatgattttc ctgagtatgg ggcaggacaa ccaggagcat 4020
ttggagatat acaatccaga acagtctcaa gctctgatct gtatgccaat accaacctag 4080
tgctgcagag acccaaagca ggagcgatcc acgtgccata cactcaggca ccttcgggtt 4140
ttgagcaatg gaagaaagat aaagctccat cattgaaatt taccgcccct ttcggatgcg 4200
aaatatatac aaaccccatt cgcgccgaaa actgtgctgt agggtcaatt ccattagcct 4260
ttgacattcc cgacgccttg ttcaccaggg tgtcagaaac accgacactt tcagcggccg 4320
aatgcactct taacgagtgc gtgtattctt ccgactttgg tgggatcgcc acggtcaagt 4380
actcggccag caagtcaggc aagtgcgcag tccatgtgcc atcagggact gctaccctaa 4440
aagaagcagc agtcgagcta accgagcaag ggtcggcgac tatccatttc tcgaccgcaa 4500
atatccaccc ggagttcagg ctccaaatat gcacatcata tgttacgtgc aaaggtgatt 4560
gtcacccccc gaaagaccat attgtgacac accctcagta tcacgcccaa acatttacag 4620
ccgcggtgtc aaaaaccgcg tggacgtggt taacatccct gctgggagga tcagccgtaa 4680
ttattataat tggcttggtg ctggctacta ttgtggccat gtacgtgctg accaaccaga 4740
aacataatta aggatctaga tctgctgtgc cttctagttg ccagccatct gttgtttgcc 4800
cctcccccgt gccttccttg accctggaag gtgccactcc cactgtcctt tcctaataaa 4860
atgaggaaat tgcatcgcat tgtctgagta ggtgtcattc tattctgggg ggtggggtgg 4920
ggcaggacag caagggggag gattgggaag acaatagcag gcatgctggg gatgcggtgg 4980
gctctatggg tacccaggtg ctgaagaatt gacccggttc ctcctgggcc agaaagaagc 5040
aggcacatcc ccttctctgt gacacaccct gtccacgccc ctggttctta gttccagccc 5100
cactcatagg acactcatag ctcaggaggg ctccgccttc aatcccaccc gctaaagtac 5160
ttggagcggt ctctccctcc ctcatcagcc caccaaacca aacctagcct ccaagagtgg 5220
gaagaaatta aagcaagata ggctattaag tgcagaggga gagaaaatgc ctccaacatg 5280
tgaggaagta atgagagaaa tcatagaatt ttaaggccat gatttaaggc catcatggcc 5340
taagcttgaa aggagatagg atcaaagctt ggcgtaatca tggtcatagc tgtttcctgt 5400
gtgaaattgt tatccgctca caattccaca caacatacga gccggaagca taaagtgtaa 5460

-continued agcctggggt gcctaatgag tgagctaact cacattaatt gcgttgcgct cactgcccgc 5520
tttccagtcg ggaaacctgt cgtgccagct gcattaatga atcggccaac gcgcggggag 5580
aggcggtttg cgtattgggc gctcttccgc ttcctcgctc actgactcgc tgcgctcggt 5640
cgttcggctg cggcgagcgg tatcagctca ctcaaaggcg gtaatacggt tatccacaga 5700
atcaggggat aacgcaggaa agaacatgtg agcaaaaggc cagcaaaagg ccaggaaccg 5760
taaaaaggcc gcgttgctgg cgtttttcca taggctccgc ccccctgacg agcatcacaa 5820
aaatcgacgc tcaagtcaga ggtggcgaaa cccgacagga ctataaagat accaggcgtt 5880
tccccctgga agctccctcg tgcgctctcc tgttccgacc ctgccgctta ccggatacct 5940
gtccgccttt ctcccttcgg gaagcgtggc gctttctcat agctcacgct gtaggtatct 6000
cagttcggtg taggtcgttc gctccaagct gggctgtgtg cacgaacccc ccgttcagcc 6060
cgaccgctgc gccttatccg gtaactatcg tcttgagtcc aacccggtaa gacacgactt 6120
atcgccactg gcagcagcca ctggtaacag gattagcaga gcgaggtatg taggcggtgc 6180
tacagagttc ttgaagtggt ggcctaacta cggctacact agaagaacag tatttggtat 6240
ctgcgctctg ctgaagccag ttaccttcgg aaaaagagtt ggtagctctt gatccggcaa 6300
acaaaccacc gctggtagcg gtggtttttt tgtttgcaag cagcagatta cgcgcagaaa 6360
aaaaggatct caagaagatc ctttgatctt ttctacgggg tctgacgctc agtggaacga 6420
aaactcacgt taagggattt tggtcatgag attatcaaaa aggatcttca cctagatcct 6480
tttaaattaa aaatgaagtt ttaaatcaat ctaaagtata tatgagtaaa cttggtctga 6540
cagttaccaa tgcttaatca gtgaggcacc tatctcagcg atctgtctat ttcgttcatc 6600
catagttgcc tgactccccg tcgtgtagat aactacgata cgggagggct taccatctgg 6660
ccccagtgct gcaatgatac cgcgagaacc acgctcaccg gctccagatt tatcagcaat 6720
aaaccagcca gccggaaggg ccgagcgcag aagtggtcct gcaactttat ccgcctccat 6780
ccagtctatt aattgttgcc gggaagctag agtaagtagt tcgccagtta atagtttgcg 6840
caacgttgtt gccattgcta caggcatcgt ggtgtcacgc tcgtcgtttg gtatggcttc 6900
attcagctcc ggttcccaac gatcaaggcg agttacatga tcccccatgt tgtgcaaaaa 6960
agcggttagc tccttcggtc ctccgatcgt tgtcagaagt aagttggccg cagtgttatc 7020
actcatggtt atggcagcac tgcataattc tcttactgtc atgccatccg taagatgctt 7080
ttctgtgact ggtgagtact caaccaagtc attctgagaa tagtgtatgc ggcgaccgag 7140
ttgctcttgc ccggcgtcaa tacgggataa taccgcgcca catagcagaa ctttaaaagt 7200
gctcatcatt ggaaaacgtt cttcggggcg aaaactctca aggatcttac cgctgttgag 7260
atccagttcg atgtaaccca ctcgtgcacc caactgatct tcagcatctt ttactttcac 7320
cagcgtttct gggtgagcaa aaacaggaag gcaaaatgcc gcaaaaaagg gaataagggc 7380
gacacggaaa tgttgaatac tcatactctt cctttttcaa tattattgaa gcatttatca 7440
gggttattgt ctcatgagcg gatacatatt tgaatgtatt tagaaaaata aacaaatagg 7500
ggttccgcgc acatttcccc gaaaagtgcc acctgacgtc taagaaacca ttattatcat 7560
gacattaacc tataaaaata ggcgtatcac gaggcccttt cgggtcgcgc gtttcggtga 7620
tgacggtgaa aacctctgac acatgcagct cccgttgacg gtcacagctt gtctgtaagc 7680
ggatgccggg agcagacaag cccgtcaggg cgcgtcagcg ggtgttggcg ggtgtcgggg 7740
ctggcttaac tatgcggcat cagagcagat tgtactgaga gtgcaccata aaattgtaaa 7800
cgttaatatt ttgttaaaat tcgcgttaaa tttttgttaa atcagctcat tttttaacca 7860
ataggccgaa atcggcaaaa tcccttataa atcaaaagaa tagcccgaga tagggttgag 7920
tgttgttcca gtttggaaca agagtccact attaaagaac gtggactcca acgtcaaagg 7980
gcgaaaaacc gtctatcagg gcgatggccc actacgtgaa ccatcaccca aatcaagttt 8040
tttggggtcg aggtgccgta aagcactaaa tcggaaccct aaagggagcc cccgatttag 8100
agcttgacgg ggaaagccgg cgaacgtggc gagaaaggaa gggaagaaag cgaaaggagc 8160
gggcgctagg gcgctggcaa gtgtagcggt cacgctgcgc gtaaccacca cacccgccgc 8220
gcttaatgcg ccgctacagg gcgcgtacta tggttgcttt gacgtatgcg gtgtgaaata 8280
ccgcacagat gcgtaaggag aaaataccgc atcaggcgcc attcgccatt caggctgcgc 8340
aactgttggg aagggcgatc ggtgcgggcc tcttcgctat tacgccagct ggcgaaaggg 8400
ggatgtgctg caaggcgatt aagttgggta acgccagggt tttcccagtc acgacgttgt 8460
aaaacgacgg ccagtgaatt ccatggtctc aacttttc 8497

<210> SEQ ID NO 60
<211> LENGTH: 90
<212> TYPE: DNA
<213> ORGANISM: Artificial Sequence
<220> FEATURE:
<223> OTHER INFORMATION: Synthetic CSP repeat antigen "74" (6 repeat of NPNA) with linker

<400> SEQUENCE: 60
tccggaggaa acccgaatgc caatcccaac gcgaacccca atgctaaccc aaatgccaac 60
ccaaacgcca accccaacgc tggtggatcc 90

<210> SEQ ID NO 61
<211> LENGTH: 62
<212> TYPE: PRT
<213> ORGANISM: Artificial Sequence
<220> FEATURE:
<223> OTHER INFORMATION: Synthetic CSP repeat antigen "76" (14 repeat of NPNA) with linker

<400> SEQUENCE: 61

Ser Gly Gly Asn Pro Asn Ala Asn Pro Asn Ala Asn Pro Asn Ala Asn
1 5 10 15

Pro Asn Ala Asn Pro Asn Ala Asn Pro Asn Ala Asn Pro Asn Ala Asn
20 25 30

Pro Asn Ala Asn Pro Asn Ala Asn Pro Asn Ala Asn Pro Asn Ala Asn
35 40 45

Pro Asn Ala Asn Pro Asn Ala Asn Pro Asn Ala Gly Gly Ser
50 55 60

<210> SEQ ID NO 62
<211> LENGTH: 186
<212> TYPE: DNA
<213> ORGANISM: Artificial Sequence
<220> FEATURE:
<223> OTHER INFORMATION: Synthetic CSP repeat antigen "76" (14 repeat of NPNA) with linker

<400> SEQUENCE: 62
tccggaggca accccaacgc caaccctaat gccaatccca acgctaatcc caatgctaac 60
cctaacgcaa atccaaatgc aaaccccaat gccaacccaa acgctaaccc taacgccaac 120
cctaacgcaa acccaaacgc caatcctaat gctaacccaa atgcaaaccc taatgctggc 180
ggatcc 186

<210> SEQ ID NO 63
<211> LENGTH: 106
<212> TYPE: PRT
<213> ORGANISM: Artificial Sequence
<220> FEATURE:
<223> OTHER INFORMATION: Synthetic CSP repeat antigen "78" (25 repeat of NPNA) with linker

<400> SEQUENCE: 63

```
Ser Gly Gly Asn Pro Asn Ala Asn Pro Asn Ala Asn Pro Asn Ala Asn
1               5                   10                  15

Pro Asn Ala Asn Pro Asn Ala Asn Pro Asn Val Asp Pro Asn Ala Asn
            20                  25                  30

Pro Asn Ala Asn Pro Asn Ala Asn Pro Asn Ala Asn Pro Asn Ala Asn
        35                  40                  45

Pro Asn Ala Asn Pro Asn Ala Asn Pro Asn Ala Asn Pro Asn Ala Asn
    50                  55                  60

Pro Asn Ala Asn Pro Asn Ala Asn Pro Asn Ala Asn Pro Asn Ala Asn
65                  70                  75                  80

Pro Asn Ala Asn Pro Asn Ala Asn Pro Asn Ala Asn Pro Asn Ala Asn
                85                  90                  95

Pro Asn Ala Asn Pro Asn Ala Gly Gly Ser
            100                 105
```

<210> SEQ ID NO 64
<211> LENGTH: 318
<212> TYPE: DNA
<213> ORGANISM: Artificial Sequence
<220> FEATURE:
<223> OTHER INFORMATION: Synthetic CSP repeat antigen "78" (25 repeat of NPNA) with linker

<400> SEQUENCE: 64

```
tccggaggaa acccgaatgc caatcccaac gcgaacccca acgctaaccc caacgccaat     60

ccgaatgcaa acccgaacgt tgacccaaac gccaacccga atgccaatcc caacgcgaac    120

cccaatgcta acccaaatgc caacccaaac gccaacccca acgctaatcc aaacgccaac    180

cctaacgcca atcccaacgc gaatcctaac gctaatccca acgcaaatcc caatgctaat    240

ccgaacgcga accctaatgc aaacccccaac gccaacccga acgctaaccc gaacgctaat    300

cccaacgccg gtggatcc                                                  318
```

<210> SEQ ID NO 65
<211> LENGTH: 90
<212> TYPE: DNA
<213> ORGANISM: Artificial Sequence
<220> FEATURE:
<223> OTHER INFORMATION: Synthetic CSP repeat antigen "261" (repeat of qgpgap)

<400> SEQUENCE: 65

```
tccggaggac agggacctgg cgctcctcag ggaccagggg caccacaggg cccaggcgcc     60

ccacaggggc ctggggcccc tgggggatcc                                      90
```

<210> SEQ ID NO 66
<211> LENGTH: 19
<212> TYPE: PRT
<213> ORGANISM: Artificial Sequence
<220> FEATURE:
<223> OTHER INFORMATION: 302R (Synthetic antigen derived from pfs25 with linker)

<400> SEQUENCE: 66

Ser Gly Gly Cys Ile Lys Ile Asp Gly Asn Pro Val Ser Tyr Ala Cys
1 5 10 15

Gly Gly Ser

<210> SEQ ID NO 67
<211> LENGTH: 57
<212> TYPE: DNA
<213> ORGANISM: Artificial Sequence
<220> FEATURE:
<223> OTHER INFORMATION: 302R (Synthetic antigen derived from pfs25 with linker)

<400> SEQUENCE: 67
tccggagggt gcatcaagat cgacggcaac cccgtgtcct acgcctgcgg gggatcc 57

<210> SEQ ID NO 68
<211> LENGTH: 20
<212> TYPE: PRT
<213> ORGANISM: Artificial Sequence
<220> FEATURE:
<223> OTHER INFORMATION: 303R (Synthetic antigen derived from pfs25 with linker)

<400> SEQUENCE: 68

Ser Gly Gly Cys Ile Leu Asp Thr Ser Asn Pro Val Lys Thr Gly Val
1 5 10 15

Cys Gly Gly Ser
20

<210> SEQ ID NO 69
<211> LENGTH: 60
<212> TYPE: DNA
<213> ORGANISM: Artificial Sequence
<220> FEATURE:
<223> OTHER INFORMATION: 303R (Synthetic antigen derived from pfs25 with linker)

<400> SEQUENCE: 69
tccggaggct gcatcctgga caccagcaac cccgtgaaaa ccggcgtgtg tggcggatcc 60

<210> SEQ ID NO 70
<211> LENGTH: 48
<212> TYPE: DNA
<213> ORGANISM: Artificial Sequence
<220> FEATURE:
<223> OTHER INFORMATION: 299 (Synthetic mousePD-L1 antigen with linker)

<400> SEQUENCE: 70
tccggaggat gcatcatcag ctacggcgga gccgactacg gaggatcc 48

<210> SEQ ID NO 71
<211> LENGTH: 17
<212> TYPE: PRT
<213> ORGANISM: Artificial Sequence
<220> FEATURE:
<223> OTHER INFORMATION: 299 (Synthetic mousePD-L1 antigen with linker)

<400> SEQUENCE: 71

Ser Gly Gly Cys Ile Ile Ser Tyr Gly Gly Ala Asp Tyr Cys Gly Gly
1 5 10 15

Ser

```
<210> SEQ ID NO 72
<211> LENGTH: 60
<212> TYPE: DNA
<213> ORGANISM: Artificial Sequence
<220> FEATURE:
<223> OTHER INFORMATION: 274 (Synthetic mousePD-1 antigen with linker)

<400> SEQUENCE: 72

tccggaggag gcgccatcag cctgcacccc aaggccaaga tcgaggaatc tggaggatcc     60


<210> SEQ ID NO 73
<211> LENGTH: 19
<212> TYPE: PRT
<213> ORGANISM: Artificial Sequence
<220> FEATURE:
<223> OTHER INFORMATION: 274 (Synthetic mousePD-1 antigen with linker)

<400> SEQUENCE: 73

Ser Gly Gly Gly Ala Ile Ser Leu His Pro Lys Ala Lys Ile Glu Glu
1               5                   10                  15

Ser Gly Ser


<210> SEQ ID NO 74
<211> LENGTH: 24
<212> TYPE: PRT
<213> ORGANISM: Artificial Sequence
<220> FEATURE:
<223> OTHER INFORMATION: Synthetic mCTLA-4 _ver2 antigen with linker

<400> SEQUENCE: 74

Ser Gly Gly Gly Gly Lys Val Glu Leu Met Tyr Pro Pro Pro Tyr Phe
1               5                   10                  15

Val Gly Met Gly Gly Gly Gly Ser
            20


<210> SEQ ID NO 75
<211> LENGTH: 261
<212> TYPE: PRT
<213> ORGANISM: Artificial Sequence
<220> FEATURE:
<223> OTHER INFORMATION: Synthetic CHIKV Capsid (OPY-1 strain)

<400> SEQUENCE: 75

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140
```

```
Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260


<210> SEQ ID NO 76
<211> LENGTH: 439
<212> TYPE: PRT
<213> ORGANISM: Artificial Sequence
<220> FEATURE:
<223> OTHER INFORMATION: Synthetic CHIKV E1 (OPY-1 strain)

<400> SEQUENCE: 76

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Val Gly Thr Val His Val Pro Tyr Ser Gln Ala Pro Ser Gly Phe
225                 230                 235                 240
```

Lys Tyr Trp Leu Lys Glu Arg Gly Ala Ser Leu Gln His Thr Ala Pro
245 250 255

Phe Gly Cys Gln Ile Ala Thr Asn Pro Val Arg Ala Val Asn Cys Ala
260 265 270

Val Gly Asn Met Pro Ile Ser Ile Asp Ile Pro Glu Ala Ala Phe Thr
275 280 285

Arg Val Val Asp Ala Pro Ser Leu Thr Asp Met Ser Cys Glu Val Pro
290 295 300

Ala Cys Thr His Ser Ser Asp Phe Gly Gly Val Ala Ile Ile Lys Tyr
305 310 315 320

Ala Ala Ser Lys Lys Gly Lys Cys Ala Val His Ser Met Thr Asn Ala
325 330 335

Val Thr Ile Arg Glu Ala Glu Ile Glu Val Glu Gly Asn Ser Gln Leu
340 345 350

Gln Ile Ser Phe Ser Thr Ala Leu Ala Ser Ala Glu Phe Arg Val Gln
355 360 365

Val Cys Ser Thr Gln Val His Cys Ala Ala Glu Cys His Pro Pro Lys
370 375 380

Asp His Ile Val Asn Tyr Pro Ala Ser His Thr Thr Leu Gly Val Gln
385 390 395 400

Asp Ile Ser Ala Thr Ala Met Ser Trp Val Gln Lys Ile Thr Gly Gly
405 410 415

Val Gly Leu Val Val Ala Val Ala Ala Leu Ile Leu Ile Val Val Leu
420 425 430

Cys Val Ser Phe Ser Arg His
435

<210> SEQ ID NO 77
<211> LENGTH: 483
<212> TYPE: PRT
<213> ORGANISM: Artificial Sequence
<220> FEATURE:
<223> OTHER INFORMATION: Synthetic CHIKV E3-insert-E2 (OPY-1 strain)
<220> FEATURE:
<221> NAME/KEY: NON_CONS
<222> LOCATION: (60)..(61)
<223> OTHER INFORMATION: antigen will be inserted

<400> SEQUENCE: 77

Ser Leu Ala Ile Pro Val Met Cys Leu Leu Ala Asn Thr Thr Phe Pro
1 5 10 15

Cys Ser Gln Pro Pro Cys Thr Pro Cys Cys Tyr Glu Lys Glu Pro Glu
20 25 30

Glu Thr Leu Arg Met Leu Glu Asp Asn Val Met Arg Pro Gly Tyr Tyr
35 40 45

Gln Leu Leu Gln Ala Ser Leu Thr Cys Ser Pro His Ser Thr Lys Asp
50 55 60

Asn Phe Asn Val Tyr Lys Ala Thr Arg Pro Tyr Leu Ala His Cys Pro
65 70 75 80

Asp Cys Gly Glu Gly His Ser Cys His Ser Pro Val Ala Leu Glu Arg
85 90 95

Ile Arg Asn Glu Ala Thr Asp Gly Thr Leu Lys Ile Gln Val Ser Leu
100 105 110

Gln Ile Gly Ile Lys Thr Asp Asp Ser His Asp Trp Thr Lys Leu Arg
115 120 125

Tyr Met Asp Asn His Met Pro Ala Asp Ala Glu Arg Ala Gly Leu Phe
130 135 140

```
Val Arg Thr Ser Ala Pro Cys Thr Ile Thr Gly Thr Met Gly His Phe
145                 150                 155                 160

Ile Leu Ala Arg Cys Pro Lys Gly Glu Thr Leu Thr Val Gly Phe Thr
                165                 170                 175

Asp Ser Arg Lys Ile Ser His Ser Cys Thr His Pro Phe His His Asp
            180                 185                 190

Pro Pro Val Ile Gly Arg Glu Lys Phe His Ser Arg Pro Gln His Gly
        195                 200                 205

Lys Glu Leu Pro Cys Ser Thr Tyr Val Gln Ser Thr Ala Ala Thr Thr
    210                 215                 220

Glu Glu Ile Glu Val His Met Pro Pro Asp Thr Pro Asp Arg Thr Leu
225                 230                 235                 240

Met Ser Gln Gln Ser Gly Asn Val Lys Ile Thr Val Asn Gly Gln Thr
                245                 250                 255

Val Arg Tyr Lys Cys Asn Cys Gly Gly Ser Asn Glu Gly Leu Thr Thr
            260                 265                 270

Thr Asp Lys Val Ile Asn Asn Cys Lys Val Asp Gln Cys His Ala Ala
        275                 280                 285

Val Thr Asn His Lys Lys Trp Gln Tyr Asn Ser Pro Leu Val Pro Arg
    290                 295                 300

Asn Ala Glu Leu Gly Asp Arg Lys Gly Lys Ile His Ile Pro Phe Pro
305                 310                 315                 320

Leu Ala Asn Val Thr Cys Arg Val Pro Lys Ala Arg Asn Pro Thr Val
                325                 330                 335

Thr Tyr Gly Lys Asn Gln Val Ile Met Leu Leu Tyr Pro Asp His Pro
            340                 345                 350

Thr Leu Leu Ser Tyr Arg Asn Met Gly Glu Glu Pro Asn Tyr Gln Glu
        355                 360                 365

Glu Trp Val Met His Lys Lys Glu Val Val Leu Thr Val Pro Thr Glu
    370                 375                 380

Gly Leu Glu Val Thr Trp Gly Asn Asn Glu Pro Tyr Lys Tyr Trp Pro
385                 390                 395                 400

Gln Leu Ser Thr Asn Gly Thr Ala His Gly His Pro His Glu Ile Ile
                405                 410                 415

Leu Tyr Tyr Tyr Glu Leu Tyr Pro Thr Met Thr Val Val Val Val Ser
            420                 425                 430

Val Ala Thr Phe Ile Leu Leu Ser Met Val Gly Met Ala Ala Gly Met
        435                 440                 445

Cys Met Cys Ala Arg Arg Arg Cys Ile Thr Pro Tyr Glu Leu Thr Pro
    450                 455                 460

Gly Ala Thr Val Pro Phe Leu Leu Ser Leu Ile Cys Cys Ile Arg Thr
465                 470                 475                 480

Ala Lys Ala
```

<210> SEQ ID NO 78
<211> LENGTH: 72
<212> TYPE: DNA
<213> ORGANISM: Artificial Sequence
<220> FEATURE:
<223> OTHER INFORMATION: Synthetic mCTLA-4 _ver2 with linker

<400> SEQUENCE: 78

```
tccggaggcg gcggcaaggt ggaactcatg tacccaccgc catactttgt gggcatgggc      60

ggcggcggat cc                                                          72
```

<210> SEQ ID NO 79
<211> LENGTH: 25
<212> TYPE: PRT
<213> ORGANISM: Artificial Sequence
<220> FEATURE:
<223> OTHER INFORMATION: Synthetic mCTLA-4 _ver4 with linker

<400> SEQUENCE: 79

Ser Gly Gly Cys Ala Thr Thr Phe Thr Glu Lys Asn Thr Val Gly Phe
1               5                   10                  15

Leu Asp Tyr Pro Phe Cys Gly Gly Ser
            20                  25

<210> SEQ ID NO 80
<211> LENGTH: 75
<212> TYPE: DNA
<213> ORGANISM: Artificial Sequence
<220> FEATURE:
<223> OTHER INFORMATION: Synthetic mCTLA-4 _ver4 with linker

<400> SEQUENCE: 80
tccggaggct gtgccacgac attcacagag aagaatacag tgggcttcct agattacccc 60
ttctgcggcg gatcc 75

<210> SEQ ID NO 81
<211> LENGTH: 23
<212> TYPE: PRT
<213> ORGANISM: Artificial Sequence
<220> FEATURE:
<223> OTHER INFORMATION: Synthetic mCTLA-4 _ver5 with linker

<400> SEQUENCE: 81

Ser Gly Gly Ala Thr Thr Phe Thr Glu Lys Asn Thr Val Gly Phe Leu
1               5                   10                  15

Asp Tyr Pro Phe Gly Gly Ser
            20

<210> SEQ ID NO 82
<211> LENGTH: 69
<212> TYPE: DNA
<213> ORGANISM: Artificial Sequence
<220> FEATURE:
<223> OTHER INFORMATION: Synthetic mCTLA-4 _ver5 with linker

<400> SEQUENCE: 82
tccggaggcg ccacgacatt cacagagaag aatacagtgg gcttcctaga ttaccccttc 60
ggcggatcc 69

<210> SEQ ID NO 83
<211> LENGTH: 9257
<212> TYPE: DNA
<213> ORGANISM: Artificial Sequence
<220> FEATURE:
<223> OTHER INFORMATION: Synthetic Expression vector for CHIKV
      containing Mouse IL2(wt) antigen in E3

<400> SEQUENCE: 83
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240

-continued

```
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt ggggggataaa  1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccca cttcaagctc cacttcaagc   1860
tctacagcgg aagcacagca gcagcagcag cagcagcagc agcagcagca cctggagcag   1920
ctgttgatgg acctacagga gctcctgagc aggatggaga attacaggaa cctgaaactc   1980
cccaggatgc tcaccttcaa attttacttg cccaagcagg ccacagaatt gaaagatctt   2040
cagtgcctag aagatgaact tggacctctg cggcatgttc tggatttgac tcaaagcaaa   2100
agctttcaat tggaagatgc tgagaatttc atcagcaata tcagagtaac tgttgtaaaa   2160
ctaaagggct ctgacaacac atttgagtgc caattcgatg atgagtcagc aactgtggtg   2220
gactttctga ggagatggat agccttctgt caaagcatca tctcaacaag ccctcaaggg   2280
ggatccagta ctaaggacaa ttttaatgtc tataaagcca caagaccata tctagctcat   2340
tgtcctgact gcggagaagg gcattcgtgc cacagcccta tcgcattgga gcgcatcaga   2400
aatgaagcaa cggacggaac gctgaaaatc caggtctctt tgcagatcgg gataaagaca   2460
gatgacagcc acgattggac caagctgcgc tatatggata gccatacgcc cgcggacgcg   2520
gagcgagccg gattgcttgt aaggacttca gcaccgtgca cgatcaccgg gaccatggga   2580
```

-continued

```
cactttattc tcgcccgatg cccgaaagga gagacgctga cagtgggatt tacggacagc   2640
agaaagatca gccacacatg cacacacccg ttccatcatg aaccacctgt gataggtagg   2700
gagaggttcc actctcgacc acaacatggt aaagagttac cttgcagcac gtacgtgcag   2760
agcaccgctg ccactgctga ggagatagag gtgcatatgc ccccagatac tcctgaccgc   2820
acgctgatga cgcagcagtc tggcaacgtg aagatcacag ttaatgggca gacggtgcgg   2880
tacaagtgca actgcggtgg ctcaaacgag ggactgacaa ccacagacaa agtgatcaat   2940
aactgcaaaa ttgatcagtg ccatgctgca gtcactaatc acaagaattg gcaatacaac   3000
tcccctttag tcccgcgcaa cgctgaactc ggggaccgta aaggaaagat ccacatccca   3060
ttcccattgg caaacgtgac ttgcagagtg ccaaaagcaa gaaaccctac agtaacttac   3120
ggaaaaaacc aagtcaccat gctgctgtat cctgaccatc cgacactctt gtcttaccgt   3180
aacatgggac aggaaccaaa ttaccacgag gagtgggtga cacacaagaa ggaggttacc   3240
ttgaccgtgc ctactgaggg tctggaggtc acttggggca acaacgaacc atacaagtac   3300
tggccgcaga tgtctacgaa cggtactgct catggtcacc cacatgagat aatcttgtac   3360
tattatgagc tgtaccccac tatgactgta gtcattgtgt cggtggcctc gttcgtgctt   3420
ctgtcgatgg tgggcacagc agtgggaatg tgtgtgtgcg cacggcgcag atgcattaca   3480
ccatatgaat taacaccagg agccactgtt cccttcctgc tcagcctgct atgctgcgtc   3540
agaacgacca aggcggccac atattacgag gctgcggcat atctatggaa cgaacagcag   3600
cccctgttct ggttgcaggc tcttatcccg ctggccgcct tgatcgtcct gtgcaactgt   3660
ctgaaactct tgccatgctg ctgtaagacc ctggcttttt tagccgtaat gagcatcggt   3720
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
gcaccgttcg gttgccagat tgcgacaaac ccggtaagag ctgtaaattg cgctgtgggg   4560
aacataccaa tttccatcga cataccggat gcggccttta ctagggttgt cgatgcaccc   4620
tctgtaacgg acatgtcatg cgaagtacca gcctgcactc actcctccga ctttgggggc   4680
gtcgccatca tcaaatacac agctagcaag aaaggtaaat gtgcagtaca ttcgatgacc   4740
aacgccgtta ccattcgaga agccgacgta gaagtagagg ggaactccca gctgcaaata   4800
tccttctcaa cagccctggc aagcgccgag tttcgcgtgc aagtgtgctc cacacaagta   4860
cactgcgcag ccgcatgcca ccctccaaag gaccacatag tcaattaccc agcatcacac   4920
accacccttg ggtccagga tatatccaca acggcaatgt cttgggtgca gaagattacg   4980
```

```
ggaggagtag gattaattgt tgctgttgct gccttaattt taattgtggt gctatgcgtg   5040
tcgtttagca ggcactaatg atccggaggg gcacccactt caagctccac ttcaagctct   5100
acagcggaag cacagcagca gcagcagcag cagcagcagc agcagcacct ggagcagctg   5160
ttgatggacc tacaggagct cctgagcagg atggagaatt acaggaacct gaaactcccc   5220
aggatgctca ccttcaaatt ttacttgccc aagcaggcca cagaattgaa agatcttcag   5280
tgcctagaag atgaacttgg acctctgcgg catgttctgg atttgactca aagcaaaagc   5340
tttcaattgg aagatgctga gaatttcatc agcaatatca gagtaactgt tgtaaaacta   5400
aagggctctg acaacacatt tgagtgccaa ttcgatgatg agtcagcaac tgtggtggac   5460
tttctgagga gatggatagc cttctgtcaa agcatcatct caacaagccc tcaaggggga   5520
tccgctgtgc cttctagttg ccagccatct gttgtttgcc cctcccccgt gccttccttg   5580
accctggaag gtgccactcc cactgtcctt tcctaataaa atgaggaaat tgcatcgcat   5640
tgtctgagta ggtgtcattc tattctgggg ggtggggtgg ggcaggacag caagggggag   5700
gattgggaag acaatagcag gcatgctggg gatgcggtgg gctctatggg tacccaggtg   5760
ctgaagaatt gacccggttc ctcctgggcc agaaagaagc aggcacatcc ccttctctgt   5820
gacacaccct gtccacgccc ctggttctta gttccagccc cactcatagg acactcatag   5880
ctcaggaggg ctccgccttc aatcccaccc gctaaagtac ttggagcggt ctctccctcc   5940
ctcatcagcc caccaaacca aacctagcct ccaagagtgg gaagaaatta aagcaagata   6000
ggctattaag tgcagaggga gagaaaatgc ctccaacatg tgaggaagta atgagagaaa   6060
tcatagaatt ttaaggccat gatttaaggc catcatggcc taagcttgaa aggagatagg   6120
atcaaagctt ggcgtaatca tggtcatagc tgtttcctgt gtgaaattgt tatccgctca   6180
caattccaca caacatacga gccggaagca taaagtgtaa agcctggggt gcctaatgag   6240
tgagctaact cacattaatt gcgttgcgct cactgcccgc tttccagtcg ggaaacctgt   6300
cgtgccagct gcattaatga atcggccaac gcgcggggag aggcggtttg cgtattgggc   6360
gctcttccgc ttcctcgctc actgactcgc tgcgctcggt cgttcggctg cggcgagcgg   6420
tatcagctca ctcaaaggcg gtaatacggt tatccacaga atcaggggat aacgcaggaa   6480
agaacatgtg agcaaaaggc cagcaaaagg ccaggaaccg taaaaaggcc gcgttgctgg   6540
cgtttttcca taggctccgc ccccctgacg agcatcacaa aaatcgacgc tcaagtcaga   6600
ggtggcgaaa cccgacagga ctataaagat accaggcgtt tccccctgga agctccctcg   6660
tgcgctctcc tgttccgacc ctgccgctta ccggatacct gtccgccttt ctcccttcgg   6720
gaagcgtggc gctttctcat agctcacgct gtaggtatct cagttcggtg taggtcgttc   6780
gctccaagct gggctgtgtg cacgaacccc ccgttcagcc cgaccgctgc gccttatccg   6840
gtaactatcg tcttgagtcc aacccggtaa gacacgactt atcgccactg gcagcagcca   6900
ctggtaacag gattagcaga gcgaggtatg taggcggtgc tacagagttc ttgaagtggt   6960
ggcctaacta cggctacact agaagaacag tatttggtat ctgcgctctg ctgaagccag   7020
ttaccttcgg aaaaagagtt ggtagctctt gatccggcaa acaaaccacc gctggtagcg   7080
gtggtttttt tgtttgcaag cagcagatta cgcgcagaaa aaaaggatct caagaagatc   7140
ctttgatctt ttctacgggg tctgacgctc agtggaacga aaactcacgt taagggattt   7200
tggtcatgag attatcaaaa aggatcttca cctagatcct tttaaattaa aaatgaagtt   7260
ttaaatcaat ctaaagtata tatgagtaaa cttggtctga cagttaccaa tgcttaatca   7320
```

-continued gtgaggcacc tatctcagcg atctgtctat ttcgttcatc catagttgcc tgactccccg 7380
tcgtgtagat aactacgata cgggagggct taccatctgg ccccagtgct gcaatgatac 7440
cgcgagaacc acgctcaccg gctccagatt tatcagcaat aaaccagcca gccggaaggg 7500
ccgagcgcag aagtggtcct gcaactttat ccgcctccat ccagtctatt aattgttgcc 7560
gggaagctag agtaagtagt tcgccagtta atagtttgcg caacgttgtt gccattgcta 7620
caggcatcgt ggtgtcacgc tcgtcgtttg gtatggcttc attcagctcc ggttcccaac 7680
gatcaaggcg agttacatga tcccccatgt tgtgcaaaaa agcggttagc tccttcggtc 7740
ctccgatcgt tgtcagaagt aagttggccg cagtgttatc actcatggtt atggcagcac 7800
tgcataattc tcttactgtc atgccatccg taagatgctt ttctgtgact ggtgagtact 7860
caaccaagtc attctgagaa tagtgtatgc ggcgaccgag ttgctcttgc ccggcgtcaa 7920
tacgggataa taccgcgcca catagcagaa ctttaaaagt gctcatcatt ggaaaacgtt 7980
cttcggggcg aaaactctca aggatcttac cgctgttgag atccagttcg atgtaaccca 8040
ctcgtgcacc caactgatct tcagcatctt ttactttcac cagcgtttct gggtgagcaa 8100
aaacaggaag gcaaaatgcc gcaaaaaagg gaataagggc gacacggaaa tgttgaatac 8160
tcatactctt cctttttcaa tattattgaa gcatttatca gggttattgt ctcatgagcg 8220
gatacatatt tgaatgtatt tagaaaaata aacaaatagg ggttccgcgc acatttcccc 8280
gaaaagtgcc acctgacgtc taagaaacca ttattatcat gacattaacc tataaaaata 8340
ggcgtatcac gaggcccttt cgggtcgcgc gtttcggtga tgacggtgaa aacctctgac 8400
acatgcagct cccgttgacg gtcacagctt gtctgtaagc ggatgccggg agcagacaag 8460
cccgtcaggg cgcgtcagcg ggtgttggcg ggtgtcgggg ctggcttaac tatgcggcat 8520
cagagcagat tgtactgaga gtgcaccata aaattgtaaa cgttaatatt ttgttaaaat 8580
tcgcgttaaa tttttgttaa atcagctcat tttttaacca ataggccgaa atcggcaaaa 8640
tcccttataa atcaaaagaa tagcccgaga tagggttgag tgttgttcca gtttggaaca 8700
agagtccact attaaagaac gtggactcca acgtcaaagg gcgaaaaacc gtctatcagg 8760
gcgatggccc actacgtgaa ccatcaccca aatcaagttt tttggggtcg aggtgccgta 8820
aagcactaaa tcggaaccct aaagggagcc cccgatttag agcttgacgg ggaaagccgg 8880
cgaacgtggc gagaaaggaa gggaagaaag cgaaaggagc gggcgctagg gcgctggcaa 8940
gtgtagcggt cacgctgcgc gtaaccacca cacccgccgc gcttaatgcg ccgctacagg 9000
gcgcgtacta tggttgcttt gacgtatgcg gtgtgaaata ccgcacagat gcgtaaggag 9060
aaaataccgc atcaggcgcc attcgccatt caggctgcgc aactgttggg aagggcgatc 9120
ggtgcgggcc tcttcgctat tacgccagct ggcgaaaggg ggatgtgctg caaggcgatt 9180
aagttgggta acgccagggt tttcccagtc acgacgttgt aaaacgacgg ccagtgaatt 9240
ccatggtctc aactttc 9257

<210> SEQ ID NO 84
<211> LENGTH: 1398
<212> TYPE: PRT
<213> ORGANISM: Artificial Sequence
<220> FEATURE:
<223> OTHER INFORMATION: Synthetic CHIKV containing Mouse IL2(wt) antigen in E3

<400> SEQUENCE: 84

Met Glu Phe Ile Pro Thr Gln Thr Phe Tyr Asn Arg Arg Tyr Gln Pro
1 5 10 15

-continued

```
Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Ser Ser Ser Thr Ala
                325                 330                 335

Glu Ala Gln Gln Gln Gln Gln Gln Gln Gln Gln Gln Gln His Leu Glu
            340                 345                 350

Gln Leu Leu Met Asp Leu Gln Glu Leu Leu Ser Arg Met Glu Asn Tyr
        355                 360                 365

Arg Asn Leu Lys Leu Pro Arg Met Leu Thr Phe Lys Phe Tyr Leu Pro
    370                 375                 380

Lys Gln Ala Thr Glu Leu Lys Asp Leu Gln Cys Leu Glu Asp Glu Leu
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430
```

```
Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
                565                 570                 575

Leu Ala Arg Cys Pro Lys Gly Glu Thr Leu Thr Val Gly Phe Thr Asp
            580                 585                 590

Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640

Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765

Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815

Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
```

```
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990

Gln Ser Val Thr Leu Glu Pro Thr  Leu Ser Leu Asp Tyr  Ile Thr Cys
        995                 1000                1005

Glu Tyr  Lys Thr Val Ile Pro  Ser Pro Tyr Val Lys  Cys Cys Gly
    1010                 1015                 1020

Thr Ala  Glu Cys Lys Asp Lys  Ser Leu Pro Asp Tyr  Ser Cys Lys
    1025                 1030                 1035

Val Phe  Thr Gly Val Tyr Pro  Phe Met Trp Gly Gly  Ala Tyr Cys
    1040                 1045                 1050

Phe Cys  Asp Ala Glu Asn Thr  Gln Leu Ser Glu Ala  His Val Glu
    1055                 1060                 1065

Lys Ser  Glu Ser Cys Lys Thr  Glu Phe Ala Ser Ala  Tyr Arg Ala
    1070                 1075                 1080

His Thr  Ala Ser Ala Ser Ala  Lys Leu Arg Val Leu  Tyr Gln Gly
    1085                 1090                 1095

Asn Asn  Ile Thr Val Ala Ala  Tyr Ala Asn Gly Asp  His Ala Val
    1100                 1105                 1110

Thr Val  Lys Asp Ala Lys Phe  Val Val Gly Pro Met  Ser Ser Ala
    1115                 1120                 1125

Trp Thr  Pro Phe Asp Asn Lys  Ile Val Val Tyr Lys  Gly Asp Val
    1130                 1135                 1140

Tyr Asn  Met Asp Tyr Pro Pro  Phe Gly Ala Gly Arg  Pro Gly Gln
    1145                 1150                 1155

Phe Gly  Asp Ile Gln Ser Arg  Thr Pro Glu Ser Lys  Asp Val Tyr
    1160                 1165                 1170

Ala Asn  Thr Gln Leu Val Leu  Gln Arg Pro Ala Ala  Gly Thr Val
    1175                 1180                 1185

His Val  Pro Tyr Ser Gln Ala  Pro Ser Gly Phe Lys  Tyr Trp Leu
    1190                 1195                 1200

Lys Glu  Arg Gly Ala Ser Leu  Gln His Thr Ala Pro  Phe Gly Cys
    1205                 1210                 1215

Gln Ile  Ala Thr Asn Pro Val  Arg Ala Val Asn Cys  Ala Val Gly
    1220                 1225                 1230

Asn Ile  Pro Ile Ser Ile Asp  Ile Pro Asp Ala Ala  Phe Thr Arg
    1235                 1240                 1245

Val Val  Asp Ala Pro Ser Val  Thr Asp Met Ser Cys  Glu Val Pro
    1250                 1255                 1260
```

Ala Cys Thr His Ser Ser Asp Phe Gly Gly Val Ala Ile Ile Lys
1265 1270 1275

Tyr Thr Ala Ser Lys Lys Gly Lys Cys Ala Val His Ser Met Thr
1280 1285 1290

Asn Ala Val Thr Ile Arg Glu Ala Asp Val Glu Val Glu Gly Asn
1295 1300 1305

Ser Gln Leu Gln Ile Ser Phe Ser Thr Ala Leu Ala Ser Ala Glu
1310 1315 1320

Phe Arg Val Gln Val Cys Ser Thr Gln Val His Cys Ala Ala Ala
1325 1330 1335

Cys His Pro Pro Lys Asp His Ile Val Asn Tyr Pro Ala Ser His
1340 1345 1350

Thr Thr Leu Gly Val Gln Asp Ile Ser Thr Thr Ala Met Ser Trp
1355 1360 1365

Val Gln Lys Ile Thr Gly Gly Val Gly Leu Ile Val Ala Val Ala
1370 1375 1380

Ala Leu Ile Leu Ile Val Val Leu Cys Val Ser Phe Ser Arg His
1385 1390 1395

<210> SEQ ID NO 85
<211> LENGTH: 9212
<212> TYPE: DNA
<213> ORGANISM: Artificial Sequence
<220> FEATURE:
<223> OTHER INFORMATION: Synthetic Expression vector for CHIKV viral structural protein containing human IL-2(wt) antigen in E3

<400> SEQUENCE: 85
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttgcggccg ctctagacac catggagttc atcccgacgc aaactttcta taacagaagg 900
taccaacccc gaccctgggc cccacgccct acaattcaag taattagacc tagaccacgt 960
ccacagaggc aggctgggca actcgcccag ctgatctccg cagtcaacaa attgaccatg 1020
cgcgcggtac ctcaacagaa gcctcgcaga aatcggaaaa acaagaagca aaggcagaag 1080
aagcaggcgc cgcaaaacga cccaaagcaa aagaagcaac caccacaaaa gaagccggct 1140
caaaagaaga agaaaccagg ccgtagggag agaatgtgca tgaaaattga aaatgattgc 1200

-continued atcttcgaag tcaagcatga aggcaaagtg atgggctacg catgcctggt gggggataaa 1260
gtaatgaaac cagcacatgt gaagggaact atcgacaatg ccgatctggc taaactggcc 1320
tttaagcggt cgtctaaata cgatcttgaa tgtgcacaga taccggtgca catgaagtct 1380
gatgcctcga agtttaccca cgagaaaccc gaggggtact ataactggca tcacggagca 1440
gtgcagtatt caggaggccg gttcactatc ccgacgggtg caggcaagcc gggagacagc 1500
ggcagaccga tcttcgacaa caaaggacgg gtggtggcca tcgtcctagg aggggccaac 1560
gaaggtgccc gcacggccct ctccgtggtg acgtggaaca aagacatcgt cacaaaaatt 1620
acccctgagg gagccgaaga gtggagcctc gccctcccgg tcttgtgcct gttggcaaac 1680
actacattcc cctgctctca gccgccttgc acaccctgct gctacgaaaa ggaaccggaa 1740
agcaccttgc gcatgcttga ggacaacgtg atgagacccg gatactacca gctactaaaa 1800
gcatcgctga cttgctctcc ccactccgga ggggcaccta cttcaagttc tacaaagaaa 1860
acacagctac aactggagca tttactgctg gatttacaga tgattttgaa tggaattaat 1920
aattacaaga atcccaaact caccaggatg ctcacattta agttttacat gcccaagaag 1980
gccacagaac tgaaacatct tcagtgtcta gaagaagaac tcaaacctct ggaggaagtg 2040
ctaaatttag ctcaaagcaa aaactttcac ttaagaccca gggacttaat cagcaatatc 2100
aacgtaatag ttctggaact aaagggatct gaaacaacat tcatgtgtga atatgctgat 2160
gagacagcaa ccattgtaga atttctgaac agatggatta ccttttgtca aagcatcatc 2220
tcaacactga ctgggggatc cagtactaag gacaatttta atgtctataa agccacaaga 2280
ccatatctag ctcattgtcc tgactgcgga gaagggcatt cgtgccacag ccctatcgca 2340
ttggagcgca tcagaaatga agcaacggac ggaacgctga aatccaggt ctctttgcag 2400 atcgggataa agacagatga cagccacgat tggaccaagc tgcgctatat ggatagccat 2460
acgcccgcgg acgcggagcg agccggattg cttgtaagga cttcagcacc gtgcacgatc 2520
accgggacca tgggacactt tattctcgcc cgatgcccga aaggagagac gctgacagtg 2580
ggatttacgg acagcagaaa gatcagccac acatgcacac acccgttcca tcatgaacca 2640
cctgtgatag gtagggagag gttccactct cgaccacaac atggtaaaga gttaccttgc 2700
agcacgtacg tgcagagcac cgctgccact gctgaggaga tagaggtgca tatgcccccca 2760 gatactcctg accgcacgct gatgacgcag cagtctggca acgtgaagat cacagttaat 2820
gggcagacgg tgcggtacaa gtgcaactgc ggtggctcaa acgagggact gacaaccaca 2880
gacaaagtga tcaataactg caaaattgat cagtgccatg ctgcagtcac taatcacaag 2940
aattggcaat acaactcccc tttagtcccg cgcaacgctg aactcgggga ccgtaaagga 3000
aagatccaca tcccattccc attggcaaac gtgacttgca gagtgccaaa agcaagaaac 3060
cctacagtaa cttacggaaa aaaccaagtc accatgctgc tgtatcctga ccatccgaca 3120
ctcttgtctt accgtaacat gggacaggaa ccaaattacc acgaggagtg ggtgacacac 3180
aagaaggagg ttaccttgac cgtgcctact gagggtctgg aggtcacttg gggcaacaac 3240
gaaccataca agtactggcc gcagatgtct acgaacggta ctgctcatgg tcacccacat 3300
gagataatct tgtactatta tgagctgtac cccactatga ctgtagtcat tgtgtcggtg 3360
gcctcgttcg tgcttctgtc gatggtgggc acagcagtgg gaatgtgtgt gtgcgcacgg 3420
cgcagatgca ttacaccata tgaattaaca ccaggagcca ctgttccctt cctgctcagc 3480
ctgctatgct gcgtcagaac gaccaaggcg gccacatatt acgaggctgc ggcatatcta 3540
tggaacgaac agcagcccct gttctggttg caggctctta tcccgctggc cgccttgatc 3600

```
gtcctgtgca actgtctgaa actcttgcca tgctgctgta agaccctggc ttttttagcc   3660
gtaatgagca tcggtgccca cactgtgagc gcgtacgaac acgtaacagt gatcccgaac   3720
acggtgggag taccgtataa gactcttgtc aacagaccgg gttacagccc catggtgttg   3780
gagatggagc tacaatcagt caccttggaa ccaacactgt cacttgacta catcacgtgc   3840
gagtacaaaa ctgtcatccc ctccccgtac gtgaagtgct gtggtacagc agagtgcaag   3900
gacaagagcc taccagacta cagctgcaag gtctttactg gagtctaccc atttatgtgg   3960
ggcggcgcct actgcttttg cgacgccgaa aatacgcaat tgagcgaggc acatgtagag   4020
aaatctgaat cttgcaaaac agagtttgca tcggcctaca gagcccacac cgcatcggcg   4080
tcggcgaagc tccgcgtcct ttaccaagga aacaacatta ccgtagctgc ctacgctaac   4140
ggtgaccatg ccgtcacagt aaaggacgcc aagtttgtcg tgggcccaat gtcctccgcc   4200
tggacacctt ttgacaacaa aatcgtggtg tacaaaggcg acgtctacaa catggactac   4260
ccaccttttg gcgcaggaag accaggacaa tttggtgaca ttcaaagtcg tacaccggaa   4320
agtaaagacg tttatgccaa cactcagttg gtactacaga ggccagcagc aggcacggta   4380
catgtaccat actctcaggc accatctggc ttcaagtatt ggctgaagga acgaggagca   4440
tcgctacagc acacggcacc gttcggttgc cagattgcga caaacccggt aagagctgta   4500
aattgcgctg tggggaacat accaatttcc atcgacatac cggatgcggc ctttactagg   4560
gttgtcgatg caccctctgt aacggacatg tcatgcgaag taccagcctg cactcactcc   4620
tccgactttg gggcgtcgc catcatcaaa tacacagcta gcaagaaagg taaatgtgca   4680
gtacattcga tgaccaacgc cgttaccatt cgagaagccg acgtagaagt agaggggaac   4740
tcccagctgc aaatatcctt ctcaacagcc ctggcaagcg ccgagtttcg cgtgcaagtg   4800
tgctccacac aagtacactg cgcagccgca tgccaccctc caaaggacca catagtcaat   4860
tacccagcat cacacaccac ccttggggtc caggatatat ccacaacggc aatgtcttgg   4920
gtgcagaaga ttacgggagg agtaggatta attgttgctg ttgctgcctt aattttaatt   4980
gtggtgctat gcgtgtcgtt tagcaggcac taatgatccg gaggggcacc cacttcaagc   5040
tccacttcaa gctctacagc ggaagcacag cagcagcagc agcagcagca gcagcagcag   5100
cacctggagc agctgttgat ggacctacag gagctcctga gcaggatgga gaattacagg   5160
aacctgaaac tccccaggat gctcaccttc aaattttact tgcccaagca ggccacagaa   5220
ttgaaagatc ttcagtgcct agaagatgaa cttggacctc tgcggcatgt tctggatttg   5280
actcaaagca aaagctttca attggaagat gctgagaatt tcatcagcaa tatcagagta   5340
actgttgtaa aactaaaggg ctctgacaac acatttgagt gccaattcga tgatgagtca   5400
gcaactgtgg tggactttct gaggagatgg atagccttct gtcaaagcat catctcaaca   5460
agccctcaag gggatccgc tgtgccttct agttgccagc catctgttgt ttgcccctcc   5520
cccgtgcctt ccttgaccct ggaaggtgcc actcccactg tcctttccta ataaaatgag   5580
gaaattgcat cgcattgtct gagtaggtgt cattctattc tggggggtgg ggtggggcag   5640
gacagcaagg gggaggattg ggaagacaat agcaggcatg ctggggatgc ggtgggctct   5700
atgggtaccc aggtgctgaa gaattgaccc ggttcctcct gggccagaaa gaagcaggca   5760
catcccctc tctgtgacac accctgtcca cgcccctggt tcttagttcc agccccactc   5820
ataggacact catagctcag gagggctccg ccttcaatcc cacccgctaa agtacttgga   5880
gcggtctctc cctccctcat cagcccacca aaccaaacct agcctccaag agtgggaaga   5940
```

-continued aattaaagca agataggcta ttaagtgcag agggagagaa aatgcctcca acatgtgagg 6000
aagtaatgag agaaatcata gaattttaag gccatgattt aaggccatca tggcctaagc 6060
ttgaaaggag ataggatcaa agcttggcgt aatcatggtc atagctgttt cctgtgtgaa 6120
attgttatcc gctcacaatt ccacacaaca tacgagccgg aagcataaag tgtaaagcct 6180
ggggtgccta atgagtgagc taactcacat taattgcgtt gcgctcactg cccgctttcc 6240
agtcgggaaa cctgtcgtgc cagctgcatt aatgaatcgg ccaacgcgcg gggagaggcg 6300
gtttgcgtat tgggcgctct tccgcttcct cgctcactga ctcgctgcgc tcggtcgttc 6360
ggctgcggcg agcggtatca gctcactcaa aggcggtaat acggttatcc acagaatcag 6420
gggataacgc aggaaagaac atgtgagcaa aaggccagca aaaggccagg aaccgtaaaa 6480
aggccgcgtt gctggcgttt ttccataggc tccgcccccc tgacgagcat cacaaaaatc 6540
gacgctcaag tcagaggtgg cgaaacccga caggactata aagataccag gcgtttcccc 6600
ctggaagctc cctcgtgcgc tctcctgttc cgaccctgcc gcttaccgga tacctgtccg 6660
cctttctccc ttcgggaagc gtggcgcttt ctcatagctc acgctgtagg tatctcagtt 6720
cggtgtaggt cgttcgctcc aagctgggct gtgtgcacga accccccgtt cagcccgacc 6780
gctgcgcctt atccggtaac tatcgtcttg agtccaaccc ggtaagacac gacttatcgc 6840
cactggcagc agccactggt aacaggatta gcagagcgag gtatgtaggc ggtgctacag 6900
agttcttgaa gtggtggcct aactacggct acactagaag aacagtattt ggtatctgcg 6960
ctctgctgaa gccagttacc ttcggaaaaa gagttggtag ctcttgatcc ggcaaacaaa 7020
ccaccgctgg tagcggtggt ttttttgttt gcaagcagca gattacgcgc agaaaaaaag 7080
gatctcaaga agatcctttg atcttttcta cggggtctga cgctcagtgg aacgaaaact 7140
cacgttaagg gattttggtc atgagattat caaaaaggat cttcacctag atccttttaa 7200
attaaaaatg aagttttaaa tcaatctaaa gtatatatga gtaaacttgg tctgacagtt 7260
accaatgctt aatcagtgag gcacctatct cagcgatctg tctatttcgt tcatccatag 7320
ttgcctgact ccccgtcgtg tagataacta cgatacggga gggcttacca tctggcccca 7380
gtgctgcaat gataccgcga gaaccacgct caccggctcc agatttatca gcaataaacc 7440
agccagccgg aagggccgag cgcagaagtg gtcctgcaac tttatccgcc tccatccagt 7500
ctattaattg ttgccgggaa gctagagtaa gtagttcgcc agttaatagt ttgcgcaacg 7560
ttgttgccat tgctacaggc atcgtggtgt cacgctcgtc gtttggtatg gcttcattca 7620
gctccggttc ccaacgatca aggcgagtta catgatcccc catgttgtgc aaaaaagcgg 7680
ttagctcctt cggtcctccg atcgttgtca gaagtaagtt ggccgcagtg ttatcactca 7740
tggttatggc agcactgcat aattctctta ctgtcatgcc atccgtaaga tgcttttctg 7800
tgactggtga gtactcaacc aagtcattct gagaatagtg tatgcggcga ccgagttgct 7860
cttgcccggc gtcaatacgg gataataccg cgccacatag cagaacttta aaagtgctca 7920
tcattggaaa acgttcttcg gggcgaaaac tctcaaggat cttaccgctg ttgagatcca 7980
gttcgatgta acccactcgt gcacccaact gatcttcagc atcttttact ttcaccagcg 8040
tttctgggtg agcaaaaaca ggaaggcaaa atgccgcaaa aaagggaata agggcgacac 8100
ggaaatgttg aatactcata ctcttccttt ttcaatatta ttgaagcatt tatcagggtt 8160
attgtctcat gagcggatac atatttgaat gtatttagaa aaataaacaa ataggggttc 8220
cgcgcacatt tccccgaaaa gtgccacctg acgtctaaga aaccattatt atcatgacat 8280
taacctataa aaataggcgt atcacgaggc cctttcgggt cgcgcgtttc ggtgatgacg 8340

```
gtgaaaacct ctgacacatg cagctcccgt tgacggtcac agcttgtctg taagcggatg   8400

ccgggagcag acaagcccgt cagggcgcgt cagcgggtgt tggcgggtgt cggggctggc   8460

ttaactatgc ggcatcagag cagattgtac tgagagtgca ccataaaatt gtaaacgtta   8520

atattttgtt aaaattcgcg ttaaattttt gttaaatcag ctcatttttt aaccaatagg   8580

ccgaaatcgg caaaatccct tataaatcaa aagaatagcc cgagataggg ttgagtgttg   8640

ttccagtttg gaacaagagt ccactattaa agaacgtgga ctccaacgtc aaagggcgaa   8700

aaaccgtcta tcagggcgat ggcccactac gtgaaccatc acccaaatca agttttttgg   8760

ggtcgaggtg ccgtaaagca ctaaatcgga accctaaagg gagcccccga tttagagctt   8820

gacggggaaa gccggcgaac gtggcgagaa aggaagggaa gaaagcgaaa ggagcgggcg   8880

ctagggcgct ggcaagtgta gcggtcacgc tgcgcgtaac caccacaccc gccgcgctta   8940

atgcgccgct acagggcgcg tactatggtt gctttgacgt atgcggtgtg aaataccgca   9000

cagatgcgta aggagaaaat accgcatcag gcgccattcg ccattcaggc tgcgcaactg   9060

ttgggaaggg cgatcggtgc gggcctcttc gctattacgc cagctggcga aaggggatg    9120

tgctgcaagg cgattaagtt gggtaacgcc agggttttcc cagtcacgac gttgtaaaac   9180

gacggccagt gaattccatg gtctcaactt tc                                 9212
```

<210> SEQ ID NO 86
<211> LENGTH: 1383
<212> TYPE: PRT
<213> ORGANISM: Artificial Sequence
<220> FEATURE:
<223> OTHER INFORMATION: Synthetic CHIKV viral structural protein containing human IL-2(wt) antigen in E3

<400> SEQUENCE: 86

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
```

-continued

```
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Lys Lys Thr Gln Leu
                325                 330                 335

Gln Leu Glu His Leu Leu Leu Asp Leu Gln Met Ile Leu Asn Gly Ile
            340                 345                 350

Asn Asn Tyr Lys Asn Pro Lys Leu Thr Arg Met Leu Thr Phe Lys Phe
        355                 360                 365

Tyr Met Pro Lys Lys Ala Thr Glu Leu Lys His Leu Gln Cys Leu Glu
    370                 375                 380

Glu Glu Leu Lys Pro Leu Glu Glu Val Leu Asn Leu Ala Gln Ser Lys
385                 390                 395                 400

Asn Phe His Leu Arg Pro Arg Asp Leu Ile Ser Asn Ile Asn Val Ile
                405                 410                 415

Val Leu Glu Leu Lys Gly Ser Glu Thr Thr Phe Met Cys Glu Tyr Ala
            420                 425                 430

Asp Glu Thr Ala Thr Ile Val Glu Phe Leu Asn Arg Trp Ile Thr Phe
        435                 440                 445

Cys Gln Ser Ile Ile Ser Thr Leu Thr Gly Gly Ser Ser Thr Lys Asp
    450                 455                 460

Asn Phe Asn Val Tyr Lys Ala Thr Arg Pro Tyr Leu Ala His Cys Pro
465                 470                 475                 480

Asp Cys Gly Glu Gly His Ser Cys His Ser Pro Ile Ala Leu Glu Arg
                485                 490                 495

Ile Arg Asn Glu Ala Thr Asp Gly Thr Leu Lys Ile Gln Val Ser Leu
            500                 505                 510

Gln Ile Gly Ile Lys Thr Asp Asp Ser His Asp Trp Thr Lys Leu Arg
        515                 520                 525

Tyr Met Asp Ser His Thr Pro Ala Asp Ala Glu Arg Ala Gly Leu Leu
    530                 535                 540

Val Arg Thr Ser Ala Pro Cys Thr Ile Thr Gly Thr Met Gly His Phe
545                 550                 555                 560

Ile Leu Ala Arg Cys Pro Lys Gly Glu Thr Leu Thr Val Gly Phe Thr
                565                 570                 575

Asp Ser Arg Lys Ile Ser His Thr Cys Thr His Pro Phe His His Glu
            580                 585                 590

Pro Pro Val Ile Gly Arg Glu Arg Phe His Ser Arg Pro Gln His Gly
        595                 600                 605

Lys Glu Leu Pro Cys Ser Thr Tyr Val Gln Ser Thr Ala Ala Thr Ala
    610                 615                 620
```

-continued

Glu Glu Ile Glu Val His Met Pro Pro Asp Thr Pro Asp Arg Thr Leu
625 630 635 640

Met Thr Gln Gln Ser Gly Asn Val Lys Ile Thr Val Asn Gly Gln Thr
645 650 655

Val Arg Tyr Lys Cys Asn Cys Gly Gly Ser Asn Glu Gly Leu Thr Thr
660 665 670

Thr Asp Lys Val Ile Asn Asn Cys Lys Ile Asp Gln Cys His Ala Ala
675 680 685

Val Thr Asn His Lys Asn Trp Gln Tyr Asn Ser Pro Leu Val Pro Arg
690 695 700

Asn Ala Glu Leu Gly Asp Arg Lys Gly Lys Ile His Ile Pro Phe Pro
705 710 715 720

Leu Ala Asn Val Thr Cys Arg Val Pro Lys Ala Arg Asn Pro Thr Val
725 730 735

Thr Tyr Gly Lys Asn Gln Val Thr Met Leu Leu Tyr Pro Asp His Pro
740 745 750

Thr Leu Leu Ser Tyr Arg Asn Met Gly Gln Glu Pro Asn Tyr His Glu
755 760 765

Glu Trp Val Thr His Lys Lys Glu Val Thr Leu Thr Val Pro Thr Glu
770 775 780

Gly Leu Glu Val Thr Trp Gly Asn Asn Glu Pro Tyr Lys Tyr Trp Pro
785 790 795 800

Gln Met Ser Thr Asn Gly Thr Ala His Gly His Pro His Glu Ile Ile
805 810 815

Leu Tyr Tyr Tyr Glu Leu Tyr Pro Thr Met Thr Val Val Ile Val Ser
820 825 830

Val Ala Ser Phe Val Leu Leu Ser Met Val Gly Thr Ala Val Gly Met
835 840 845

Cys Val Cys Ala Arg Arg Arg Cys Ile Thr Pro Tyr Glu Leu Thr Pro
850 855 860

Gly Ala Thr Val Pro Phe Leu Leu Ser Leu Leu Cys Cys Val Arg Thr
865 870 875 880

Thr Lys Ala Ala Thr Tyr Tyr Glu Ala Ala Ala Tyr Leu Trp Asn Glu
885 890 895

Gln Gln Pro Leu Phe Trp Leu Gln Ala Leu Ile Pro Leu Ala Ala Leu
900 905 910

Ile Val Leu Cys Asn Cys Leu Lys Leu Leu Pro Cys Cys Cys Lys Thr
915 920 925

Leu Ala Phe Leu Ala Val Met Ser Ile Gly Ala His Thr Val Ser Ala
930 935 940

Tyr Glu His Val Thr Val Ile Pro Asn Thr Val Gly Val Pro Tyr Lys
945 950 955 960

Thr Leu Val Asn Arg Pro Gly Tyr Ser Pro Met Val Leu Glu Met Glu
965 970 975

Leu Gln Ser Val Thr Leu Glu Pro Thr Leu Ser Leu Asp Tyr Ile Thr
980 985 990

Cys Glu Tyr Lys Thr Val Ile Pro Ser Pro Tyr Val Lys Cys Cys Gly
995 1000 1005

Thr Ala Glu Cys Lys Asp Lys Ser Leu Pro Asp Tyr Ser Cys Lys
1010 1015 1020

Val Phe Thr Gly Val Tyr Pro Phe Met Trp Gly Gly Ala Tyr Cys
1025 1030 1035

```
Phe Cys  Asp Ala Glu Asn Thr  Gln Leu Ser Glu Ala  His Val Glu
    1040                 1045                 1050

Lys Ser  Glu Ser Cys Lys Thr  Glu Phe Ala Ser Ala  Tyr Arg Ala
    1055                 1060                 1065

His Thr  Ala Ser Ala Ser Ala  Lys Leu Arg Val Leu  Tyr Gln Gly
    1070                 1075                 1080

Asn Asn  Ile Thr Val Ala Ala  Tyr Ala Asn Gly Asp  His Ala Val
    1085                 1090                 1095

Thr Val  Lys Asp Ala Lys Phe  Val Val Gly Pro Met  Ser Ser Ala
    1100                 1105                 1110

Trp Thr  Pro Phe Asp Asn Lys  Ile Val Val Tyr Lys  Gly Asp Val
    1115                 1120                 1125

Tyr Asn  Met Asp Tyr Pro Pro  Phe Gly Ala Gly Arg  Pro Gly Gln
    1130                 1135                 1140

Phe Gly  Asp Ile Gln Ser Arg  Thr Pro Glu Ser Lys  Asp Val Tyr
    1145                 1150                 1155

Ala Asn  Thr Gln Leu Val Leu  Gln Arg Pro Ala Ala  Gly Thr Val
    1160                 1165                 1170

His Val  Pro Tyr Ser Gln Ala  Pro Ser Gly Phe Lys  Tyr Trp Leu
    1175                 1180                 1185

Lys Glu  Arg Gly Ala Ser Leu  Gln His Thr Ala Pro  Phe Gly Cys
    1190                 1195                 1200

Gln Ile  Ala Thr Asn Pro Val  Arg Ala Val Asn Cys  Ala Val Gly
    1205                 1210                 1215

Asn Ile  Pro Ile Ser Ile Asp  Ile Pro Asp Ala Ala  Phe Thr Arg
    1220                 1225                 1230

Val Val  Asp Ala Pro Ser Val  Thr Asp Met Ser Cys  Glu Val Pro
    1235                 1240                 1245

Ala Cys  Thr His Ser Ser Asp  Phe Gly Gly Val Ala  Ile Ile Lys
    1250                 1255                 1260

Tyr Thr  Ala Ser Lys Lys Gly  Lys Cys Ala Val His  Ser Met Thr
    1265                 1270                 1275

Asn Ala  Val Thr Ile Arg Glu  Ala Asp Val Glu Val  Glu Gly Asn
    1280                 1285                 1290

Ser Gln  Leu Gln Ile Ser Phe  Ser Thr Ala Leu Ala  Ser Ala Glu
    1295                 1300                 1305

Phe Arg  Val Gln Val Cys Ser  Thr Gln Val His Cys  Ala Ala Ala
    1310                 1315                 1320

Cys His  Pro Pro Lys Asp His  Ile Val Asn Tyr Pro  Ala Ser His
    1325                 1330                 1335

Thr Thr  Leu Gly Val Gln Asp  Ile Ser Thr Thr Ala  Met Ser Trp
    1340                 1345                 1350

Val Gln  Lys Ile Thr Gly Gly  Val Gly Leu Ile Val  Ala Val Ala
    1355                 1360                 1365

Ala Leu  Ile Leu Ile Val Val  Leu Cys Val Ser Phe  Ser Arg His
    1370                 1375                 1380
```

<210> SEQ ID NO 87
<211> LENGTH: 9257
<212> TYPE: DNA
<213> ORGANISM: Artificial Sequence
<220> FEATURE:
<223> OTHER INFORMATION: Synthetic Expression vector for CHIKV viral
      structural protein containing mouse IL-2 (F54A) antigen in E3

<400> SEQUENCE: 87

-continued

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt ggggggataaa  1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccca cttcaagctc cacttcaagc   1860
tctacagcgg aagcacagca gcagcagcag cagcagcagc agcagcagca cctggagcag   1920
ctgttgatgg acctacagga gctcctgagc aggatggaga attacaggaa cctgaaactc   1980
cccaggatgc tcaccgccaa attttacttg cccaagcagg ccacagaatt gaaagatctt   2040
cagtgcctag aagatgaact tggacctctg cggcatgttc tggatttgac tcaaagcaaa   2100
agctttcaat tggaagatgc tgagaatttc atcagcaata tcagagtaac tgttgtaaaa   2160
ctaaagggct ctgacaacac atttgagtgc caattcgatg atgagtcagc aactgtggtg   2220
gactttctga ggagatggat agccttctgt caaagcatca tctcaacaag ccctcaaggg   2280
ggatccagta ctaaggacaa ttttaatgtc tataaagcca caagaccata tctagctcat   2340
```

-continued

```
tgtcctgact gcggagaagg gcattcgtgc cacagcccta tcgcattgga gcgcatcaga   2400
aatgaagcaa cggacggaac gctgaaaatc caggtctctt tgcagatcgg gataaagaca   2460
gatgacagcc acgattggac caagctgcgc tatatggata gccatacgcc cgcggacgcg   2520
gagcgagccg gattgcttgt aaggacttca gcaccgtgca cgatcaccgg gaccatggga   2580
cactttattc tcgcccgatg cccgaaagga gagacgctga cagtgggatt tacggacagc   2640
agaaagatca gccacacatg cacacacccg ttccatcatg aaccacctgt gataggtagg   2700
gagaggttcc actctcgacc acaacatggt aaagagttac cttgcagcac gtacgtgcag   2760
agcaccgctg ccactgctga ggagatagag gtgcatatgc ccccagatac tcctgaccgc   2820
acgctgatga cgcagcagtc tggcaacgtg aagatcacag ttaatgggca gacggtgcgg   2880
tacaagtgca actgcggtgg ctcaaacgag ggactgacaa ccacagacaa agtgatcaat   2940
aactgcaaaa ttgatcagtg ccatgctgca gtcactaatc acaagaattg gcaatacaac   3000
tcccctttag tcccgcgcaa cgctgaactc ggggaccgta aaggaaagat ccacatccca   3060
ttcccattgg caaacgtgac ttgcagagtg ccaaaagcaa gaaaccctac agtaacttac   3120
ggaaaaaacc aagtcaccat gctgctgtat cctgaccatc cgacactctt gtcttaccgt   3180
aacatgggac aggaaccaaa ttaccacgag gagtgggtga cacacaagaa ggaggttacc   3240
ttgaccgtgc ctactgaggg tctggaggtc acttggggca acaacgaacc atacaagtac   3300
tggccgcaga tgtctacgaa cggtactgct catggtcacc cacatgagat aatcttgtac   3360
tattatgagc tgtaccccac tatgactgta gtcattgtgt cggtggcctc gttcgtgctt   3420
ctgtcgatgg tgggcacagc agtgggaatg tgtgtgtgcg cacggcgcag atgcattaca   3480
ccatatgaat taacaccagg agccactgtt cccttcctgc tcagcctgct atgctgcgtc   3540
agaacgacca aggcggccac atattacgag gctgcggcat atctatggaa cgaacagcag   3600
cccctgttct ggttgcaggc tcttatcccg ctggccgcct tgatcgtcct gtgcaactgt   3660
ctgaaactct tgccatgctg ctgtaagacc ctggcttttt tagccgtaat gagcatcggt   3720
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
gcaccgttcg gttgccagat tgcgacaaac ccggtaagag ctgtaaattg cgctgtgggg   4560
aacataccaa tttccatcga cataccggat gcggccttta ctagggttgt cgatgcaccc   4620
tctgtaacgg acatgtcatg cgaagtacca gcctgcactc actcctccga ctttgggggc   4680
gtcgccatca tcaaatacac agctagcaag aaaggtaaat gtgcagtaca ttcgatgacc   4740
```

```
aacgccgtta ccattcgaga agccgacgta gaagtagagg ggaactccca gctgcaaata   4800
tccttctcaa cagccctggc aagcgccgag tttcgcgtgc aagtgtgctc cacacaagta   4860
cactgcgcag ccgcatgcca ccctccaaag gaccacatag tcaattaccc agcatcacac   4920
accacccttg ggtccagga tatatccaca acggcaatgt cttgggtgca gaagattacg    4980
ggaggagtag gattaattgt tgctgttgct gccttaattt taattgtggt gctatgcgtg   5040
tcgtttagca ggcactaatg atccggaggg gcacccactt caagctccac ttcaagctct   5100
acagcggaag cacagcagca gcagcagcag cagcagcagc agcagcacct ggagcagctg   5160
ttgatggacc tacaggagct cctgagcagg atggagaatt acaggaacct gaaactcccc   5220
aggatgctca ccttcaaatt ttacttgccc aagcaggcca cagaattgaa agatcttcag   5280
tgcctagaag atgaacttgg acctctgcgg catgttctgg atttgactca aagcaaaagc   5340
tttcaattgg aagatgctga gaatttcatc agcaatatca gagtaactgt tgtaaaacta   5400
aagggctctg acaacacatt tgagtgccaa ttcgatgatg agtcagcaac tgtggtggac   5460
tttctgagga gatggatagc cttctgtcaa agcatcatct caacaagccc tcaaggggga   5520
tccgctgtgc cttctagttg ccagccatct gttgtttgcc cctcccccgt gccttccttg   5580
accctggaag gtgccactcc cactgtcctt tcctaataaa atgaggaaat tgcatcgcat   5640
tgtctgagta ggtgtcattc tattctgggg ggtggggtgg ggcaggacag caagggggag   5700
gattgggaag acaatagcag gcatgctggg gatgcggtgg gctctatggg tacccaggtg   5760
ctgaagaatt gacccggttc ctcctgggcc agaaagaagc aggcacatcc ccttctctgt   5820
gacacaccct gtccacgccc ctggttctta gttccagccc cactcatagg acactcatag   5880
ctcaggaggg ctccgccttc aatcccaccc gctaaagtac ttggagcggt ctctccctcc   5940
ctcatcagcc caccaaacca aacctagcct ccaagagtgg gaagaaatta aagcaagata   6000
ggctattaag tgcagaggga gagaaaatgc ctccaacatg tgaggaagta atgagagaaa   6060
tcatagaatt ttaaggccat gatttaaggc catcatggcc taagcttgaa aggagatagg   6120
atcaaagctt ggcgtaatca tggtcatagc tgtttcctgt gtgaaattgt tatccgctca   6180
caattccaca caacatacga gccggaagca taaagtgtaa agcctggggt gcctaatgag   6240
tgagctaact cacattaatt gcgttgcgct cactgcccgc tttccagtcg ggaaacctgt   6300
cgtgccagct gcattaatga atcggccaac gcgcggggag aggcggtttg cgtattgggc   6360
gctcttccgc ttcctcgctc actgactcgc tgcgctcggt cgttcggctg cggcgagcgg   6420
tatcagctca ctcaaaggcg gtaatacggt tatccacaga atcaggggat aacgcaggaa   6480
agaacatgtg agcaaaaggc cagcaaaagg ccaggaaccg taaaaaggcc gcgttgctgg   6540
cgtttttcca taggctccgc ccccctgacg agcatcacaa aaatcgacgc tcaagtcaga   6600
ggtggcgaaa cccgacagga ctataaagat accaggcgtt tccccctgga agctccctcg   6660
tgcgctctcc tgttccgacc ctgccgctta ccggatacct gtccgccttt ctcccttcgg   6720
gaagcgtggc gctttctcat agctcacgct gtaggtatct cagttcggtg taggtcgttc   6780
gctccaagct gggctgtgtg cacgaacccc ccgttcagcc cgaccgctgc gccttatccg   6840
gtaactatcg tcttgagtcc aacccggtaa gacacgactt atcgccactg gcagcagcca   6900
ctggtaacag gattagcaga gcgaggtatg taggcggtgc tacagagttc ttgaagtggt   6960
ggcctaacta cggctacact agaagaacag tatttggtat ctgcgctctg ctgaagccag   7020
ttaccttcgg aaaaagagtt ggtagctctt gatccggcaa acaaaccacc gctggtagcg   7080
```

-continued

```
gtggtttttt tgtttgcaag cagcagatta cgcgcagaaa aaaaggatct caagaagatc   7140
ctttgatctt ttctacgggg tctgacgctc agtggaacga aaactcacgt taagggattt   7200
tggtcatgag attatcaaaa aggatcttca cctagatcct tttaaattaa aaatgaagtt   7260
ttaaatcaat ctaaagtata tatgagtaaa cttggtctga cagttaccaa tgcttaatca   7320
gtgaggcacc tatctcagcg atctgtctat ttcgttcatc catagttgcc tgactccccg   7380
tcgtgtagat aactacgata cgggagggct taccatctgg ccccagtgct gcaatgatac   7440
cgcgagaacc acgctcaccg gctccagatt tatcagcaat aaaccagcca gccggaaggg   7500
ccgagcgcag aagtggtcct gcaactttat ccgcctccat ccagtctatt aattgttgcc   7560
gggaagctag agtaagtagt tcgccagtta atagtttgcg caacgttgtt gccattgcta   7620
caggcatcgt ggtgtcacgc tcgtcgtttg gtatggcttc attcagctcc ggttcccaac   7680
gatcaaggcg agttacatga tcccccatgt tgtgcaaaaa agcggttagc tccttcggtc   7740
ctccgatcgt tgtcagaagt aagttggccg cagtgttatc actcatggtt atggcagcac   7800
tgcataattc tcttactgtc atgccatccg taagatgctt ttctgtgact ggtgagtact   7860
caaccaagtc attctgagaa tagtgtatgc ggcgaccgag ttgctcttgc ccggcgtcaa   7920
tacgggataa taccgcgcca catagcagaa ctttaaaagt gctcatcatt ggaaaacgtt   7980
cttcggggcg aaaactctca aggatcttac cgctgttgag atccagttcg atgtaaccca   8040
ctcgtgcacc caactgatct tcagcatctt ttactttcac cagcgtttct gggtgagcaa   8100
aaacaggaag gcaaaatgcc gcaaaaaagg gaataagggc gacacggaaa tgttgaatac   8160
tcatactctt cctttttcaa tattattgaa gcatttatca gggttattgt ctcatgagcg   8220
gatacatatt tgaatgtatt tagaaaaata aacaaatagg ggttccgcgc acatttcccc   8280
gaaaagtgcc acctgacgtc taagaaacca ttattatcat gacattaacc tataaaaata   8340
ggcgtatcac gaggcccttt cggtcgcgc gtttcggtga tgacggtgaa aacctctgac   8400
acatgcagct cccgttgacg gtcacagctt gtctgtaagc ggatgccggg agcagacaag   8460
cccgtcaggg cgcgtcagcg ggtgttggcg ggtgtcgggg ctggcttaac tatgcggcat   8520
cagagcagat tgtactgaga gtgcaccata aaattgtaaa cgttaatatt ttgttaaaat   8580
tcgcgttaaa tttttgttaa atcagctcat tttttaacca ataggccgaa atcggcaaaa   8640
tcccttataa atcaaaagaa tagcccgaga tagggttgag tgttgttcca gtttggaaca   8700
agagtccact attaaagaac gtggactcca acgtcaaagg gcgaaaaacc gtctatcagg   8760
gcgatggccc actacgtgaa ccatcaccca aatcaagttt tttggggtcg aggtgccgta   8820
aagcactaaa tcggaaccct aaagggagcc cccgatttag agcttgacgg ggaaagccgg   8880
cgaacgtggc gagaaaggaa gggaagaaag cgaaaggagc gggcgctagg gcgctggcaa   8940
gtgtagcggt cacgctgcgc gtaaccacca cacccgccgc gcttaatgcg ccgctacagg   9000
gcgcgtacta tggttgcttt gacgtatgcg gtgtgaaata ccgcacagat gcgtaaggag   9060
aaaataccgc atcaggcgcc attcgccatt caggctgcgc aactgttggg aagggcgatc   9120
ggtgcgggcc tcttcgctat tacgccagct ggcgaaaggg ggatgtgctg caaggcgatt   9180
aagttgggta acgccagggt tttcccagtc acgacgttgt aaaacgacgg ccagtgaatt   9240
ccatggtctc aactttc                                                  9257
```

<210> SEQ ID NO 88
<211> LENGTH: 1398
<212> TYPE: PRT
<213> ORGANISM: Artificial Sequence
<220> FEATURE:
<223> OTHER INFORMATION: Synthetic CHIKV viral structural protein
containing mouse IL-2 (F54A) antigen in E3

<400> SEQUENCE: 88

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Ser Ser Ser Thr Ala
                325                 330                 335

Glu Ala Gln Gln Gln Gln Gln Gln Gln Gln Gln Gln Gln His Leu Glu
            340                 345                 350

Gln Leu Leu Met Asp Leu Gln Glu Leu Leu Ser Arg Met Glu Asn Tyr
        355                 360                 365

Arg Asn Leu Lys Leu Pro Arg Met Leu Thr Ala Lys Phe Tyr Leu Pro
    370                 375                 380

Lys Gln Ala Thr Glu Leu Lys Asp Leu Gln Cys Leu Glu Asp Glu Leu
```

-continued

```
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430

Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
                565                 570                 575

Leu Ala Arg Cys Pro Lys Gly Glu Thr Leu Thr Val Gly Phe Thr Asp
            580                 585                 590

Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640

Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765

Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815
```

```
Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990

Gln Ser Val Thr Leu Glu Pro Thr  Leu Ser Leu Asp Tyr  Ile Thr Cys
        995                 1000                1005

Glu Tyr  Lys Thr Val Ile Pro  Ser Pro Tyr Val Lys  Cys Cys Gly
    1010                 1015                 1020

Thr Ala  Glu Cys Lys Asp Lys  Ser Leu Pro Asp Tyr  Ser Cys Lys
    1025                 1030                 1035

Val Phe  Thr Gly Val Tyr Pro  Phe Met Trp Gly Gly  Ala Tyr Cys
    1040                 1045                 1050

Phe Cys  Asp Ala Glu Asn Thr  Gln Leu Ser Glu Ala  His Val Glu
    1055                 1060                 1065

Lys Ser  Glu Ser Cys Lys Thr  Glu Phe Ala Ser Ala  Tyr Arg Ala
    1070                 1075                 1080

His Thr  Ala Ser Ala Ser Ala  Lys Leu Arg Val Leu  Tyr Gln Gly
    1085                 1090                 1095

Asn Asn  Ile Thr Val Ala Ala  Tyr Ala Asn Gly Asp  His Ala Val
    1100                 1105                 1110

Thr Val  Lys Asp Ala Lys Phe  Val Val Gly Pro Met  Ser Ser Ala
    1115                 1120                 1125

Trp Thr  Pro Phe Asp Asn Lys  Ile Val Val Tyr Lys  Gly Asp Val
    1130                 1135                 1140

Tyr Asn  Met Asp Tyr Pro Pro  Phe Gly Ala Gly Arg  Pro Gly Gln
    1145                 1150                 1155

Phe Gly  Asp Ile Gln Ser Arg  Thr Pro Glu Ser Lys  Asp Val Tyr
    1160                 1165                 1170

Ala Asn  Thr Gln Leu Val Leu  Gln Arg Pro Ala Ala  Gly Thr Val
    1175                 1180                 1185

His Val  Pro Tyr Ser Gln Ala  Pro Ser Gly Phe Lys  Tyr Trp Leu
    1190                 1195                 1200

Lys Glu  Arg Gly Ala Ser Leu  Gln His Thr Ala Pro  Phe Gly Cys
    1205                 1210                 1215
```

Gln Ile Ala Thr Asn Pro Val Arg Ala Val Asn Cys Ala Val Gly
1220 1225 1230

Asn Ile Pro Ile Ser Ile Asp Ile Pro Asp Ala Ala Phe Thr Arg
1235 1240 1245

Val Val Asp Ala Pro Ser Val Thr Asp Met Ser Cys Glu Val Pro
1250 1255 1260

Ala Cys Thr His Ser Ser Asp Phe Gly Gly Val Ala Ile Ile Lys
1265 1270 1275

Tyr Thr Ala Ser Lys Lys Gly Lys Cys Ala Val His Ser Met Thr
1280 1285 1290

Asn Ala Val Thr Ile Arg Glu Ala Asp Val Glu Val Glu Gly Asn
1295 1300 1305

Ser Gln Leu Gln Ile Ser Phe Ser Thr Ala Leu Ala Ser Ala Glu
1310 1315 1320

Phe Arg Val Gln Val Cys Ser Thr Gln Val His Cys Ala Ala Ala
1325 1330 1335

Cys His Pro Pro Lys Asp His Ile Val Asn Tyr Pro Ala Ser His
1340 1345 1350

Thr Thr Leu Gly Val Gln Asp Ile Ser Thr Thr Ala Met Ser Trp
1355 1360 1365

Val Gln Lys Ile Thr Gly Gly Val Gly Leu Ile Val Ala Val Ala
1370 1375 1380

Ala Leu Ile Leu Ile Val Val Leu Cys Val Ser Phe Ser Arg His
1385 1390 1395

<210> SEQ ID NO 89
<211> LENGTH: 9257
<212> TYPE: DNA
<213> ORGANISM: Artificial Sequence
<220> FEATURE:
<223> OTHER INFORMATION: Synthetic Expression vector for CHIKV viral structural protein containing mouse IL-2 (D34K) antigen in E3

<400> SEQUENCE: 89
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttgcggccg ctctagacac catggagttc atcccgacgc aaactttcta taacagaagg 900
taccaacccc gaccctgggc cccacgccct acaattcaag taattagacc tagaccacgt 960

-continued

```
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggggcaccca cttcaagctc cacttcaagc   1860
tctacagcgg aagcacagca gcagcagcag cagcagcagc agcagcagca cctggagcag   1920
ctgttgatga agctacagga gctcctgagc aggatggaga attacaggaa cctgaaactc   1980
cccaggatgc tcaccttcaa attttacttg cccaagcagg ccacagaatt gaaagatctt   2040
cagtgcctag aagatgaact tggacctctg cggcatgttc tggatttgac tcaaagcaaa   2100
agctttcaat tggaagatgc tgagaatttc atcagcaata tcagagtaac tgttgtaaaa   2160
ctaaagggct ctgacaacac atttgagtgc caattcgatg atgagtcagc aactgtggtg   2220
gactttctga ggagatggat agccttctgt caaagcatca tctcaacaag ccctcaaggg   2280
ggatccagta ctaaggacaa ttttaatgtc tataaagcca caagaccata tctagctcat   2340
tgtcctgact gcggagaagg gcattcgtgc cacagcccta tcgcattgga gcgcatcaga   2400
aatgaagcaa cggacggaac gctgaaaatc caggtctctt tgcagatcgg gataaagaca   2460
gatgacagcc acgattggac caagctgcgc tatatggata gccatacgcc cgcggacgcg   2520
gagcgagccg gattgcttgt aaggacttca gcaccgtgca cgatcaccgg gaccatggga   2580
cactttattc tcgcccgatg cccgaaagga gagacgctga cagtgggatt tacggacagc   2640
agaaagatca gccacacatg cacacacccg ttccatcatg aaccacctgt gataggtagg   2700
gagaggttcc actctcgacc acaacatggt aaagagttac cttgcagcac gtacgtgcag   2760
agcaccgctg ccactgctga ggagatagag gtgcatatgc ccccagatac tcctgaccgc   2820
acgctgatga cgcagcagtc tggcaacgtg aagatcacag ttaatgggca gacggtgcgg   2880
tacaagtgca actgcggtgg ctcaaacgag ggactgacaa ccacagacaa agtgatcaat   2940
aactgcaaaa ttgatcagtg ccatgctgca gtcactaatc acaagaattg gcaatacaac   3000
tcccctttag tcccgcgcaa cgctgaactc ggggaccgta aaggaaagat ccacatccca   3060
ttcccattgg caaacgtgac ttgcagagtg ccaaaagcaa gaaaccctac agtaacttac   3120
ggaaaaaacc aagtcaccat gctgctgtat cctgaccatc cgacactctt gtcttaccgt   3180
aacatgggac aggaaccaaa ttaccacgag gagtgggtga cacacaagaa ggaggttacc   3240
ttgaccgtgc ctactgaggg tctggaggtc acttggggca acaacgaacc atacaagtac   3300
tggccgcaga tgtctacgaa cggtactgct catggtcacc cacatgagat aatcttgtac   3360
```

-continued

```
tattatgagc tgtaccccac tatgactgta gtcattgtgt cggtggcctc gttcgtgctt   3420
ctgtcgatgg tgggcacagc agtgggaatg tgtgtgtgcg cacggcgcag atgcattaca   3480
ccatatgaat taacaccagg agccactgtt cccttcctgc tcagcctgct atgctgcgtc   3540
agaacgacca aggcggccac atattacgag gctgcggcat atctatggaa cgaacagcag   3600
cccctgttct ggttgcaggc tcttatcccg ctggccgcct tgatcgtcct gtgcaactgt   3660
ctgaaactct tgccatgctg ctgtaagacc ctggcttttt tagccgtaat gagcatcggt   3720
gcccacactg tgagcgcgta cgaacacgta acagtgatcc cgaacacggt gggagtaccg   3780
tataagactc ttgtcaacag accgggttac agccccatgg tgttggagat ggagctacaa   3840
tcagtcacct tggaaccaac actgtcactt gactacatca cgtgcgagta caaaactgtc   3900
atcccctccc cgtacgtgaa gtgctgtggt acagcagagt gcaaggacaa gagcctacca   3960
gactacagct gcaaggtctt tactggagtc tacccattta tgtggggcgg cgcctactgc   4020
ttttgcgacg ccgaaaatac gcaattgagc gaggcacatg tagagaaatc tgaatcttgc   4080
aaaacagagt ttgcatcggc ctacagagcc cacaccgcat cggcgtcggc gaagctccgc   4140
gtcctttacc aaggaaacaa cattaccgta gctgcctacg ctaacggtga ccatgccgtc   4200
acagtaaagg acgccaagtt tgtcgtgggc ccaatgtcct ccgcctggac accttttgac   4260
aacaaaatcg tggtgtacaa aggcgacgtc tacaacatgg actacccacc ttttggcgca   4320
ggaagaccag gacaatttgg tgacattcaa agtcgtacac cggaaagtaa agacgtttat   4380
gccaacactc agttggtact acagaggcca gcagcaggca cggtacatgt accatactct   4440
caggcaccat ctggcttcaa gtattggctg aaggaacgag gagcatcgct acagcacacg   4500
gcaccgttcg gttgccagat tgcgacaaac ccggtaagag ctgtaaattg cgctgtgggg   4560
aacataccaa tttccatcga cataccggat gcggccttta ctagggttgt cgatgcaccc   4620
tctgtaacgg acatgtcatg cgaagtacca gcctgcactc actcctccga ctttgggggc   4680
gtcgccatca tcaaatacac agctagcaag aaaggtaaat gtgcagtaca ttcgatgacc   4740
aacgccgtta ccattcgaga agccgacgta gaagtagagg ggaactccca gctgcaaata   4800
tccttctcaa cagccctggc aagcgccgag tttcgcgtgc aagtgtgctc cacacaagta   4860
cactgcgcag ccgcatgcca ccctccaaag gaccacatag tcaattaccc agcatcacac   4920
accacccttg ggtccagga tatatccaca acggcaatgt cttgggtgca gaagattacg   4980
ggaggagtag gattaattgt tgctgttgct gccttaattt taattgtggt gctatgcgtg   5040
tcgtttagca ggcactaatg atccggaggg gcacccactt caagctccac ttcaagctct   5100
acagcggaag cacagcagca gcagcagcag cagcagcagc agcagcacct ggagcagctg   5160
ttgatggacc tacaggagct cctgagcagg atggagaatt acaggaacct gaaactcccc   5220
aggatgctca ccttcaaatt ttacttgccc aagcaggcca cagaattgaa agatcttcag   5280
tgcctagaag atgaacttgg acctctgcgg catgttctgg atttgactca aagcaaaagc   5340
tttcaattgg aagatgctga gaatttcatc agcaatatca gagtaactgt tgtaaaacta   5400
aagggctctg acaacacatt tgagtgccaa ttcgatgatg agtcagcaac tgtggtggac   5460
tttctgagga gatggatagc cttctgtcaa agcatcatct caacaagccc tcaaggggga   5520
tccgctgtgc cttctagttg ccagccatct gttgtttgcc cctcccccgt gccttccttg   5580
accctggaag gtgccactcc cactgtcctt tcctaataaa atgaggaaat tgcatcgcat   5640
tgtctgagta ggtgtcattc tattctgggg ggtggggtgg ggcaggacag caagggggag   5700
```

-continued

```
gattgggaag acaatagcag gcatgctggg gatgcggtgg gctctatggg tacccaggtg   5760
ctgaagaatt gacccggttc ctcctgggcc agaaagaagc aggcacatcc ccttctctgt   5820
gacacaccct gtccacgccc ctggttctta gttccagccc cactcatagg acactcatag   5880
ctcaggaggg ctccgccttc aatcccaccc gctaaagtac ttggagcggt ctctccctcc   5940
ctcatcagcc caccaaacca aacctagcct ccaagagtgg gaagaaatta aagcaagata   6000
ggctattaag tgcagaggga gagaaaatgc ctccaacatg tgaggaagta atgagagaaa   6060
tcatagaatt ttaaggccat gatttaaggc catcatggcc taagcttgaa aggagatagg   6120
atcaaagctt ggcgtaatca tggtcatagc tgtttcctgt gtgaaattgt tatccgctca   6180
caattccaca caacatacga gccggaagca taaagtgtaa agcctggggt gcctaatgag   6240
tgagctaact cacattaatt gcgttgcgct cactgcccgc tttccagtcg ggaaacctgt   6300
cgtgccagct gcattaatga atcggccaac gcgcggggag aggcggtttg cgtattgggc   6360
gctcttccgc ttcctcgctc actgactcgc tgcgctcggt cgttcggctg cggcgagcgg   6420
tatcagctca ctcaaaggcg gtaatacggt tatccacaga atcaggggat aacgcaggaa   6480
agaacatgtg agcaaaaggc cagcaaaagg ccaggaaccg taaaaaggcc gcgttgctgg   6540
cgtttttcca taggctccgc ccccctgacg agcatcacaa aaatcgacgc tcaagtcaga   6600
ggtggcgaaa cccgacagga ctataaagat accaggcgtt tccccctgga agctccctcg   6660
tgcgctctcc tgttccgacc ctgccgctta ccggatacct gtccgccttt ctcccttcgg   6720
gaagcgtggc gctttctcat agctcacgct gtaggtatct cagttcggtg taggtcgttc   6780
gctccaagct gggctgtgtg cacgaacccc ccgttcagcc cgaccgctgc gccttatccg   6840
gtaactatcg tcttgagtcc aacccggtaa gacacgactt atcgccactg gcagcagcca   6900
ctggtaacag gattagcaga gcgaggtatg taggcggtgc tacagagttc ttgaagtggt   6960
ggcctaacta cggctacact agaagaacag tatttggtat ctgcgctctg ctgaagccag   7020
ttaccttcgg aaaaagagtt ggtagctctt gatccggcaa acaaaccacc gctggtagcg   7080
gtggtttttt tgtttgcaag cagcagatta cgcgcagaaa aaaaggatct caagaagatc   7140
ctttgatctt ttctacgggg tctgacgctc agtggaacga aaactcacgt taagggattt   7200
tggtcatgag attatcaaaa aggatcttca cctagatcct tttaaattaa aaatgaagtt   7260
ttaaatcaat ctaaagtata tatgagtaaa cttggtctga cagttaccaa tgcttaatca   7320
gtgaggcacc tatctcagcg atctgtctat ttcgttcatc catagttgcc tgactccccg   7380
tcgtgtagat aactacgata cgggagggct taccatctgg ccccagtgct gcaatgatac   7440
cgcgagaacc acgctcaccg gctccagatt tatcagcaat aaaccagcca gccggaaggg   7500
ccgagcgcag aagtggtcct gcaactttat ccgcctccat ccagtctatt aattgttgcc   7560
gggaagctag agtaagtagt tcgccagtta atagtttgcg caacgttgtt gccattgcta   7620
caggcatcgt ggtgtcacgc tcgtcgtttg gtatggcttc attcagctcc ggttcccaac   7680
gatcaaggcg agttacatga tcccccatgt tgtgcaaaaa agcggttagc tccttcggtc   7740
ctccgatcgt tgtcagaagt aagttggccg cagtgttatc actcatggtt atggcagcac   7800
tgcataattc tcttactgtc atgccatccg taagatgctt ttctgtgact ggtgagtact   7860
caaccaagtc attctgagaa tagtgtatgc ggcgaccgag ttgctcttgc ccggcgtcaa   7920
tacgggataa taccgcgcca catagcagaa ctttaaaagt gctcatcatt ggaaaacgtt   7980
cttcggggcg aaaactctca aggatcttac cgctgttgag atccagttcg atgtaaccca   8040
ctcgtgcacc caactgatct tcagcatctt ttactttcac cagcgtttct gggtgagcaa   8100
```

```
aaacaggaag gcaaaatgcc gcaaaaaagg gaataagggc gacacggaaa tgttgaatac   8160

tcatactctt cctttttcaa tattattgaa gcatttatca gggttattgt ctcatgagcg   8220

gatacatatt tgaatgtatt tagaaaaata aacaaatagg ggttccgcgc acatttcccc   8280

gaaaagtgcc acctgacgtc taagaaacca ttattatcat gacattaacc tataaaaata   8340

ggcgtatcac gaggcccttt cggtcgcgc gtttcggtga tgacggtgaa aacctctgac   8400

acatgcagct cccgttgacg gtcacagctt gtctgtaagc ggatgccggg agcagacaag   8460

cccgtcaggg cgcgtcagcg ggtgttggcg ggtgtcgggg ctggcttaac tatgcggcat   8520

cagagcagat tgtactgaga gtgcaccata aaattgtaaa cgttaatatt ttgttaaaat   8580

tcgcgttaaa tttttgttaa atcagctcat tttttaacca ataggccgaa atcggcaaaa   8640

tcccttataa atcaaaagaa tagcccgaga tagggttgag tgttgttcca gtttggaaca   8700

agagtccact attaaagaac gtggactcca acgtcaaagg gcgaaaaacc gtctatcagg   8760

gcgatggccc actacgtgaa ccatcaccca aatcaagttt tttggggtcg aggtgccgta   8820

aagcactaaa tcggaaccct aaagggagcc cccgatttag agcttgacgg ggaaagccgg   8880

cgaacgtggc gagaaaggaa gggaagaaag cgaaaggagc gggcgctagg gcgctggcaa   8940

gtgtagcggt cacgctgcgc gtaaccacca cacccgccgc gcttaatgcg ccgctacagg   9000

gcgcgtacta tggttgcttt gacgtatgcg gtgtgaaata ccgcacagat gcgtaaggag   9060

aaaataccgc atcaggcgcc attcgccatt caggctgcgc aactgttggg aagggcgatc   9120

ggtgcgggcc tcttcgctat tacgccagct ggcgaaaggg ggatgtgctg caaggcgatt   9180

aagttgggta acgccagggt tttcccagtc acgacgttgt aaaacgacgg ccagtgaatt   9240

ccatggtctc aactttc                                                  9257
```

<210> SEQ ID NO 90
<211> LENGTH: 1398
<212> TYPE: PRT
<213> ORGANISM: Artificial Sequence
<220> FEATURE:
<223> OTHER INFORMATION: Synthetic CHIKV viral structural protein containing mouse IL-2 (D34K) antigen in E3

<400> SEQUENCE: 90

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140
```

-continued

```
Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Ala Pro Thr Ser Ser Ser Thr Ser Ser Ser Thr Ala
                325                 330                 335

Glu Ala Gln Gln Gln Gln Gln Gln Gln Gln Gln Gln Gln His Leu Glu
            340                 345                 350

Gln Leu Leu Met Lys Leu Gln Glu Leu Leu Ser Arg Met Glu Asn Tyr
        355                 360                 365

Arg Asn Leu Lys Leu Pro Arg Met Leu Thr Phe Lys Phe Tyr Leu Pro
    370                 375                 380

Lys Gln Ala Thr Glu Leu Lys Asp Leu Gln Cys Leu Glu Asp Glu Leu
385                 390                 395                 400

Gly Pro Leu Arg His Val Leu Asp Leu Thr Gln Ser Lys Ser Phe Gln
                405                 410                 415

Leu Glu Asp Ala Glu Asn Phe Ile Ser Asn Ile Arg Val Thr Val Val
            420                 425                 430

Lys Leu Lys Gly Ser Asp Asn Thr Phe Glu Cys Gln Phe Asp Asp Glu
        435                 440                 445

Ser Ala Thr Val Val Asp Phe Leu Arg Arg Trp Ile Ala Phe Cys Gln
    450                 455                 460

Ser Ile Ile Ser Thr Ser Pro Gln Gly Gly Ser Ser Thr Lys Asp Asn
465                 470                 475                 480

Phe Asn Val Tyr Lys Ala Thr Arg Pro Tyr Leu Ala His Cys Pro Asp
                485                 490                 495

Cys Gly Glu Gly His Ser Cys His Ser Pro Ile Ala Leu Glu Arg Ile
            500                 505                 510

Arg Asn Glu Ala Thr Asp Gly Thr Leu Lys Ile Gln Val Ser Leu Gln
        515                 520                 525

Ile Gly Ile Lys Thr Asp Asp Ser His Asp Trp Thr Lys Leu Arg Tyr
    530                 535                 540

Met Asp Ser His Thr Pro Ala Asp Ala Glu Arg Ala Gly Leu Leu Val
545                 550                 555                 560

Arg Thr Ser Ala Pro Cys Thr Ile Thr Gly Thr Met Gly His Phe Ile
```

-continued

```
                565                 570                 575

Leu Ala Arg Cys Pro Lys Gly Glu Thr Leu Thr Val Gly Phe Thr Asp
            580                 585                 590

Ser Arg Lys Ile Ser His Thr Cys Thr His Pro Phe His His Glu Pro
        595                 600                 605

Pro Val Ile Gly Arg Glu Arg Phe His Ser Arg Pro Gln His Gly Lys
    610                 615                 620

Glu Leu Pro Cys Ser Thr Tyr Val Gln Ser Thr Ala Ala Thr Ala Glu
625                 630                 635                 640

Glu Ile Glu Val His Met Pro Pro Asp Thr Pro Asp Arg Thr Leu Met
                645                 650                 655

Thr Gln Gln Ser Gly Asn Val Lys Ile Thr Val Asn Gly Gln Thr Val
            660                 665                 670

Arg Tyr Lys Cys Asn Cys Gly Gly Ser Asn Glu Gly Leu Thr Thr Thr
        675                 680                 685

Asp Lys Val Ile Asn Asn Cys Lys Ile Asp Gln Cys His Ala Ala Val
    690                 695                 700

Thr Asn His Lys Asn Trp Gln Tyr Asn Ser Pro Leu Val Pro Arg Asn
705                 710                 715                 720

Ala Glu Leu Gly Asp Arg Lys Gly Lys Ile His Ile Pro Phe Pro Leu
                725                 730                 735

Ala Asn Val Thr Cys Arg Val Pro Lys Ala Arg Asn Pro Thr Val Thr
            740                 745                 750

Tyr Gly Lys Asn Gln Val Thr Met Leu Leu Tyr Pro Asp His Pro Thr
        755                 760                 765

Leu Leu Ser Tyr Arg Asn Met Gly Gln Glu Pro Asn Tyr His Glu Glu
    770                 775                 780

Trp Val Thr His Lys Lys Glu Val Thr Leu Thr Val Pro Thr Glu Gly
785                 790                 795                 800

Leu Glu Val Thr Trp Gly Asn Asn Glu Pro Tyr Lys Tyr Trp Pro Gln
                805                 810                 815

Met Ser Thr Asn Gly Thr Ala His Gly His Pro His Glu Ile Ile Leu
            820                 825                 830

Tyr Tyr Tyr Glu Leu Tyr Pro Thr Met Thr Val Val Ile Val Ser Val
        835                 840                 845

Ala Ser Phe Val Leu Leu Ser Met Val Gly Thr Ala Val Gly Met Cys
    850                 855                 860

Val Cys Ala Arg Arg Arg Cys Ile Thr Pro Tyr Glu Leu Thr Pro Gly
865                 870                 875                 880

Ala Thr Val Pro Phe Leu Leu Ser Leu Leu Cys Cys Val Arg Thr Thr
                885                 890                 895

Lys Ala Ala Thr Tyr Tyr Glu Ala Ala Ala Tyr Leu Trp Asn Glu Gln
            900                 905                 910

Gln Pro Leu Phe Trp Leu Gln Ala Leu Ile Pro Leu Ala Ala Leu Ile
        915                 920                 925

Val Leu Cys Asn Cys Leu Lys Leu Leu Pro Cys Cys Cys Lys Thr Leu
    930                 935                 940

Ala Phe Leu Ala Val Met Ser Ile Gly Ala His Thr Val Ser Ala Tyr
945                 950                 955                 960

Glu His Val Thr Val Ile Pro Asn Thr Val Gly Val Pro Tyr Lys Thr
                965                 970                 975

Leu Val Asn Arg Pro Gly Tyr Ser Pro Met Val Leu Glu Met Glu Leu
            980                 985                 990
```

-continued

Gln Ser Val Thr Leu Glu Pro Thr Leu Ser Leu Asp Tyr Ile Thr Cys
995 1000 1005

Glu Tyr Lys Thr Val Ile Pro Ser Pro Tyr Val Lys Cys Cys Gly
1010 1015 1020

Thr Ala Glu Cys Lys Asp Lys Ser Leu Pro Asp Tyr Ser Cys Lys
1025 1030 1035

Val Phe Thr Gly Val Tyr Pro Phe Met Trp Gly Gly Ala Tyr Cys
1040 1045 1050

Phe Cys Asp Ala Glu Asn Thr Gln Leu Ser Glu Ala His Val Glu
1055 1060 1065

Lys Ser Glu Ser Cys Lys Thr Glu Phe Ala Ser Ala Tyr Arg Ala
1070 1075 1080

His Thr Ala Ser Ala Ser Ala Lys Leu Arg Val Leu Tyr Gln Gly
1085 1090 1095

Asn Asn Ile Thr Val Ala Ala Tyr Ala Asn Gly Asp His Ala Val
1100 1105 1110

Thr Val Lys Asp Ala Lys Phe Val Val Gly Pro Met Ser Ser Ala
1115 1120 1125

Trp Thr Pro Phe Asp Asn Lys Ile Val Val Tyr Lys Gly Asp Val
1130 1135 1140

Tyr Asn Met Asp Tyr Pro Pro Phe Gly Ala Gly Arg Pro Gly Gln
1145 1150 1155

Phe Gly Asp Ile Gln Ser Arg Thr Pro Glu Ser Lys Asp Val Tyr
1160 1165 1170

Ala Asn Thr Gln Leu Val Leu Gln Arg Pro Ala Ala Gly Thr Val
1175 1180 1185

His Val Pro Tyr Ser Gln Ala Pro Ser Gly Phe Lys Tyr Trp Leu
1190 1195 1200

Lys Glu Arg Gly Ala Ser Leu Gln His Thr Ala Pro Phe Gly Cys
1205 1210 1215

Gln Ile Ala Thr Asn Pro Val Arg Ala Val Asn Cys Ala Val Gly
1220 1225 1230

Asn Ile Pro Ile Ser Ile Asp Ile Pro Asp Ala Ala Phe Thr Arg
1235 1240 1245

Val Val Asp Ala Pro Ser Val Thr Asp Met Ser Cys Glu Val Pro
1250 1255 1260

Ala Cys Thr His Ser Ser Asp Phe Gly Gly Val Ala Ile Ile Lys
1265 1270 1275

Tyr Thr Ala Ser Lys Lys Gly Lys Cys Ala Val His Ser Met Thr
1280 1285 1290

Asn Ala Val Thr Ile Arg Glu Ala Asp Val Glu Val Glu Gly Asn
1295 1300 1305

Ser Gln Leu Gln Ile Ser Phe Ser Thr Ala Leu Ala Ser Ala Glu
1310 1315 1320

Phe Arg Val Gln Val Cys Ser Thr Gln Val His Cys Ala Ala Ala
1325 1330 1335

Cys His Pro Pro Lys Asp His Ile Val Asn Tyr Pro Ala Ser His
1340 1345 1350

Thr Thr Leu Gly Val Gln Asp Ile Ser Thr Thr Ala Met Ser Trp
1355 1360 1365

Val Gln Lys Ile Thr Gly Gly Val Gly Leu Ile Val Ala Val Ala
1370 1375 1380

Ala Leu Ile Leu Ile Val Val Leu Cys Val Ser Phe Ser Arg His
1385 1390 1395

<210> SEQ ID NO 91
<211> LENGTH: 9212
<212> TYPE: DNA
<213> ORGANISM: Artificial Sequence
<220> FEATURE:
<223> OTHER INFORMATION: Synthetic Expression vector for CHIKV viral structural protein containing human IL-2 (FDVVFmutant) antigen in E3

<400> SEQUENCE: 91
gaattcccat tgcatacgtt gtatccatat cataatatgt acatttatat tggctcatgt 60
ccaacattac cgccatgttg acattgatta ttgactagtt attaatagta atcaattacg 120
gggtcattag ttcatagccc atatatggag ttccgcgtta cataacttac ggtaaatggc 180
ccgcctggct gaccgcccaa cgacccccgc ccattgacgt caataatgac gtatgttccc 240
atagtaacgc caatagggac tttccattga cgtcaatggg tggagtattt acggtaaact 300
gcccacttgg cagtacatca agtgtatcat atgccaagta cgccccctat tgacgtcaat 360
gacggtaaat ggcccgcctg gcattatgcc cagtacatga ccttatggga ctttcctact 420
tggcagtaca tctacgtatt agtcatcgct attaccatgg tgatgcggtt ttggcagtac 480
atcaatgggc gtggatagcg gtttgactca cggggatttc caagtctcca ccccattgac 540
gtcaatggga gtttgttttg gcaccaaaat caacgggact ttccaaaatg tcgtaacaac 600
tccgccccat tgacgcaaat gggcggtagg cgtgtacggt gggaggtcta tataagcaga 660
gctcgtttag tgaaccgtca gatcgcctgg agacgccatc cacgctgttt tgacctccat 720
agaagacacc gggaccgatc cagcctccgt taacggtgga gggcagtgta gtctgagcag 780
tactcgttgc tgccgcgcgc gccaccagac ataatagctg acagactaac agactgttcc 840
tttgcggccg ctctagacac catggagttc atcccgacgc aaactttcta taacagaagg 900
taccaacccc gaccctgggc cccacgccct acaattcaag taattagacc tagaccacgt 960
ccacagaggc aggctgggca actcgcccag ctgatctccg cagtcaacaa attgaccatg 1020
cgcgcggtac ctcaacagaa gcctcgcaga aatcggaaaa acaagaagca aaggcagaag 1080
aagcaggcgc cgcaaaacga cccaaagcaa aagaagcaac caccacaaaa gaagccggct 1140
caaaagaaga agaaaccagg ccgtagggag agaatgtgca tgaaaattga aaatgattgc 1200
atcttcgaag tcaagcatga aggcaaagtg atgggctacg catgcctggt gggggataaa 1260
gtaatgaaac cagcacatgt gaagggaact atcgacaatg ccgatctggc taaactggcc 1320
tttaagcggt cgtctaaata cgatcttgaa tgtgcacaga taccggtgca catgaagtct 1380
gatgcctcga agtttaccca cgagaaaccc gaggggtact ataactggca tcacggagca 1440
gtgcagtatt caggaggccg gttcactatc ccgacgggtg caggcaagcc gggagacagc 1500
ggcagaccga tcttcgacaa caaaggacgg gtggtggcca tcgtcctagg aggggccaac 1560
gaaggtgccc gcacggccct ctccgtggtg acgtggaaca aagacatcgt cacaaaaatt 1620
acccctgagg gagccgaaga gtggagcctc gccctcccgg tcttgtgcct gttggcaaac 1680
actacattcc cctgctctca gccgccttgc acaccctgct gctacgaaaa ggaaccggaa 1740
agcaccttgc gcatgcttga ggacaacgtg atgagacccg gatactacca gctactaaaa 1800
gcatcgctga cttgctctcc ccactccgga ggcgccccta caagcagcag caccaagaaa 1860
acccagctgc agctggaaca tctgctgctg gacctgcaga tgatcctgaa cggcatcaac 1920

-continued

```
aactacaaga accccaagct gacccggatg ctgaccttca agttctacat gcccaagaag   1980
gccaccgaac tgaaacatct gcagtgcctg gaagaggaac tgaagcccct ggaagaagtg   2040
ctgaacctgg cccagagcaa gaacttccac ttcgaccccc gggacgtggt gtccaacatc   2100
aacgtgttcg tgctggaact gaaaggcagc gagacaacct tcatgtgcga gtacgccgac   2160
gagacagcta ccatcgtgga atttctgaat cggtggatca ccttctgcca gagcatcatc   2220
agcaccctga ccggcggatc cagtactaag gacaatttta atgtctataa agccacaaga   2280
ccatatctag ctcattgtcc tgactgcgga gaagggcatt cgtgccacag ccctatcgca   2340
ttggagcgca tcagaaatga agcaacggac ggaacgctga aatccaggt ctctttgcag   2400
atcgggataa agacagatga cagccacgat tggaccaagc tgcgctatat ggatagccat   2460
acgcccgcgg acgcggagcg agccggattg cttgtaagga cttcagcacc gtgcacgatc   2520
accgggacca tgggacactt tattctcgcc cgatgcccga aaggagagac gctgacagtg   2580
ggatttacgg acagcagaaa gatcagccac acatgcacac acccgttcca tcatgaacca   2640
cctgtgatag gtagggagag gttccactct cgaccacaac atggtaaaga gttaccttgc   2700
agcacgtacg tgcagagcac cgctgccact gctgaggaga tagaggtgca tatgcccccca   2760
gatactcctg accgcacgct gatgacgcag cagtctggca acgtgaagat cacagttaat   2820
gggcagacgg tgcggtacaa gtgcaactgc ggtggctcaa acgagggact gacaaccaca   2880
gacaaagtga tcaataactg caaaattgat cagtgccatg ctgcagtcac taatcacaag   2940
aattggcaat acaactcccc tttagtcccg cgcaacgctg aactcgggga ccgtaaagga   3000
aagatccaca tcccattccc attggcaaac gtgacttgca gagtgccaaa agcaagaaac   3060
cctacagtaa cttacggaaa aaaccaagtc accatgctgc tgtatcctga ccatccgaca   3120
ctcttgtctt accgtaacat gggacaggaa ccaaattacc acgaggagtg ggtgacacac   3180
aagaaggagg ttaccttgac cgtgcctact gagggtctgg aggtcacttg gggcaacaac   3240
gaaccataca agtactggcc gcagatgtct acgaacggta ctgctcatgg tcacccacat   3300
gagataatct tgtactatta tgagctgtac cccactatga ctgtagtcat tgtgtcggtg   3360
gcctcgttcg tgcttctgtc gatggtgggc acagcagtgg gaatgtgtgt gtgcgcacgg   3420
cgcagatgca ttacaccata tgaattaaca ccaggagcca ctgttccctt cctgctcagc   3480
ctgctatgct gcgtcagaac gaccaaggcg gccacatatt acgaggctgc ggcatatcta   3540
tggaacgaac agcagcccct gttctggttg caggctctta tcccgctggc cgccttgatc   3600
gtcctgtgca actgtctgaa actcttgcca tgctgctgta agaccctggc tttttagcc   3660
gtaatgagca tcggtgccca cactgtgagc gcgtacgaac acgtaacagt gatcccgaac   3720
acggtgggag taccgtataa gactcttgtc aacagaccgg gttacagccc catggtgttg   3780
gagatggagc tacaatcagt caccttggaa ccaacactgt cacttgacta catcacgtgc   3840
gagtacaaaa ctgtcatccc ctccccgtac gtgaagtgct gtggtacagc agagtgcaag   3900
gacaagagcc taccagacta cagctgcaag gtctttactg gagtctaccc atttatgtgg   3960
ggcggcgcct actgcttttg cgacgccgaa aatacgcaat tgagcgaggc acatgtagag   4020
aaatctgaat cttgcaaaac agagtttgca tcggcctaca gagcccacac cgcatcggcg   4080
tcggcgaagc tccgcgtcct ttaccaagga aacaacatta ccgtagctgc ctacgctaac   4140
ggtgaccatg ccgtcacagt aaaggacgcc aagtttgtcg tgggcccaat gtcctccgcc   4200
tggacacctt ttgacaacaa aatcgtggtg tacaaaggcg acgtctacaa catggactac   4260
ccaccttttg gcgcaggaag accaggacaa tttggtgaca ttcaaagtcg tacaccggaa   4320
```

agtaaagacg tttatgccaa cactcagttg gtactacaga ggccagcagc aggcacggta 4380
catgtaccat actctcaggc accatctggc ttcaagtatt ggctgaagga acgaggagca 4440
tcgctacagc acacggcacc gttcggttgc cagattgcga caaacccggt aagagctgta 4500
aattgcgctg tggggaacat accaatttcc atcgacatac cggatgcggc ctttactagg 4560
gttgtcgatg caccctctgt aacggacatg tcatgcgaag taccagcctg cactcactcc 4620
tccgactttg gggcgtcgc catcatcaaa tacacagcta gcaagaaagg taaatgtgca 4680
gtacattcga tgaccaacgc cgttaccatt cgagaagccg acgtagaagt agaggggaac 4740
tcccagctgc aaatatcctt ctcaacagcc ctggcaagcg ccgagtttcg cgtgcaagtg 4800
tgctccacac aagtacactg cgcagccgca tgccaccctc caaaggacca catagtcaat 4860
tacccagcat cacacaccac ccttggggtc caggatatat ccacaacggc aatgtcttgg 4920
gtgcagaaga ttacgggagg agtaggatta attgttgctg ttgctgcctt aattttaatt 4980
gtggtgctat gcgtgtcgtt tagcaggcac taatgatccg gaggggcacc cacttcaagc 5040
tccacttcaa gctctacagc ggaagcacag cagcagcagc agcagcagca gcagcagcag 5100
cacctggagc agctgttgat ggacctacag gagctcctga gcaggatgga gaattacagg 5160
aacctgaaac tccccaggat gctcaccttc aaattttact tgcccaagca ggccacagaa 5220
ttgaaagatc ttcagtgcct agaagatgaa cttggacctc tgcggcatgt tctggatttg 5280
actcaaagca aaagctttca attggaagat gctgagaatt tcatcagcaa tatcagagta 5340
actgttgtaa aactaaaggg ctctgacaac acatttgagt gccaattcga tgatgagtca 5400
gcaactgtgg tggactttct gaggagatgg atagccttct gtcaaagcat catctcaaca 5460
agccctcaag gggatccgc tgtgccttct agttgccagc catctgttgt ttgcccctcc 5520
cccgtgcctt ccttgaccct ggaaggtgcc actcccactg tcctttccta ataaaatgag 5580
gaaattgcat cgcattgtct gagtaggtgt cattctattc tggggggtgg ggtggggcag 5640
gacagcaagg gggaggattg ggaagacaat agcaggcatg ctggggatgc ggtgggctct 5700
atgggtaccc aggtgctgaa gaattgaccc ggttcctcct gggccagaaa gaagcaggca 5760
catccccttc tctgtgacac accctgtcca cgcccctggt tcttagttcc agccccactc 5820
ataggacact catagctcag gagggctccg ccttcaatcc cacccgctaa agtacttgga 5880
gcggtctctc cctccctcat cagcccacca aaccaaacct agcctccaag agtgggaaga 5940
aattaaagca agataggcta ttaagtgcag agggagagaa aatgcctcca acatgtgagg 6000
aagtaatgag agaaatcata gaattttaag gccatgattt aaggccatca tggcctaagc 6060
ttgaaaggag ataggatcaa agcttggcgt aatcatggtc atagctgttt cctgtgtgaa 6120
attgttatcc gctcacaatt ccacacaaca tacgagccgg aagcataaag tgtaaagcct 6180
ggggtgccta atgagtgagc taactcacat taattgcgtt gcgctcactg cccgctttcc 6240
agtcgggaaa cctgtcgtgc cagctgcatt aatgaatcgg ccaacgcgcg gggagaggcg 6300
gtttgcgtat tgggcgctct tccgcttcct cgctcactga ctcgctgcgc tcggtcgttc 6360
ggctgcggcg agcggtatca gctcactcaa aggcggtaat acggttatcc acagaatcag 6420
gggataacgc aggaaagaac atgtgagcaa aaggccagca aaaggccagg aaccgtaaaa 6480
aggccgcgtt gctggcgttt ttccataggc tccgcccccc tgacgagcat cacaaaaatc 6540
gacgctcaag tcagaggtgg cgaaacccga caggactata aagataccag gcgtttcccc 6600
ctggaagctc cctcgtgcgc tctcctgttc cgaccctgcc gcttaccgga tacctgtccg 6660

```
cctttctccc ttcgggaagc gtggcgcttt ctcatagctc acgctgtagg tatctcagtt   6720

cggtgtaggt cgttcgctcc aagctgggct gtgtgcacga accccccgtt cagcccgacc   6780

gctgcgcctt atccggtaac tatcgtcttg agtccaaccc ggtaagacac gacttatcgc   6840

cactggcagc agccactggt aacaggatta gcagagcgag gtatgtaggc ggtgctacag   6900

agttcttgaa gtggtggcct aactacggct acactagaag aacagtattt ggtatctgcg   6960

ctctgctgaa gccagttacc ttcggaaaaa gagttggtag ctcttgatcc ggcaaacaaa   7020

ccaccgctgg tagcggtggt ttttttgttt gcaagcagca gattacgcgc agaaaaaaag   7080

gatctcaaga agatcctttg atcttttcta cggggtctga cgctcagtgg aacgaaaact   7140

cacgttaagg gattttggtc atgagattat caaaaaggat cttcacctag atccttttaa   7200

attaaaaatg aagttttaaa tcaatctaaa gtatatatga gtaaacttgg tctgacagtt   7260

accaatgctt aatcagtgag gcacctatct cagcgatctg tctatttcgt tcatccatag   7320

ttgcctgact ccccgtcgtg tagataacta cgatacggga gggcttacca tctggcccca   7380

gtgctgcaat gataccgcga gaaccacgct caccggctcc agatttatca gcaataaacc   7440

agccagccgg aagggccgag cgcagaagtg gtcctgcaac tttatccgcc tccatccagt   7500

ctattaattg ttgccgggaa gctagagtaa gtagttcgcc agttaatagt ttgcgcaacg   7560

ttgttgccat tgctacaggc atcgtggtgt cacgctcgtc gtttggtatg gcttcattca   7620

gctccggttc ccaacgatca aggcgagtta catgatcccc catgttgtgc aaaaaagcgg   7680

ttagctcctt cggtcctccg atcgttgtca gaagtaagtt ggccgcagtg ttatcactca   7740

tggttatggc agcactgcat aattctctta ctgtcatgcc atccgtaaga tgcttttctg   7800

tgactggtga gtactcaacc aagtcattct gagaatagtg tatgcggcga ccgagttgct   7860

cttgcccggc gtcaatacgg gataataccg cgccacatag cagaacttta aaagtgctca   7920

tcattggaaa acgttcttcg gggcgaaaac tctcaaggat cttaccgctg ttgagatcca   7980

gttcgatgta acccactcgt gcacccaact gatcttcagc atcttttact ttcaccagcg   8040

tttctgggtg agcaaaaaca ggaaggcaaa atgccgcaaa aaagggaata agggcgacac   8100

ggaaatgttg aatactcata ctcttccttt ttcaatatta ttgaagcatt tatcagggtt   8160

attgtctcat gagcggatac atatttgaat gtatttagaa aaataaacaa ataggggttc   8220

cgcgcacatt tccccgaaaa gtgccacctg acgtctaaga aaccattatt atcatgacat   8280

taacctataa aaataggcgt atcacgaggc cctttcgggt cgcgcgtttc ggtgatgacg   8340

gtgaaaacct ctgacacatg cagctcccgt tgacggtcac agcttgtctg taagcggatg   8400

ccgggagcag acaagcccgt cagggcgcgt cagcgggtgt tggcgggtgt cggggctggc   8460

ttaactatgc ggcatcagag cagattgtac tgagagtgca ccataaaatt gtaaacgtta   8520

atattttgtt aaaattcgcg ttaaattttt gttaaatcag ctcatttttt aaccaatagg   8580

ccgaaatcgg caaaatccct tataaatcaa aagaatagcc cgagataggg ttgagtgttg   8640

ttccagtttg gaacaagagt ccactattaa agaacgtgga ctccaacgtc aaagggcgaa   8700

aaaccgtcta tcagggcgat ggcccactac gtgaaccatc acccaaatca agttttttgg   8760

ggtcgaggtg ccgtaaagca ctaaatcgga accctaaagg gagcccccga tttagagctt   8820

gacggggaaa gccggcgaac gtggcgagaa aggaagggaa gaaagcgaaa ggagcgggcg   8880

ctagggcgct ggcaagtgta gcggtcacgc tgcgcgtaac caccacaccc gccgcgctta   8940

atgcgccgct acagggcgcg tactatggtt gctttgacgt atgcggtgtg aaataccgca   9000

cagatgcgta aggagaaaat accgcatcag gcgccattcg ccattcaggc tgcgcaactg   9060
```

ttgggaaggg cgatcggtgc gggcctcttc gctattacgc cagctggcga aagggggatg 9120
tgctgcaagg cgattaagtt gggtaacgcc agggttttcc cagtcacgac gttgtaaaac 9180
gacggccagt gaattccatg gtctcaactt tc 9212

<210> SEQ ID NO 92
<211> LENGTH: 1383
<212> TYPE: PRT
<213> ORGANISM: Artificial Sequence
<220> FEATURE:
<223> OTHER INFORMATION: Synthetic CHIKV viral structural protein containing human IL-2 (FDVVFmutant) antigen in E3

<400> SEQUENCE: 92

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Leu Pro Val Leu Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Ser Thr Leu Arg Met Leu Glu Asp Asn Val Met
290 295 300

Arg Pro Gly Tyr Tyr Gln Leu Leu Lys Ala Ser Leu Thr Cys Ser Pro
305 310 315 320

His Ser Gly Gly Ala Pro Thr Ser Ser Ser Thr Lys Lys Thr Gln Leu

-continued

```
                325                 330                 335

Gln Leu Glu His Leu Leu Leu Asp Leu Gln Met Ile Leu Asn Gly Ile
            340                 345                 350

Asn Asn Tyr Lys Asn Pro Lys Leu Thr Arg Met Leu Thr Phe Lys Phe
        355                 360                 365

Tyr Met Pro Lys Lys Ala Thr Glu Leu Lys His Leu Gln Cys Leu Glu
    370                 375                 380

Glu Glu Leu Lys Pro Leu Glu Glu Val Leu Asn Leu Ala Gln Ser Lys
385                 390                 395                 400

Asn Phe His Phe Asp Pro Arg Asp Val Val Ser Asn Ile Asn Val Phe
                405                 410                 415

Val Leu Glu Leu Lys Gly Ser Glu Thr Thr Phe Met Cys Glu Tyr Ala
            420                 425                 430

Asp Glu Thr Ala Thr Ile Val Glu Phe Leu Asn Arg Trp Ile Thr Phe
        435                 440                 445

Cys Gln Ser Ile Ile Ser Thr Leu Thr Gly Gly Ser Ser Thr Lys Asp
    450                 455                 460

Asn Phe Asn Val Tyr Lys Ala Thr Arg Pro Tyr Leu Ala His Cys Pro
465                 470                 475                 480

Asp Cys Gly Glu Gly His Ser Cys His Ser Pro Ile Ala Leu Glu Arg
                485                 490                 495

Ile Arg Asn Glu Ala Thr Asp Gly Thr Leu Lys Ile Gln Val Ser Leu
            500                 505                 510

Gln Ile Gly Ile Lys Thr Asp Asp Ser His Asp Trp Thr Lys Leu Arg
        515                 520                 525

Tyr Met Asp Ser His Thr Pro Ala Asp Ala Glu Arg Ala Gly Leu Leu
    530                 535                 540

Val Arg Thr Ser Ala Pro Cys Thr Ile Thr Gly Thr Met Gly His Phe
545                 550                 555                 560

Ile Leu Ala Arg Cys Pro Lys Gly Glu Thr Leu Thr Val Gly Phe Thr
                565                 570                 575

Asp Ser Arg Lys Ile Ser His Thr Cys Thr His Pro Phe His His Glu
            580                 585                 590

Pro Pro Val Ile Gly Arg Glu Arg Phe His Ser Arg Pro Gln His Gly
        595                 600                 605

Lys Glu Leu Pro Cys Ser Thr Tyr Val Gln Ser Thr Ala Ala Thr Ala
    610                 615                 620

Glu Glu Ile Glu Val His Met Pro Pro Asp Thr Pro Asp Arg Thr Leu
625                 630                 635                 640

Met Thr Gln Gln Ser Gly Asn Val Lys Ile Thr Val Asn Gly Gln Thr
                645                 650                 655

Val Arg Tyr Lys Cys Asn Cys Gly Gly Ser Asn Glu Gly Leu Thr Thr
            660                 665                 670

Thr Asp Lys Val Ile Asn Asn Cys Lys Ile Asp Gln Cys His Ala Ala
        675                 680                 685

Val Thr Asn His Lys Asn Trp Gln Tyr Asn Ser Pro Leu Val Pro Arg
    690                 695                 700

Asn Ala Glu Leu Gly Asp Arg Lys Gly Lys Ile His Ile Pro Phe Pro
705                 710                 715                 720

Leu Ala Asn Val Thr Cys Arg Val Pro Lys Ala Arg Asn Pro Thr Val
                725                 730                 735

Thr Tyr Gly Lys Asn Gln Val Thr Met Leu Leu Tyr Pro Asp His Pro
            740                 745                 750
```

-continued

```
Thr Leu Leu Ser Tyr Arg Asn Met Gly Gln Glu Pro Asn Tyr His Glu
        755                 760                 765

Glu Trp Val Thr His Lys Lys Glu Val Thr Leu Thr Val Pro Thr Glu
    770                 775                 780

Gly Leu Glu Val Thr Trp Gly Asn Asn Glu Pro Tyr Lys Tyr Trp Pro
785                 790                 795                 800

Gln Met Ser Thr Asn Gly Thr Ala His Gly His Pro His Glu Ile Ile
                805                 810                 815

Leu Tyr Tyr Tyr Glu Leu Tyr Pro Thr Met Thr Val Val Ile Val Ser
            820                 825                 830

Val Ala Ser Phe Val Leu Leu Ser Met Val Gly Thr Ala Val Gly Met
        835                 840                 845

Cys Val Cys Ala Arg Arg Arg Cys Ile Thr Pro Tyr Glu Leu Thr Pro
    850                 855                 860

Gly Ala Thr Val Pro Phe Leu Leu Ser Leu Leu Cys Cys Val Arg Thr
865                 870                 875                 880

Thr Lys Ala Ala Thr Tyr Tyr Glu Ala Ala Ala Tyr Leu Trp Asn Glu
                885                 890                 895

Gln Gln Pro Leu Phe Trp Leu Gln Ala Leu Ile Pro Leu Ala Ala Leu
            900                 905                 910

Ile Val Leu Cys Asn Cys Leu Lys Leu Leu Pro Cys Cys Cys Lys Thr
        915                 920                 925

Leu Ala Phe Leu Ala Val Met Ser Ile Gly Ala His Thr Val Ser Ala
    930                 935                 940

Tyr Glu His Val Thr Val Ile Pro Asn Thr Val Gly Val Pro Tyr Lys
945                 950                 955                 960

Thr Leu Val Asn Arg Pro Gly Tyr Ser Pro Met Val Leu Glu Met Glu
                965                 970                 975

Leu Gln Ser Val Thr Leu Glu Pro Thr Leu Ser Leu Asp Tyr Ile Thr
            980                 985                 990

Cys Glu Tyr Lys Thr Val Ile Pro  Ser Pro Tyr Val Lys  Cys Cys Gly
        995                 1000                1005

Thr Ala  Glu Cys Lys Asp Lys  Ser Leu Pro Asp Tyr  Ser Cys Lys
    1010                1015                1020

Val Phe  Thr Gly Val Tyr Pro  Phe Met Trp Gly Gly  Ala Tyr Cys
    1025                1030                1035

Phe Cys  Asp Ala Glu Asn Thr  Gln Leu Ser Glu Ala  His Val Glu
    1040                1045                1050

Lys Ser  Glu Ser Cys Lys Thr  Glu Phe Ala Ser Ala  Tyr Arg Ala
    1055                1060                1065

His Thr  Ala Ser Ala Ser Ala  Lys Leu Arg Val Leu  Tyr Gln Gly
    1070                1075                1080

Asn Asn  Ile Thr Val Ala Ala  Tyr Ala Asn Gly Asp  His Ala Val
    1085                1090                1095

Thr Val  Lys Asp Ala Lys Phe  Val Val Gly Pro Met  Ser Ser Ala
    1100                1105                1110

Trp Thr  Pro Phe Asp Asn Lys  Ile Val Val Tyr Lys  Gly Asp Val
    1115                1120                1125

Tyr Asn  Met Asp Tyr Pro Pro  Phe Gly Ala Gly Arg  Pro Gly Gln
    1130                1135                1140

Phe Gly  Asp Ile Gln Ser Arg  Thr Pro Glu Ser Lys  Asp Val Tyr
    1145                1150                1155
```

```
Ala Asn  Thr Gln Leu Val Leu  Gln Arg Pro Ala Ala  Gly Thr Val
    1160                 1165                 1170

His Val  Pro Tyr Ser Gln Ala  Pro Ser Gly Phe Lys  Tyr Trp Leu
    1175                 1180                 1185

Lys Glu  Arg Gly Ala Ser Leu  Gln His Thr Ala Pro  Phe Gly Cys
    1190                 1195                 1200

Gln Ile  Ala Thr Asn Pro Val  Arg Ala Val Asn Cys  Ala Val Gly
    1205                 1210                 1215

Asn Ile  Pro Ile Ser Ile Asp  Ile Pro Asp Ala Ala  Phe Thr Arg
    1220                 1225                 1230

Val Val  Asp Ala Pro Ser Val  Thr Asp Met Ser Cys  Glu Val Pro
    1235                 1240                 1245

Ala Cys  Thr His Ser Ser Asp  Phe Gly Gly Val Ala  Ile Ile Lys
    1250                 1255                 1260

Tyr Thr  Ala Ser Lys Lys Gly  Lys Cys Ala Val His  Ser Met Thr
    1265                 1270                 1275

Asn Ala  Val Thr Ile Arg Glu  Ala Asp Val Glu Val  Glu Gly Asn
    1280                 1285                 1290

Ser Gln  Leu Gln Ile Ser Phe  Ser Thr Ala Leu Ala  Ser Ala Glu
    1295                 1300                 1305

Phe Arg  Val Gln Val Cys Ser  Thr Gln Val His Cys  Ala Ala Ala
    1310                 1315                 1320

Cys His  Pro Pro Lys Asp His  Ile Val Asn Tyr Pro  Ala Ser His
    1325                 1330                 1335

Thr Thr  Leu Gly Val Gln Asp  Ile Ser Thr Thr Ala  Met Ser Trp
    1340                 1345                 1350

Val Gln  Lys Ile Thr Gly Gly  Val Gly Leu Ile Val  Ala Val Ala
    1355                 1360                 1365

Ala Leu  Ile Leu Ile Val Val  Leu Cys Val Ser Phe  Ser Arg His
    1370                 1375                 1380
```

<210> SEQ ID NO 93
<211> LENGTH: 30
<212> TYPE: PRT
<213> ORGANISM: Artificial Sequence
<220> FEATURE:
<223> OTHER INFORMATION: Synthetic mouse malaria (Plasmodium yoelii) CSP epitope 4X(261) with linker

<400> SEQUENCE: 93

```
Ser Gly Gly Gln Gly Pro Gly Ala Pro Gln Gly Pro Gly Ala Pro Gln
1               5                   10                  15

Gly Pro Gly Ala Pro Gln Gly Pro Gly Ala Pro Gly Gly Ser
            20                  25                  30
```

<210> SEQ ID NO 94
<211> LENGTH: 90
<212> TYPE: DNA
<213> ORGANISM: Artificial Sequence
<220> FEATURE:
<223> OTHER INFORMATION: Synthetic mouse malaria (Plasmodium yoelii) CSP epitope 4X(261) with linker

<400> SEQUENCE: 94

```
tccggaggac agggacctgg cgctcctcag ggaccagggg caccacaggg cccaggcgcc     60

ccacaggggc ctggggcccc tgggggatcc                                       90
```

<210> SEQ ID NO 95

-continued

<211> LENGTH: 90
<212> TYPE: PRT
<213> ORGANISM: Artificial Sequence
<220> FEATURE:
<223> OTHER INFORMATION: Synthetic mouse malaria (Plasmodium yoelii) CSP epitope 14X(264) with linker

<400> SEQUENCE: 95

Ser Gly Gly Gln Gly Pro Gly Ala Pro Gln Gly Pro Gly Ala Pro Gln
1 5 10 15

Gly Pro Gly Ala Pro Gln Gly Pro Gly Ala Pro Gln Gly Pro Gly Ala
20 25 30

Pro Gln Gly Pro Gly Ala Pro Gln Gly Pro Gly Ala Pro Gln Gly Pro
35 40 45

Gly Ala Pro Gln Gly Pro Gly Ala Pro Gln Gly Pro Gly Ala Pro Gln
50 55 60

Gly Pro Gly Ala Pro Gln Gly Pro Gly Ala Pro Gln Gly Pro Gly Ala
65 70 75 80

Pro Gln Gly Pro Gly Ala Pro Gly Gly Ser
85 90

<210> SEQ ID NO 96
<211> LENGTH: 270
<212> TYPE: DNA
<213> ORGANISM: Artificial Sequence
<220> FEATURE:
<223> OTHER INFORMATION: Synthetic mouse malaria (Plasmodium yoelii) CSP epitope 14X(264) with linker

<400> SEQUENCE: 96
tccggaggac agggacctgg cgctcctcag ggaccagggg caccacaggg cccaggcgcc 60
ccacaggggc ctggggcacc ccagggacct ggggctccac aggggcctgg cgcacctcag 120
ggcccaggcg ctcctcaggg acctggcgct ccacagggac ccggcgctcc tcaggggcct 180
ggggcccctc agggacccgg cgcacctcag ggaccaggcg caccccaggg gccaggggct 240
cctcagggcc caggggctcc aggcggatcc 270

<210> SEQ ID NO 97
<211> LENGTH: 1303
<212> TYPE: PRT
<213> ORGANISM: Artificial Sequence
<220> FEATURE:
<223> OTHER INFORMATION: Synthetic CHIKV viral structural protein containing CSP epitope 4X(261) in E2 and E3 (261 dual)

<400> SEQUENCE: 97

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

```
Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Gln Gly Pro Gly Ala Pro Gln Gly Pro Gly Ala Pro
                325                 330                 335

Gln Gly Pro Gly Ala Pro Gln Gly Pro Gly Ala Pro Gly Gly Ser Ser
            340                 345                 350

Thr Lys Asp Asn Phe Asn Val Tyr Lys Ala Thr Arg Pro Tyr Leu Ala
        355                 360                 365

His Cys Pro Asp Cys Gly Glu Gly His Ser Cys His Ser Pro Ile Ala
    370                 375                 380

Leu Glu Arg Ile Arg Asn Glu Ala Thr Asp Gly Thr Leu Lys Ile Gln
385                 390                 395                 400

Val Ser Leu Gln Ile Gly Ile Lys Thr Asp Asp Ser His Asp Trp Thr
                405                 410                 415

Lys Leu Arg Tyr Met Asp Ser His Thr Pro Ala Asp Ala Glu Arg Ala
            420                 425                 430

Gly Leu Leu Val Arg Thr Ser Ala Pro Cys Thr Ile Thr Gly Thr Met
        435                 440                 445

Gly His Phe Ile Leu Ala Arg Cys Pro Lys Gly Glu Thr Leu Thr Val
    450                 455                 460

Gly Phe Thr Asp Ser Arg Lys Ile Ser His Thr Cys Thr His Pro Phe
465                 470                 475                 480

His His Glu Pro Pro Val Ile Gly Arg Glu Arg Phe His Ser Arg Pro
                485                 490                 495

Gln His Gly Lys Glu Leu Pro Cys Ser Thr Tyr Val Gln Ser Thr Ala
            500                 505                 510

Ala Thr Ala Glu Glu Ile Glu Val His Met Pro Pro Asp Thr Pro Asp
        515                 520                 525
```

```
Arg Thr Leu Met Thr Gln Gln Ser Gly Asn Val Lys Ile Thr Val Asn
    530                 535                 540

Gly Gln Thr Val Arg Tyr Lys Cys Asn Cys Gly Gly Ser Gly Gly Gln
545                 550                 555                 560

Gly Pro Gly Ala Pro Gln Gly Pro Gly Ala Pro Gln Gly Pro Gly Ala
                565                 570                 575

Pro Gln Gly Pro Gly Ala Pro Gly Gly Ser Asn Glu Gly Leu Thr Thr
            580                 585                 590

Thr Asp Lys Val Ile Asn Asn Cys Lys Ile Asp Gln Cys His Ala Ala
        595                 600                 605

Val Thr Asn His Lys Asn Trp Gln Tyr Asn Ser Pro Leu Val Pro Arg
    610                 615                 620

Asn Ala Glu Leu Gly Asp Arg Lys Gly Lys Ile His Ile Pro Phe Pro
625                 630                 635                 640

Leu Ala Asn Val Thr Cys Arg Val Pro Lys Ala Arg Asn Pro Thr Val
                645                 650                 655

Thr Tyr Gly Lys Asn Gln Val Thr Met Leu Leu Tyr Pro Asp His Pro
            660                 665                 670

Thr Leu Leu Ser Tyr Arg Asn Met Gly Gln Glu Pro Asn Tyr His Glu
        675                 680                 685

Glu Trp Val Thr His Lys Lys Glu Val Thr Leu Thr Val Pro Thr Glu
    690                 695                 700

Gly Leu Glu Val Thr Trp Gly Asn Asn Glu Pro Tyr Lys Tyr Trp Pro
705                 710                 715                 720

Gln Met Ser Thr Asn Gly Thr Ala His Gly His Pro His Glu Ile Ile
                725                 730                 735

Leu Tyr Tyr Tyr Glu Leu Tyr Pro Thr Met Thr Val Val Ile Val Ser
            740                 745                 750

Val Ala Ser Phe Val Leu Leu Ser Met Val Gly Thr Ala Val Gly Met
        755                 760                 765

Cys Val Cys Ala Arg Arg Arg Cys Ile Thr Pro Tyr Glu Leu Thr Pro
    770                 775                 780

Gly Ala Thr Val Pro Phe Leu Leu Ser Leu Leu Cys Cys Val Arg Thr
785                 790                 795                 800

Thr Lys Ala Ala Thr Tyr Tyr Glu Ala Ala Ala Tyr Leu Trp Asn Glu
                805                 810                 815

Gln Gln Pro Leu Phe Trp Leu Gln Ala Leu Ile Pro Leu Ala Ala Leu
            820                 825                 830

Ile Val Leu Cys Asn Cys Leu Lys Leu Leu Pro Cys Cys Cys Lys Thr
        835                 840                 845

Leu Ala Phe Leu Ala Val Met Ser Ile Gly Ala His Thr Val Ser Ala
    850                 855                 860

Tyr Glu His Val Thr Val Ile Pro Asn Thr Val Gly Val Pro Tyr Lys
865                 870                 875                 880

Thr Leu Val Asn Arg Pro Gly Tyr Ser Pro Met Val Leu Glu Met Glu
                885                 890                 895

Leu Gln Ser Val Thr Leu Glu Pro Thr Leu Ser Leu Asp Tyr Ile Thr
            900                 905                 910

Cys Glu Tyr Lys Thr Val Ile Pro Ser Pro Tyr Val Lys Cys Cys Gly
        915                 920                 925

Thr Ala Glu Cys Lys Asp Lys Ser Leu Pro Asp Tyr Ser Cys Lys Val
    930                 935                 940

Phe Thr Gly Val Tyr Pro Phe Met Trp Gly Gly Ala Tyr Cys Phe Cys
```

```
945                 950                 955                 960

Asp Ala Glu Asn Thr Gln Leu Ser Glu Ala His Val Glu Lys Ser Glu
                965                 970                 975

Ser Cys Lys Thr Glu Phe Ala Ser Ala Tyr Arg Ala His Thr Ala Ser
            980                 985                 990

Ala Ser Ala Lys Leu Arg Val Leu  Tyr Gln Gly Asn Asn  Ile Thr Val
        995                 1000                1005

Ala Ala  Tyr Ala Asn Gly Asp  His Ala Val Thr Val  Lys Asp Ala
    1010                 1015                 1020

Lys Phe  Val Val Gly Pro Met  Ser Ser Ala Trp Thr  Pro Phe Asp
    1025                 1030                 1035

Asn Lys  Ile Val Val Tyr Lys  Gly Asp Val Tyr Asn  Met Asp Tyr
    1040                 1045                 1050

Pro Pro  Phe Gly Ala Gly Arg  Pro Gly Gln Phe Gly  Asp Ile Gln
    1055                 1060                 1065

Ser Arg  Thr Pro Glu Ser Lys  Asp Val Tyr Ala Asn  Thr Gln Leu
    1070                 1075                 1080

Val Leu  Gln Arg Pro Ala Ala  Gly Thr Val His Val  Pro Tyr Ser
    1085                 1090                 1095

Gln Ala  Pro Ser Gly Phe Lys  Tyr Trp Leu Lys Glu  Arg Gly Ala
    1100                 1105                 1110

Ser Leu  Gln His Thr Ala Pro  Phe Gly Cys Gln Ile  Ala Thr Asn
    1115                 1120                 1125

Pro Val  Arg Ala Val Asn Cys  Ala Val Gly Asn Ile  Pro Ile Ser
    1130                 1135                 1140

Ile Asp  Ile Pro Asp Ala Ala  Phe Thr Arg Val Val  Asp Ala Pro
    1145                 1150                 1155

Ser Val  Thr Asp Met Ser Cys  Glu Val Pro Ala Cys  Thr His Ser
    1160                 1165                 1170

Ser Asp  Phe Gly Gly Val Ala  Ile Ile Lys Tyr Thr  Ala Ser Lys
    1175                 1180                 1185

Lys Gly  Lys Cys Ala Val His  Ser Met Thr Asn Ala  Val Thr Ile
    1190                 1195                 1200

Arg Glu  Ala Asp Val Glu Val  Glu Gly Asn Ser Gln  Leu Gln Ile
    1205                 1210                 1215

Ser Phe  Ser Thr Ala Leu Ala  Ser Ala Glu Phe Arg  Val Gln Val
    1220                 1225                 1230

Cys Ser  Thr Gln Val His Cys  Ala Ala Ala Cys His  Pro Pro Lys
    1235                 1240                 1245

Asp His  Ile Val Asn Tyr Pro  Ala Ser His Thr Thr  Leu Gly Val
    1250                 1255                 1260

Gln Asp  Ile Ser Thr Thr Ala  Met Ser Trp Val Gln  Lys Ile Thr
    1265                 1270                 1275

Gly Gly  Val Gly Leu Ile Val  Ala Val Ala Ala Leu  Ile Leu Ile
    1280                 1285                 1290

Val Val  Leu Cys Val Ser Phe  Ser Arg His
    1295                 1300
```

<210> SEQ ID NO 98
<211> LENGTH: 8972
<212> TYPE: DNA
<213> ORGANISM: Artificial Sequence
<220> FEATURE:
<223> OTHER INFORMATION: Synthetic Expression Vector for CHIKV viral
structural protein containing CSP epitope 4X(261) in E2 and E3

-continued (261.261.58)

<400> SEQUENCE: 98

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggacagggac ctggcgctcc tcagggacca   1860
ggggcaccac agggcccagg cgccccacag gggcctgggg cccctggggg atccagtact   1920
aaggacaatt ttaatgtcta taaagccaca agaccatatc tagctcattg tcctgactgc   1980
ggagaagggc attcgtgcca cagccctatc gcattggagc gcatcagaaa tgaagcaacg   2040
gacggaacgc tgaaaatcca ggtctctttg cagatcggga taaagacaga tgacagccac   2100
gattggacca agctgcgcta tatggatagc catacgcccg cggacgcgga gcgagccgga   2160
ttgcttgtaa ggacttcagc accgtgcacg atcaccggga ccatgggaca ctttattctc   2220
gcccgatgcc cgaaaggaga gacgctgaca gtgggattta cggacagcag aaagatcagc   2280
```

-continued

```
cacacatgca cacacccgtt ccatcatgaa ccacctgtga taggtaggga gaggttccac   2340
tctcgaccac aacatggtaa agagttacct tgcagcacgt acgtgcagag caccgctgcc   2400
actgctgagg agatagaggt gcatatgccc ccagatactc ctgaccgcac gctgatgacg   2460
cagcagtctg gcaacgtgaa gatcacagtt aatgggcaga cggtgcggta caagtgcaac   2520
tgcggtggct ccggaggaca gggacctggc gctcctcagg gaccaggggc accacagggc   2580
ccaggcgccc cacaggggcc tggggcccct gggggatcca acgagggact gacaaccaca   2640
gacaaagtga tcaataactg caaaattgat cagtgccatg ctgcagtcac taatcacaag   2700
aattggcaat acaactcccc tttagtcccg cgcaacgctg aactcgggga ccgtaaagga   2760
aagatccaca tcccattccc attggcaaac gtgacttgca gagtgccaaa agcaagaaac   2820
cctacagtaa cttacggaaa aaaccaagtc accatgctgc tgtatcctga ccatccgaca   2880
ctcttgtctt accgtaacat gggacaggaa ccaaattacc acgaggagtg ggtgacacac   2940
aagaaggagg ttaccttgac cgtgcctact gagggtctgg aggtcacttg gggcaacaac   3000
gaaccataca agtactggcc gcagatgtct acgaacggta ctgctcatgg tcacccacat   3060
gagataatct tgtactatta tgagctgtac cccactatga ctgtagtcat tgtgtcggtg   3120
gcctcgttcg tgcttctgtc gatggtgggc acagcagtgg gaatgtgtgt gtgcgcacgg   3180
cgcagatgca ttacaccata tgaattaaca ccaggagcca ctgttccctt cctgctcagc   3240
ctgctatgct gcgtcagaac gaccaaggcg gccacatatt acgaggctgc ggcatatcta   3300
tggaacgaac agcagcccct gttctggttg caggctctta tcccgctggc cgccttgatc   3360
gtcctgtgca actgtctgaa actcttgcca tgctgctgta agaccctggc tttttttagcc  3420
gtaatgagca tcggtgccca cactgtgagc gcgtacgaac acgtaacagt gatcccgaac   3480
acggtgggag taccgtataa gactcttgtc aacagaccgg gttacagccc catggtgttg   3540
gagatggagc tacaatcagt caccttggaa ccaacactgt cacttgacta catcacgtgc   3600
gagtacaaaa ctgtcatccc ctccccgtac gtgaagtgct gtggtacagc agagtgcaag   3660
gacaagagcc taccagacta cagctgcaag gtctttactg gagtctaccc atttatgtgg   3720
ggcggcgcct actgcttttg cgacgccgaa aatacgcaat tgagcgaggc acatgtagag   3780
aaatctgaat cttgcaaaac agagtttgca tcggcctaca gagcccacac cgcatcggcg   3840
tcggcgaagc tccgcgtcct ttaccaagga aacaacatta ccgtagctgc ctacgctaac   3900
ggtgaccatg ccgtcacagt aaaggacgcc aagtttgtcg tgggcccaat gtcctccgcc   3960
tggacacctt ttgacaacaa aatcgtggtg tacaaaggcg acgtctacaa catggactac   4020
ccacctttttg gcgcaggaag accaggacaa tttggtgaca ttcaaagtcg tacaccggaa  4080
agtaaagacg tttatgccaa cactcagttg gtactacaga ggccagcagc aggcacggta   4140
catgtaccat actctcaggc accatctggc ttcaagtatt ggctgaagga acgaggagca   4200
tcgctacagc acacggcacc gttcggttgc cagattgcga caaacccggt aagagctgta   4260
aattgcgctg tggggaacat accaatttcc atcgacatac cggatgcggc ctttactagg   4320
gttgtcgatg caccctctgt aacggacatg tcatgcgaag taccagcctg cactcactcc   4380
tccgactttg ggggcgtcgc catcatcaaa tacacagcta gcaagaaagg taaatgtgca   4440
gtacattcga tgaccaacgc cgttaccatt cgagaagccg acgtagaagt agaggggaac   4500
tcccagctgc aaatatcctt ctcaacagcc ctggcaagcg ccgagtttcg cgtgcaagtg   4560
tgctccacac aagtacactg cgcagccgca tgccaccctc caaaggacca catagtcaat   4620
```

-continued

```
tacccagcat cacacaccac ccttggggtc caggatatat ccacaacggc aatgtcttgg   4680
gtgcagaaga ttacgggagg agtaggatta attgttgctg ttgctgcctt aattttaatt   4740
gtggtgctat gcgtgtcgtt tagcaggcac taatgatccg gaggggcacc cacttcaagc   4800
tccacttcaa gctctacagc ggaagcacag cagcagcagc agcagcagca gcagcagcag   4860
cacctggagc agctgttgat ggacctacag gagctcctga gcaggatgga gaattacagg   4920
aacctgaaac tccccaggat gctcaccttc aaattttact tgcccaagca ggccacagaa   4980
ttgaaagatc ttcagtgcct agaagatgaa cttggacctc tgcggcatgt tctggatttg   5040
actcaaagca aaagctttca attggaagat gctgagaatt tcatcagcaa tatcagagta   5100
actgttgtaa aactaaaggg ctctgacaac acatttgagt gccaattcga tgatgagtca   5160
gcaactgtgg tggactttct gaggagatgg atagccttct gtcaaagcat catctcaaca   5220
agccctcaag gggatccgc tgtgccttct agttgccagc catctgttgt ttgcccctcc   5280
cccgtgcctt ccttgaccct ggaaggtgcc actcccactg tcctttccta ataaaatgag   5340
gaaattgcat cgcattgtct gagtaggtgt cattctattc tggggggtgg ggtggggcag   5400
gacagcaagg gggaggattg ggaagacaat agcaggcatg ctggggatgc ggtgggctct   5460
atgggtaccc aggtgctgaa gaattgaccc ggttcctcct gggccagaaa gaagcaggca   5520
catccccttc tctgtgacac accctgtcca cgcccctggt tcttagttcc agccccactc   5580
ataggacact catagctcag gagggctccg ccttcaatcc cacccgctaa agtacttgga   5640
gcggtctctc cctccctcat cagcccacca aaccaaacct agcctccaag agtgggaaga   5700
aattaaagca agataggcta ttaagtgcag agggagagaa aatgcctcca acatgtgagg   5760
aagtaatgag agaaatcata gaattttaag gccatgattt aaggccatca tggcctaagc   5820
ttgaaaggag ataggatcaa agcttggcgt aatcatggtc atagctgttt cctgtgtgaa   5880
attgttatcc gctcacaatt ccacacaaca tacgagccgg aagcataaag tgtaaagcct   5940
ggggtgccta atgagtgagc taactcacat taattgcgtt gcgctcactg cccgctttcc   6000
agtcgggaaa cctgtcgtgc cagctgcatt aatgaatcgg ccaacgcgcg gggagaggcg   6060
gtttgcgtat tgggcgctct tccgcttcct cgctcactga ctcgctgcgc tcggtcgttc   6120
ggctgcggcg agcggtatca gctcactcaa aggcggtaat acggttatcc acagaatcag   6180
gggataacgc aggaaagaac atgtgagcaa aaggccagca aaaggccagg aaccgtaaaa   6240
aggccgcgtt gctggcgttt ttccataggc tccgcccccc tgacgagcat cacaaaaatc   6300
gacgctcaag tcagaggtgg cgaaacccga caggactata aagataccag gcgtttcccc   6360
ctggaagctc cctcgtgcgc tctcctgttc cgaccctgcc gcttaccgga tacctgtccg   6420
cctttctccc ttcgggaagc gtggcgcttt ctcatagctc acgctgtagg tatctcagtt   6480
cggtgtaggt cgttcgctcc aagctgggct gtgtgcacga accccccgtt cagcccgacc   6540
gctgcgcctt atccggtaac tatcgtcttg agtccaaccc ggtaagacac gacttatcgc   6600
cactggcagc agccactggt aacaggatta gcagagcgag gtatgtaggc ggtgctacag   6660
agttcttgaa gtggtggcct aactacggct acactagaag aacagtattt ggtatctgcg   6720
ctctgctgaa gccagttacc ttcggaaaaa gagttggtag ctcttgatcc ggcaaacaaa   6780
ccaccgctgg tagcggtggt ttttttgttt gcaagcagca gattacgcgc agaaaaaaag   6840
gatctcaaga agatcctttg atcttttcta cggggtctga cgctcagtgg aacgaaaact   6900
cacgttaagg gattttggtc atgagattat caaaaaggat cttcacctag atccttttaa   6960
attaaaaatg aagttttaaa tcaatctaaa gtatatatga gtaaacttgg tctgacagtt   7020
```

```
accaatgctt aatcagtgag gcacctatct cagcgatctg tctatttcgt tcatccatag   7080

ttgcctgact ccccgtcgtg tagataacta cgatacggga gggcttacca tctggcccca   7140

gtgctgcaat gataccgcga gaaccacgct caccggctcc agatttatca gcaataaacc   7200

agccagccgg aagggccgag cgcagaagtg gtcctgcaac tttatccgcc tccatccagt   7260

ctattaattg ttgccgggaa gctagagtaa gtagttcgcc agttaatagt ttgcgcaacg   7320

ttgttgccat tgctacaggc atcgtggtgt cacgctcgtc gtttggtatg gcttcattca   7380

gctccggttc ccaacgatca aggcgagtta catgatcccc catgttgtgc aaaaaagcgg   7440

ttagctcctt cggtcctccg atcgttgtca gaagtaagtt ggccgcagtg ttatcactca   7500

tggttatggc agcactgcat aattctctta ctgtcatgcc atccgtaaga tgcttttctg   7560

tgactggtga gtactcaacc aagtcattct gagaatagtg tatgcggcga ccgagttgct   7620

cttgcccggc gtcaatacgg gataataccg cgccacatag cagaacttta aaagtgctca   7680

tcattggaaa acgttcttcg gggcgaaaac tctcaaggat cttaccgctg ttgagatcca   7740

gttcgatgta acccactcgt gcacccaact gatcttcagc atcttttact ttcaccagcg   7800

tttctgggtg agcaaaaaca ggaaggcaaa atgccgcaaa aaagggaata agggcgacac   7860

ggaaatgttg aatactcata ctcttccttt ttcaatatta ttgaagcatt tatcagggtt   7920

attgtctcat gagcggatac atatttgaat gtatttagaa aaataaacaa ataggggttc   7980

cgcgcacatt tccccgaaaa gtgccacctg acgtctaaga aaccattatt atcatgacat   8040

taacctataa aaataggcgt atcacgaggc cctttcgggt cgcgcgtttc ggtgatgacg   8100

gtgaaaacct ctgacacatg cagctcccgt tgacggtcac agcttgtctg taagcggatg   8160

ccgggagcag acaagcccgt cagggcgcgt cagcgggtgt tggcgggtgt cggggctggc   8220

ttaactatgc ggcatcagag cagattgtac tgagagtgca ccataaaatt gtaaacgtta   8280

atattttgtt aaaattcgcg ttaaattttt gttaaatcag ctcatttttt aaccaatagg   8340

ccgaaatcgg caaaatccct tataaatcaa aagaatagcc cgagataggg ttgagtgttg   8400

ttccagtttg gaacaagagt ccactattaa agaacgtgga ctccaacgtc aaagggcgaa   8460

aaaccgtcta tcagggcgat ggcccactac gtgaaccatc acccaaatca agttttttgg   8520

ggtcgaggtg ccgtaaagca ctaaatcgga accctaaagg gagcccccga tttagagctt   8580

gacggggaaa gccggcgaac gtggcgagaa aggaagggaa gaaagcgaaa ggagcgggcg   8640

ctagggcgct ggcaagtgta gcggtcacgc tgcgcgtaac caccacaccc gccgcgctta   8700

atgcgccgct acagggcgcg tactatggtt gctttgacgt atgcggtgtg aaataccgca   8760

cagatgcgta aggagaaaat accgcatcag gcgccattcg ccattcaggc tgcgcaactg   8820

ttgggaaggg cgatcggtgc gggcctcttc gctattacgc cagctggcga aagggggatg   8880

tgctgcaagg cgattaagtt gggtaacgcc agggttttcc cagtcacgac gttgtaaaac   8940

gacggccagt gaattccatg gtctcaactt tc                                 8972
```

```
<210> SEQ ID NO 99
<211> LENGTH: 1423
<212> TYPE: PRT
<213> ORGANISM: Artificial Sequence
<220> FEATURE:
<223> OTHER INFORMATION: Synthetic CHIKV 264.264.58 (264 dual)

<400> SEQUENCE: 99

Met Glu Phe Ile Pro Thr Gln Thr Phe Tyr Asn Arg Arg Tyr Gln Pro
1               5                   10                  15
```

```
Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Gln Gly Pro Gly Ala Pro Gln Gly Pro Gly Ala Pro
                325                 330                 335

Gln Gly Pro Gly Ala Pro Gln Gly Pro Gly Ala Pro Gln Gly Pro Gly
            340                 345                 350

Ala Pro Gln Gly Pro Gly Ala Pro Gln Gly Pro Gly Ala Pro Gln Gly
        355                 360                 365

Pro Gly Ala Pro Gln Gly Pro Gly Ala Pro Gln Gly Pro Gly Ala Pro
    370                 375                 380

Gln Gly Pro Gly Ala Pro Gln Gly Pro Gly Ala Pro Gln Gly Pro Gly
385                 390                 395                 400

Ala Pro Gln Gly Pro Gly Ala Pro Gly Gly Ser Ser Thr Lys Asp Asn
                405                 410                 415

Phe Asn Val Tyr Lys Ala Thr Arg Pro Tyr Leu Ala His Cys Pro Asp
            420                 425                 430
```

-continued

```
Cys Gly Glu Gly His Ser Cys His Ser Pro Ile Ala Leu Glu Arg Ile
        435                 440                 445

Arg Asn Glu Ala Thr Asp Gly Thr Leu Lys Ile Gln Val Ser Leu Gln
    450                 455                 460

Ile Gly Ile Lys Thr Asp Asp Ser His Asp Trp Thr Lys Leu Arg Tyr
465                 470                 475                 480

Met Asp Ser His Thr Pro Ala Asp Ala Glu Arg Ala Gly Leu Leu Val
                485                 490                 495

Arg Thr Ser Ala Pro Cys Thr Ile Thr Gly Thr Met Gly His Phe Ile
            500                 505                 510

Leu Ala Arg Cys Pro Lys Gly Glu Thr Leu Thr Val Gly Phe Thr Asp
        515                 520                 525

Ser Arg Lys Ile Ser His Thr Cys Thr His Pro Phe His His Glu Pro
    530                 535                 540

Pro Val Ile Gly Arg Glu Arg Phe His Ser Arg Pro Gln His Gly Lys
545                 550                 555                 560

Glu Leu Pro Cys Ser Thr Tyr Val Gln Ser Thr Ala Ala Thr Ala Glu
                565                 570                 575

Glu Ile Glu Val His Met Pro Pro Asp Thr Pro Asp Arg Thr Leu Met
            580                 585                 590

Thr Gln Gln Ser Gly Asn Val Lys Ile Thr Val Asn Gly Gln Thr Val
        595                 600                 605

Arg Tyr Lys Cys Asn Cys Gly Gly Ser Gly Gly Gln Gly Pro Gly Ala
    610                 615                 620

Pro Gln Gly Pro Gly Ala Pro Gln Gly Pro Gly Ala Pro Gln Gly Pro
625                 630                 635                 640

Gly Ala Pro Gln Gly Pro Gly Ala Pro Gln Gly Pro Gly Ala Pro Gln
                645                 650                 655

Gly Pro Gly Ala Pro Gln Gly Pro Gly Ala Pro Gln Gly Pro Gly Ala
            660                 665                 670

Pro Gln Gly Pro Gly Ala Pro Gln Gly Pro Gly Ala Pro Gln Gly Pro
        675                 680                 685

Gly Ala Pro Gln Gly Pro Gly Ala Pro Gln Gly Pro Gly Ala Pro Gly
    690                 695                 700

Gly Ser Asn Glu Gly Leu Thr Thr Thr Asp Lys Val Ile Asn Asn Cys
705                 710                 715                 720

Lys Ile Asp Gln Cys His Ala Ala Val Thr Asn His Lys Asn Trp Gln
                725                 730                 735

Tyr Asn Ser Pro Leu Val Pro Arg Asn Ala Glu Leu Gly Asp Arg Lys
            740                 745                 750

Gly Lys Ile His Ile Pro Phe Pro Leu Ala Asn Val Thr Cys Arg Val
        755                 760                 765

Pro Lys Ala Arg Asn Pro Thr Val Thr Tyr Gly Lys Asn Gln Val Thr
    770                 775                 780

Met Leu Leu Tyr Pro Asp His Pro Thr Leu Leu Ser Tyr Arg Asn Met
785                 790                 795                 800

Gly Gln Glu Pro Asn Tyr His Glu Glu Trp Val Thr His Lys Lys Glu
                805                 810                 815

Val Thr Leu Thr Val Pro Thr Glu Gly Leu Glu Val Thr Trp Gly Asn
            820                 825                 830

Asn Glu Pro Tyr Lys Tyr Trp Pro Gln Met Ser Thr Asn Gly Thr Ala
        835                 840                 845

His Gly His Pro His Glu Ile Ile Leu Tyr Tyr Tyr Glu Leu Tyr Pro
```

850 855 860

Thr Met Thr Val Val Ile Val Ser Val Ala Ser Phe Val Leu Leu Ser
865 870 875 880

Met Val Gly Thr Ala Val Gly Met Cys Val Cys Ala Arg Arg Arg Cys
885 890 895

Ile Thr Pro Tyr Glu Leu Thr Pro Gly Ala Thr Val Pro Phe Leu Leu
900 905 910

Ser Leu Leu Cys Cys Val Arg Thr Thr Lys Ala Ala Thr Tyr Tyr Glu
915 920 925

Ala Ala Ala Tyr Leu Trp Asn Glu Gln Gln Pro Leu Phe Trp Leu Gln
930 935 940

Ala Leu Ile Pro Leu Ala Ala Leu Ile Val Leu Cys Asn Cys Leu Lys
945 950 955 960

Leu Leu Pro Cys Cys Cys Lys Thr Leu Ala Phe Leu Ala Val Met Ser
965 970 975

Ile Gly Ala His Thr Val Ser Ala Tyr Glu His Val Thr Val Ile Pro
980 985 990

Asn Thr Val Gly Val Pro Tyr Lys Thr Leu Val Asn Arg Pro Gly Tyr
995 1000 1005

Ser Pro Met Val Leu Glu Met Glu Leu Gln Ser Val Thr Leu Glu
1010 1015 1020

Pro Thr Leu Ser Leu Asp Tyr Ile Thr Cys Glu Tyr Lys Thr Val
1025 1030 1035

Ile Pro Ser Pro Tyr Val Lys Cys Cys Gly Thr Ala Glu Cys Lys
1040 1045 1050

Asp Lys Ser Leu Pro Asp Tyr Ser Cys Lys Val Phe Thr Gly Val
1055 1060 1065

Tyr Pro Phe Met Trp Gly Gly Ala Tyr Cys Phe Cys Asp Ala Glu
1070 1075 1080

Asn Thr Gln Leu Ser Glu Ala His Val Glu Lys Ser Glu Ser Cys
1085 1090 1095

Lys Thr Glu Phe Ala Ser Ala Tyr Arg Ala His Thr Ala Ser Ala
1100 1105 1110

Ser Ala Lys Leu Arg Val Leu Tyr Gln Gly Asn Asn Ile Thr Val
1115 1120 1125

Ala Ala Tyr Ala Asn Gly Asp His Ala Val Thr Val Lys Asp Ala
1130 1135 1140

Lys Phe Val Val Gly Pro Met Ser Ser Ala Trp Thr Pro Phe Asp
1145 1150 1155

Asn Lys Ile Val Val Tyr Lys Gly Asp Val Tyr Asn Met Asp Tyr
1160 1165 1170

Pro Pro Phe Gly Ala Gly Arg Pro Gly Gln Phe Gly Asp Ile Gln
1175 1180 1185

Ser Arg Thr Pro Glu Ser Lys Asp Val Tyr Ala Asn Thr Gln Leu
1190 1195 1200

Val Leu Gln Arg Pro Ala Ala Gly Thr Val His Val Pro Tyr Ser
1205 1210 1215

Gln Ala Pro Ser Gly Phe Lys Tyr Trp Leu Lys Glu Arg Gly Ala
1220 1225 1230

Ser Leu Gln His Thr Ala Pro Phe Gly Cys Gln Ile Ala Thr Asn
1235 1240 1245

Pro Val Arg Ala Val Asn Cys Ala Val Gly Asn Ile Pro Ile Ser
1250 1255 1260

```
Ile Asp  Ile Pro Asp Ala Ala  Phe Thr Arg Val Val  Asp Ala Pro
    1265                 1270                 1275

Ser Val  Thr Asp Met Ser Cys  Glu Val Pro Ala Cys  Thr His Ser
    1280                 1285                 1290

Ser Asp  Phe Gly Gly Val Ala  Ile Ile Lys Tyr Thr  Ala Ser Lys
    1295                 1300                 1305

Lys Gly  Lys Cys Ala Val His  Ser Met Thr Asn Ala  Val Thr Ile
    1310                 1315                 1320

Arg Glu  Ala Asp Val Glu Val  Glu Gly Asn Ser Gln  Leu Gln Ile
    1325                 1330                 1335

Ser Phe  Ser Thr Ala Leu Ala  Ser Ala Glu Phe Arg  Val Gln Val
    1340                 1345                 1350

Cys Ser  Thr Gln Val His Cys  Ala Ala Ala Cys His  Pro Pro Lys
    1355                 1360                 1365

Asp His  Ile Val Asn Tyr Pro  Ala Ser His Thr Thr  Leu Gly Val
    1370                 1375                 1380

Gln Asp  Ile Ser Thr Thr Ala  Met Ser Trp Val Gln  Lys Ile Thr
    1385                 1390                 1395

Gly Gly  Val Gly Leu Ile Val  Ala Val Ala Ala Leu  Ile Leu Ile
    1400                 1405                 1410

Val Val  Leu Cys Val Ser Phe  Ser Arg His
    1415                 1420
```

<210> SEQ ID NO 100
<211> LENGTH: 9332
<212> TYPE: DNA
<213> ORGANISM: Artificial Sequence
<220> FEATURE:
<223> OTHER INFORMATION: Synthetic Expression Vector for CHIKV viral structural protein containing CSP epitope 14X(264) in E2 and E3 (264 dual)

<400> SEQUENCE: 100

```
gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttgcggccg ctctagacac catggagttc atcccgacgc aaactttcta taacagaagg    900

taccaacccc gaccctgggc cccacgccct acaattcaag taattagacc tagaccacgt    960

ccacagaggc aggctgggca actcgcccag ctgatctccg cagtcaacaa attgaccatg   1020
```

```
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt gggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggacagggac ctggcgctcc tcagggacca   1860
ggggcaccac agggcccagg cgccccacag gggcctgggg caccccaggg acctggggct   1920
ccacaggggc ctggcgcacc tcagggccca ggcgctcctc agggacctgg cgctccacag   1980
ggacccggcg ctcctcaggg gcctggggcc cctcagggac ccggcgcacc tcagggacca   2040
ggcgcacccc aggggccagg ggctcctcag ggcccagggg ctccaggcgg atccagtact   2100
aaggacaatt ttaatgtcta taaagccaca agaccatatc tagctcattg tcctgactgc   2160
ggagaagggc attcgtgcca cagccctatc gcattggagc gcatcagaaa tgaagcaacg   2220
gacggaacgc tgaaaatcca ggtctctttg cagatcggga taaagacaga tgacagccac   2280
gattggacca agctgcgcta tatggatagc catacgcccg cggacgcgga gcgagccgga   2340
ttgcttgtaa ggacttcagc accgtgcacg atcaccggga ccatgggaca ctttattctc   2400
gcccgatgcc cgaaaggaga gacgctgaca gtgggattta cggacagcag aaagatcagc   2460
cacacatgca cacacccgtt ccatcatgaa ccacctgtga taggtaggga gaggttccac   2520
tctcgaccac aacatggtaa agagttacct tgcagcacgt acgtgcagag caccgctgcc   2580
actgctgagg agatagaggt gcatatgccc ccagatactc ctgaccgcac gctgatgacg   2640
cagcagtctg gcaacgtgaa gatcacagtt aatgggcaga cggtgcggta caagtgcaac   2700
tgcggtggct ccggaggaca gggacctggc gctcctcagg gaccaggggc accacagggc   2760
ccaggcgccc cacaggggcc tggggcaccc cagggacctg gggctccaca ggggcctggc   2820
gcacctcagg gcccaggcgc tcctcaggga cctggcgctc cacagggacc cggcgctcct   2880
caggggcctg gggcccctca gggacccggc gcacctcagg gaccaggcgc accccagggg   2940
ccaggggctc ctcagggccc aggggctcca ggcggatcca acgagggact gacaaccaca   3000
gacaaagtga tcaataactg caaaattgat cagtgccatg ctgcagtcac taatcacaag   3060
aattggcaat acaactcccc tttagtcccg cgcaacgctg aactcgggga ccgtaaagga   3120
aagatccaca tcccattccc attggcaaac gtgacttgca gagtgccaaa agcaagaaac   3180
cctacagtaa cttacggaaa aaaccaagtc accatgctgc tgtatcctga ccatccgaca   3240
ctcttgtctt accgtaacat gggacaggaa ccaaattacc acgaggagtg ggtgacacac   3300
aagaaggagg ttaccttgac cgtgcctact gagggtctgg aggtcacttg ggcaacaac    3360
```

-continued

```
gaaccataca agtactggcc gcagatgtct acgaacggta ctgctcatgg tcacccacat   3420
gagataatct tgtactatta tgagctgtac cccactatga ctgtagtcat tgtgtcggtg   3480
gcctcgttcg tgcttctgtc gatggtgggc acagcagtgg gaatgtgtgt gtgcgcacgg   3540
cgcagatgca ttacaccata tgaattaaca ccaggagcca ctgttccctt cctgctcagc   3600
ctgctatgct gcgtcagaac gaccaaggcg gccacatatt acgaggctgc ggcatatcta   3660
tggaacgaac agcagcccct gttctggttg caggctctta tcccgctggc cgccttgatc   3720
gtcctgtgca actgtctgaa actcttgcca tgctgctgta agaccctggc tttttagcc    3780
gtaatgagca tcggtgccca cactgtgagc gcgtacgaac acgtaacagt gatcccgaac   3840
acggtgggag taccgtataa gactcttgtc aacagaccgg gttacagccc catggtgttg   3900
gagatggagc tacaatcagt caccttggaa ccaacactgt cacttgacta catcacgtgc   3960
gagtacaaaa ctgtcatccc ctccccgtac gtgaagtgct gtggtacagc agagtgcaag   4020
gacaagagcc taccagacta cagctgcaag gtctttactg gagtctaccc atttatgtgg   4080
ggcggcgcct actgcttttg cgacgccgaa aatacgcaat tgagcgaggc acatgtagag   4140
aaatctgaat cttgcaaaac agagtttgca tcggcctaca gagcccacac cgcatcggcg   4200
tcggcgaagc tccgcgtcct ttaccaagga aacaacatta ccgtagctgc ctacgctaac   4260
ggtgaccatg ccgtcacagt aaaggacgcc aagtttgtcg tgggcccaat gtcctccgcc   4320
tggacacctt ttgacaacaa aatcgtggtg tacaaaggcg acgtctacaa catggactac   4380
ccacctttttg gcgcaggaag accaggacaa tttggtgaca ttcaaagtcg tacaccggaa   4440
agtaaagacg tttatgccaa cactcagttg gtactacaga ggccagcagc aggcacggta   4500
catgtaccat actctcaggc accatctggc ttcaagtatt ggctgaagga acgaggagca   4560
tcgctacagc acacggcacc gttcggttgc cagattgcga caaacccggt aagagctgta   4620
aattgcgctg tggggaacat accaatttcc atcgacatac cggatgcggc ctttactagg   4680
gttgtcgatg caccctctgt aacggacatg tcatgcgaag taccagcctg cactcactcc   4740
tccgactttg gggcgtcgc catcatcaaa tacacagcta gcaagaaagg taaatgtgca    4800
gtacattcga tgaccaacgc cgttaccatt cgagaagccg acgtagaagt agaggggaac   4860
tcccagctgc aaatatcctt ctcaacagcc ctggcaagcg ccgagtttcg cgtgcaagtg   4920
tgctccacac aagtacactg cgcagccgca tgccaccctc caaaggacca catagtcaat   4980
tacccagcat cacacaccac ccttggggtc caggatatat ccacaacggc aatgtcttgg   5040
gtgcagaaga ttacgggagg agtaggatta attgttgctg ttgctgcctt aattttaatt   5100
gtggtgctat gcgtgtcgtt tagcaggcac taatgatccg gaggggcacc cacttcaagc   5160
tccacttcaa gctctacagc ggaagcacag cagcagcagc agcagcagca gcagcagcag   5220
cacctggagc agctgttgat ggacctacag gagctcctga gcaggatgga gaattacagg   5280
aacctgaaac tccccaggat gctcaccttc aaattttact tgcccaagca ggccacagaa   5340
ttgaaagatc ttcagtgcct agaagatgaa cttggacctc tgcggcatgt tctggatttg   5400
actcaaagca aaagctttca attggaagat gctgagaatt tcatcagcaa tatcagagta   5460
actgttgtaa aactaaaggg ctctgacaac acatttgagt gccaattcga tgatgagtca   5520
gcaactgtgg tggactttct gaggagatgg atagccttct gtcaaagcat catctcaaca   5580
agccctcaag gggatccgc tgtgccttct agttgccagc catctgttgt ttgcccctcc    5640
cccgtgcctt ccttgaccct ggaaggtgcc actcccactg tcctttccta ataaaatgag   5700
gaaattgcat cgcattgtct gagtaggtgt cattctattc tggggggtgg ggtggggcag   5760
```

```
gacagcaagg gggaggattg ggaagacaat agcaggcatg ctggggatgc ggtgggctct   5820
atgggtaccc aggtgctgaa gaattgaccc ggttcctcct gggccagaaa gaagcaggca   5880
catccccttc tctgtgacac accctgtcca cgcccctggt tcttagttcc agccccactc   5940
ataggacact catagctcag gagggctccg ccttcaatcc cacccgctaa agtacttgga   6000
gcggtctctc cctccctcat cagcccacca aaccaaacct agcctccaag agtgggaaga   6060
aattaaagca agataggcta ttaagtgcag agggagagaa aatgcctcca acatgtgagg   6120
aagtaatgag agaaatcata gaattttaag gccatgattt aaggccatca tggcctaagc   6180
ttgaaaggag ataggatcaa agcttggcgt aatcatggtc atagctgttt cctgtgtgaa   6240
attgttatcc gctcacaatt ccacacaaca tacgagccgg aagcataaag tgtaaagcct   6300
ggggtgccta atgagtgagc taactcacat taattgcgtt gcgctcactg cccgctttcc   6360
agtcgggaaa cctgtcgtgc cagctgcatt aatgaatcgg ccaacgcgcg gggagaggcg   6420
gtttgcgtat tgggcgctct tccgcttcct cgctcactga ctcgctgcgc tcggtcgttc   6480
ggctgcggcg agcggtatca gctcactcaa aggcggtaat acggttatcc acagaatcag   6540
gggataacgc aggaaagaac atgtgagcaa aaggccagca aaaggccagg aaccgtaaaa   6600
aggccgcgtt gctggcgttt ttccataggc tccgcccccc tgacgagcat cacaaaaatc   6660
gacgctcaag tcagaggtgg cgaaacccga caggactata aagataccag gcgtttcccc   6720
ctggaagctc cctcgtgcgc tctcctgttc cgaccctgcc gcttaccgga tacctgtccg   6780
cctttctccc ttcgggaagc gtggcgcttt ctcatagctc acgctgtagg tatctcagtt   6840
cggtgtaggt cgttcgctcc aagctgggct gtgtgcacga accccccgtt cagcccgacc   6900
gctgcgcctt atccggtaac tatcgtcttg agtccaaccc ggtaagacac gacttatcgc   6960
cactggcagc agccactggt aacaggatta gcagagcgag gtatgtaggc ggtgctacag   7020
agttcttgaa gtggtggcct aactacggct acactagaag aacagtattt ggtatctgcg   7080
ctctgctgaa gccagttacc ttcggaaaaa gagttggtag ctcttgatcc ggcaaacaaa   7140
ccaccgctgg tagcggtggt ttttttgttt gcaagcagca gattacgcgc agaaaaaaag   7200
gatctcaaga agatcctttg atcttttcta cggggtctga cgctcagtgg aacgaaaact   7260
cacgttaagg gattttggtc atgagattat caaaaaggat cttcacctag atccttttaa   7320
attaaaaatg aagttttaaa tcaatctaaa gtatatatga gtaaacttgg tctgacagtt   7380
accaatgctt aatcagtgag gcacctatct cagcgatctg tctatttcgt tcatccatag   7440
ttgcctgact ccccgtcgtg tagataacta cgatacggga gggcttacca tctggcccca   7500
gtgctgcaat gataccgcga gaaccacgct caccggctcc agatttatca gcaataaacc   7560
agccagccgg aagggccgag cgcagaagtg gtcctgcaac tttatccgcc tccatccagt   7620
ctattaattg ttgccgggaa gctagagtaa gtagttcgcc agttaatagt ttgcgcaacg   7680
ttgttgccat tgctacaggc atcgtggtgt cacgctcgtc gtttggtatg gcttcattca   7740
gctccggttc ccaacgatca aggcgagtta catgatcccc catgttgtgc aaaaaagcgg   7800
ttagctcctt cggtcctccg atcgttgtca gaagtaagtt ggccgcagtg ttatcactca   7860
tggttatggc agcactgcat aattctctta ctgtcatgcc atccgtaaga tgcttttctg   7920
tgactggtga gtactcaacc aagtcattct gagaatagtg tatgcggcga ccgagttgct   7980
cttgcccggc gtcaatacgg gataataccg cgccacatag cagaacttta aaagtgctca   8040
tcattggaaa acgttcttcg gggcgaaaac tctcaaggat cttaccgctg ttgagatcca   8100
```

```
gttcgatgta acccactcgt gcacccaact gatcttcagc atcttttact ttcaccagcg   8160

tttctgggtg agcaaaaaca ggaaggcaaa atgccgcaaa aaagggaata agggcgacac   8220

ggaaatgttg aatactcata ctcttccttt ttcaatatta ttgaagcatt tatcagggtt   8280

attgtctcat gagcggatac atatttgaat gtatttagaa aaataaacaa ataggggttc   8340

cgcgcacatt tccccgaaaa gtgccacctg acgtctaaga aaccattatt atcatgacat   8400

taacctataa aaataggcgt atcacgaggc cctttcgggt cgcgcgtttc ggtgatgacg   8460

gtgaaaacct ctgacacatg cagctcccgt tgacggtcac agcttgtctg taagcggatg   8520

ccgggagcag acaagcccgt cagggcgcgt cagcgggtgt tggcgggtgt cggggctggc   8580

ttaactatgc ggcatcagag cagattgtac tgagagtgca ccataaaatt gtaaacgtta   8640

atattttgtt aaaattcgcg ttaaattttt gttaaatcag ctcatttttt aaccaatagg   8700

ccgaaatcgg caaaatccct tataaatcaa aagaatagcc cgagataggg ttgagtgttg   8760

ttccagtttg gaacaagagt ccactattaa agaacgtgga ctccaacgtc aaagggcgaa   8820

aaaccgtcta tcagggcgat ggcccactac gtgaaccatc acccaaatca agttttttgg   8880

ggtcgaggtg ccgtaaagca ctaaatcgga accctaaagg gagcccccga tttagagctt   8940

gacggggaaa gccggcgaac gtggcgagaa aggaagggaa gaaagcgaaa ggagcgggcg   9000

ctagggcgct ggcaagtgta gcggtcacgc tgcgcgtaac caccacaccc gccgcgctta   9060

atgcgccgct acagggcgcg tactatggtt gctttgacgt atgcggtgtg aaataccgca   9120

cagatgcgta aggagaaaat accgcatcag gcgccattcg ccattcaggc tgcgcaactg   9180

ttgggaaggg cgatcggtgc gggcctcttc gctattacgc cagctggcga aaggggggatg  9240

tgctgcaagg cgattaagtt gggtaacgcc agggttttcc cagtcacgac gttgtaaaac   9300

gacggccagt gaattccatg gtctcaactt tc                                 9332
```

<210> SEQ ID NO 101
<211> LENGTH: 1303
<212> TYPE: PRT
<213> ORGANISM: Artificial Sequence
<220> FEATURE:
<223> OTHER INFORMATION: Synthetic CHIKV viral structural protein containing CSP antigen 74 in E2 and E3 (74 dual)

<400> SEQUENCE: 101

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140
```

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp Ser Leu Ala Leu Pro Val Leu Cys Leu Leu Ala
260 265 270

Asn Thr Thr Phe Pro Cys Ser Gln Pro Pro Cys Thr Pro Cys Cys Tyr
275 280 285

Glu Lys Glu Pro Glu Ser Thr Leu Arg Met Leu Glu Asp Asn Val Met
290 295 300

Arg Pro Gly Tyr Tyr Gln Leu Leu Lys Ala Ser Leu Thr Cys Ser Pro
305 310 315 320

His Ser Gly Gly Asn Pro Asn Ala Asn Pro Asn Ala Asn Pro Asn Ala
325 330 335

Asn Pro Asn Ala Asn Pro Asn Ala Asn Pro Asn Ala Gly Gly Ser Ser
340 345 350

Thr Lys Asp Asn Phe Asn Val Tyr Lys Ala Thr Arg Pro Tyr Leu Ala
355 360 365

His Cys Pro Asp Cys Gly Glu Gly His Ser Cys His Ser Pro Ile Ala
370 375 380

Leu Glu Arg Ile Arg Asn Glu Ala Thr Asp Gly Thr Leu Lys Ile Gln
385 390 395 400

Val Ser Leu Gln Ile Gly Ile Lys Thr Asp Asp Ser His Asp Trp Thr
405 410 415

Lys Leu Arg Tyr Met Asp Ser His Thr Pro Ala Asp Ala Glu Arg Ala
420 425 430

Gly Leu Leu Val Arg Thr Ser Ala Pro Cys Thr Ile Thr Gly Thr Met
435 440 445

Gly His Phe Ile Leu Ala Arg Cys Pro Lys Gly Glu Thr Leu Thr Val
450 455 460

Gly Phe Thr Asp Ser Arg Lys Ile Ser His Thr Cys Thr His Pro Phe
465 470 475 480

His His Glu Pro Pro Val Ile Gly Arg Glu Arg Phe His Ser Arg Pro
485 490 495

Gln His Gly Lys Glu Leu Pro Cys Ser Thr Tyr Val Gln Ser Thr Ala
500 505 510

Ala Thr Ala Glu Glu Ile Glu Val His Met Pro Pro Asp Thr Pro Asp
515 520 525

Arg Thr Leu Met Thr Gln Gln Ser Gly Asn Val Lys Ile Thr Val Asn
530 535 540

Gly Gln Thr Val Arg Tyr Lys Cys Asn Cys Gly Gly Ser Gly Gly Asn
545 550 555 560

-continued

```
Pro Asn Ala Asn Pro Asn Ala Asn Pro Asn Ala Asn Pro Asn Ala Asn
                565                 570                 575

Pro Asn Ala Asn Pro Asn Ala Gly Gly Ser Asn Glu Gly Leu Thr Thr
            580                 585                 590

Thr Asp Lys Val Ile Asn Asn Cys Lys Ile Asp Gln Cys His Ala Ala
        595                 600                 605

Val Thr Asn His Lys Asn Trp Gln Tyr Asn Ser Pro Leu Val Pro Arg
    610                 615                 620

Asn Ala Glu Leu Gly Asp Arg Lys Gly Lys Ile His Ile Pro Phe Pro
625                 630                 635                 640

Leu Ala Asn Val Thr Cys Arg Val Pro Lys Ala Arg Asn Pro Thr Val
                645                 650                 655

Thr Tyr Gly Lys Asn Gln Val Thr Met Leu Leu Tyr Pro Asp His Pro
            660                 665                 670

Thr Leu Leu Ser Tyr Arg Asn Met Gly Gln Glu Pro Asn Tyr His Glu
        675                 680                 685

Glu Trp Val Thr His Lys Lys Glu Val Thr Leu Thr Val Pro Thr Glu
    690                 695                 700

Gly Leu Glu Val Thr Trp Gly Asn Asn Glu Pro Tyr Lys Tyr Trp Pro
705                 710                 715                 720

Gln Met Ser Thr Asn Gly Thr Ala His Gly His Pro His Glu Ile Ile
                725                 730                 735

Leu Tyr Tyr Tyr Glu Leu Tyr Pro Thr Met Thr Val Val Ile Val Ser
            740                 745                 750

Val Ala Ser Phe Val Leu Leu Ser Met Val Gly Thr Ala Val Gly Met
        755                 760                 765

Cys Val Cys Ala Arg Arg Arg Cys Ile Thr Pro Tyr Glu Leu Thr Pro
    770                 775                 780

Gly Ala Thr Val Pro Phe Leu Leu Ser Leu Leu Cys Cys Val Arg Thr
785                 790                 795                 800

Thr Lys Ala Ala Thr Tyr Tyr Glu Ala Ala Ala Tyr Leu Trp Asn Glu
                805                 810                 815

Gln Gln Pro Leu Phe Trp Leu Gln Ala Leu Ile Pro Leu Ala Ala Leu
            820                 825                 830

Ile Val Leu Cys Asn Cys Leu Lys Leu Leu Pro Cys Cys Cys Lys Thr
        835                 840                 845

Leu Ala Phe Leu Ala Val Met Ser Ile Gly Ala His Thr Val Ser Ala
    850                 855                 860

Tyr Glu His Val Thr Val Ile Pro Asn Thr Val Gly Val Pro Tyr Lys
865                 870                 875                 880

Thr Leu Val Asn Arg Pro Gly Tyr Ser Pro Met Val Leu Glu Met Glu
                885                 890                 895

Leu Gln Ser Val Thr Leu Glu Pro Thr Leu Ser Leu Asp Tyr Ile Thr
            900                 905                 910

Cys Glu Tyr Lys Thr Val Ile Pro Ser Pro Tyr Val Lys Cys Cys Gly
        915                 920                 925

Thr Ala Glu Cys Lys Asp Lys Ser Leu Pro Asp Tyr Ser Cys Lys Val
    930                 935                 940

Phe Thr Gly Val Tyr Pro Phe Met Trp Gly Gly Ala Tyr Cys Phe Cys
945                 950                 955                 960

Asp Ala Glu Asn Thr Gln Leu Ser Glu Ala His Val Glu Lys Ser Glu
                965                 970                 975

Ser Cys Lys Thr Glu Phe Ala Ser Ala Tyr Arg Ala His Thr Ala Ser
```

```
            980                 985                 990

Ala Ser Ala Lys Leu Arg Val Leu  Tyr Gln Gly Asn Asn  Ile Thr Val
        995                 1000                1005

Ala Ala  Tyr Ala Asn Gly Asp  His Ala Val Thr Val  Lys Asp Ala
    1010                 1015                 1020

Lys Phe  Val Val Gly Pro Met  Ser Ser Ala Trp Thr  Pro Phe Asp
    1025                 1030                 1035

Asn Lys  Ile Val Val Tyr Lys  Gly Asp Val Tyr Asn  Met Asp Tyr
    1040                 1045                 1050

Pro Pro  Phe Gly Ala Gly Arg  Pro Gly Gln Phe Gly  Asp Ile Gln
    1055                 1060                 1065

Ser Arg  Thr Pro Glu Ser Lys  Asp Val Tyr Ala Asn  Thr Gln Leu
    1070                 1075                 1080

Val Leu  Gln Arg Pro Ala Ala  Gly Thr Val His Val  Pro Tyr Ser
    1085                 1090                 1095

Gln Ala  Pro Ser Gly Phe Lys  Tyr Trp Leu Lys Glu  Arg Gly Ala
    1100                 1105                 1110

Ser Leu  Gln His Thr Ala Pro  Phe Gly Cys Gln Ile  Ala Thr Asn
    1115                 1120                 1125

Pro Val  Arg Ala Val Asn Cys  Ala Val Gly Asn Ile  Pro Ile Ser
    1130                 1135                 1140

Ile Asp  Ile Pro Asp Ala Ala  Phe Thr Arg Val Val  Asp Ala Pro
    1145                 1150                 1155

Ser Val  Thr Asp Met Ser Cys  Glu Val Pro Ala Cys  Thr His Ser
    1160                 1165                 1170

Ser Asp  Phe Gly Gly Val Ala  Ile Ile Lys Tyr Thr  Ala Ser Lys
    1175                 1180                 1185

Lys Gly  Lys Cys Ala Val His  Ser Met Thr Asn Ala  Val Thr Ile
    1190                 1195                 1200

Arg Glu  Ala Asp Val Glu Val  Glu Gly Asn Ser Gln  Leu Gln Ile
    1205                 1210                 1215

Ser Phe  Ser Thr Ala Leu Ala  Ser Ala Glu Phe Arg  Val Gln Val
    1220                 1225                 1230

Cys Ser  Thr Gln Val His Cys  Ala Ala Ala Cys His  Pro Pro Lys
    1235                 1240                 1245

Asp His  Ile Val Asn Tyr Pro  Ala Ser His Thr Thr  Leu Gly Val
    1250                 1255                 1260

Gln Asp  Ile Ser Thr Thr Ala  Met Ser Trp Val Gln  Lys Ile Thr
    1265                 1270                 1275

Gly Gly  Val Gly Leu Ile Val  Ala Val Ala Ala Leu  Ile Leu Ile
    1280                 1285                 1290

Val Val  Leu Cys Val Ser Phe  Ser Arg His
    1295                 1300
```

<210> SEQ ID NO 102
<211> LENGTH: 8972
<212> TYPE: DNA
<213> ORGANISM: Artificial Sequence
<220> FEATURE:
<223> OTHER INFORMATION: Synthetic Expression vector for CHIKV viral structural protein containing CSP antigen 74 in E2 and E3 (74 dual) (CHIKV 74.74.58)

<400> SEQUENCE: 102

```
gaattcccat tgcatacgtt gtatccatat cataatatgt acatttatat tggctcatgt     60
```

-continued

```
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttgcggccg ctctagacac catggagttc atcccgacgc aaactttcta taacagaagg    900
taccaacccc gaccctgggc cccacgccct acaattcaag taattagacc tagaccacgt    960
ccacagaggc aggctgggca actcgcccag ctgatctccg cagtcaacaa attgaccatg   1020
cgcgcggtac ctcaacagaa gcctcgcaga aatcggaaaa acaagaagca aaggcagaag   1080
aagcaggcgc cgcaaaacga cccaaagcaa aagaagcaac caccacaaaa gaagccggct   1140
caaaagaaga agaaaccagg ccgtagggag agaatgtgca tgaaaattga aaatgattgc   1200
atcttcgaag tcaagcatga aggcaaagtg atgggctacg catgcctggt ggggggataaa   1260
gtaatgaaac cagcacatgt gaagggaact atcgacaatg ccgatctggc taaactggcc   1320
tttaagcggt cgtctaaata cgatcttgaa tgtgcacaga taccggtgca catgaagtct   1380
gatgcctcga agtttaccca cgagaaaccc gaggggtact ataactggca tcacggagca   1440
gtgcagtatt caggaggccg gttcactatc ccgacgggtg caggcaagcc gggagacagc   1500
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggaaacccga atgccaatcc caacgcgaac   1860
cccaatgcta acccaaatgc caacccaaac gccaacccca acgctggtgg atccagtact   1920
aaggacaatt ttaatgtcta taaagccaca agaccatatc tagctcattg tcctgactgc   1980
ggagaagggc attcgtgcca cagccctatc gcattggagc gcatcagaaa tgaagcaacg   2040
gacggaacgc tgaaaatcca ggtctctttg cagatcggga taaagacaga tgacagccac   2100
gattggacca agctgcgcta tatggatagc catacgcccg cggacgcgga gcgagccgga   2160
ttgcttgtaa ggacttcagc accgtgcacg atcaccggga ccatgggaca ctttattctc   2220
gcccgatgcc cgaaaggaga gacgctgaca gtgggattta cggacagcag aaagatcagc   2280
cacacatgca cacacccgtt ccatcatgaa ccacctgtga taggtaggga gaggttccac   2340
tctcgaccac aacatggtaa agagttacct tgcagcacgt acgtgcagag caccgctgcc   2400
actgctgagg agatagaggt gcatatgccc ccagatactc ctgaccgcac gctgatgacg   2460
```

-continued

```
cagcagtctg gcaacgtgaa gatcacagtt aatgggcaga cggtgcggta caagtgcaac   2520
tgcggtggct ccggaggaaa cccgaatgcc aatcccaacg cgaaccccaa tgctaaccca   2580
aatgccaacc caaacgccaa ccccaacgct ggtggatcca acgagggact gacaaccaca   2640
gacaaagtga tcaataactg caaaattgat cagtgccatg ctgcagtcac taatcacaag   2700
aattggcaat acaactcccc tttagtcccg cgcaacgctg aactcgggga ccgtaaagga   2760
aagatccaca tcccattccc attggcaaac gtgacttgca gagtgccaaa agcaagaaac   2820
cctacagtaa cttacggaaa aaaccaagtc accatgctgc tgtatcctga ccatccgaca   2880
ctcttgtctt accgtaacat gggacaggaa ccaaattacc acgaggagtg ggtgacacac   2940
aagaaggagg ttaccttgac cgtgcctact gagggtctgg aggtcacttg gggcaacaac   3000
gaaccataca agtactggcc gcagatgtct acgaacggta ctgctcatgg tcacccacat   3060
gagataatct tgtactatta tgagctgtac cccactatga ctgtagtcat tgtgtcggtg   3120
gcctcgttcg tgcttctgtc gatggtgggc acagcagtgg gaatgtgtgt gtgcgcacgg   3180
cgcagatgca ttacaccata tgaattaaca ccaggagcca ctgttccctt cctgctcagc   3240
ctgctatgct gcgtcagaac gaccaaggcg gccacatatt acgaggctgc ggcatatcta   3300
tggaacgaac agcagcccct gttctggttg caggctctta tcccgctggc cgccttgatc   3360
gtcctgtgca actgtctgaa actcttgcca tgctgctgta agaccctggc tttttagcc    3420
gtaatgagca tcggtgccca cactgtgagc gcgtacgaac acgtaacagt gatcccgaac   3480
acggtgggag taccgtataa gactcttgtc aacagaccgg gttacagccc catggtgttg   3540
gagatggagc tacaatcagt caccttggaa ccaacactgt cacttgacta catcacgtgc   3600
gagtacaaaa ctgtcatccc ctccccgtac gtgaagtgct gtggtacagc agagtgcaag   3660
gacaagagcc taccagacta cagctgcaag gtctttactg gagtctaccc atttatgtgg   3720
ggcggcgcct actgcttttg cgacgccgaa aatacgcaat tgagcgaggc acatgtagag   3780
aaatctgaat cttgcaaaac agagtttgca tcggcctaca gagcccacac cgcatcggcg   3840
tcggcgaagc tccgcgtcct ttaccaagga aacaacatta ccgtagctgc ctacgctaac   3900
ggtgaccatg ccgtcacagt aaaggacgcc aagtttgtcg tgggcccaat gtcctccgcc   3960
tggacacctt ttgacaacaa aatcgtggtg tacaaaggcg acgtctacaa catggactac   4020
ccaccttttg gcgcaggaag accaggacaa tttggtgaca ttcaaagtcg tacaccggaa   4080
agtaaagacg tttatgccaa cactcagttg gtactacaga ggccagcagc aggcacggta   4140
catgtaccat actctcaggc accatctggc ttcaagtatt ggctgaagga acgaggagca   4200
tcgctacagc acacggcacc gttcggttgc cagattgcga caaacccggt aagagctgta   4260
aattgcgctg tggggaacat accaatttcc atcgacatac cggatgcggc ctttactagg   4320
gttgtcgatg caccctctgt aacggacatg tcatgcgaag taccagcctg cactcactcc   4380
tccgactttg gggcgtcgc catcatcaaa tacacagcta gcaagaaagg taaatgtgca    4440
gtacattcga tgaccaacgc cgttaccatt cgagaagccg acgtagaagt agaggggaac   4500
tcccagctgc aaatatcctt ctcaacagcc ctggcaagcg ccgagtttcg cgtgcaagtg   4560
tgctccacac aagtacactg cgcagccgca tgccaccctc caaaggacca catagtcaat   4620
tacccagcat cacacaccac ccttggggtc caggatatat ccacaacggc aatgtcttgg   4680
gtgcagaaga ttacgggagg agtaggatta attgttgctg ttgctgcctt aattttaatt   4740
gtggtgctat gcgtgtcgtt tagcaggcac taatgatccg gaggggcacc cacttcaagc   4800
```

-continued

```
tccacttcaa gctctacagc ggaagcacag cagcagcagc agcagcagca gcagcagcag   4860
cacctggagc agctgttgat ggacctacag gagctcctga gcaggatgga gaattacagg   4920
aacctgaaac tccccaggat gctcaccttc aaattttact tgcccaagca ggccacagaa   4980
ttgaaagatc ttcagtgcct agaagatgaa cttggacctc tgcggcatgt tctggatttg   5040
actcaaagca aaagctttca attggaagat gctgagaatt tcatcagcaa tatcagagta   5100
actgttgtaa aactaaaggg ctctgacaac acatttgagt gccaattcga tgatgagtca   5160
gcaactgtgg tggactttct gaggagatgg atagccttct gtcaaagcat catctcaaca   5220
agccctcaag gggatccgc tgtgccttct agttgccagc catctgttgt ttgcccctcc   5280
cccgtgcctt ccttgaccct ggaaggtgcc actcccactg tcctttccta ataaaatgag   5340
gaaattgcat cgcattgtct gagtaggtgt cattctattc tggggggtgg ggtggggcag   5400
gacagcaagg gggaggattg ggaagacaat agcaggcatg ctggggatgc ggtgggctct   5460
atgggtaccc aggtgctgaa gaattgaccc ggttcctcct gggccagaaa gaagcaggca   5520
catccccttc tctgtgacac accctgtcca cgcccctggt tcttagttcc agccccactc   5580
ataggacact catagctcag gagggctccg ccttcaatcc cacccgctaa agtacttgga   5640
gcggtctctc cctccctcat cagcccacca aaccaaacct agcctccaag agtgggaaga   5700
aattaaagca agataggcta ttaagtgcag agggagagaa aatgcctcca acatgtgagg   5760
aagtaatgag agaaatcata gaattttaag gccatgattt aaggccatca tggcctaagc   5820
ttgaaaggag ataggatcaa agcttggcgt aatcatggtc atagctgttt cctgtgtgaa   5880
attgttatcc gctcacaatt ccacacaaca tacgagccgg aagcataaag tgtaaagcct   5940
ggggtgccta atgagtgagc taactcacat taattgcgtt gcgctcactg cccgctttcc   6000
agtcgggaaa cctgtcgtgc cagctgcatt aatgaatcgg ccaacgcgcg gggagaggcg   6060
gtttgcgtat tgggcgctct tccgcttcct cgctcactga ctcgctgcgc tcggtcgttc   6120
ggctgcggcg agcggtatca gctcactcaa aggcggtaat acggttatcc acagaatcag   6180
gggataacgc aggaaagaac atgtgagcaa aaggccagca aaaggccagg aaccgtaaaa   6240
aggccgcgtt gctggcgttt ttccataggc tccgcccccc tgacgagcat cacaaaaatc   6300
gacgctcaag tcagaggtgg cgaaacccga caggactata aagataccag gcgtttcccc   6360
ctggaagctc cctcgtgcgc tctcctgttc cgaccctgcc gcttaccgga tacctgtccg   6420
cctttctccc ttcgggaagc gtggcgcttt ctcatagctc acgctgtagg tatctcagtt   6480
cggtgtaggt cgttcgctcc aagctgggct gtgtgcacga accccccgtt cagcccgacc   6540
gctgcgcctt atccggtaac tatcgtcttg agtccaaccc ggtaagacac gacttatcgc   6600
cactggcagc agccactggt aacaggatta gcagagcgag gtatgtaggc ggtgctacag   6660
agttcttgaa gtggtggcct aactacggct acactagaag aacagtattt ggtatctgcg   6720
ctctgctgaa gccagttacc ttcggaaaaa gagttggtag ctcttgatcc ggcaaacaaa   6780
ccaccgctgg tagcggtggt ttttttgttt gcaagcagca gattacgcgc agaaaaaaag   6840
gatctcaaga agatcctttg atcttttcta cggggtctga cgctcagtgg aacgaaaact   6900
cacgttaagg gattttggtc atgagattat caaaaaggat cttcacctag atccttttaa   6960
attaaaaatg aagttttaaa tcaatctaaa gtatatatga gtaaacttgg tctgacagtt   7020
accaatgctt aatcagtgag gcacctatct cagcgatctg tctatttcgt tcatccatag   7080
ttgcctgact ccccgtcgtg tagataacta cgatacggga gggcttacca tctggcccca   7140
gtgctgcaat gataccgcga gaaccacgct caccggctcc agatttatca gcaataaacc   7200
```

agccagccgg aagggccgag cgcagaagtg gtcctgcaac tttatccgcc tccatccagt 7260
ctattaattg ttgccgggaa gctagagtaa gtagttcgcc agttaatagt ttgcgcaacg 7320
ttgttgccat tgctacaggc atcgtggtgt cacgctcgtc gtttggtatg gcttcattca 7380
gctccggttc ccaacgatca aggcgagtta catgatcccc catgttgtgc aaaaaagcgg 7440
ttagctcctt cggtcctccg atcgttgtca gaagtaagtt ggccgcagtg ttatcactca 7500
tggttatggc agcactgcat aattctctta ctgtcatgcc atccgtaaga tgcttttctg 7560
tgactggtga gtactcaacc aagtcattct gagaatagtg tatgcggcga ccgagttgct 7620
cttgcccggc gtcaatacgg gataataccg cgccacatag cagaacttta aaagtgctca 7680
tcattggaaa acgttcttcg gggcgaaaac tctcaaggat cttaccgctg ttgagatcca 7740
gttcgatgta acccactcgt gcacccaact gatcttcagc atcttttact ttcaccagcg 7800
tttctgggtg agcaaaaaca ggaaggcaaa atgccgcaaa aaagggaata agggcgacac 7860
ggaaatgttg aatactcata ctcttccttt ttcaatatta ttgaagcatt tatcagggtt 7920
attgtctcat gagcggatac atatttgaat gtatttagaa aaataaacaa ataggggttc 7980
cgcgcacatt tccccgaaaa gtgccacctg acgtctaaga aaccattatt atcatgacat 8040
taacctataa aaataggcgt atcacgaggc cctttcgggt cgcgcgtttc ggtgatgacg 8100
gtgaaaacct ctgacacatg cagctcccgt tgacggtcac agcttgtctg taagcggatg 8160
ccgggagcag acaagcccgt cagggcgcgt cagcgggtgt tggcgggtgt cggggctggc 8220
ttaactatgc ggcatcagag cagattgtac tgagagtgca ccataaaatt gtaaacgtta 8280
atattttgtt aaaattcgcg ttaaattttt gttaaatcag ctcatttttt aaccaatagg 8340
ccgaaatcgg caaaatccct tataaatcaa aagaatagcc cgagataggg ttgagtgttg 8400
ttccagtttg gaacaagagt ccactattaa agaacgtgga ctccaacgtc aaagggcgaa 8460
aaaccgtcta tcagggcgat ggcccactac gtgaaccatc acccaaatca agttttttgg 8520
ggtcgaggtg ccgtaaagca ctaaatcgga accctaaagg gagcccccga tttagagctt 8580
gacggggaaa gccggcgaac gtggcgagaa aggaagggaa gaaagcgaaa ggagcgggcg 8640
ctagggcgct ggcaagtgta gcggtcacgc tgcgcgtaac caccacaccc gccgcgctta 8700
atgcgccgct acagggcgcg tactatggtt gctttgacgt atgcggtgtg aaataccgca 8760
cagatgcgta aggagaaaat accgcatcag gcgccattcg ccattcaggc tgcgcaactg 8820
ttgggaaggg cgatcggtgc gggcctcttc gctattacgc cagctggcga aaggggggatg 8880 tgctgcaagg cgattaagtt gggtaacgcc agggttttcc cagtcacgac gttgtaaaac 8940
gacggccagt gaattccatg gtctcaactt tc 8972

<210> SEQ ID NO 103
<211> LENGTH: 1367
<212> TYPE: PRT
<213> ORGANISM: Artificial Sequence
<220> FEATURE:
<223> OTHER INFORMATION: Synthetic CHIKV viral structural protein
      containing CSP antigen 76 in E2 and E3 (76 Dual)

<400> SEQUENCE: 103

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val

```
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Ser Gly Gly Asn Pro Asn Ala Asn Pro Asn Ala Asn Pro Asn Ala
                325                 330                 335

Asn Pro Asn Ala Asn Pro Asn Ala Asn Pro Asn Ala Asn Pro Asn Ala
            340                 345                 350

Asn Pro Asn Ala Asn Pro Asn Ala Asn Pro Asn Ala Asn Pro Asn Ala
        355                 360                 365

Asn Pro Asn Ala Asn Pro Asn Ala Asn Pro Asn Ala Gly Gly Ser Ser
    370                 375                 380

Thr Lys Asp Asn Phe Asn Val Tyr Lys Ala Thr Arg Pro Tyr Leu Ala
385                 390                 395                 400

His Cys Pro Asp Cys Gly Glu Gly His Ser Cys His Ser Pro Ile Ala
                405                 410                 415

Leu Glu Arg Ile Arg Asn Glu Ala Thr Asp Gly Thr Leu Lys Ile Gln
            420                 425                 430

Val Ser Leu Gln Ile Gly Ile Lys Thr Asp Asp Ser His Asp Trp Thr
        435                 440                 445

Lys Leu Arg Tyr Met Asp Ser His Thr Pro Ala Asp Ala Glu Arg Ala
    450                 455                 460
```

-continued

```
Gly Leu Leu Val Arg Thr Ser Ala Pro Cys Thr Ile Thr Gly Thr Met
465                 470                 475                 480

Gly His Phe Ile Leu Ala Arg Cys Pro Lys Gly Glu Thr Leu Thr Val
                485                 490                 495

Gly Phe Thr Asp Ser Arg Lys Ile Ser His Thr Cys Thr His Pro Phe
            500                 505                 510

His His Glu Pro Pro Val Ile Gly Arg Glu Arg Phe His Ser Arg Pro
        515                 520                 525

Gln His Gly Lys Glu Leu Pro Cys Ser Thr Tyr Val Gln Ser Thr Ala
    530                 535                 540

Ala Thr Ala Glu Glu Ile Glu Val His Met Pro Pro Asp Thr Pro Asp
545                 550                 555                 560

Arg Thr Leu Met Thr Gln Gln Ser Gly Asn Val Lys Ile Thr Val Asn
                565                 570                 575

Gly Gln Thr Val Arg Tyr Lys Cys Asn Cys Gly Gly Ser Gly Gly Asn
            580                 585                 590

Pro Asn Ala Asn Pro Asn Ala Asn Pro Asn Ala Asn Pro Asn Ala Asn
        595                 600                 605

Pro Asn Ala Asn Pro Asn Ala Asn Pro Asn Ala Asn Pro Asn Ala Asn
    610                 615                 620

Pro Asn Ala Asn Pro Asn Ala Asn Pro Asn Ala Asn Pro Asn Ala Asn
625                 630                 635                 640

Pro Asn Ala Asn Pro Asn Ala Gly Gly Ser Asn Glu Gly Leu Thr Thr
                645                 650                 655

Thr Asp Lys Val Ile Asn Asn Cys Lys Ile Asp Gln Cys His Ala Ala
            660                 665                 670

Val Thr Asn His Lys Asn Trp Gln Tyr Asn Ser Pro Leu Val Pro Arg
        675                 680                 685

Asn Ala Glu Leu Gly Asp Arg Lys Gly Lys Ile His Ile Pro Phe Pro
    690                 695                 700

Leu Ala Asn Val Thr Cys Arg Val Pro Lys Ala Arg Asn Pro Thr Val
705                 710                 715                 720

Thr Tyr Gly Lys Asn Gln Val Thr Met Leu Leu Tyr Pro Asp His Pro
                725                 730                 735

Thr Leu Leu Ser Tyr Arg Asn Met Gly Gln Glu Pro Asn Tyr His Glu
            740                 745                 750

Glu Trp Val Thr His Lys Lys Glu Val Thr Leu Thr Val Pro Thr Glu
        755                 760                 765

Gly Leu Glu Val Thr Trp Gly Asn Asn Glu Pro Tyr Lys Tyr Trp Pro
    770                 775                 780

Gln Met Ser Thr Asn Gly Thr Ala His Gly His Pro His Glu Ile Ile
785                 790                 795                 800

Leu Tyr Tyr Tyr Glu Leu Tyr Pro Thr Met Thr Val Val Ile Val Ser
                805                 810                 815

Val Ala Ser Phe Val Leu Leu Ser Met Val Gly Thr Ala Val Gly Met
            820                 825                 830

Cys Val Cys Ala Arg Arg Arg Cys Ile Thr Pro Tyr Glu Leu Thr Pro
        835                 840                 845

Gly Ala Thr Val Pro Phe Leu Leu Ser Leu Leu Cys Cys Val Arg Thr
    850                 855                 860

Thr Lys Ala Ala Thr Tyr Tyr Glu Ala Ala Ala Tyr Leu Trp Asn Glu
865                 870                 875                 880
```

-continued

```
Gln Gln Pro Leu Phe Trp Leu Gln Ala Leu Ile Pro Leu Ala Ala Leu
                885                 890                 895

Ile Val Leu Cys Asn Cys Leu Lys Leu Leu Pro Cys Cys Cys Lys Thr
            900                 905                 910

Leu Ala Phe Leu Ala Val Met Ser Ile Gly Ala His Thr Val Ser Ala
        915                 920                 925

Tyr Glu His Val Thr Val Ile Pro Asn Thr Val Gly Val Pro Tyr Lys
    930                 935                 940

Thr Leu Val Asn Arg Pro Gly Tyr Ser Pro Met Val Leu Glu Met Glu
945                 950                 955                 960

Leu Gln Ser Val Thr Leu Glu Pro Thr Leu Ser Leu Asp Tyr Ile Thr
                965                 970                 975

Cys Glu Tyr Lys Thr Val Ile Pro Ser Pro Tyr Val Lys Cys Cys Gly
            980                 985                 990

Thr Ala Glu Cys Lys Asp Lys Ser  Leu Pro Asp Tyr Ser  Cys Lys Val
        995                 1000                1005

Phe Thr  Gly Val Tyr Pro Phe  Met Trp Gly Gly Ala  Tyr Cys Phe
    1010                1015                1020

Cys Asp  Ala Glu Asn Thr Gln  Leu Ser Glu Ala His  Val Glu Lys
    1025                1030                1035

Ser Glu  Ser Cys Lys Thr Glu  Phe Ala Ser Ala Tyr  Arg Ala His
    1040                1045                1050

Thr Ala  Ser Ala Ser Ala Lys  Leu Arg Val Leu Tyr  Gln Gly Asn
    1055                1060                1065

Asn Ile  Thr Val Ala Ala Tyr  Ala Asn Gly Asp His  Ala Val Thr
    1070                1075                1080

Val Lys  Asp Ala Lys Phe Val  Val Gly Pro Met Ser  Ser Ala Trp
    1085                1090                1095

Thr Pro  Phe Asp Asn Lys Ile  Val Val Tyr Lys Gly  Asp Val Tyr
    1100                1105                1110

Asn Met  Asp Tyr Pro Pro Phe  Gly Ala Gly Arg Pro  Gly Gln Phe
    1115                1120                1125

Gly Asp  Ile Gln Ser Arg Thr  Pro Glu Ser Lys Asp  Val Tyr Ala
    1130                1135                1140

Asn Thr  Gln Leu Val Leu Gln  Arg Pro Ala Ala Gly  Thr Val His
    1145                1150                1155

Val Pro  Tyr Ser Gln Ala Pro  Ser Gly Phe Lys Tyr  Trp Leu Lys
    1160                1165                1170

Glu Arg  Gly Ala Ser Leu Gln  His Thr Ala Pro Phe  Gly Cys Gln
    1175                1180                1185

Ile Ala  Thr Asn Pro Val Arg  Ala Val Asn Cys Ala  Val Gly Asn
    1190                1195                1200

Ile Pro  Ile Ser Ile Asp Ile  Pro Asp Ala Ala Phe  Thr Arg Val
    1205                1210                1215

Val Asp  Ala Pro Ser Val Thr  Asp Met Ser Cys Glu  Val Pro Ala
    1220                1225                1230

Cys Thr  His Ser Ser Asp Phe  Gly Gly Val Ala Ile  Ile Lys Tyr
    1235                1240                1245

Thr Ala  Ser Lys Lys Gly Lys  Cys Ala Val His Ser  Met Thr Asn
    1250                1255                1260

Ala Val  Thr Ile Arg Glu Ala  Asp Val Glu Val Glu  Gly Asn Ser
    1265                1270                1275

Gln Leu  Gln Ile Ser Phe Ser  Thr Ala Leu Ala Ser  Ala Glu Phe
```

```
    1280                1285                1290

Arg Val  Gln Val Cys Ser Thr  Gln Val His Cys Ala  Ala Ala Cys
    1295                1300                1305

His Pro  Pro Lys Asp His Ile  Val Asn Tyr Pro Ala  Ser His Thr
    1310                1315                1320

Thr Leu  Gly Val Gln Asp Ile  Ser Thr Thr Ala Met  Ser Trp Val
    1325                1330                1335

Gln Lys  Ile Thr Gly Gly Val  Gly Leu Ile Val Ala  Val Ala Ala
    1340                1345                1350

Leu Ile  Leu Ile Val Val Leu  Cys Val Ser Phe Ser  Arg His
    1355                1360                1365


<210> SEQ ID NO 104
<211> LENGTH: 9164
<212> TYPE: DNA
<213> ORGANISM: Artificial Sequence
<220> FEATURE:
<223> OTHER INFORMATION: Synthetic Expression vector for CHIKV viral
      structural protein containing CSP antigen 76 in E2 and E3
      (76.76.58)

<400> SEQUENCE: 104

gaattcccat tgcatacgtt gtatccatat cataatatgt acatttatat tggctcatgt     60

ccaacattac cgccatgttg acattgatta ttgactagtt attaatagta atcaattacg    120

gggtcattag ttcatagccc atatatggag ttccgcgtta cataacttac ggtaaatggc    180

ccgcctggct gaccgcccaa cgacccccgc ccattgacgt caataatgac gtatgttccc    240

atagtaacgc caatagggac tttccattga cgtcaatggg tggagtattt acggtaaact    300

gcccacttgg cagtacatca agtgtatcat atgccaagta cgccccctat tgacgtcaat    360

gacggtaaat ggcccgcctg gcattatgcc cagtacatga ccttatggga ctttcctact    420

tggcagtaca tctacgtatt agtcatcgct attaccatgg tgatgcggtt ttggcagtac    480

atcaatgggc gtggatagcg gtttgactca cggggatttc caagtctcca ccccattgac    540

gtcaatggga gtttgttttg gcaccaaaat caacgggact ttccaaaatg tcgtaacaac    600

tccgccccat tgacgcaaat gggcggtagg cgtgtacggt gggaggtcta tataagcaga    660

gctcgtttag tgaaccgtca gatcgcctgg agacgccatc cacgctgttt tgacctccat    720

agaagacacc gggaccgatc cagcctccgt taacggtgga gggcagtgta gtctgagcag    780

tactcgttgc tgccgcgcgc gccaccagac ataatagctg acagactaac agactgttcc    840

tttgcggccg ctctagacac catggagttc atcccgacgc aaactttcta taacagaagg    900

taccaacccc gaccctgggc cccacgccct acaattcaag taattagacc tagaccacgt    960

ccacagaggc aggctgggca actcgcccag ctgatctccg cagtcaacaa attgaccatg   1020

cgcgcggtac ctcaacagaa gcctcgcaga aatcggaaaa acaagaagca aaggcagaag   1080

aagcaggcgc cgcaaaacga cccaaagcaa aagaagcaac caccacaaaa gaagccggct   1140

caaaagaaga agaaaccagg ccgtagggag agaatgtgca tgaaaattga aaatgattgc   1200

atcttcgaag tcaagcatga aggcaaagtg atgggctacg catgcctggt gggggataaa   1260

gtaatgaaac cagcacatgt gaagggaact atcgacaatg ccgatctggc taaactggcc   1320

tttaagcggt cgtctaaata cgatcttgaa tgtgcacaga taccggtgca catgaagtct   1380

gatgcctcga agtttaccca cgagaaaccc gaggggtact ataactggca tcacggagca   1440

gtgcagtatt caggaggccg gttcactatc ccgacgggtg caggcaagcc gggagacagc   1500
```

-continued

```
ggcagaccga tcttcgacaa caaaggacgg gtggtggcca tcgtcctagg aggggccaac   1560
gaaggtgccc gcacggccct ctccgtggtg acgtggaaca aagacatcgt cacaaaaatt   1620
acccctgagg gagccgaaga gtggagcctc gccctcccgg tcttgtgcct gttggcaaac   1680
actacattcc cctgctctca gccgccttgc acaccctgct gctacgaaaa ggaaccggaa   1740
agcaccttgc gcatgcttga ggacaacgtg atgagacccg gatactacca gctactaaaa   1800
gcatcgctga cttgctctcc ccactccgga ggcaacccca acgccaaccc taatgccaat   1860
cccaacgcta atcccaatgc taaccctaac gcaaatccaa atgcaaaccc caatgccaac   1920
ccaaacgcta accctaacgc caaccctaac gcaaacccaa acgccaatcc taatgctaac   1980
ccaaatgcaa accctaatgc tggcggatcc agtactaagg acaattttaa tgtctataaa   2040
gccacaagac catatctagc tcattgtcct gactgcggag aagggcattc gtgccacagc   2100
cctatcgcat tggagcgcat cagaaatgaa gcaacggacg gaacgctgaa aatccaggtc   2160
tctttgcaga tcgggataaa gacagatgac agccacgatt ggaccaagct gcgctatatg   2220
gatagccata cgcccgcgga cgcggagcga gccggattgc ttgtaaggac ttcagcaccg   2280
tgcacgatca ccgggaccat gggacacttt attctcgccc gatgcccgaa aggagagacg   2340
ctgacagtgg gatttacgga cagcagaaag atcagccaca catgcacaca cccgttccat   2400
catgaaccac ctgtgatagg tagggagagg ttccactctc gaccacaaca tggtaaagag   2460
ttaccttgca gcacgtacgt gcagagcacc gctgccactg ctgaggagat agaggtgcat   2520
atgcccccag atactcctga ccgcacgctg atgacgcagc agtctggcaa cgtgaagatc   2580
acagttaatg ggcagacggt gcggtacaag tgcaactgcg gtggctccgg aggcaacccc   2640
aacgccaacc ctaatgccaa tcccaacgct aatcccaatg ctaaccctaa cgcaaatcca   2700
aatgcaaacc ccaatgccaa cccaaacgct aaccctaacg ccaaccctaa cgcaaaccca   2760
aacgccaatc ctaatgctaa cccaaatgca aaccctaatg ctggcggatc caacgaggga   2820
ctgacaacca cagacaaagt gatcaataac tgcaaaattg atcagtgcca tgctgcagtc   2880
actaatcaca agaattggca atacaactcc cctttagtcc cgcgcaacgc tgaactcggg   2940
gaccgtaaag gaaagatcca catcccattc ccattggcaa acgtgacttg cagagtgcca   3000
aaagcaagaa accctacagt aacttacgga aaaaaccaag tcaccatgct gctgtatcct   3060
gaccatccga cactcttgtc ttaccgtaac atgggacagg aaccaaatta ccacgaggag   3120
tgggtgacac acaagaagga ggttaccttg accgtgccta ctgagggtct ggaggtcact   3180
tggggcaaca acgaaccata caagtactgg ccgcagatgt ctacgaacgg tactgctcat   3240
ggtcacccac atgagataat cttgtactat tatgagctgt accccactat gactgtagtc   3300
attgtgtcgg tggcctcgtt cgtgcttctg tcgatggtgg gcacagcagt gggaatgtgt   3360
gtgtgcgcac ggcgcagatg cattacacca tatgaattaa caccaggagc cactgttccc   3420
ttcctgctca gcctgctatg ctgcgtcaga acgaccaagg cggccacata ttacgaggct   3480
gcggcatatc tatggaacga acagcagccc ctgttctggt tgcaggctct tatcccgctg   3540
gccgccttga tcgtcctgtg caactgtctg aaactcttgc catgctgctg taagaccctg   3600
gctttttttag ccgtaatgag catcggtgcc cacactgtga gcgcgtacga acacgtaaca   3660
gtgatcccga acacggtggg agtaccgtat aagactcttg tcaacagacc gggttacagc   3720
cccatggtgt tggagatgga gctacaatca gtcaccttgg aaccaacact gtcacttgac   3780
tacatcacgt gcgagtacaa aactgtcatc ccctccccgt acgtgaagtg ctgtggtaca   3840
gcagagtgca aggacaagag cctaccagac tacagctgca aggtctttac tggagtctac   3900
```

```
ccatttatgt ggggcggcgc ctactgcttt tgcgacgccg aaaatacgca attgagcgag   3960
gcacatgtag agaaatctga atcttgcaaa acagagtttg catcggccta cagagcccac   4020
accgcatcgg cgtcggcgaa gctccgcgtc ctttaccaag gaaacaacat taccgtagct   4080
gcctacgcta acggtgacca tgccgtcaca gtaaaggacg ccaagtttgt cgtgggccca   4140
atgtcctccg cctggacacc ttttgacaac aaaatcgtgg tgtacaaagg cgacgtctac   4200
aacatggact acccaccttt tggcgcagga agaccaggac aatttggtga cattcaaagt   4260
cgtacaccgg aaagtaaaga cgtttatgcc aacactcagt tggtactaca gaggccagca   4320
gcaggcacgg tacatgtacc atactctcag gcaccatctg gcttcaagta ttggctgaag   4380
gaacgaggag catcgctaca gcacacggca ccgttcggtt gccagattgc gacaaacccg   4440
gtaagagctg taaattgcgc tgtggggaac ataccaattt ccatcgacat accggatgcg   4500
gcctttacta gggttgtcga tgcaccctct gtaacggaca tgtcatgcga agtaccagcc   4560
tgcactcact cctccgactt tgggggcgtc gccatcatca aatacacagc tagcaagaaa   4620
ggtaaatgtg cagtacattc gatgaccaac gccgttacca ttcgagaagc cgacgtagaa   4680
gtagagggga actcccagct gcaaatatcc ttctcaacag ccctggcaag cgccgagttt   4740
cgcgtgcaag tgtgctccac acaagtacac tgcgcagccg catgccaccc tccaaaggac   4800
cacatagtca attacccagc atcacacacc acccttgggg tccaggatat atccacaacg   4860
gcaatgtctt gggtgcagaa gattacggga ggagtaggat taattgttgc tgttgctgcc   4920
ttaattttaa ttgtggtgct atgcgtgtcg tttagcaggc actaatgatc cggaggggca   4980
cccacttcaa gctccacttc aagctctaca gcggaagcac agcagcagca gcagcagcag   5040
cagcagcagc agcacctgga gcagctgttg atggacctac aggagctcct gagcaggatg   5100
gagaattaca ggaacctgaa actccccagg atgctcacct tcaaatttta cttgcccaag   5160
caggccacag aattgaaaga tcttcagtgc ctagaagatg aacttggacc tctgcggcat   5220
gttctggatt tgactcaaag caaaagcttt caattggaag atgctgagaa tttcatcagc   5280
aatatcagag taactgttgt aaaactaaag ggctctgaca acacatttga gtgccaattc   5340
gatgatgagt cagcaactgt ggtggacttt ctgaggagat ggatagcctt ctgtcaaagc   5400
atcatctcaa caagccctca agggggatcc gctgtgcctt ctagttgcca gccatctgtt   5460
gtttgcccct cccccgtgcc ttccttgacc ctggaaggtg ccactcccac tgtcctttcc   5520
taataaaatg aggaaattgc atcgcattgt ctgagtaggt gtcattctat tctggggggt   5580
ggggtggggc aggacagcaa gggggaggat tgggaagaca atagcaggca tgctggggat   5640
gcggtgggct ctatgggtac ccaggtgctg aagaattgac ccggttcctc ctgggccaga   5700
aagaagcagg cacatcccct tctctgtgac acaccctgtc cacgcccctg gttcttagtt   5760
ccagccccac tcataggaca ctcatagctc aggagggctc cgccttcaat cccacccgct   5820
aaagtacttg gagcggtctc tccctccctc atcagcccac caaaccaaac ctagcctcca   5880
agagtgggaa gaaattaaag caagataggc tattaagtgc agagggagag aaaatgcctc   5940
caacatgtga ggaagtaatg agagaaatca tagaatttta aggccatgat ttaaggccat   6000
catggcctaa gcttgaaagg agataggatc aaagcttggc gtaatcatgg tcatagctgt   6060
ttcctgtgtg aaattgttat ccgctcacaa ttccacacaa catacgagcc ggaagcataa   6120
agtgtaaagc ctggggtgcc taatgagtga gctaactcac attaattgcg ttgcgctcac   6180
tgcccgcttt ccagtcggga aacctgtcgt gccagctgca ttaatgaatc ggccaacgcg   6240
```

-continued

```
cggggagagg cggtttgcgt attgggcgct cttccgcttc ctcgctcact gactcgctgc   6300
gctcggtcgt tcggctgcgg cgagcggtat cagctcactc aaaggcggta atacggttat   6360
ccacagaatc aggggataac gcaggaaaga acatgtgagc aaaaggccag caaaaggcca   6420
ggaaccgtaa aaaggccgcg ttgctggcgt ttttccatag gctccgcccc cctgacgagc   6480
atcacaaaaa tcgacgctca agtcagaggt ggcgaaaccc gacaggacta taaagatacc   6540
aggcgtttcc ccctggaagc tccctcgtgc gctctcctgt tccgaccctg ccgcttaccg   6600
gatacctgtc cgcctttctc ccttcgggaa gcgtggcgct ttctcatagc tcacgctgta   6660
ggtatctcag ttcggtgtag gtcgttcgct ccaagctggg ctgtgtgcac gaaccccccg   6720
ttcagcccga ccgctgcgcc ttatccggta actatcgtct tgagtccaac ccggtaagac   6780
acgacttatc gccactggca gcagccactg gtaacaggat tagcagagcg aggtatgtag   6840
gcggtgctac agagttcttg aagtggtggc ctaactacgg ctacactaga agaacagtat   6900
ttggtatctg cgctctgctg aagccagtta ccttcggaaa aagagttggt agctcttgat   6960
ccggcaaaca aaccaccgct ggtagcggtg gtttttttgt ttgcaagcag cagattacgc   7020
gcagaaaaaa aggatctcaa gaagatcctt tgatcttttc tacggggtct gacgctcagt   7080
ggaacgaaaa ctcacgttaa gggattttgg tcatgagatt atcaaaaagg atcttcacct   7140
agatcctttt aaattaaaaa tgaagtttta aatcaatcta aagtatatat gagtaaactt   7200
ggtctgacag ttaccaatgc ttaatcagtg aggcacctat ctcagcgatc tgtctatttc   7260
gttcatccat agttgcctga ctccccgtcg tgtagataac tacgatacgg gagggcttac   7320
catctggccc cagtgctgca atgataccgc gagaaccacg ctcaccggct ccagatttat   7380
cagcaataaa ccagccagcc ggaagggccg agcgcagaag tggtcctgca actttatccg   7440
cctccatcca gtctattaat tgttgccggg aagctagagt aagtagttcg ccagttaata   7500
gtttgcgcaa cgttgttgcc attgctacag gcatcgtggt gtcacgctcg tcgtttggta   7560
tggcttcatt cagctccggt tcccaacgat caaggcgagt tacatgatcc cccatgttgt   7620
gcaaaaaagc ggttagctcc ttcggtcctc cgatcgttgt cagaagtaag ttggccgcag   7680
tgttatcact catggttatg gcagcactgc ataattctct tactgtcatg ccatccgtaa   7740
gatgcttttc tgtgactggt gagtactcaa ccaagtcatt ctgagaatag tgtatgcggc   7800
gaccgagttg ctcttgcccg gcgtcaatac gggataatac cgcgccacat agcagaactt   7860
taaaagtgct catcattgga aaacgttctt cggggcgaaa actctcaagg atcttaccgc   7920
tgttgagatc cagttcgatg taacccactc gtgcacccaa ctgatcttca gcatctttta   7980
ctttcaccag cgtttctggg tgagcaaaaa caggaaggca aaatgccgca aaaaagggaa   8040
taagggcgac acggaaatgt tgaatactca tactcttcct ttttcaatat tattgaagca   8100
tttatcaggg ttattgtctc atgagcggat acatatttga atgtatttag aaaaataaac   8160
aaataggggt tccgcgcaca tttccccgaa aagtgccacc tgacgtctaa gaaaccatta   8220
ttatcatgac attaacctat aaaaataggc gtatcacgag gccctttcgg gtcgcgcgtt   8280
tcggtgatga cggtgaaaac ctctgacaca tgcagctccc ggtgacggtc acagcttgtc   8340
tgtaagcgga tgccgggagc agacaagccc gtcagggcgc gtcagcgggt gttggcgggt   8400
gtcggggctg gcttaactat gcggcatcag agcagattgt actgagagtg caccataaaa   8460
ttgtaaacgt taatattttg ttaaaattcg cgttaaattt ttgttaaatc agctcatttt   8520
ttaaccaata ggccgaaatc ggcaaaatcc cttataaatc aaaagaatag cccgagatag   8580
ggttgagtgt tgttccagtt tggaacaaga gtccactatt aaagaacgtg gactccaacg   8640
```

tcaaagggcg aaaaaccgtc tatcagggcg atggcccact acgtgaacca tcacccaaat 8700
caagtttttt ggggtcgagg tgccgtaaag cactaaatcg gaaccctaaa gggagccccc 8760
gatttagagc ttgacgggga aagccggcga acgtggcgag aaaggaaggg aagaaagcga 8820
aaggagcggg cgctagggcg ctggcaagtg tagcggtcac gctgcgcgta accaccacac 8880
ccgccgcgct taatgcgccg ctacagggcg cgtactatgg ttgctttgac gtatgcggtg 8940
tgaaataccg cacagatgcg taaggagaaa ataccgcatc aggcgccatt cgccattcag 9000
gctgcgcaac tgttgggaag ggcgatcggt gcgggcctct tcgctattac gccagctggc 9060
gaaaggggga tgtgctgcaa ggcgattaag ttgggtaacg ccagggtttt cccagtcacg 9120
acgttgtaaa acgacggcca gtgaattcca tggtctcaac tttc 9164

<210> SEQ ID NO 105
<211> LENGTH: 33
<212> TYPE: PRT
<213> ORGANISM: Artificial Sequence
<220> FEATURE:
<223> OTHER INFORMATION: Synthetic DISC1_451 antigen with linker

<400> SEQUENCE: 105

Ser Gly Gly Leu Leu Ile Gln Ser Leu Gln Leu Gln Glu Ala Arg Gly
1 5 10 15

Glu Leu Ser Val Glu Asp Glu Arg Gln Met Asp Asp Leu Glu Gly Gly
20 25 30

Ser

<210> SEQ ID NO 106
<211> LENGTH: 24
<212> TYPE: PRT
<213> ORGANISM: Artificial Sequence
<220> FEATURE:
<223> OTHER INFORMATION: Synthetic DISC1_452 antigen with linker

<400> SEQUENCE: 106

Ser Gly Gly Glu Ala Arg Gly Glu Leu Ser Val Glu Asp Glu Arg Gln
1 5 10 15

Met Asp Asp Leu Glu Gly Gly Ser
20

<210> SEQ ID NO 107
<211> LENGTH: 15
<212> TYPE: PRT
<213> ORGANISM: Artificial Sequence
<220> FEATURE:
<223> OTHER INFORMATION: Synthetic DISC1_454 antigen with linker

<400> SEQUENCE: 107

Ser Gly Gly Glu Ala Arg Gly Glu Leu Ser Val Glu Gly Gly Ser
1 5 10 15

<210> SEQ ID NO 108
<211> LENGTH: 18
<212> TYPE: PRT
<213> ORGANISM: Artificial Sequence
<220> FEATURE:
<223> OTHER INFORMATION: Synthetic HER2 antigen with linker

<400> SEQUENCE: 108

Ser Gly Gly Val Thr Tyr Asn Thr Asp Thr Phe Glu Ser Met Pro Gly
1 5 10 15

Gly Ser

<210> SEQ ID NO 109
<211> LENGTH: 16
<212> TYPE: PRT
<213> ORGANISM: Artificial Sequence
<220> FEATURE:
<223> OTHER INFORMATION: Synthetic HER2 antigen with linker

<400> SEQUENCE: 109

Ser Gly Gly Glu Tyr Val Asn Ala Arg His Cys Leu Pro Gly Gly Ser
1 5 10 15

<210> SEQ ID NO 110
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 110

Ser Gly Gly Tyr Val Asn Ala Arg His Cys Leu Gly Gly Ser
1 5 10

<210> SEQ ID NO 111
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 111

Ser Gly Gly Tyr Val Asn Ala Arg His Gly Leu Gly Gly Ser
1 5 10

<210> SEQ ID NO 112
<211> LENGTH: 20
<212> TYPE: PRT
<213> ORGANISM: Artificial Sequence
<220> FEATURE:
<223> OTHER INFORMATION: Synthetic HER2 antigen with linker

<400> SEQUENCE: 112

Ser Gly Gly Lys Phe Pro Asp Glu Glu Gly Ala Cys Gln Pro Cys Pro
1 5 10 15

Ile Gly Gly Ser
20

<210> SEQ ID NO 113
<211> LENGTH: 17
<212> TYPE: PRT
<213> ORGANISM: Artificial Sequence
<220> FEATURE:
<223> OTHER INFORMATION: Synthetic HER2 antigen with linker

<400> SEQUENCE: 113

Ser Gly Gly Lys Phe Pro Asp Glu Glu Gly Ala Cys Gln Pro Gly Gly
1 5 10 15

Ser

<210> SEQ ID NO 114
<211> LENGTH: 13
<212> TYPE: PRT
<213> ORGANISM: Artificial Sequence
<220> FEATURE:
<223> OTHER INFORMATION: Synthetic HER2 antigen with linker

<400> SEQUENCE: 114

Ser Gly Gly Lys Asp Pro Pro Phe Cys Val Gly Gly Ser
1 5 10

<210> SEQ ID NO 115
<211> LENGTH: 15
<212> TYPE: PRT
<213> ORGANISM: Artificial Sequence
<220> FEATURE:
<223> OTHER INFORMATION: Synthetic HER2 antigen with linker

<400> SEQUENCE: 115

Ser Gly Gly Tyr Lys Asp Pro Pro Phe Cys Val Ala Gly Gly Ser
1 5 10 15

<210> SEQ ID NO 116
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 116

Ser Gly Gly Tyr Lys Asp Pro Pro Phe Cys Val Gly Gly Ser
1 5 10

<210> SEQ ID NO 117
<211> LENGTH: 99
<212> TYPE: DNA
<213> ORGANISM: Artificial Sequence
<220> FEATURE:
<223> OTHER INFORMATION: Synthetic DISC1_451 with linker

<400> SEQUENCE: 117
tccggagggc tgctgatcca gtctctgcag ctgcaggaag ccagaggcga gctgagcgtg 60
gaagatgagc ggcagatgga cgacctggaa gggggatcc 99

<210> SEQ ID NO 118
<211> LENGTH: 72
<212> TYPE: DNA
<213> ORGANISM: Artificial Sequence
<220> FEATURE:
<223> OTHER INFORMATION: Synthetic DISC1_452 with linker

<400> SEQUENCE: 118
tccggagggg aagccagagg cgagctgagc gtggaagatg agcggcagat ggacgacctg 60
gaagggggat cc 72

<210> SEQ ID NO 119
<211> LENGTH: 45
<212> TYPE: DNA
<213> ORGANISM: Artificial Sequence
<220> FEATURE:
<223> OTHER INFORMATION: Synthetic DISC1_454 with linker

<400> SEQUENCE: 119
tccggagggg aagccagagg cgagctgagc gtggaagggg gatcc 45

<210> SEQ ID NO 120
<211> LENGTH: 63
<212> TYPE: DNA
<213> ORGANISM: Artificial Sequence
<220> FEATURE:
<223> OTHER INFORMATION: Synthetic hHER2 antigen with linker

<400> SEQUENCE: 120
aaaaaatccg gaggcgtcac ctacaacaca gacacgtttg agtccatgcc cggcggatcc 60
aaa 63

<210> SEQ ID NO 121
<211> LENGTH: 51
<212> TYPE: DNA
<213> ORGANISM: Artificial Sequence
<220> FEATURE:
<223> OTHER INFORMATION: Synthetic hHER2 antigen with linker

<400> SEQUENCE: 121
aaaaaatccg gaggctatgt gaatgccagg cactgtttgg gcggatccaa a 51

<210> SEQ ID NO 122
<211> LENGTH: 51
<212> TYPE: DNA
<213> ORGANISM: Artificial Sequence
<220> FEATURE:
<223> OTHER INFORMATION: Synthetic HER2 antigen with linker

<400> SEQUENCE: 122
aaaaaatccg gaggctatgt gaatgccagg cacggtttgg gcggatccaa a 51

<210> SEQ ID NO 123
<211> LENGTH: 69
<212> TYPE: DNA
<213> ORGANISM: artificial sequence
<220> FEATURE:
<223> OTHER INFORMATION: Synthetic HER2 antigen with linker

<400> SEQUENCE: 123
aaaaaatccg gaggcaagtt tccagatgag gagggcgcat gccagccttg ccccatcggc 60
ggatccaaa 69

<210> SEQ ID NO 124
<211> LENGTH: 60
<212> TYPE: DNA
<213> ORGANISM: Artificial Sequence
<220> FEATURE:
<223> OTHER INFORMATION: Synthetic HER2 antigen

<400> SEQUENCE: 124
aaaaaatccg gaggcaagtt tccagatgag gagggcgcat gccagcctgg cggatccaaa 60

<210> SEQ ID NO 125
<211> LENGTH: 48
<212> TYPE: DNA
<213> ORGANISM: Artificial Sequence
<220> FEATURE:
<223> OTHER INFORMATION: Synthetic HER2 antigen with linker

<400> SEQUENCE: 125
aaaaaatccg gaggcaagga ccctcccttc tgcgtgggcg gatccaaa 48

<210> SEQ ID NO 126
<211> LENGTH: 54
<212> TYPE: DNA
<213> ORGANISM: Artificial Sequence
<220> FEATURE:
<223> OTHER INFORMATION: Synthetic HER2 antigen with linker

<400> SEQUENCE: 126
aaaaaatccg gaggctataa ggaccctccc ttctgcgtgg cgggcggatc caaa 54

<210> SEQ ID NO 127
<211> LENGTH: 51
<212> TYPE: DNA
<213> ORGANISM: Artificial Sequence
<220> FEATURE:
<223> OTHER INFORMATION: Synthetic HER2 antigen with linker

<400> SEQUENCE: 127
aaaaaatccg gaggctataa ggaccctccc ttctgcgtgg gcggatccaa a 51

<210> SEQ ID NO 128
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 128

Ser Gly Gly Tyr Val Asn Ala Arg His Gly Leu Gly Gly Ser
1 5 10

<210> SEQ ID NO 129
<211> LENGTH: 18
<212> TYPE: PRT
<213> ORGANISM: Artificial Sequence
<220> FEATURE:
<223> OTHER INFORMATION: Synthetic HER2 antigen with linker

<400> SEQUENCE: 129

Ser Gly Gly Cys Gly Tyr Val Asn Ala Arg His Gly Leu Gly Cys Gly
1 5 10 15

Gly Ser

<210> SEQ ID NO 130
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 130

Ser Gly Gly Tyr Lys Asp Pro Pro Phe Cys Val Gly Gly Ser
1 5 10

<210> SEQ ID NO 131
<211> LENGTH: 14
<212> TYPE: PRT
<213> ORGANISM: Artificial Sequence
<220> FEATURE:
<223> OTHER INFORMATION: Synthetic HER2 antigen with linker

<400> SEQUENCE: 131

Ser Gly Gly Tyr Lys Asp Pro Pro Phe Gly Val Gly Gly Ser
1 5 10

<210> SEQ ID NO 132
<211> LENGTH: 14
<212> TYPE: PRT
<213> ORGANISM: Artificial Sequence
<220> FEATURE:
<223> OTHER INFORMATION: Synthetic hBTLA antigen with linker

<400> SEQUENCE: 132

Ser Gly Gly Cys Lys Leu Asn Gly Thr Thr Cys Gly Gly Ser 1 5 10

<210> SEQ ID NO 133
<211> LENGTH: 20
<212> TYPE: PRT
<213> ORGANISM: Artificial Sequence
<220> FEATURE:
<223> OTHER INFORMATION: Synthetic hHVEM antigen

<400> SEQUENCE: 133

Ser Gly Gly Cys Val Lys Glu Ala Ser Gly Glu Leu Thr Gly Thr Val
1 5 10 15

Cys Gly Gly Ser
20

<210> SEQ ID NO 134
<211> LENGTH: 25
<212> TYPE: PRT
<213> ORGANISM: Artificial Sequence
<220> FEATURE:
<223> OTHER INFORMATION: Synthetic hHVEM antigen with linker

<400> SEQUENCE: 134

Ser Gly Gly Cys Tyr Arg Val Lys Glu Ala Ser Gly Glu Leu Thr Gly
1 5 10 15

Thr Val Ser Glu Pro Cys Gly Gly Ser
20 25

<210> SEQ ID NO 135
<211> LENGTH: 19
<212> TYPE: PRT
<213> ORGANISM: Artificial Sequence
<220> FEATURE:
<223> OTHER INFORMATION: Synthetic hHVEM antigen with linker

<400> SEQUENCE: 135

Ser Gly Gly Cys Ser Arg Asn Ser Ser Arg Thr Glu Asn Ala Val Cys
1 5 10 15

Gly Gly Ser

<210> SEQ ID NO 136
<211> LENGTH: 21
<212> TYPE: PRT
<213> ORGANISM: Artificial Sequence
<220> FEATURE:
<223> OTHER INFORMATION: Synthetic hHVEM antigen with linker

<400> SEQUENCE: 136

Ser Gly Gly Cys Gln Met Ser Asp Pro Ala Met Gly Leu Arg Ser Arg
1 5 10 15

Asn Cys Gly Gly Ser
20

<210> SEQ ID NO 137
<211> LENGTH: 61
<212> TYPE: PRT
<213> ORGANISM: Artificial Sequence
<220> FEATURE:
<223> OTHER INFORMATION: Synthetic CHIKV OPY-1 strain 6K sequence

<400> SEQUENCE: 137

Ala Thr Tyr Gln Glu Ala Ala Ile Tyr Leu Trp Asn Glu Gln Gln Pro
1 5 10 15

Leu Phe Trp Leu Gln Ala Leu Ile Pro Leu Ala Ala Leu Ile Val Leu

```
            20                  25                  30

Cys Asn Cys Leu Arg Leu Leu Pro Cys Cys Cys Lys Thr Leu Ala Phe
        35                  40                  45

Leu Ala Val Met Ser Val Gly Ala His Thr Val Ser Ala
    50                  55                  60


<210> SEQ ID NO 138
<211> LENGTH: 61
<212> TYPE: PRT
<213> ORGANISM: Artificial Sequence
<220> FEATURE:
<223> OTHER INFORMATION: Synthetic CHIKV 37997 strain 6K sequence

<400> SEQUENCE: 138

Ala Thr Tyr Tyr Glu Ala Ala Ala Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Lys Leu Leu Pro Cys Cys Cys Lys Thr Leu Ala Phe
        35                  40                  45

Leu Ala Val Met Ser Ile Gly Ala His Thr Val Ser Ala
    50                  55                  60


<210> SEQ ID NO 139
<211> LENGTH: 56
<212> TYPE: PRT
<213> ORGANISM: Artificial Sequence
<220> FEATURE:
<223> OTHER INFORMATION: Synthetic VEEV TC-83 strain 6K sequence

<400> SEQUENCE: 139

Glu Thr Thr Trp Glu Ser Leu Asp His Leu Trp Asn Asn Asn Gln Gln
1               5                   10                  15

Met Phe Trp Ile Gln Leu Leu Ile Pro Leu Ala Ala Leu Ile Val Val
            20                  25                  30

Thr Arg Leu Leu Arg Cys Val Cys Cys Val Val Pro Phe Leu Val Met
        35                  40                  45

Ala Gly Ala Ala Gly Ala Gly Ala
    50                  55


<210> SEQ ID NO 140
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(4)
<223> OTHER INFORMATION: amino acid residues 1 to 4 may repeat 4 to 30
      times

<400> SEQUENCE: 140

Asn Pro Asn Ala
1


<210> SEQ ID NO 141
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 141
```

Asp Asp Asp Asp Lys
1 5

<210> SEQ ID NO 142
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 142

Asn Pro Asn Ala
1

<210> SEQ ID NO 143
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 143

Arg Xaa Xaa Arg
1

<210> SEQ ID NO 144
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 144

Gln Gly Pro Gly Ala Pro
1 5

<210> SEQ ID NO 145
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 145

Ala Asn Gly Ala Gly Asn Gln Pro Gly
1 5

<210> SEQ ID NO 146
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 146

Asn Ala Ala Gly
1

<210> SEQ ID NO 147
<211> LENGTH: 4
<212> TYPE: PRT
<213> ORGANISM: Artificial Sequence
<220> FEATURE:

<223> OTHER INFORMATION: Synthetic peptide sequence

<400> SEQUENCE: 147

Ser Gly Ser Gly
1

<210> SEQ ID NO 148
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 148

Arg Lys Arg Arg
1

<210> SEQ ID NO 149
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 149

Thr Arg Gly Gly Ser
1 5

<210> SEQ ID NO 150
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 150

Arg Gln Arg Arg
1

<210> SEQ ID NO 151
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 151

Ser Gly Gly Gly Ser
1 5

<210> SEQ ID NO 152
<211> LENGTH: 4
<212> TYPE: PRT
<213> ORGANISM: Artificial Sequence
<220> FEATURE:
<223> OTHER INFORMATION: Synthetic peptide

<400> SEQUENCE: 152

Ile Asp Gly Arg
1

<210> SEQ ID NO 153
<211> LENGTH: 4
<212> TYPE: PRT
<213> ORGANISM: Artificial Sequence
<220> FEATURE:
<223> OTHER INFORMATION: Synthetic peptide sequence -continued

```
<400> SEQUENCE: 153

Ile Glu Gly Arg
1


<210> SEQ ID NO 154
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 154

Asn Ala Asn Pro
1
```

VIRUS LIKE PARTICLE COMPRISING MODIFIED ENVELOPE PROTEIN E3

CROSS REFERENCE TO RELATED APPLICATIONS

This application is a continuation-in-part of U.S. application Ser. No. 14/820,785 filed Aug. 7, 2015 (now U.S. Pat. No. 9,969,986), which claims the benefit of U.S. Provisional Applications No. 62/035,037 filed Aug. 8, 2014, No. 62/079,128 filed Nov. 13, 2014, No. 62/101,514 filed Jan. 9, 2015, No. 62/120,569 filed Feb. 25, 2015 and 62/198,949 filed Jul. 30, 2015. The contents of those non-provisional application and 5 provisional applications are herein incorporated by reference.

TECHNICAL FIELD

The present application relates to a virus like particle comprising a modified envelope protein E3, and use thereof.

BACKGROUND ART

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination.

Up to now, VLP-based vaccines have been produced for more than 30 different viruses that infect human and other animals. The examples include AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, JC polyomavirus, Marburg, MS2, IPCV (Indian peanut clump virus), NDV (Newcastle disease virus), No (Norovirus) Nv (Norwalk virus), PhMV (Physalis mottle virus), Polyomavirus, PPV (Porcine parvovirus), RHDV (Rabbit hemorrhagic disease virus), Rotavirus, SARS, SIV (Simian immunodeficiency virus), SV40 (Simian virus 40), SVDV (Swine vesicular disease virus) and so on. (Expert Rev. Vaccines 9(10), 1149-1176, 2010).

To quickly generate large quantity of VLPs or vaccines for both pre-clinical and clinical trials, almost all drug development will face the same challenging obstacle of rapidly generating a high stable producer. Developing and identifying a stable cell line is a critical part of the development. However, to generate a stable cell line with high titer and good product quality is not so easily accomplished until now.

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya viral structural proteins which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF INVENTION

According to the present application, followings are provided:

(1) A virus like particle comprising a viral structural protein which comprises modified envelope protein E3.

(2) The virus like particle according to (1), wherein the viral structural protein is derived from alphavirus or flavivirus.

(3) The virus like particle according to (2), wherein the viral structural protein is derived from Chikungunya virus or Venezuelan equine encephalitis virus.

(4) The virus like particle according to (3), wherein the virus like particle is derived from Chikungunya virus strain 37997 or strain OPY-1, or Venezuelan equine encephalitis virus strain TC-83.

(5) The virus like particle according to any one of (1)-(4), wherein one or more amino acid residues in the envelope protein E3 are replaced, added and/or deleted in amino acid sequence of the viral structural protein.

(6) The virus like particle according to (5), wherein one or more amino acid residues are replaced, added and/or deleted in amino acid sequence at furin site in the envelope protein E3.

(7) The virus like particle according to any one of (1)-(6), wherein the viral structural protein comprises capsid, envelope protein E1, envelope protein E2 and envelope protein E3.

(8) The virus like particle according to any one of (1)-(7), wherein an at least one antigen is inserted into the envelope protein E3.

(9) The virus like particle according to (8), wherein the at least one antigen is further inserted into the envelope protein E2.

(10) The virus like particle according to (8) or (9), wherein the at least one antigen is inserted between residues corresponding to 321 and 326 of SEQ ID NO: 1, residues 321 and 326 of SEQ ID NO: 2 or residues 330 and 335 of SEQ ID NO: 3.

(11) The virus like particle according to any one of (8)-(10), wherein the at least one antigen is derived from *Plasmodium falciparum* circumsporozoite protein, PD-1, PD-L1, CTLA-4, DISC1, IL-2, HER2, BTLA or HVEM.

(12) The virus like particle according to (11), wherein a peptide selected from (NPNA)n (n=4-30) (SEQ ID NO:

140), amino acid sequence represented by SEQ ID Nos.6-9 and 15-29 is inserted into the envelope E3 protein.

(13) The virus like particle according to any one of (8)-(12), wherein the virus like particle is Chikungunya virus like particle comprises the following amino acid sequences or an amino acid sequence having 90% or more identity to the following sequences:

a capsid which consists of an amino acid sequence represented by SEQ ID NO: 31 or SEQ ID NO: 75;

an E1 which consists of an amino acid sequence represented by SEQ ID NO: 32 or SEQ ID NO: 76; and a complex of E2 and E3 which consists of an amino acid sequence represented by SEQ ID NO: 33 or SEQ ID NO: 77, wherein an amino acid sequence of the at least one antigen is inserted between residues corresponding to residues 321 and 326 of SEQ ID NO: 2.

(14) The virus like particle according to any one of (8)-(12), wherein the virus like particle is Venezuelan equine encephalitis virus like particle comprises the following amino acid sequences or an amino acid sequence having 90% or more identity to the following sequences:

a capsid which consists of an amino acid sequence represented by SEQ ID NO: 35;

an E1 which consists of an amino acid sequence represented by SEQ ID NO: 36; and a complex of E2 and E3 which consists of an amino acid sequence represented by SEQ ID NO: 37, wherein an amino acid sequence of the at least one antigen is inserted between residues corresponding to the residues 330 and 335 of SEQ ID NO: 3.

(15) The virus like particle according to any one of (8)-(12), wherein the virus like particle is Chikungunya virus like particle and the structure of the virus like particle comprises any one of the following sequences (1)-(4) or an amino acid sequence having 90% or more identity to any one of the following sequences (1)-(4):

(1)

an E1 which consists of an amino acid sequence represented by SEQ ID NO: 32;

a complex of E2 and E3 into which a malaria antigen is inserted, which consists of an amino acid sequence represented by SEQ ID NO: 46; and and a capsid which consists of an amino acid sequence represented by SEQ ID NO: 31;

(2)

an E1 which consists of an amino acid sequence represented by SEQ ID NO: 32;

a complex of E2 and E3 into which a PD-1 antigen is inserted, which consists of an amino acid sequence represented by SEQ ID NO: 47; and a capsid which consists of an amino acid sequence represented by SEQ ID NO: 31;

(3)

an E1 which consists of an amino acid sequence represented by SEQ ID NO: 32;

a complex of E2 and E3 into which a PD-L1 ligand antigen is inserted, which consists of an amino acid sequence represented by SEQ ID NO: 48; and a capsid which consists of an amino acid sequence represented by SEQ ID NO: 31; or (4)

an E1 which consists of an amino acid sequence represented by SEQ ID NO: 32;

a complex of E2 and E3 into which a CTLA-4 antigen is inserted, which consists of an amino acid sequence represented by SEQ ID NO: 49; and a capsid which consists of an amino acid sequence represented by SEQ ID NO: 31.

(16) The virus like particle according to any one of (8)-(12), wherein the virus like particle is Venezuelan equine encephalitis virus like particle and the structure of the virus like particle comprises any one of the following sequences (1)-(4) or an amino acid sequence having 90% or more identity to any one of the following sequences (1)-(4):

(1)

an E1 which consists of an amino acid sequence represented by SEQ ID NO: 36;

a complex of E2 and E3 into which a malaria antigen is inserted, which consists of an amino acid sequence represented by SEQ ID NO: 50; and a capsid which consists of an amino acid sequence represented by SEQ ID NO: 35;

(2)

an E1 which consists of an amino acid sequence represented by SEQ ID NO: 36;

a complex of E2 and E3 into which a PD-1 antigen is inserted, which consists of an amino acid sequence represented by SEQ ID NO: 51; and a capsid which consists of an amino acid sequence represented by SEQ ID NO: 35;

(3)

an E1 which consists of an amino acid sequence represented by SEQ ID NO: 36;

a complex of E2 and E3 into which a PD-L1 antigen is inserted, which consists of an amino acid sequence represented by SEQ ID NO: 52; and a capsid which consists of an amino acid sequence represented by SEQ ID NO: 35; or (4)

an E1 which consists of an amino acid sequence represented by SEQ ID NO: 36;

a complex of E2 and E3 into which a CTLA-4 antigen is inserted, which consists of an amino acid sequence represented by SEQ ID NO: 53; and a capsid which consists of an amino acid sequence represented by SEQ ID NO: 35.

(17) The virus like particle according to any one of (1)-(5), wherein furin cleavage site located in envelope protein E3 is altered or mutated to prevent the furin site from cleaving.

(18). An isolated nucleic acid molecule comprising a nucleotide sequence encoding the virus like particle according to any one of (1)-(17).

(19) An isolated nucleic acid molecule consisting of a nucleotide sequence which has a sequence identity of 90% or more with a nucleotide sequence represented by any one of SEQ ID Nos.38-45.

(20) The nucleic acid molecule according to (19), wherein the nucleic acid molecule consists of a nucleotide sequence represented by any one of SEQ ID Nos.:38-45.

(21) A vector comprising the nucleic acid molecule according to any one of (18)-(20), wherein the vector optionally comprises an expression control sequence operably linked to the nucleic acid molecule.

(22) A vector comprising a nucleic acid molecule which comprises:

a nucleotide sequence represented by SEQ ID NO: 54 or SEQ ID NO: 55, wherein a nucleotide sequence encoding at least one antigen is inserted between residues 963 and 969 of SEQ ID NO: 54 or between residues 990 and 1006 of SEQ ID NO: 55; and an expression control sequence operably linked to the nucleic acid molecule.

(23) A pharmaceutical composition comprising
(a) the virus like particle according to any one of (1)-(17), the nucleic acid molecule according to any one of (18)-(20) and/or the vector according to (21) or (22); and
(b) a pharmaceutically acceptable carrier.
(24) A vaccine composition comprising the virus like particle according to any one of (1)-(17) and a pharmaceutically acceptable carrier.
(25) A method of producing the virus like particle according to any one of (1)-(17), comprising the steps of:
culturing a cell which is transfected with the vector according to (21)-22) to express the virus like particle; and
purifying the generated particle.
(26) A method of enhancing the production of a virus like particle comprising a viral structural protein and at least one antigen, comprising
(1) inserting the at least one antigen into an envelope protein E3 of the viral structural protein, and
(2) isolating the virus like particle wherein at least one antigen is inserted into the envelope protein E3 of the viral structural protein.
(27) The method according to (26), wherein the step (1) is achieved by a method comprising preparing a nucleic acid molecule comprising a nucleotide sequence encoding the virus like particle wherein at least one antigen is inserted into the envelope protein E3 of the viral structural protein; and allow the nucleic acid molecule to be expressed using cells.
(28) The method according to (26) or (27), wherein the virus like particle is the virus like particle according to any one of (1)-(17).
(29) A method of treating or preventing cancer, neurological disease, infectious disease or malaria; producing an antibody against the at least one antigen in a mammal; modulating an immune response; immunostimulation; inhibiting function of the at least one antigen; or presenting an antigen on macrophage, comprising administering the virus like particle according to any one of (1)-(17), the nucleic acid molecule according to any one of (18)-(20), the vector according to (21) or (22) and/or the composition according to (23) or (24) to a subject in need thereof.
(30) Use of the virus like particle according to any one of (1)-(17), the nucleic acid molecule according to any one of (18)-(20) or the vector according to (21) or (22) for the manufacture of a pharmaceutical composition or a kit for treating or preventing cancer, infectious disease or malaria; producing an antibody against the at least one antigen in a mammal; modulating an immune response; immunostimulation; inhibiting function of the at least one antigen; or presenting an antigen on macrophage.
(31) A cell line expressing a virus like particle, wherein the virus like particle comprises a viral structural protein which comprises an alternation/mutation to the amino acid sequence at the furin site in the envelope protein E3.
(32) The cell line of (31), the alternation to the amino acid sequence at furin site is an alternation to Ile-Glu/Asp-Gly-Arg or Asp-Asp-Asp-Asp-Lys (SEQ ID NO: 141).
(33) The cell line of (31) or (32), wherein the cell line is a stable cell line.
(34) A method for producing a cell line expressing a virus like particle, which comprising the step of:

transfecting a cell line with an expression vector comprising a nucleic acid molecule encoding a viral structural protein whose furin site in an envelope protein E3 is altered to a specific protease recognition site.

(35) The method of (34), wherein the furin site is altered to Factor Xa or Enterokinase recognition site.
(36) The method of (34) or (35), wherein the method provides a stable cell line.
(37) A method for producing a mature virus like particle, which comprises the steps of:
i) generating an immature virus like particle produced by the cell line according to any one of (31)-(33); and
ii) removing the E3 from the immature virus like particle.
(38) The method of (37), wherein the E3 is removed by a protease.
(39) The method of (38), wherein the protease is Factor Xa or Enterokinase.
(40) The cell line of (31), wherein the virus like particle is the virus like particle according to any one of (1)-(17).

In a first aspect, the present application provides a virus like particle comprising a modified envelope protein E3.

In a second aspect, the present application provides a nucleic acid molecule comprising or consisting of a nucleotide sequence encoding a virus like particle comprising a modified envelope protein E3.

In a third aspect, the present application provides a pharmaceutical composition and a kit comprising the pharmaceutical composition, wherein the pharmaceutical composition comprises (i) a virus like particle comprising a modified envelope protein E3 and/or (ii) a nucleic acid molecule comprising or consisting of a nucleotide sequence encoding a virus like particle comprising a modified envelope protein E3.

In a fourth aspect, the present application provides a method of producing a virus like particle comprising a modified envelope protein E3, comprising culturing a cell which is transfected with a vector to express the virus like particle; and purifying the particle generated by the cell.

In a fifth aspect, the present application provides a method of enhancing the production of a virus like particle comprising a viral structural protein with a modified envelop protein E3. In one embodiment, the virus like particle comprises a viral structural protein and at least one foreign antigen, comprising:
(1) inserting the at least one foreign antigen into an envelope protein E3 of the viral structural protein, and
(2) isolating the virus like particle wherein at least one antigen is inserted into the envelope protein E3 of the viral structural protein.

In a sixth aspect, the present application provides use of (i) a virus like particle comprising a modified envelope protein E3 and/or (ii) a nucleic acid molecule consisting of a nucleotide sequence encoding a virus like particle comprising a modified envelope protein E3 for the manufacture of a pharmaceutical composition or a kit for treating or preventing cancer, neurological disease, infectious disease or malaria; producing an antibody against at least one antigen in a mammal; modulating an immune response; immunostimulation; inhibiting function of at least one antigen; or presenting an antigen on macrophage.

In all aspect, the envelope protein E3 may be modified to comprise at least one antigen or an alternation/mutation to the amino acid sequence at the furin site.

In a seventh aspect, the present application provides a cell line that expresses a viral structural protein and can generate virus like particle, wherein the viral structural protein comprises an alternation/mutation to the amino acid sequence at the furin site, and the method for producing thereof.

In an eighth aspect, the present application provides a method for producing a mature virus like particle, which comprises the steps of:
i) generating an immature virus like particle produced by the cell line described above;
ii) removing the E3 from the immature virus like particle.

74: Malaria CSP repeat antigen (repeat ×6)

76: Malaria CSP repeat antigen (repeat ×14)

78: Malaria CSP repeat antigen (repeat ×25)

In the figure, "74" indicates that inserted antigen is 6 repeats of NPNA (SEQ ID NO: 142), "76" indicates that inserted antigen is 14 repeats of NPNA (SEQ ID NO: 142), and "78" indicates that inserted antigen is 25 repeats of NPNA (SEQ ID NO: 142); and "21" indicates that the antigen is inserted in E2 and "26" indicates that the antigen is inserted in E3.

Figure 4:
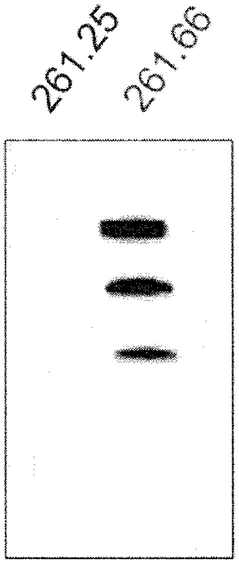

FIG. 4 shows results of western blotting. A mouse malaria CSP repeat antigen was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody. In the figure, "261.25" indicates VEEV VLP comprising E2 into which mouse malaria CSP repeat antigen was inserted, and "261.66" indicates VEEV VLP comprising E3 into which mouse malaria CSP repeat antigen was inserted.

Figure 5:
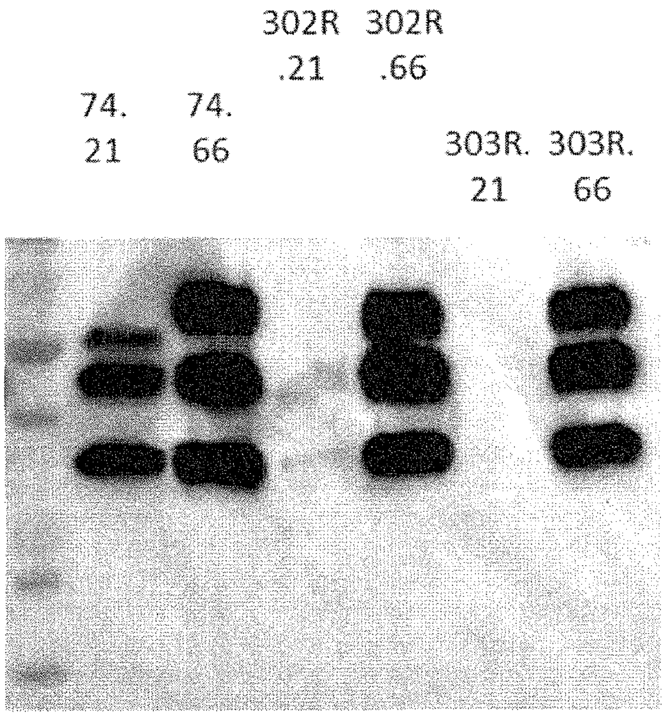

FIG. 5 shows results of western blotting. A CSP repeat sequence, malaria pfs25 domain 1 epitope or malaria pfs25 domain 2 epitope was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody. In the figure, "74" indicates that inserted antigen is malaria CSP repeat epitope, "302R" indicates that inserted antigen is malaria pfs25 domain 1 epitope, and "303R" indicates that inserted antigen is malaria pfs25 domain 2 epitope; and "21" indicates that the antigen is inserted in E2 and "26" indicates that the antigen is inserted in E3.

Figure 6:
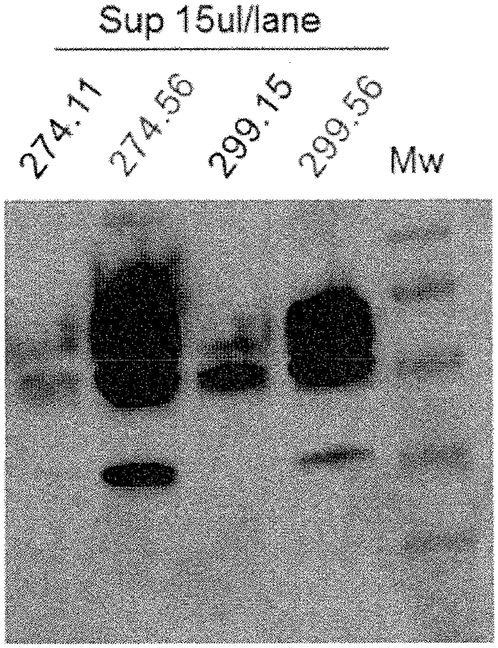

FIG. 6 shows results of western blotting. PD-1 epitope or PD-L1 epitope was inserted into E2 or E3 of virus like particle of Chikungunya virus (CHIKV) (strain 37997). The antigen-inserted CHIKV virus like particle expressed in 293F cells was confirmed by western blotting using mouse anti-CHIKV antibody. In the figure, "274.11" indicates CHIKV VLP comprising E2 into which PD-1 epitope was inserted, "274.56" indicates CHIKV VLP comprising E3 into which mouse PD-1 epitope was inserted, "299.15" indicates CHIKV VLP comprising E2 into which PD-L1 epitope was inserted, and "299.56" indicates CHIKV VLP comprising E3 into which mouse PD-L1 epitope was inserted.

Figure 7:
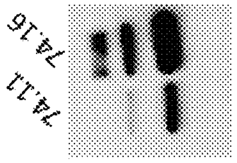

FIG. 7 shows results of western blotting. Malaria CSP repeat epitope was inserted into E2 or E3 of virus like particle of Chikungunya virus (CHIKV) (strain 37997). The antigen-inserted CHIKV virus like particle expressed in 293F cells was confirmed by western blotting using mouse anti-CHIKV antibody. In the figure, "74.11" indicates CHIKV VLP comprising E2 into which malaria CSP repeat epitope was inserted, "74.16" indicates CHIKV VLP comprising E3 into which mouse malaria CSP epitope was inserted.

Figure 8:
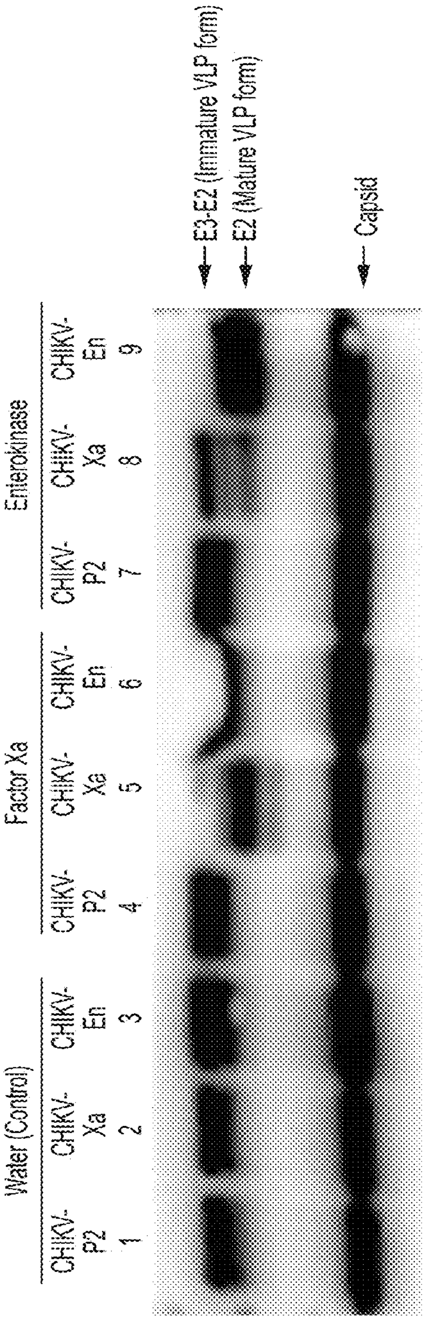

FIG. 8 shows results of western blotting regarding CHIKV immature construct from transient transfection.

Figure 9:
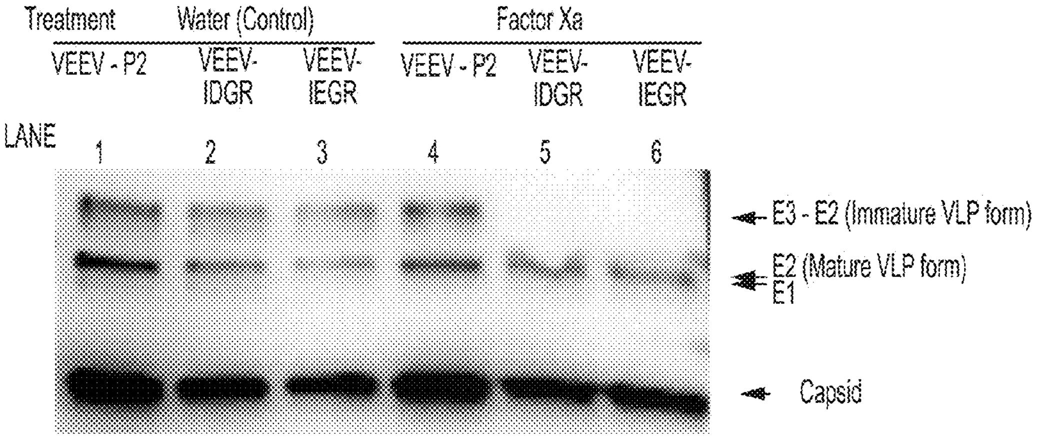

FIG. 9 shows results of western blotting regarding VEEV immature construct from transient transfection.

Figure 10:
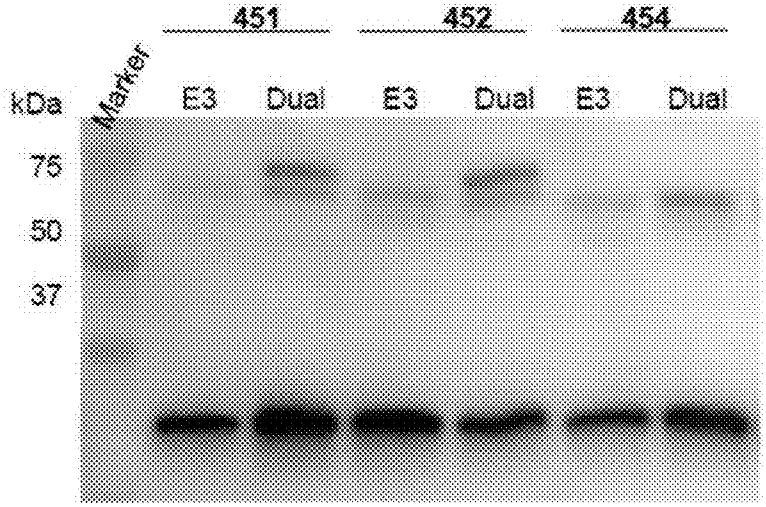

FIG. 10 shows results of western blotting indicating that DISC1_451, _452 and _454-inserted VLPs were produced when those antigens were inserted into E3 and into both E2 and E3 (dual).

Figure 11:
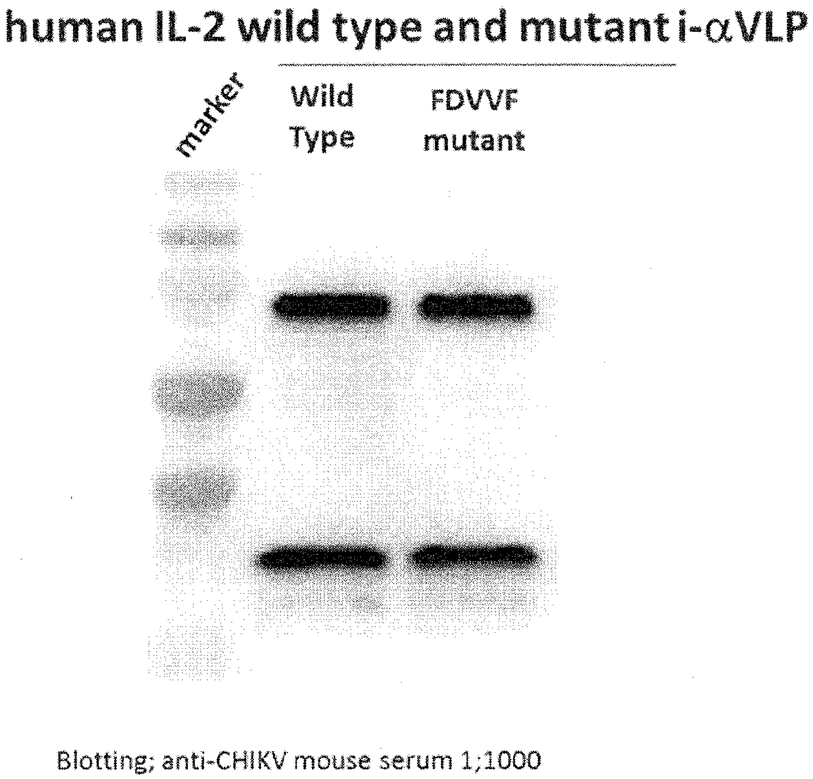

FIG. 11 shows results of western blotting indicating that human IL-2 wild type and human IL-2 mutant-inserted VLPs were produced when those antigens were inserted into E3.

Figure 12:
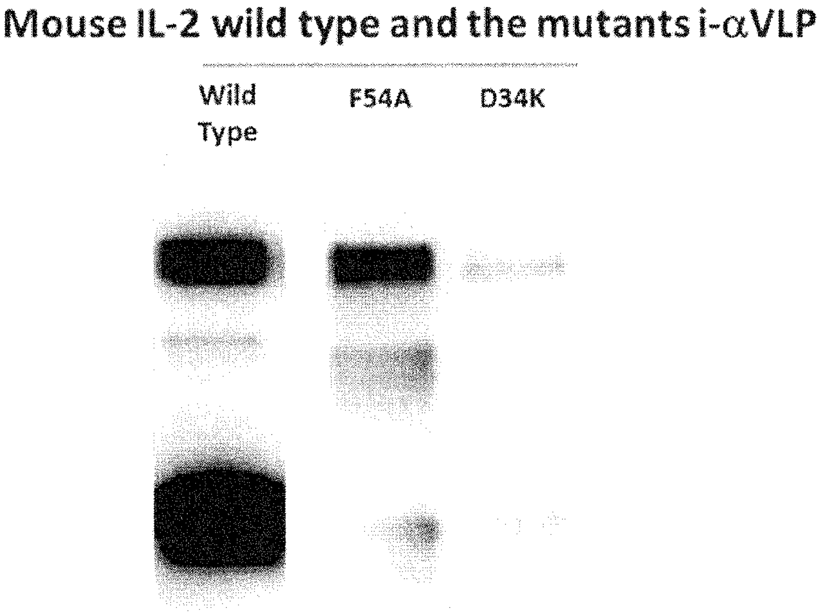

FIG. 12 shows results of western blotting indicating that mouse IL-2 wild type and mouse IL-2 mutant-inserted VLPs were produced when those antigens were inserted into E3.

Figure 13:
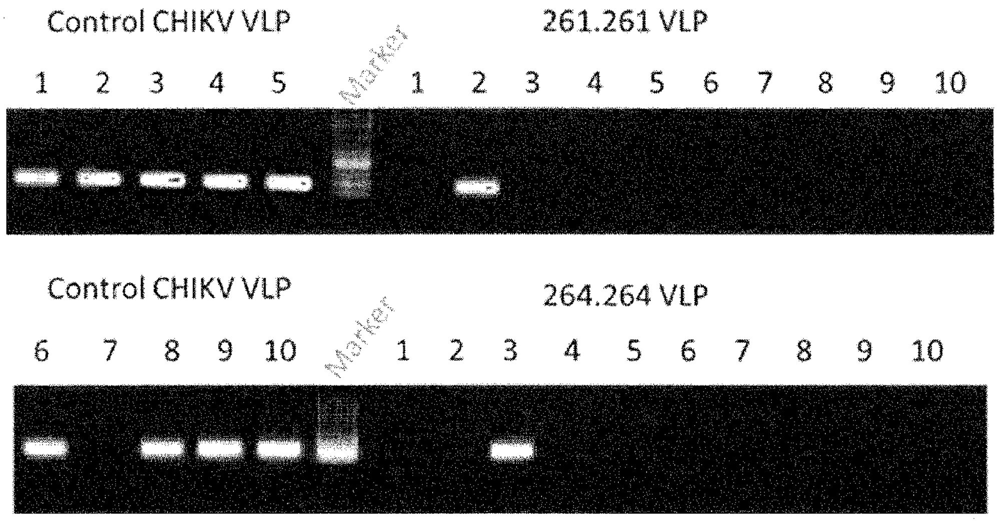

FIG. 13 shows results of the PCR, indicating that among 10 mice immunized with Control VLP, 9 mice were infected with malaria; among 10 mice immunized with Chikungunya VLP comprising Malaria CSP 4X repeat inserted into both envelop proteins E2 and E3 (261.261 VLP), 9 mice were not infected with malaria; and among 10 mice immunized with Chikungunya VLP comprising Malaria CSP 14X repeat inserted into both envelop proteins E2 and E3, 9 mice were not infected with malaria.

Figure 14:
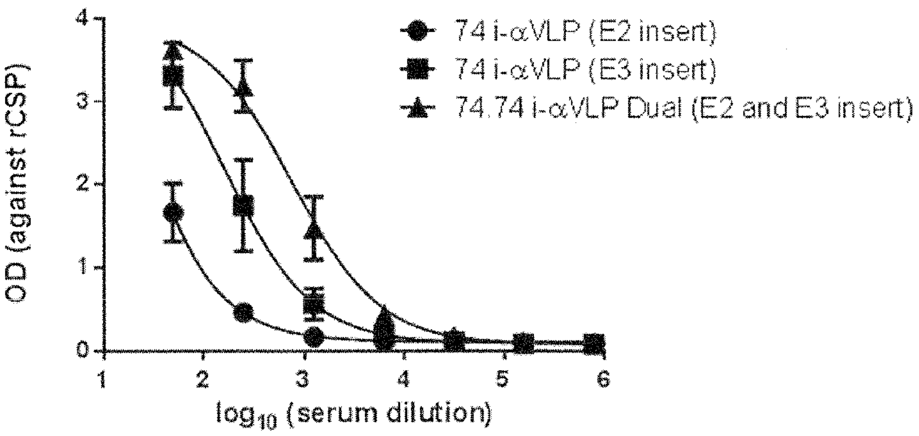

FIG. 14 shows results of ELISA, indicating that E3-inserted as well as E2- and E3-inserted VLPs have higher titer than E2-inserted VLP.

Figure 15:
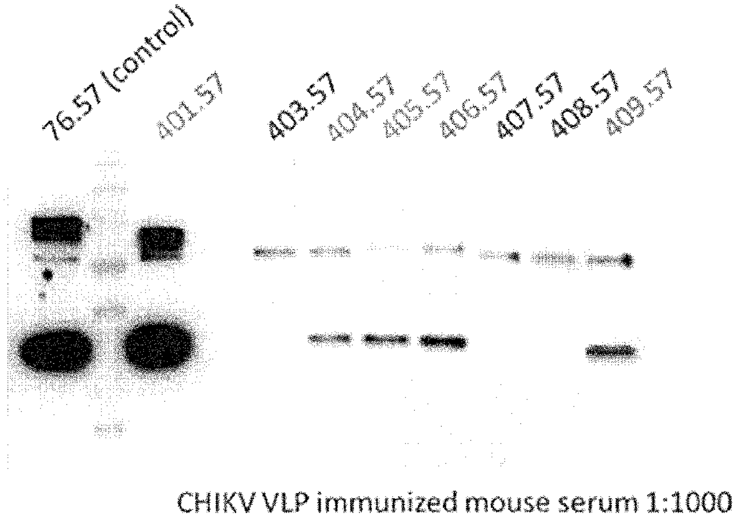

FIG. 15 shows western blotting indicating that hHER2-inserted VLPs were produced.

Figure 16:
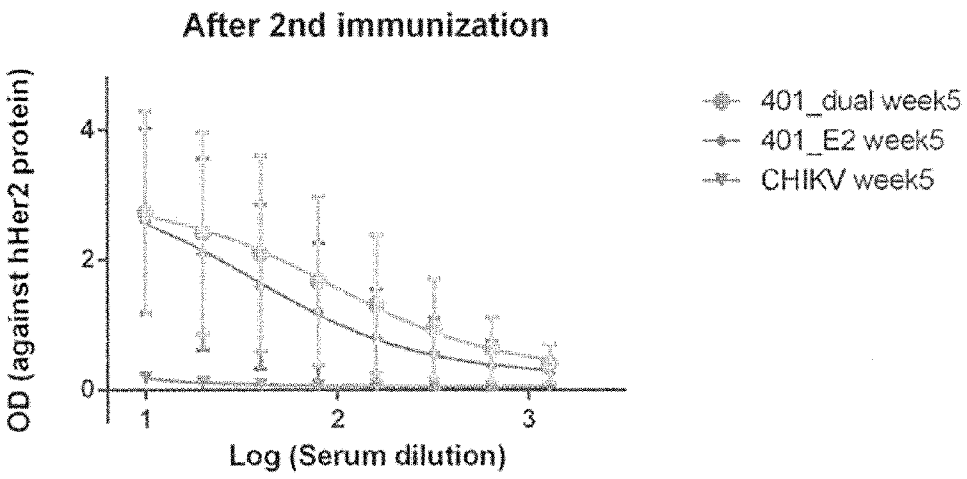

FIG. 16 shows results of ELISA, indicating that E2- and E3-inserted VLP has higher titer than E2-inserted VLP.

Figure 17:
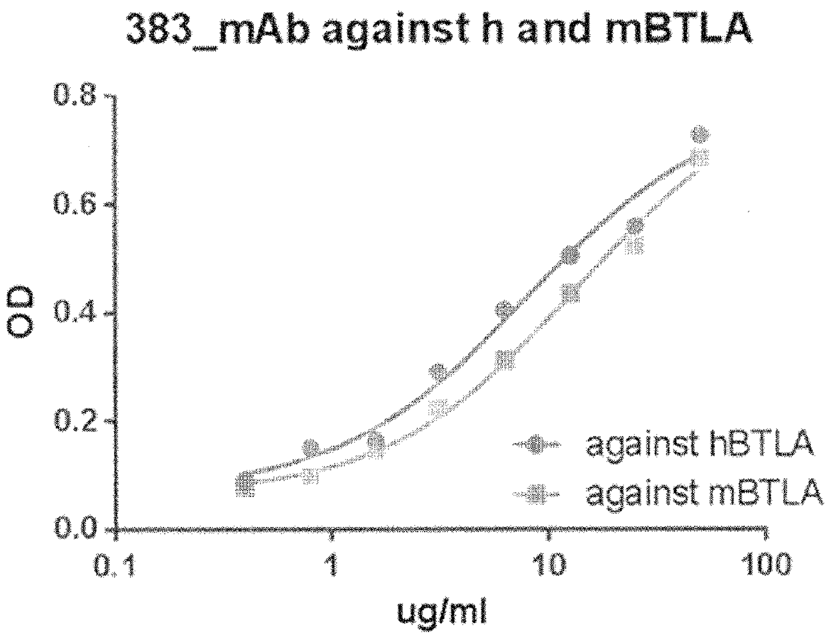

FIG. 17 shows that monoclonal antibody was obtained by using CHIKV-VLP comprising hBTLA antigen.

Figure 18:
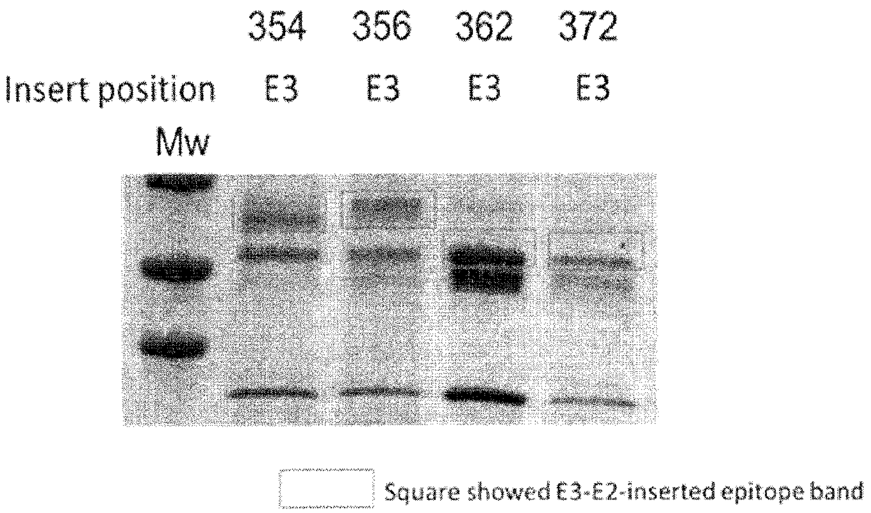

FIG. 18 shows result of western blotting indicating that human hHVEM inserted VLPs were produced when those antigens were inserted into E3.

Figure 19:
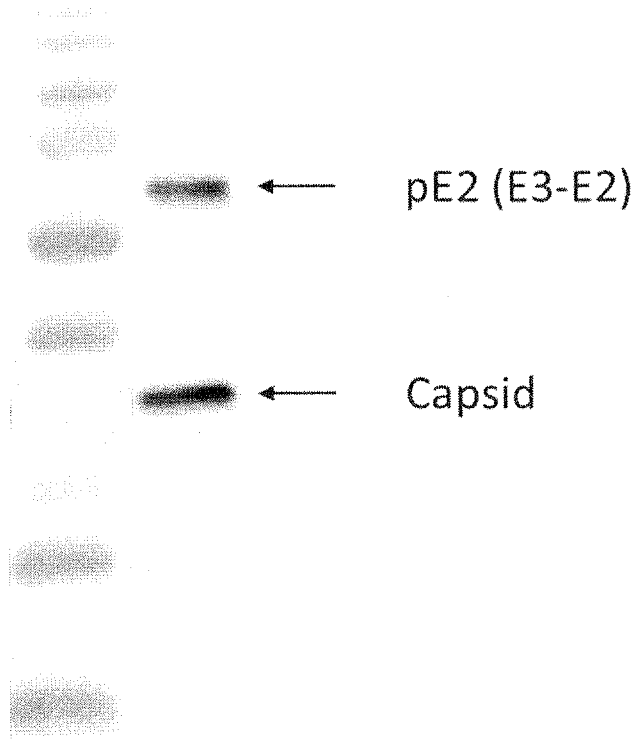

FIG. 19 shows that a cell line that express immature Chikungunya VLP whose furin site in the E3 envelope protein is modified could generate the immature VLP even after 3 months culture.

Figure 20:
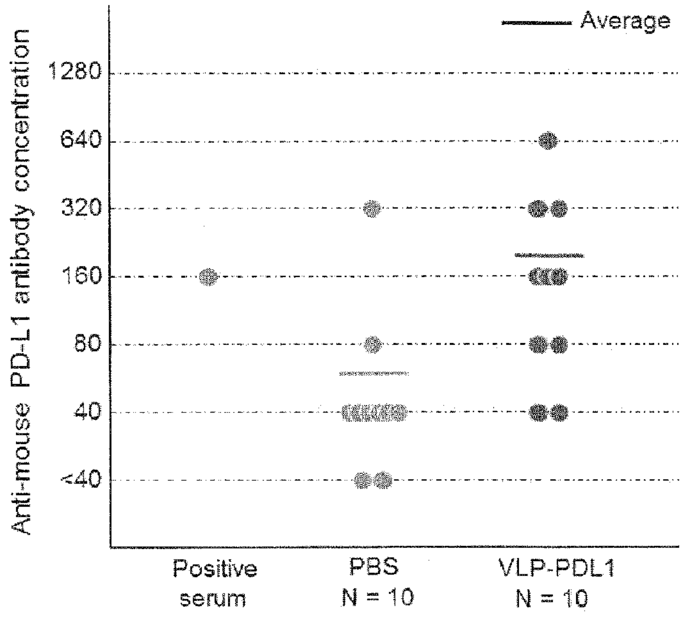

FIG. 20 shows the amount of anti PD-L1 antibody in mouse serum induced by intramuscular injection of PD-L1 inserted VLP.

Figure 21:
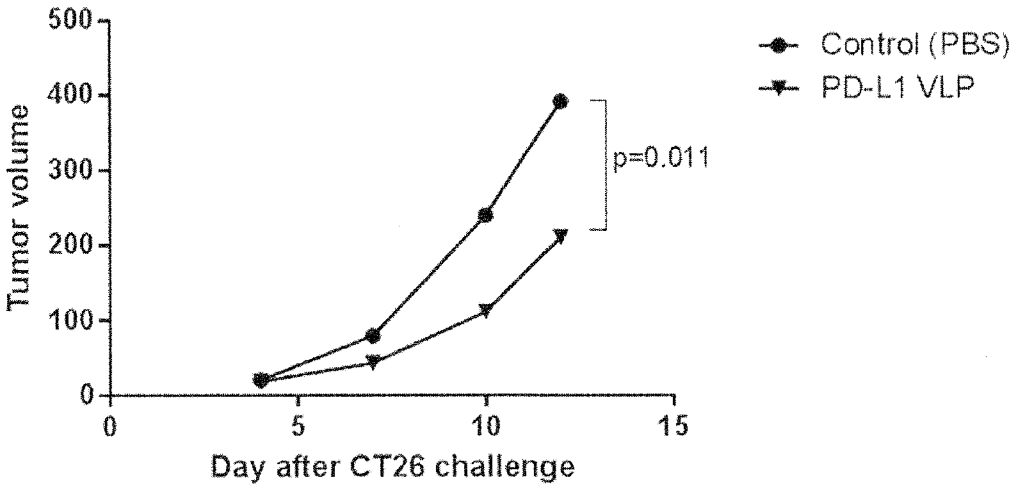

FIG. 21 shows the effect of intramuscular injection of PD-L1 inserted VLP on CT-26 tumor inoculated mice.

Figure 22:
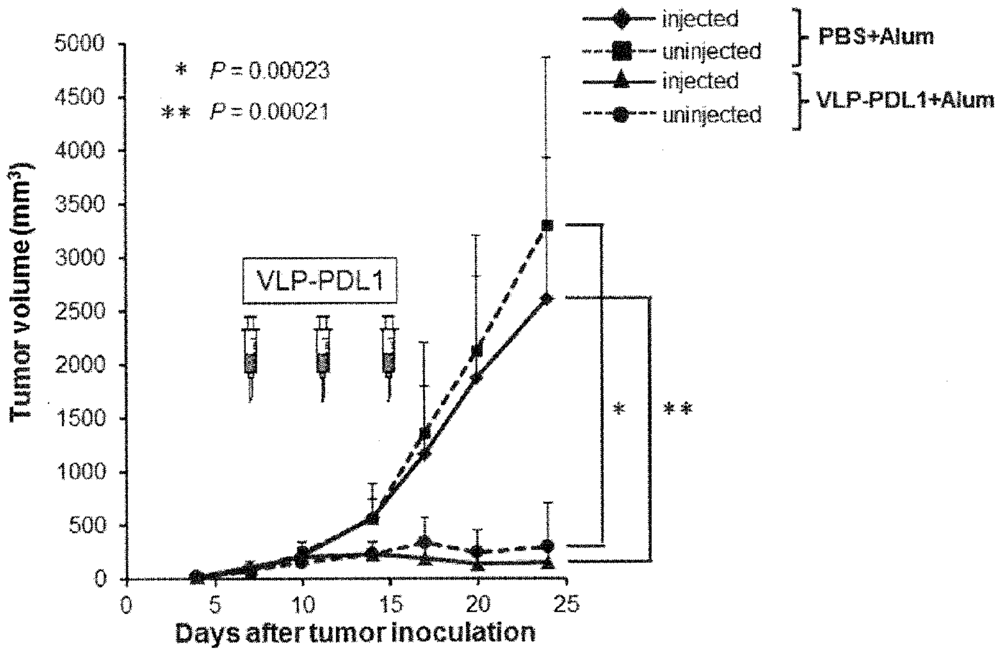

FIG. 22 shows the effect of intratumoral injection of PD-L1 inserted VLP on CT-26 tumor inoculated mice.

Figure 23:
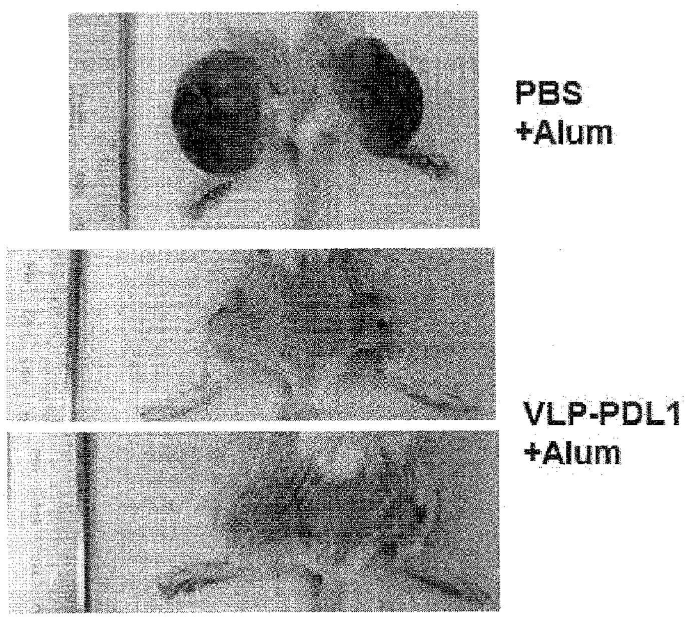

FIG. 23 shows the effect of intratumoral injection of PD-L1 inserted VLP on CT-26 tumor inoculated mice. The intratumoral injection of PD-L1 VLP effectively suppressed growth of tumors not only those directly injected with the VLP and but also those distant from the injected site.

Figure 24:
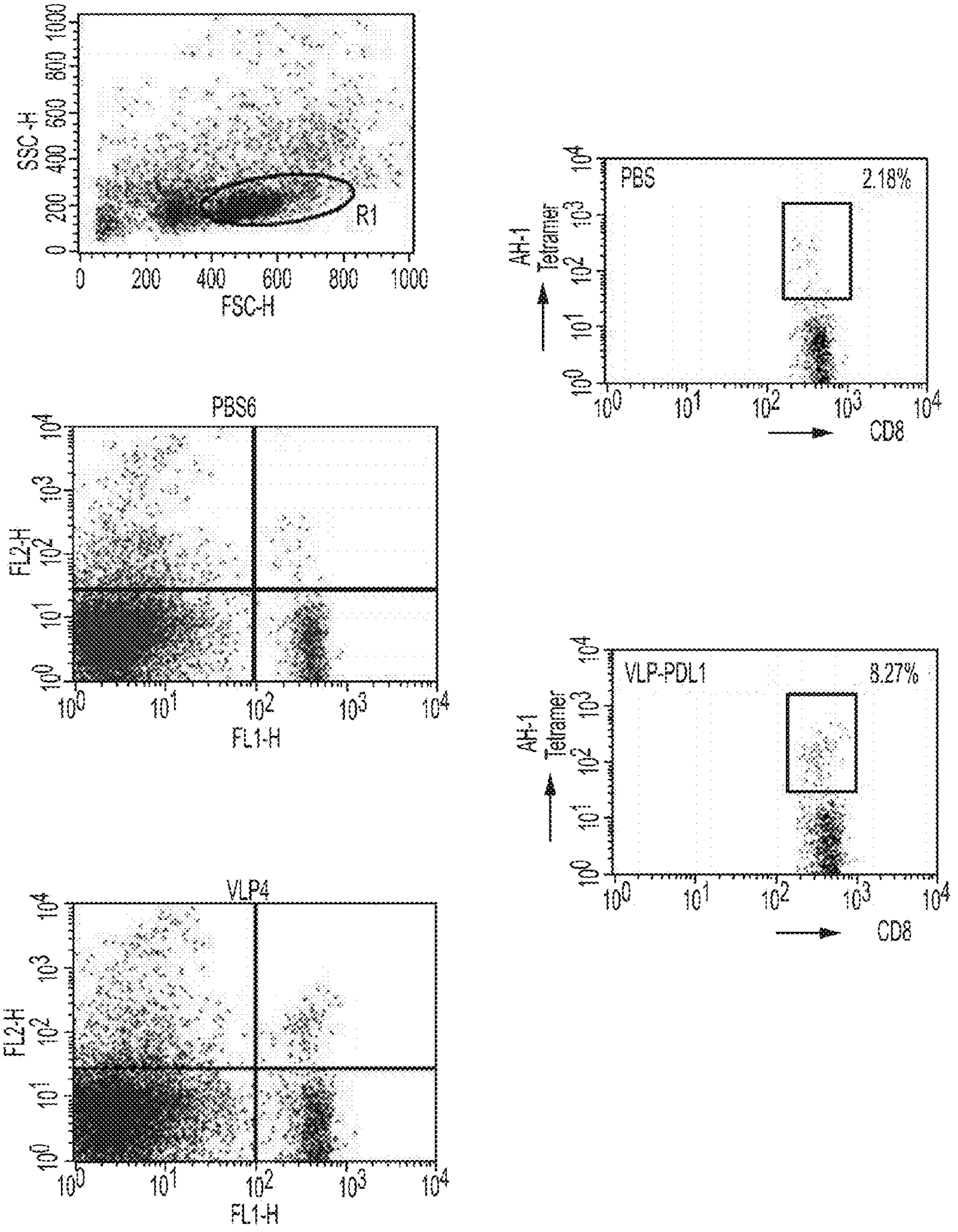

FIG. 24 shows the effect of intratumoral injection of PD-L1 inserted VLP on mice bearing CT-26 tumor. PD-L1 VLP effectively induced CT-26 specific CD8 positive cells in the mice.

Figure 25:
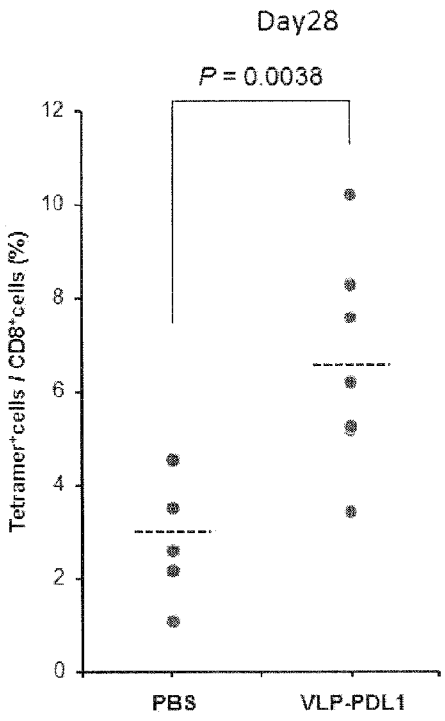

FIG. 25 shows the percentage of AH-1 tetramer positive and CD8 positive cells induced by intratumoral injection of PD-L1 VLP in mice bearing CT-26 tumor.

Figure 26:
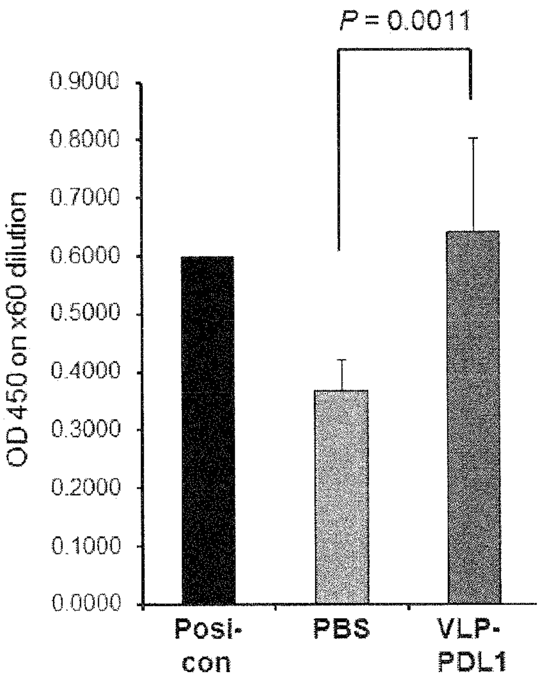

FIG. 26 shows the amount of anti PD-L1 antibody in mouse serum induced by intratumoral injection of PD-L1 inserted VLP.

Figure 27:
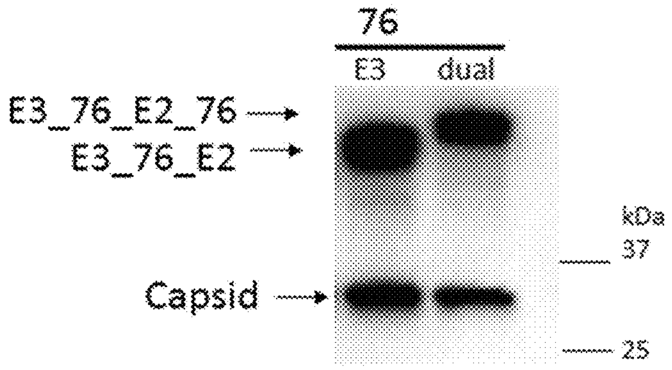

FIG. 27 shows result of Western Blot indicating that CHIKV-VLP CSP repeat antigen inserted VLPs were prepared.

Figure 28:
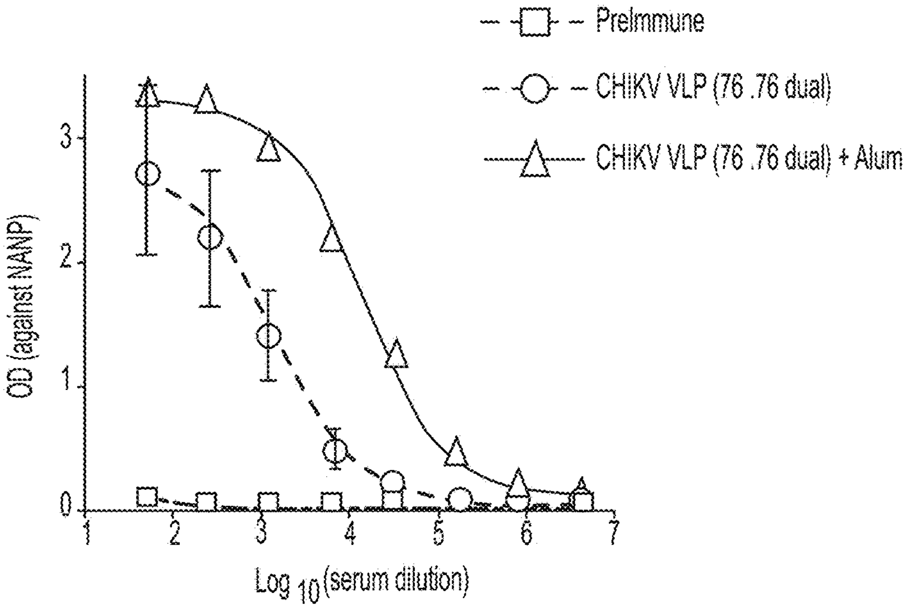

FIG. 28 shows malaria CSP repeat antigen 76 inserted VLP stimulated the production of anti CSP antigen antibodies in mice.

DESCRIPTION OF EMBODIMENTS

(1) Virus Like Particle Comprising a Modified Envelope Protein E3

In a first aspect, the present application provides a virus like particle comprising a modified envelope protein E3.

In this aspect, the envelope protein E3 may be modified to comprise at least one antigen or an alternation/mutation to the amino acid sequence at the furin site (Arg-X-X-Arg) (SEQ ID NO: 143).

The term "Arg-X-X-Arg" (SEQ ID NO: 143) indicates the minimal cleavage site of furin and "X-X" includes any two amino acids.

A virus like particle is composed of one or more viral structural proteins that spontaneously assemble into a particulate structure.

A viral structural protein used for the present application may be any viral structural protein as long as it expresses a furin site.

In a seventh aspect, the present application provides a cell line, especially stable cell line expressing a virus like particle, wherein the virus like particle comprises an alternation/mutation to the amino acid sequence at the furin site (Arg-X-X-Arg) (SEQ ID NO: 143), and the method for producing thereof. Example of the alternation to the amino acid sequence at furin site includes the alternation to Ile-Glu/Asp-Gly-Arg or Asp-Asp-Asp-Asp-Lys (SEQ ID NO: 141).

In one embodiment, the present application provides a method for producing a cell line expressing a virus like particle, wherein the furin site of the virus like particle is altered to a protease recognition site. In this embodiment, the cell line generated by this method could be a stable cell line. For example, the stable cell line obtained by this embodiment may maintain the ability to express and generate the VLP for relatively long time, such as more than three months.

In one embodiment, the present application provides an immature virus like particle produced by the cell line described above.

In an eighth aspect, the present application provides a method for producing a mature virus like particle, which comprises the steps of:

i) providing an immature virus like particle produced by the cell line described above;

ii) removing the E3 from the immature virus particle.

In one embodiment, the E3 in the immature virus like particle is removed by digestion of the protease recognition site. In one embodiment, the E3 in the immature virus like particle is removed by a protease. Examples of proteases include, but not limited to, Arg-C proteinase, Asp-N endopeptidase, Asp-N endopeptidase+N-terminal Glu, BNPS-Skatole, Caspasel to Caspase10, Chymotrypsin, Clostripain (Clostridiopeptidase B), CNBr, Enterokinase, Factor Xa, Formic acid, Glutamyl endopeptidase, GranzymeB, Hydroxylamine, Iodosobenzoic acid, LysC, LysN, NTCB (2-nitro-5-thiocyanobenzoic acid), Neutrophil elastase, Pepsin, Proline-endopeptidase, PreScission Protease (PSP), Proteinase K, Staphylococcal peptidase I, Tobacco etch virus protease, Thermolysin, Thrombin and Trypsin. Preferred examples of the protease include Factor Xa, Enterokinase and PreScission Protease (PSP), especially, Factor Xa and Enterokinase (e.g. Enterokinase (enteropeptidase), light chain).

In another aspect, the present application provides a virus like particle comprising an envelope protein E3, wherein the envelope protein E3 is modified to comprise at least one antigen. The at least one antigen may be a peptide that is not derived from the virus from which the viral structural protein is derived or a peptide that is derived from the same virus that provides the viral structural protein.

A derivative of the above-described virus like particle which can be prepared by modifying the above-described particle is also provided by the present application. Examples of the modification include, but are not limited to, addition, deletion or replacement of one or more amino acid residues.

The particle provided by the present application may be a particle which consists of or comprises i) at least one viral structural protein and ii) at least one antigen, wherein the at least one antigen is inserted into the envelope protein E3 of the viral structural protein. The at least one viral structural protein may consist of one or more kinds of protein or peptide and spontaneously assembles to form a particle. In one embodiment, the particle provided by the present application has a diameter of at least 10 nm, for example, at least 20 nm, preferably at least 50 nm. In one embodiment, molecular weight of the particle is from 100 kDa to 100,000 kDa, preferably from 400 kDa to 30,000 kDa.

One or more amino acid residues can be replaced, added and/or deleted in amino acid sequence of the viral structural protein to allow expression of a virus like particle comprising an envelope protein E3 where at least one antigen is inserted.

In one preferred embodiment, the virus like particle provided by the present application comprising at least one antigen in an envelope protein E3 can be expressed more efficiently in a eukaryotic cell (e.g. 293F cells) than a virus like particle comprising said at least one antigen in an envelope protein E2.

A viral structural protein used for the present application may be a viral structural protein derived from Alphavirus or Flavivirus. Thus, the particle provided by the present application may be a virus like particle including a virus like particle derived from Alphavirus or Flavivirus.

Examples of Alphavirus and Flavivirus include, but not limited to, Aura virus, Babanki virus, Barmah Forest virus (BFV), Bebaruvirus, Cabassouvirus, Chikungunyavirus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

The particle provided by the present application may be a virus like particle derived from Chikungunya virus or Venezuelan equine encephalitis virus. Chikungunya virus may be Chikungunya virus 37997 strain or OPY-1 strain. Venezuelan equine encephalitis virus may be Venezuelan equine encephalitis virus TC-83 strain.

Viral structural protein may be a capsid protein, an envelope protein, a fragment thereof or a complex thereof. Thus, viral structural protein used for the present application may consist of or comprise a capsid protein and/or an envelope protein and/or a fragment or derivative thereof. In one embodiment, the virus like particle provided by the present application consists of or comprises capsid, E3, E2 and E1 proteins, and an antigen is inserted into E3. For example, the virus like particle provided by the present application may be formed by assembling 240 capsids, 240 E1 proteins, 240 E2 proteins and 240 E3 proteins where an antigen is inserted into each of E3 proteins.

Under physiological conditions, E3 can be dissociated from E2 after furin cleavage. In one embodiment, the furin cleavage site located in E3 may be mutated to prevent furin site from cleaving. For example, an antigen can be inserted into the furin cleavage site to introduce a mutation in the furin cleavage site. In this embodiment, the virus like particle provided may consist of or comprises capsid, E3, E2 and E1 proteins, where E3 is bound to E2 to form a single protein and an antigen is inserted into E3 region. For example, the virus like particle provided by the present application may be formed by assembling 240 capsids, 240 E1 proteins, 240 proteins in each of which E2 is bound to E3 and an antigen is inserted into each of E3 regions.

Antigen may be a molecule capable of being bound by an antibody or a T cell receptor (TCR) if it is presented with MHC molecules. Antigen can encompass B-cell epitopes and T-cell epitopes. Antigen disclosed in U.S. patent publication No.: US 2013/0251744 filed Feb. 15, 2013, the entire contents of which are incorporated herein by reference, may be used for the present application. Examples of antigen used for the present application include, but are not limited to, allergens, self-antigens, haptens, cancer antigens, infectious disease antigens and small organic molecules, and fragments and derivatives thereof.

Antigen may be a naturally occurring and/or modified protein, a fragment thereof or derivative of the naturally occurring protein or its fragment. A fragment of a naturally occurring and/or modified protein for use as an antigen contained in the particle provided by the present application may be selected based on the amino acid sequence of the naturally occurring and/or modified protein and/or tertiary structure thereof. For example, a fragment for use as an antigen may consist of or comprise a fragment located in the surface of a naturally occurring protein. Preferably, an antibody against an antigen contained in the particle provided by the present application may inhibit function of the antigen. An antigen (e.g. a fragment of a naturally occurring protein) may be 10-300 amino acid residues (e.g. 10-120, 10-30 or 15-30 amino acid residues) in length. A derivative of a naturally occurring protein or its fragment may be prepared by addition, deletion or replacement of one or several amino acid residues in the naturally occurring protein or its fragment. In one embodiment, a derivative of a naturally occurring protein or its fragment has at least 70%, 75%, 80%, 85%, 90%, 95% or 98% amino acid sequence identity to the corresponding naturally occurring protein or its fragment. In one embodiment, a derivative of a naturally occurring protein or its fragment is a mutant where at most 10% of the amino acids are deleted, substituted, and/or added based on the corresponding naturally occurring protein or its fragment.

In one embodiment, an antigen or epitope (e.g. a fragment of a naturally occurring protein) may be selected so that spatial distance between the N-terminal residue and C-terminal residue of the antigen is 30 Å or less when the distance is determined in a crystal of the antigen or a naturally occurring protein containing the antigen or modified peptide therefrom. For example, an antigen used for the particle provided by the present application can be designed using a free software including PyMOL (e.g. PyMOL v0.99: http://www.pymol.org). In one embodiment, a spatial distance between N-terminal residue and C-terminal residue of the antigen is 30 Å (angstrom) or less, 20 Å or less, or 10 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

In one embodiment, an antigen or epitope which may be used for the present application may be malaria antigen, PD-1 antigen, PD-1 ligand antigen, CTLA-4 antigen, IL-2 antigen DISC1 antigen, HER2 antigen, BTLA antigen, HVEM antigen, PCSK9 antigen or DPP-4 antigen.

As used herein, "malaria antigen" refers to an antigen or epitope derived from *Plasmodium* parasite. The *plasmodium* parasite may be selected from any of the known *Plasmodium* (P.) species, for example, *P. falciparum, P. malariae, P. ovale, P. vivax, P. knowlesi, P. berghei, P. chabaudi* and *P. yoelii.*

In one embodiment, malaria antigen is a *Plasmodium falciparum* circumsporozoite protein B cell epitope (hereinafter, referred as CSP protein, Malaria CSP protein, or CSP). Example of *Plasmodium falciparum* circumsporozoite protein B cell epitope may be a repeat sequence of NPNA (SEQ ID NO: 142), including (NPNA) 4-30 (SEQ ID NO: 140) (i.e. 4×NPNA, 5×NPNA, 6×NPNA, 7×NPNA, 8×NPNA, 9×NPNA, 10×NPNA, 11×NPNA, 12×NPNA, 13×NPNA 14×NPNA, 15×NPNA, 16×NPNA, 17×NPNA, 18×NPNA, 19×NPNA, 20×NPNA, 21×NPNA, 22×NPNA, 23×NPNA, 24×NPNA, 25×NPNA, 26×NPNA, 27×NPNA, 28×NPNA, 29×NPNA or 30×NPNA).

In one embodiment, malaria antigen is a *Plasmodium yoelii* circumsporozoite protein B cell epitope including 3 to 12 repeats of (QGPGAP)(SEQ ID NO: 144).

In one embodiment, malaria antigen is a *Plasmodium vivax* circumsporozoite protein B cell epitope including 1 to 12 repeats of (ANGAGNQPG)(SEQ ID NO: 145).

In one embodiment, malaria antigen is a *Plasmodium malariae* circumsporozoite protein B cell epitope including 4 to 30 repeats of (NAAG)(SEQ ID NO: 146).

In one embodiment, malaria antigen is a *Plasmodium falciparum* circumsporozoite protein T cell epitope. Example of *Plasmodium falciparum* circumsporozoite protein T cell epitope may be EYLNKIQNSLSTEWSPCSVT (SEQ ID NO: 4). 1 to 6 repeats of EYLNKIQNSLSTEWSPCSVT (SEQ ID NO: 4) may be also used as a malaria antigen.

In one embodiment, malaria antigen is a *Plasmodium yoelii* circumsporozoite protein T cell epitope which is YNRNIVNRLLGDALNGPEEK (SEQ ID NO: 5). 1 to 6 repeats of YNRNIVNRLLGDALNGPEEK (SEQ ID NO: 5) may be also used as a malaria antigen.

As used herein, the term "PD-1 antigen" refers to an antigen or epitope derived from PD-1. Preferably, PD-1 is a human PD-1. An antigen derived from PD-1 may be a fragment of PD-1 or a derivative of a fragment of PD-1.

As used herein, the term "PD-1 ligand antigen" refers to an antigen or epitope derived from a ligand of PD-1. Examples of a ligand of PD-1 include, but are not limited to, PD-L1 and PD-L2. Preferably, a ligand of PD-1 is human PD-L1 or human PD-L2. An antigen derived from PD-L1 may be a fragment of PD-L1 or PD-L2; or a derivative of a fragment of PD-L1 or PD-L2.

Examples of PD-1 antigen for use as an antigen include, but are not limited to, lnwyrmspsnqtdklaaf (SEQ ID NO: 6), mlnwyrmspsnqtdklaafs (SEQ ID NO: 7), vlnwyrmspsnqtdklaafp (SEQ ID NO: 8), gaislhpkakiees (SEQ ID NO: 9), cgaislhpkakieec (SEQ ID NO: 10), VLNWYRMSPSNQTDKLAAF (SEQ ID NO: 11), GAISLAPKAQIKES (SEQ ID NO: 12), RNDSGTYLCGAISLAPKAQIKESLRAELRVT (SEQ ID NO: 13) and RNDSGIYLCGAISLHPKAKIEESPGAELVVT (SEQ ID NO: 14). Examples of PD-1 ligand antigen for use as an antigen include, but are not limited to, ciisyggadyc (SEQ ID NO: 15), CMISYGGADYC (SEQ ID NO: 16), LQDAGVYRCMISYGGADYKRITVKVN (SEQ ID NO: 17), LQDAGVYRAMISYGGADYKRITVKVN (SEQ ID NO: 18), DLAALIVYWEMEDKNIIQFVH (SEQ ID NO: 19), DLAALIVYWEMEDKNIIQFVHGG (SEQ ID NO: 20), FTVTVPKDLYVVEYGSNMTIECKFPVE (SEQ ID NO: 21), Lqdagvycciisyggadykritlkvn (SEQ ID NO: 22), lqdagvyaaiisyggadykritlkvn (SEQ ID NO: 23), dllalvvywekedeqviqfva (SEQ ID NO: 24), dllalvvywekedeqviqfvagg (SEQ ID NO: 25) and ftitapkdlyvveygsnvtmecrfpve (SEQ ID NO: 26).

As used herein, the term "CTLA-4 antigen" refers to an antigen or epitope derived from CTLA-4 (cytotoxic T-lymphocyte-associated antigen 4). Preferably, CTLA-4 is a human CTLA-4. An antigen derived from CTLA-4 may be a fragment of CTLA-4 or a derivative of a fragment of CTLA-4. Examples of CTLA-4 antigen for use as an antigen include, but are not limited to, ggkvelmypppyfvgmgg (SEQ ID NO: 27), cattftekntvgfldypfc (SEQ ID NO: 28) and attftekntvgfldypf (SEQ ID NO: 29).

As used herein, the term "DISC1 antigen" refers to an antigen or epitope derived from DISC1. Examples of DISC1 antigen for use as an antigen include, but are not limited to, SGGLLIQSLQLQEARGELSVEDERQMDDLEGGS (DISC1_451)(SEQ ID NO: 105), SGGEARGELSVEDERQMDDLEGGS (DISC1_452)(SEQ ID NO: 106) and SGGEARGELSVEGGS (DISC1_454)(SEQ ID NO: 107).

As used herein, the term "HER2 antigen" refers to an antigen or epitope derived from HER2. Examples of HER2 antigen for use as an antigen include, but are not limited to, SGGVTYNTDTFESMPGGS (SEQ ID NO: 108), SGGEYVNARHCLPGGS(SEQ ID NO: 109), SGGYVNARHCLGGS(SEQ ID NO: 110), SGGYVNARHGLGGS(SEQ ID NO: 111), SGGKFPDEEGACQPCPIGGS(SEQ ID NO: 112), SGGKFPDEEGACQPGGS(SEQ ID NO: 113), SGGKDPPFCVGGS(SEQ ID NO:114), SGGYKDPPFCVAGGS (SEQ ID NO: 115), and SGGYKDPPFCVGGS(SEQ ID NO: 116).

As used herein, the term "BTLA antigen" refers to an antigen or epitope derived from BTLA. Examples of BTLA antigen for use as an antigen include, are not limited to, SGGCKLNGTTCGGS (SEQ ID NO: 132).

As used herein, the term "HVEM antigen" refers to an antigen or epitope derived from HVEM. Examples of HVEM antigen for use as an antigen include, are not limited to, SGGCVKEASGELTGTVCGGS (SEQ ID NO: 133), SGGCYRVKEASGELTGTVSEPCGGS (SEQ ID NO: 134), SGGCSRNSSRTENAVCGGS (SEQ ID NO: 135), and SGGCQMSDPAMGLRSRNCGGS (SEQ ID NO: 136).

In the particle as provided by the present application, a viral structural protein and an antigen may be linked through at least one first attachment site which is present in the viral structural protein and at least one second attachment site which is present in the antigen.

As used herein, each of "a first attachment site" and "a second attachment site" refers to a site where more than one substance is linked each other.

A viral structural protein and an antigen may be directly or indirectly fused. In one embodiment, one or two linkers may intervene between N-terminal residue of an antigen and a viral structural protein and/or between C-terminal residue of an antigen and a viral structural protein.

An antigen or a viral structural protein can be truncated and replaced by short linkers. In some embodiments, an antigen or a viral structural protein include one or more peptide linkers. Typically, a linker consists of from 2 to 25 amino acids (e.g. 2, 3, 4, 5 or 6 amino acids). Usually, it is from 2 to 15 amino acids in length, although in certain circumstances, it can be only one, such as a single glycine residue.

In one embodiment, a nucleic acid molecule, in which polynucleotide encoding the viral structural protein is genetically fused with polynucleotide encoding the antigen, is expressed in a host cell (e.g. mammalian cells (e.g. 293F cells)) so that the first attachment site and the second attachment site are linked through a peptide bond. In this case, the viral structural protein and the antigen are linked through a peptide bond. Relating to this embodiment, the first attachment site and/or the second attachment site may be genetically modified from the original protein or antigen. For example, the first attachment site is modified from the viral structural protein so that through a linker peptide including SG, GS, SGG, GGS and SGSG (SEQ ID NO: 147), the protein is conjugated with the antigen. When the viral structural protein are chemically conjugated with the antigen, the first attachment site and the second attachment site may be linked through a chemical cross-linker which is a chemical compound. Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

Preferably, an antigen may be linked to the Chikungunya viral structural protein or Venezuelan equine encephalitis viral structural protein as a fusion protein produced by way of genetic engineering.

A Chikungunya viral structural protein or Venezuelan equine encephalitis viral structural protein used in the present application may be a Chikungunya or Venezuelan equine encephalitis virus envelope protein or a capsid or a complex of one or more envelope proteins and/or a capsid protein.

Examples of Chikungunya virus include, but are not limited to, strains 37997 and strain LR2006 OPY-1. Examples of Venezuelan equine encephalitis virus include, but are not limited to, strain TC-83.

Chikungunya viral structural protein or Venezuelan equine encephalitis viral structural protein used in the present application may be a naturally occurring viral structural protein or modified protein thereof. The modified protein may be a fragment of the naturally occurring viral structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis viral structural protein used in the present application.

Chikungunya or Venezuelan equine encephalitis viral structural protein may consist of or comprise a capsid, E3, E2 and E1 proteins. E3 and E2 proteins may be expressed together so that E2 and E3 can form one protein.

Examples of Chikungunya viral structural protein include, but are not limited to, Capsid-E3-E2-E1 of Chikungunya virus Strain 37997, and Capsid-E3-E2-E1 of Chikungunya virus LR2006 OPY-1.

Examples of Venezuelan equine encephalitis viral structural protein include, but are not limited to, Capsid-E3-E2-E1 of Venezuelan equine encephalitis virus Strain TC-83.

An exemplary Chikungunya viral structural protein sequence is provided at Genbank Accession No. ABX40006.1, which is described below (SEQ ID NO: 1):

```
mefiptqtfynrryqprpwtprptiqvirprprpqrqagqlaqlisavnk
ltmravpqqkprrnrknkkqkqkqqapqnntnqkkqppkkkpaqkkkkpg
rrermcmkiendcifevkhegkvtgyaclvgdkvmkpahvkgtidnadla
klafkrsskydlecaqipvhmksdaskfthekpegyynwhhgavqysggr
ftiptgagkpgdsgrpifdnkgrvvaivlgganegartalsvvtwnkdiv
tkitpegaeewslaipvmcllanttfpcsqppctpccyekepeetlrmle
dnvmrpgyyqllqasltcaphrqrrstkdnfnvykatrpylahcpdcgeg
hschspvalerirneatdgtlkiqvslqigiktddshdwtklrymdnhmp
adaeraglfvrtsapctitgtmghfilarcpkgetltvgftdsrkishsc
thpfhhdppvigrekfhsrpqhgkelpcstyvqstaatteeievhmppdt
pdrtlmsqqsgnvkitvngqtvrykcncggsneglttdkvinnckvdqc
haavtnhkkwqynsplvprnaelgdrkgkihipfplanvtcrvpkarnpt
vtygknqvimllypdhptllsyrnmgeepnyqeewvmhkkevvltvpteg
levtwgnnepykywpqlstngtahghpheiilyyyelyptmtvvvvsvat
fillsmvgmaagmcmcarrrcitpyeltpgatvpfllsliccirtakaat
yqeaaiylwneqqplfwlqaliplaalivlcnclrllpccktlaflavm
svgahtvsayehvtvipntvgvpyktlvnrpgyspmvlemellsvtlept
lsldyitceyktvipspyvkccgtaeckdknlpdysckvftgvypfmwgg
aycfcdaentqlseahveksescktefasayrahtasasaklrvlyqgnn
itvtayangdhavtvkdakfivgpmssawtpfdnkivvykgdvynmdypp
fgagrpgqfgdiqsrtpeskdvyantqlvlqrpavgtvhvpysqapsgfk
ywlkergaslqhtapfgcqiatnpvravncavgnmpisidipeaaftrvv
dapsltdmscevpacthssdfggvaiikyaaskkgkcavhsmtnavtire
aeievegnsqlqisfstalasaefrvqvcstqvhcaaechppkdhivnyp
ashttlgvqdisatamswvqkitggvglvvavaalilivvlcvsfsrh
```

Another exemplary Chikungunya viral structural protein sequence is provided at Genbank Accession No. ABX40011.1, which is described below (SEQ ID NO: 2):

```
mefiptqtfynrryqprpwaprptiqvirprprpqrqagqlaqlisavnk
ltmravpqqkprrnrknkkqrqkkqapqndpkqkkqppqkkpaqkkkkpg
rrermcmkiendcifevkhegkvmgyaclvgdknmkpahvkgtidnadla
```

-continued

```
klafkrsskydlecaqipvhmksdaskfthekpegyynwhhgavqysggr
ftiptgagkpgdsgrpifdnkgrvvaivlgganegartalsvvtwnkdiv
tkitpegaeewslalpvlcllanttfpcsqppctpccyekepestlrmle
dnvmrpgyyqllkasltcsphrqrrstkdnfnvykatrpylahcpdcgeg
hschspialerirneatdgtlkiqvslqigiktddshdwtklrymdshtp
adaeraglllvrtsapctitgtmghfilarcpkgetltvgftdsrkishtc
thpfhheppvigrerfhsrpqhgkelpcstyvqstaataeeievhmppdt
pdrtlmtqqsgnvkitvngqtvrykcncggsneglttdkvinnckidqc
haavtnhknwqynsplvprnaelgdrkgkihipfplanvtcrvpkarnpt
vtygknqvtmllypdhptllsyrnmgqepnyheewvthkkevtltvpteg
levtwgnnepykywpqmstngtahghpheiilyyyelyptmtvvivsvas
fvllsmvgtavmgcvcarrrcitpteltpgatvpfllsllccvrttkaat
yyeaaaylwneqqplfwlqaliplaalivlcnclkllpccktlaflavm
sigahtvsayehvtvipntvgvpyktlvnrpgyspmvlemelqsvtlept
lsldyitceyktvipspyvkccgtaeckdkslpdysckvftgvypfmwgg
aycfcdaentqlseahveksescktefasayrahtasasaklrvlyqgnn
itvaayangdhavtvkdakfvvgpmssawtpfdnkivvykgdvynmdypp
fgagrpgqfgdiqsrtpeskdvyantqlvlqrpaagtvhvpysqapsgfk
ywlkergaslqhtapfgcqiatnpvravncavgnipisidipdaaftrvv
dapsvtdmscevpacthssdfggvaiikytaskkgkcavhsmtnavtire
advevegnsqlqisfstalasaefrvqvcstqvhcaaachppkdhivnyp
ashttlgvqdisttamswvqkitggvglivavaalilivvlcvsfsrh.
```

An exemplary Venezuelan equine encephalitis viral structural protein is described below (SEQ ID NO: 3):

```
mfpfqpmypmqpmpyrnpfaaprrpwfprtdpflamqvqeltrsmanltf
kqrrdappegpsaakpkkeasqkqkgggqgkkkknqgkkkaktqppnpka
qngnkkktnkkpgkrqrmvmklesdktfpimlegkingyacvvggklfrp
mhvegkidndvlaalktkkaskydleyadvpqnmradtfkythekpqgyy
swhhgavqyengrftvpkgvgakgdsgrpildnqgrvvaivlggvnegsr
talsvvmwnekgvtvkytpenceqwslvttmcllanvtfpcaqppicydr
kpaetlamlsvnvdnpgydelleaavkcpgrkrrsteelfneykltrpym
arcircavgschspiaieavksdghdgyvrlqtssqygldssgnlkgrtm
rydmhgtikeiplhqvslytsrpchivdghgyfllarcpagdsitmefkk
dsvrhscsvpyevkfnpvgrelythppehgveqacqvyahdaqnrgayve
mhlpgsevdsslvslsgssvtvtppdgtsalvececggtkisetinktkq
fsqctkkeqcrayrlqndkwvynsdklpkaagatlkgklhvpflladgkc
tvplapepmitfgfrsvslklhpknptylitrqladephythelisepav
rnftvtekgwefvwgnhppkrfwaqetapgnphglphrvithyyhrypms
tilglsicaaiatvsvaastwlfcrsrvacltpyrltpnaripfclavlc
cartaraettwesldhlwnnnqqmfwiqlliplaalivvtrllrcvccvv
```

-continued

```
pflvmapaapapayehattmpsqagisyntivnragyaplpisitptkik

liptvnleyvtchyktgmdspaikccgsqectptyrpdeqckvftgvypf

mwggaycfcdtentqvskayvmksddcladhaeaykahtasvqaflnitv

gehsivttvyvngetpvnfngvkitagplstawtpfdrkivqyageiyny

dfpeygagqpgafgdiqsrtvsssdlyantnlvlqrpkagaihvpytqap

sgfeqwkkdkapslkftapfgceiytnpiraencavgsiplafdipdalf

trvsetptlsaaectlnecvyssdfggiatvkysasksgkcavhvpsgta

tlkeaavelteqgsatihfstanihpefrlqictsyvtckgdchppkdhi

vthpgyhaqtftaavsktawtwltsllggsaviiiiglvlativamyvlt

nqkhn.
```

In one embodiment, a first attachment site comprises an amino group, preferably an amino group of a lysine residue. In one embodiment, the second attachment site comprises sulfhydryl group, preferably, a sulfhydryl group of a cysteine.

According to the present application, a Chikungunya virus like particle or Venezuelan equine encephalitis virus like particle comprising a Chikungunya or Venezuelan equine encephalitis viral structural protein and at least one antigen, wherein the at least one antigen is inserted in E3 of the viral structural protein, and the Chikungunya viral structural protein or Venezuelan equine encephalitis viral structural protein and the antigen are expressed as a fusion protein can be provided. The antigen may be inserted directly or indirectly in E3 of the viral structural protein.

Figure 1:
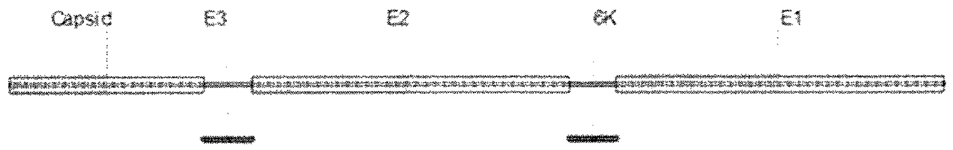
FIG. 1 shows structure of CHIKV or VEEV viral structural protein.

The viral structural protein of Chikungunya virus as well as Venezuelan equine encephalitis consist of E1, E2, 6K and E3. 6K is naturally cleaved during the process of assemble and removed from the VLPs. The mature VLPs consists of capsid, E1 and E2 (See FIG. 1). In the present specification and claims, "viral structural protein" refers not only those having 6K but also after 6K is removed.

6K sequences of the CHIKV and VEEV strains used in the working examples are as follows:

```
CHIKV OPY-1 Strain, 6K: 749-809aa of SEQ ID NO: 1
                                      (SEQ ID NO: 137)
atyqeaaiylwneqqplfwlqaliplaalivlcnclrilpccckt lafla

vmsvgahtvsa

CHIKV 37997 strain, 6K: 749-809aa of SEQ ID NO: 2
                                      (SEQ ID NO: 138)
atyyeaaaylwneqqplfwlqaliplaalivlcnckllpccckt laflav

msigahtvsa

VEEV TC-83strain, 6K: 758-813aa of SEQ ID NO: 3
                                      (SEQ ID NO: 139)
ettwesldhlwnnnqqmfwiglliplaalivvtrllrcvccvvpflvmag

aagaga
```

Regarding Chikungunya viral structural protein, at least one antigen may be inserted instead of furin site (RKRR) (SEQ ID NO: 148) from 322R to 325R of SEQ ID NO: 1 or 2. For example, regarding Chikungunya viral structural protein, at least one antigen is inserted between residues H at 321-position and S at 326-position of SEQ ID NO: 1 or 2; between P at 320-position and S at 326-position of SEQ ID NO: 1 or 2; or between S at 319-position and S at 326-position of SEQ ID NO: 1 or 2. VLP_CHI 0.56 vector (SEQ ID NO: 30) may be used for preparing Chikungunya virus like particle where the antigen is inserted between residues 321 and 326 of SEQ ID Nos.1 or 2. When an antigen is inserted between residues 321 and 326 of SEQ ID Nos.1 or 2, the virus like particle provided by the present application may be Chikungunya virus like particle consisting of a complex of E2 and E3, capsid and E1, and wherein the at least one antigen is inserted into E3 region, and wherein the capsid consists of an amino acid sequence represented by SEQ ID NO: 31 (or SEQ ID NO: 75); the E1 consists of an amino acid sequence represented by SEQ ID NO: 32 or SEQ ID NO: 76; and the complex of E2 and E3 consists of an amino acid sequence represented by SEQ ID NO: 33 or SEQ ID NO: 77 provided that an amino acid sequence of the at least one antigen is inserted between residues corresponding to 321 and 326 of SEQ ID NO: 1 or 2.

Venezuelan equine encephalitis viral structural protein, at least one antigen may be inserted instead of furin site (RKRR) (SEQ ID NO: 148) from 331R to 334R of SEQ ID NO: 3. For example, regarding Venezuelan equine encephalitis viral structural protein, at least one antigen is inserted between G at 330-position and S at 335-position of SEQ ID NO: 3; between P at 329-position and S at 335-position of SEQ ID NO: 3; or between C at 328-position and S at 335-position of SEQ ID NO: 3. VLP_VEEV 0.66 vector (SEQ ID No: 34) may be used for preparing Venezuelan equine encephalitis virus like particle where the antigen is inserted between residues 330 and 335 of SEQ ID NO: 3. When an antigen is inserted between residues 330 and 335 of SEQ ID NO: 3, the virus like particle provided by the present application may be Venezuelan equine encephalitis virus like particle consisting of a complex of E2 and E3, capsid and E1, and wherein the at least one antigen is inserted into E3 region, and wherein the capsid consists of an amino acid sequence represented by SEQ ID NO: 35; the E1 consists of an amino acid sequence represented by SEQ ID NO: 36; and the complex of E2 and E3 consists of an amino acid sequence represented by SEQ ID NO: 37 provided that an amino acid sequence of the at least one antigen is inserted between residues 330 and 335 of SEQ ID NO: 3.

In one embodiment, at least one antigen selected from an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA, an antigen derived from HVEM, an antigen derived from PCSK9 or an antigen derived from DPP-4 is inserted into E3 of Chikungunya viral structural protein or Venezuelan equine encephalitis viral structural protein.

The fusion protein may be expressed using a conventional technique in the art. A variety of expression systems can be used for the expression of the fusion protein. For example, the fusion protein can be expressed in 293F cells, Sf9 cells, *E. coli*, insect cell or Baculovirus.

A protein derived from Chikungunya virus (CHIKV) or Venezuelan equine encephalitis virus (VEEV) may be a naturally occurring viral protein or modified protein thereof.

When a protein derived from a virus is conjugated with a protein derived from an antigen, a linker peptide including SG, GS, SGG, GGS SGSG (SEQ ID NO: 147) and TRGGS (SEQ ID NO: 149) may be used. Examples of conjugation of the protein derived from a virus (referred to as "PFV" below) with the protein derived from the antigen (referred to as "PFA" below) include, but not limited to: PFV-SG-PFA-GS-PFV; PFV-SG-PFA-GGS-PFV; PFV-SSG-PFA-GS- PFV; PFV-SGG-PFA-GGS-PFV; PFV-SGSG (SEQ ID NO: 147)-PFA-GS-PFV; and PFA-SGG-PFA-TRGGS(SEQ ID NO: 149)-PFV.

In one embodiment, the present application provides a virus like particle comprising a fusion protein of a protein derived from Chikungunya virus (CHIKV) or Venezuelan equine encephalitis virus (VEEV) and a protein derived from *Plasmodium falciparum* circumsporozoite protein, PD-1, PD-L1, CTLA-4, an antigen derived from IL-2, an antigen derived from DISC1, an antigen derived from HER2, an antigen derived from BTLA, an antigen derived from HVEM, an antigen derived from PCSK9 and an antigen derived from DPP-4, wherein the virus like particle is prepared by transfecting an expression vector comprising a nucleic acid molecule comprising a nucleotide sequence represented by SEQ ID Nos.:38-45 into a mammalian cell (e.g. 293F cell). Regarding this embodiment, modified fusion protein can be prepared by transfecting an expression vector comprising a nucleic acid molecule comprising a nucleotide sequence having at least 70%, 75%, 80%, 85%, 90%, 95% or 98% amino acid sequence identity to SEQ ID Nos.: 38-45 into a mammalian cell (e.g. 293F cell).

In one embodiment, the present application provides a virus like particle comprising or consisting of:

one or more capsid of Chikungunya virus (CHIKV) or Venezuelan equine encephalitis virus (VEEV);

one or more E1 of Chikungunya virus (CHIKV) or Venezuelan equine encephalitis virus (VEEV);

one or more E2 of Chikungunya virus (CHIKV) or Venezuelan equine encephalitis virus (VEEV); and one or more E3 of Chikungunya virus (CHIKV) or Venezuelan equine encephalitis virus (VEEV), wherein each of E2 is bound to each of E3, and an antigen selected from the group consisting of an antigen derived from *Plasmodium falciparum* circumsporozoite protein, an antigen derived from PD-1, an antigen derived from a ligand of PD-1 (e.g. PD-L1, PD-L2), an antigen derived from CTLA-4, an antigen derived from IL-2, an antigen derived from DISC1, an antigen derived from HER2, an antigen derived from BTLA, an antigen derived from HVEM, an antigen derived from PCSK9, and an antigen derived from DPP-4 is inserted into E3 of Chikungunya virus (CHIKV) or Venezuelan equine encephalitis virus (VEEV). For example, present application provides a virus like particle comprising or consisting of:

240 capsids of Chikungunya virus (CHIKV) or Venezuelan equine encephalitis virus (VEEV);

240 E1s of Chikungunya virus (CHIKV) or Venezuelan equine encephalitis virus (VEEV); and 240 E2s of Chikungunya virus (CHIKV) or Venezuelan equine encephalitis virus (VEEV);

240s E3s of Chikungunya virus (CHIKV) or Venezuelan equine encephalitis virus (VEEV), wherein each of E2 is bound to each of E3, and an antigen selected from the group consisting of an antigen derived from *Plasmodium falciparum* circumsporozoite protein, PD-1, an antigen derived from a ligand of PD-1 (e.g. PD-L1, PD-L2), an antigen derived from CTLA-4, an antigen derived from IL-2, an antigen derived from DISC1, an antigen derived from HER2, an antigen derived from BTLA an antigen derived from HVEM, an antigen derived from PCSK9 and antigen derived from DPP-4 is inserted into each of E3s of Chikungunya virus (CHIKV) or Venezuelan equine encephalitis virus (VEEV).

Virus like particle may work as a carrier of an antigen, which can be administered to human body. Examples of CHIKV VLP, which can work as a carrier of an antigen, include, but are not limited to, Chikungunya virus like particle comprising or consisting of a complex of E2 and E3, capsid and E1, wherein the capsid consists of an amino acid sequence represented by SEQ ID NO: 31 (or SEQ ID NO: 75); the E1 consists of an amino acid sequence represented by SEQ ID NO: 32 (or SEQ ID NO: 76); and the complex of E2 and E3 consists of an amino acid sequence represented by SEQ ID NO: 33 (or SEQ ID NO: 77) provided that an amino acid sequence of the at least one antigen is inserted between residues corresponding to 321 and 326 of SEQ ID NO: 1 or SEQ ID NO: 2. Examples of VEEV VLP, which can work as a carrier of an antigen, include, but are not limited to, Venezuelan equine encephalitis virus like particle comprising or consisting of a complex of E2 and E3, capsid and E1, wherein the capsid consists of an amino acid sequence represented by SEQ ID NO: 35; the E1 consists of an amino acid sequence represented by SEQ ID NO: 36; and the complex of E2 and E3 consists of an amino acid sequence represented by SEQ ID NO: 37 provided that an amino acid sequence of the at least one antigen is inserted between residues corresponding to 330 and 335 of SEQ ID NO: 3.

Examples of a virus like particle comprising Chikungunya viral structural protein and an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA an antigen derived from HVEM, an antigen derived from PCSK9 and an antigen derived from DPP-4 include, but are not limited to, Chikungunya virus like particle consisting of a complex of E2 and E3 into which the at least one antigen is inserted, capsid and E1, and wherein the at least one antigen is inserted into E3 region, and wherein amino acid sequence of each of the capsid, E1, complex of E2 and E3 into which the at least one antigen is inserted is described below:

(1)

amino acid sequence of E1 is represented by SEQ ID NO: 32;

amino acid sequence of the complex of E2 and E3 into which the malaria antigen is inserted is represented by SEQ ID NO: 46; and amino acid sequence of capsid is represented by SEQ ID NO: 31;

(2)

amino acid sequence of E1 is represented by SEQ ID NO: 32;

amino acid sequence of the complex of E2 and E3 into which the PD-1 antigen is inserted is represented by SEQ ID NO: 47; and amino acid sequence of capsid is represented by SEQ ID NO: 31;

(3)

amino acid sequence of E1 is represented by SEQ ID NO: 32;

amino acid sequence of the complex of E2 and E3 into which the PD-L1 antigen is inserted is represented by SEQ ID NO: 48; and amino acid sequence of capsid is represented by SEQ ID NO: 31; or (4)

amino acid sequence of E1 is represented by SEQ ID NO: 32;

amino acid sequence of the complex of E2 and E3 into which the CTLA-4 antigen is inserted is represented by SEQ ID NO: 49; and amino acid sequence of capsid is represented by SEQ ID NO: 31.

Examples of a virus like particle comprising Venezuelan equine encephalitis viral structural protein and an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA, an antigen derived from HVEM an antigen derived from PCSK9 or an antigen derived from DPP-4 include, but are not limited to, Venezuelan equine encephalitis virus like particle consisting of a complex of E2 and E3 into which the at least one antigen is inserted, capsid and E1, and wherein amino acid sequence of each of the capsid, E1, the complex of E2 and E3 into which the at least one antigen is inserted is described below:

(1)

amino acid sequence of E1 is represented by SEQ ID NO: 36;

amino acid sequence of the complex of E2 and E3 into which the malaria antigen is inserted is represented by SEQ ID NO: 50; and amino acid sequence of capsid is represented by SEQ ID NO: 35;

(2)

amino acid sequence of E1 is represented by SEQ ID NO: 36;

amino acid sequence of the complex of E2 and E3 into which the PD-1 antigen is inserted is represented by SEQ ID NO: 51; and amino acid sequence of capsid is represented by SEQ ID NO: 35;

(3)

amino acid sequence of E1 is represented by SEQ ID NO: 36;

amino acid sequence of the complex of E2 and E3 into which the PD-L1 antigen is inserted is represented by SEQ ID NO: 52; and amino acid sequence of capsid is represented by SEQ ID NO: 35; or (4)

amino acid sequence of E1 is represented by SEQ ID NO: 36;

amino acid sequence of the complex of E2 and E3 into which the CTLA-4 antigen is inserted is represented by SEQ ID NO: 53; and amino acid sequence of capsid is represented by SEQ ID NO: 35.

Further, regarding these embodiments, modified capsid of Chikungunya virus (CHIKV) or Venezuelan equine encephalitis virus (VEEV), modified E1 of Chikungunya virus (CHIKV) or Venezuelan equine encephalitis virus (VEEV) and/or modified complex of E2 and E3 of Chikungunya virus (CHIKV) or Venezuelan equine encephalitis virus (VEEV) may be used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 31 (or SEQ ID NO: 75) or SEQ ID NO: 35; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID NO: 32 (or SEQ ID NO: 76) or SEQ ID NO: 36; and/or the modified complex of E2 and E3 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID Nos.:33 (or SEQ ID NO: 77) or SEQ ID Nos.:37. Also, the modified capsid, E1 and/or a complex of E2 and E3 may be a mutant where at most 10% of the amino acids are deleted, substituted, and/or added based on the capsid consisting of an amino acid sequence represented by SEQ ID NO: 31 (or SEQ ID NO: 75) or SEQ ID NO: 35; E1 consisting of an amino acid sequence represented by SEQ ID NO: 32 (or SEQ ID NO: 76) or SEQ ID NO: 36; and/or a complex of E2 and E3 consisting of consisting of an amino acid sequence represented by SEQ ID NO: 33 (or SEQ ID NO: 77) or SEQ ID NO: 37.

Virus like particle may be prepared by introducing an expression vector comprising a DNA molecule having a nucleotide sequence encoding the virus like particle into a cell (e.g. 293F cell), culturing the cell and recovering the virus like particle from the conditioned medium using ultracentrifugal method.

(2) Nucleotide, Vector

In a second aspect, the present application provides a nucleic acid molecule comprising or consisting of a nucleotide sequence encoding a virus like particle comprising a modified envelope protein E3.

A derivative of the above-described nucleic acid molecule which can be prepared by modifying the above-described nucleic acid molecule is also provided by the present application. The derivative may consist of a nucleotide sequence which has a sequence identity of 70%, 80%, 90%, 95% or 98% or more with the nucleotide sequence of the above-described nucleic acid molecule.

The nucleic acid molecule provided by the present application may be an isolated nucleic acid molecule encoding a virus like particle (e.g. a Chikungunya virus like particle, Venezuelan equine encephalitis virus like particle) which comprises a viral structural protein with a modified envelope protein E3. One embodiment, the virus like particle comprises a viral structural protein and at least one antigen wherein the at least one antigen is inserted into the envelope protein E3 of the viral structural protein.

One skilled in the art may prepare the nucleic acid molecule provided by the present application described above based on an exemplary nucleotide sequences of Chikungunya or Venezuelan equine viral structural protein that encode capsid and/or envelope represented by SEQ ID Nos.:54-55.

In one embodiment, a nucleotide sequence encoding an antigen can be inserted into nucleotide sequence encoding E3 of Chikungunya or Venezuelan equine viral structural protein. For example, nucleotide sequence encoding an antigen is inserted between residues 963 and 969 of SEQ ID NO: 54 (for CHIKV) or between residues 990 and 1006 of SEQ ID NO: 55 (for VEEV) to prepare a nucleic acid molecule consisting of a nucleotide sequence encoding a virus like particle comprising an envelope protein E3, wherein the envelope protein E3 is modified to comprise at least one antigen. Examples of the nucleic acid molecule provided by the present application include, but are not limited to, a nucleic acid molecule consisting of a nucleotide sequence represented by any one of SEQ ID NOs.:38-45. A nucleic acid molecule consisting of a nucleotide sequence which has a sequence identity of 70%, 80%, 90%, 95% or 98% or more with the nucleotide sequence represented by any one of SEQ IDs.:38-45 is also provided.

In one embodiment, the present application provides a vector comprising the nucleic acid molecule as described above, wherein the vector optionally comprises an expression control sequence operably linked to the nucleic acid molecule. A vector used herein may alter a promoter including enhancer sequence, polyadenylation signal, and antibiotic resistance genes. For example, a vector comprising a nucleic acid molecule which consists of a nucleotide sequence represented by SEQ ID NO: 54 or SEQ ID NO: 55, wherein a nucleotide sequence encoding at least one antigen is inserted between residues 963 and 969 of SEQ ID NO: 54 (for CHIKV VLP) or between residues 990 and 1006 of SEQ ID NO: 55 (for VEEV-VLP); and an expression control sequence operably linked to the nucleic acid molecule is provided.

Examples of an expression control sequence include, but are not limited to, promoter such as CMV promoter, phage lambda PL promoter, the *E. coli* lac, phoA and tac promoters, the SV40 early and late promoters, and promoters of retroviral LTRs.

In this embodiment, the vector comprising an expression control sequence operably linked to the nucleic acid molecule as described above can be used as an expression vector for preparing the particle provided by the present application.

The expression vectors can be prepared by a person skilled in the art based on WO2012/006180, the entire contents of which are incorporated by reference herein.

Examples of vectors which can be used for expressing a virus like particle comprising a fusion protein of a protein derived from Chikungunya virus (CHIKV) and an antigen include a vector shown in VLP_CHI 0.56 vector (SEQ ID NO: 30).

Based on the VLP_CHI 0.56 vector (SEQ ID NO: 30), a skilled person can prepare vectors which can be used for expressing a virus like particle comprising a fusion protein of a protein derived from Chikungunya virus (CHIKV) and a desired antigen. For example, when a skilled person prepares CHIKV VLP comprising a malaria antigen (Sggnpnanpnanpnanpnanpnanpnaggs (SEQ ID NO: 56))-inserted E3, based on the VLP_CHI 0.56 vector, a skilled person can prepare a vector as described below (SEQ ID NO: 57) where nucleotide encoding the antigen is underlined.

gaattcccattgcatacgttgtatccatatcataatatgtacatttatattggctcatgtccaacattaccgccatgt tgacattgattattgactagttattaatagtaatcaattacggggtcattagttcatagcccatatatggagttccgc gttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggca gtacatcaagtgtatcatatgccaagtacgccccctattgacgtcaatgacggtaaatggcccgcctggcattatgcc cagtacatgaccttatgggactttcctacttggcagtacatctacgtattagtcatcgctattaccatggtgatgcgg ttttggcagtacatcaatgggcgtggatagcggtttgactcacggggatttccaagtctccaccccattgacgtcaat gggagtttgttttggcaccaaaatcaacgggactttccaaaatgtcgtaacaactccgccccattgacgcaaatgggc ggtaggcgtgtacggtgggaggtctatataagcagagctcgtttagtgaaccgtcagatcgcctggagacgccatcca cgctgttttgacctccatagaagacaccgggaccgatccagcctccgttaacggtggagggcagtgtagtctgagcag tactcgttgctgccgcgcgcgccaccagacataatagctgacagactaacagactgttcctttccatgggtcttttct gcagtcaccgtcgtcgacacgtgtgatcagatatcgcggccgccaccatggagttcatcccgacgcaaactttctata acagaaggtaccaaccccgaccctgggccccacgccctacaattcaagtaattagacctagaccacgtccacagaggc aggctgggcaactcgcccagctgatctccgcagtcaacaaattgaccatgcgcgcggtacctcaacagaagcctcgca gaaatcggaaaaacaagaagcaaaggcagaagaagcaggcgccgcaaaacgacccaaagcaaaagaagcaaccaccac aaaagaagccggctcaaaagaagaagaaaccaggccgtagggagagaatgtgcatgaaaattgaaaatgattgcatct tcgaagtcaagcatgaaggcaaagtgatgggctacgcatgcctggtgggggataaagtaatgaaaccagcacatgtga agggaactatcgacaatgccgatctggctaaactggcctttaagcggtcgtctaaatacgatcttgaatgtgcacaga taccggtgcacatgaagtctgatgcctcgaagtttacccacgagaaacccgaggggtactataactggcatcacggag cagtgcagtattcaggaggccggttcactatcccgacgggtgcaggcaagccgggagacagcggcagaccgatcttcg acaacaaaggacgggtggtggccatcgtcctaggaggggccaacgaaggtgcccgcacggccctctccgtggtgacgt ggaacaaagacatcgtcacaaaaattacccctgagggagccgaagagtggagcctcgccctcccggtcttgtgcctgt tggcaaacactacattcccctgctctcagccgccttgcacaccctgctgctacgaaaaggaaccggaaagcaccttgc gcatgcttgaggacaacgtgatgagacccggatactaccagctactaaaagcatcgctgacttgctctccccactccg gaggaaacccgaatgccaatcccaacgcgaaccccaatgctaacccaaatgccaacccaaacgccaaccccaacgctg gtggatccagtactaaggacaattttaatgtctataaagccacaagaccatatctagctcattgtcctgactgcggag aagggcattcgtgccacagccctatcgcattggagcgcatcagaaatgaagcaacggacggaacgctgaaaatccagg -continued tctctttgcagatcgggataaagacagatgacagccacgattggaccaagctgcgctatatggatagccatacgcccg cggacgcggagcgagccggattgcttgtaaggacttcagcaccgtgcacgatcaccgggaccatgggacactttattc tcgcccgatgcccgaaaggagagacgctgacagtgggatttacggacagcagaaagatcagccacacatgcacacacc cgttccatcatgaaccacctgtgataggtagggagaggttccactctcgaccacaacatggtaaagagttaccttgca gcacgtacgtgcagagcaccgctgccactgctgaggagatagaggtgcatatgcccccagatactcctgaccgcacgc tgatgacgcagcagtctggcaacgtgaagatcacagttaatgggcagacggtgcggtacaagtgcaactgcggtggct caaacgagggactgacaaccacagacaaagtgatcaataactgcaaaattgatcagtgccatgctgcagtcactaatc acaagaattggcaatacaactcccctttagtcccgcgcaacgctgaactcggggaccgtaaaggaaagatccacatcc cattcccattggcaaacgtgacttgcagagtgccaaaagcaagaaaccctacagtaacttacggaaaaaaccaagtca ccatgctgctgtatcctgaccatccgacactcttgtcttaccgtaacatgggacaggaaccaaattaccacgaggagt gggtgacacacaagaaggaggttaccttgaccgtgcctactgagggtctggaggtcacttggggcaacaacgaaccat acaagtactggccgcagatgtctacgaacggtactgctcatggtcacccacatgagataatcttgtactattatgagc tgtaccccactatgactgtagtcattgtgtcggtggcctcgttcgtgcttctgtcgatggtgggcacagcagtgggaa tgtgtgtgtgcgcacggcgcagatgcattacaccatatgaattaacaccaggagccactgttcccttcctgctcagcc tgctatgctgcgtcagaacgaccaaggcggccacatattacgaggctgcggcatatctatggaacgaacagcagcccc tgttctggttgcaggctcttatcccgctggccgccttgatcgtcctgtgcaactgtctgaaactcttgccatgctgct gtaagaccctggctttttttagccgtaatgagcatcggtgcccacactgtgagcgcgtacgaacacgtaacagtgatcc cgaacacggtgggagtaccgtataagactcttgtcaacagaccgggttacagccccatggtgttggagatggagctac aatcagtcaccttggaaccaacactgtcacttgactacatcacgtgcgagtacaaaactgtcatcccctccccgtacg tgaagtgctgtggtacagcagagtgcaaggacaagagcctaccagactacagctgcaaggtctttactggagtctacc catttatgtggggcggcgcctactgcttttgcgacgccgaaaatacgcaattgagcgaggcacatgtagagaaatctg aatcttgcaaaacagagtttgcatcggcctacagagcccacaccgcatcggcgtcggcgaagctccgcgtcctttacc aaggaaacaacattaccgtagctgcctacgctaacggtgaccatgccgtcacagtaaaggacgccaagtttgtcgtgg gcccaatgtcctccgcctggacaccttttgacaacaaaatcgtggtgtacaaaggcgacgtctacaacatggactacc caccttttggcgcaggaagaccaggacaatttggtgacattcaaagtcgtacaccggaaagtaaagacgtttatgcca acactcagttggtactacagaggccagcagcaggcacggtacatgtaccatactctcaggcaccatctggcttcaagt attggctgaaggaacgaggagcatcgctacagcacacggcaccgttcggttgccagattgcgacaaacccggtaagag ctgtaaattgcgctgtggggaacataccaatttccatcgacataccggatgcggcctttactagggttgtcgatgcac cctctgtaacggacatgtcatgcgaagtaccagcctgcactcactcctccgactttgggggcgtcgccatcatcaaat acacagctagcaagaaaggtaaatgtgcagtacattcgatgaccaacgccgttaccattcgagaagccgacgtagaag tagaggggaactcccagctgcaaatatccttctcaacagccctggcaagcgccgagtttcgcgtgcaagtgtgctcca cacaagtacactgcgcagccgcatgccaccctccaaaggaccacatagtcaattacccagcatcacacaccacccttg gggtccaggatatatccacaacggcaatgtcttgggtgcagaagattacgggaggagtaggattaattgttgctgttg ctgccttaattttaattgtggtgctatgcgtgtcgtttagcaggcactaaggatctagatctgctgtgccttctagtt gccagccatctgttgtttgcccctcccccgtgccttccttgaccctggaaggtgccactcccactgtcctttcctaat aaaatgaggaaattgcatcgcattgtctgagtaggtgtcattctattctggggggtggggtggggcaggacagcaagg gggaggattgggaagacaatagcaggcatgctggggatgcggtgggctctatgggtacccaggtgctgaagaattgac ccggttcctcctgggccagaaagaagcaggcacatccccttctctgtgacacaccctgtccacgcccctggttcttag ttccagccccactcataggacactcatagctcaggagggctccgccttcaatcccacccgctaaagtacttggagcgg tctctccctccctcatcagcccaccaaaccaaacctagcctccaagagtgggaagaaattaaagcaagataggctatt aagtgcagagggagagaaaatgcctccaacatgtgaggaagtaatgagagaaatcatagaattttaaggccatgattt -continued aaggccatcatggcctaagcttgaaaggagataggatcaaagcttggcgtaatcatggtcatagctgtttcctgtgtg aaattgttatccgctcacaattccacacaacatacgagccggaagcataaagtgtaaagcctggggtgcctaatgagt gagctaactcacattaattgcgttgcgctcactgcccgctttccagtcgggaaacctgtcgtgccagctgcattaatg aatcggccaacgcgcggggagaggcggtttgcgtattgggcgctcttccgcttcctcgctcactgactcgctgcgctc ggtcgttcggctgcggcgagcggtatcagctcactcaaaggcggtaatacggttatccacagaatcaggggataacgc aggaaagaacatgtgagcaaaaggccagcaaaaggccaggaaccgtaaaaaggccgcgttgctggcgtttttccatag gctccgcccccctgacgagcatcacaaaaatcgacgctcaagtcagaggtggcgaaacccgacaggactataaagata ccaggcgtttccccctggaagctccctcgtgcgctctcctgttccgaccctgccgcttaccggatacctgtccgcctt tctcccttcgggaagcgtggcgctttctcatagctcacgctgtaggtatctcagttcggtgtaggtcgttcgctccaa gctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgctac agagttcttgaagtggtggcctaactacggctacactagaagaacagtatttggtatctgcgctctgctgaagccagt taccttcggaaaaagagttggtagctcttgatccggcaaacaaaccaccgctggtagcggtggtttttttgtttgcaa gcagcagattacgcgcagaaaaaaaggatctcaagaagatcctttgatcttttctacggggtctgacgctcagtggaa cgaaaactcacgttaagggattttggtcatgagattatcaaaaaggatcttcacctagatccttttaaattaaaaatg aagttttaaatcaatctaaagtatatatgagtaaacttggtctgacagttaccaatgcttaatcagtgaggcacctat ctcagcgatctgtctatttcgttcatccatagttgcctgactccccgtcgtgtagataactacgatacgggagggctt accatctggccccagtgctgcaatgataccgcgagaaccacgctcaccggctccagatttatcagcaataaaccagcc agccggaagggccgagcgcagaagtggtcctgcaactttatccgcctccatccagtctattaattgttgccgggaagc tagagtaagtagttcgccagttaatagtttgcgcaacgttgttgccattgctacaggcatcgtggtgtcacgctcgtc gtttggtatggcttcattcagctccggttcccaacgatcaaggcgagttacatgatcccccatgttgtgcaaaaaagc ggttagctccttcggtcctccgatcgttgtcagaagtaagttggccgcagtgttatcactcatggttatggcagcact gcataattctcttactgtcatgccatccgtaagatgcttttctgtgactggtgagtactcaaccaagtcattctgaga atagtgtatgcggcgaccgagttgctcttgcccggcgtcaatacgggataataccgcgccacatagcagaactttaaa agtgctcatcattggaaaacgttcttcggggcgaaaactctcaaggatcttaccgctgttgagatccagttcgatgta acccactcgtgcacccaactgatcttcagcatcttttactttcaccagcgtttctgggtgagcaaaaacaggaaggca aaatgccgcaaaaaagggaataagggcgacacggaaatgttgaatactcatactcttcctttttcaatattattgaag catttatcagggttattgtctcatgagcggatacatatttgaatgtatttagaaaaataaacaaataggggttccgcg cacatttccccgaaaagtgccacctgacgtctaagaaaccattattatcatgacattaacctataaaaataggcgtat cacgaggccctttcgggtcgcgcgtttcggtgatgacggtgaaaacctctgacacatgcagctcccgttgacggtcac agcttgtctgtaagcggatgccgggagcagacaagcccgtcagggcgcgtcagcgggtgttggcgggtgtcggggctg gcttaactatgcggcatcagagcagattgtactgagagtgcaccataaaattgtaaacgttaatattttgttaaaatt cgcgttaaatttttgttaaatcagctcattttttaaccaataggccgaaatcggcaaaatcccttataaatcaaaaga atagcccgagatagggttgagtgttgttccagtttggaacaagagtccactattaaagaacgtggactccaacgtcaa agggcgaaaaaccgtctatcagggcgatggcccactacgtgaaccatcacccaaatcaagttttttggggtcgaggtg ccgtaaagcactaaatcggaaccctaaagggagcccccgatttagagcttgacggggaaagccggcgaacgtggcgag aaaggaagggaagaaagcgaaaggagcgggcgctagggcgctggcaagtgtagcggtcacgctgcgcgtaaccaccac acccgccgcgcttaatgcgccgctacagggcgcgtactatggttgctttgacgtatgcggtgtgaaataccgcacaga tgcgtaaggagaaaataccgcatcaggcgccattcgccattcaggctgcgcaactgttgggaagggcgatcggtgcgg -continued gcctcttcgctattacgccagctggcgaaagggggatgtgctgcaaggcgattaagttgggtaacgccagggttttcc cagtcacgacgttgtaaaacgacggccagtgaattccatggtctcaactttc Examples of vectors which can be used for expressing a virus like particle comprising a fusion protein of a protein derived from Venezuelan equine encephalitis virus (VEEV) and an antigen include a vector shown in VLP_VEEV 0.66 vector (SEQ ID NO: 34).

Figure 2:
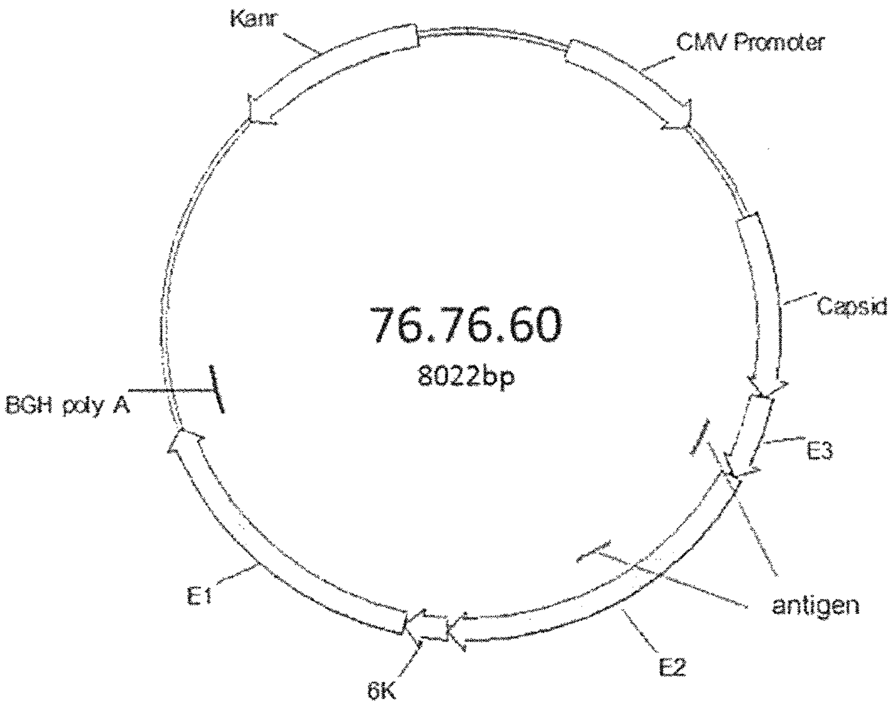
FIG. 2 shows representative structure of expression vector for a viral structural protein with modified E3 and E2 envelope proteins.

Based on the VLP_VEEV 0.66 vector (SEQ ID NO: 34), a skilled person can prepare vectors which can be used for expressing a virus like particle comprising a fusion protein of a protein derived from Venezuelan equine encephalitis virus (VEEV) and a desired antigen. For example, when a skilled person prepares VEEV VLP comprising a malaria antigen (SGG-qgpgapqgpgapqgpgapqgpgap-GGS (SEQ ID NO: 58))-inserted E3, based on the VLP_VEEV 0.66 vector, a skilled person can prepare a vector as described below (SEQ ID NO: 59) where nucleotide encoding the antigen is underlined.

gaattcccattgcatacgttgtatccatatcataatatgtacatttatattggctcatgtccaacattaccgccatgt tgacattgattattgactagttattaatagtaatcaattacggggtcattagttcatagcccatatatggagttccgc gttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggca gtacatcaagtgtatcatatgccaagtacgccccctattgacgtcaatgacggtaaatggcccgcctggcattatgcc cagtacatgaccttatgggactttcctacttggcagtacatctacgtattagtcatcgctattaccatggtgatgcgg ttttggcagtacatcaatgggcgtggatagcggtttgactcacggggatttccaagtctccaccccattgacgtcaat gggagtttgttttggcaccaaaatcaacgggactttccaaaatgtcgtaacaactccgccccattgacgcaaatgggc ggtaggcgtgtacggtgggaggtctatataagcagagctcgtttagtgaaccgtcagatcgcctggagacgccatcca cgctgttttgacctccatagaagacaccgggaccgatccagcctccgttaacggtggagggcagtgtagtctgagcag tactcgttgctgccgcgcgcgccaccagacataatagctgacagactaacagactgttcctttccatgggtcttttct gcagtcaccgtcgtcgacacgtgtgatcagatatcgcggccgccaccatgttcccgttccagccaatgtatccgatgc agccaatgccctatcgcaacccgttcgcggccccgcgcaggccctggttccccagaaccgacccttttctggcgatgc aggtgcaggaattaacccgctcgatggctaacctgacgttcaagcaacgccgggacgcgccacctgaggggccatccg ctaataaaccgaagaaggaggcctcgcaaaaacagaaaggggggaggccaagggaagaagaagaagaaccaagggaaga agaaggctaagacagggccgcctaatccgaaggcacagaatggaaacaagaagaagaccaacaagaaaccaggcaaga gacagcgcatggtcatgaaattggaatctgacaagacgttcccaatcatgttggaagggaagataaacggctacgctt gtgtggtcggagggaagttattcaggccgatgcatgtggaaggcaagatcgacaacgacgttctggccgcgcttaaga cgaagaaagcatccaaatacgatcttgagtatgcagatgtgccacagaacatgcgggccgatacattcaaatacaccc atgagaaaccccaaggctattacaggtggcatcatggagcagtccaatatgaaaatgggcgtttcacggtgccgaaag gagttggggccaagggagacagcggacgacccattctggataaccagggacgggtggtcgctattgtgctgggaggtg tgaatgaaggatctaggacagccctttcagtcgtcatgtggaacgagaagggagttaccgtgaagtatactccagaga actgcgagcaatggtcactagtgaccaccatgtgtctgctcgccaatgtgacgttcccatgtgctcaaccaccaattt gctacgacagaaaaccagcagagactttggccatgctcagcgttaacgttgacaacccgggctacgatgagctgctgg aagcagctgttaagtgccccgggtccggaggacagggacctggcgctcctcagggaccaggggcaccacagggcccag gcgccccacagggggcctggggcccccgggggatcctccaccgaggagctgtttaatgagtataagctaacgcgccctt acatggccagatgcatcagatgtgcagttgggagctgccatagtccaatagcaatcgaggcagtaaagagcgacgggc acgacggttatgttagacttcagacttcctcgcagtatggcctggattcctccggcaacttaaagggcaggaccatgc ggtatgacatgcacgggaccattaaagagataccactacatcaagtgtcactctatacatctcgcccgtgtcacattg tggatgggcacggttatttcctgcttgccaggtgcccggcaggggactccatcaccatggaatttaagaaagattccg tcagacactcctgctcggtgccgtatgaagtgaaatttaatcctgtaggcagagaactctatactcatccccccagaac acggagtagagcaagcgtgccaagtctacgcacatgatgcacagaacagaggagcttatgtcgagatgcacctcccgg -continued gctcagaagtggacagcagtttggtttccttgagcggcagttcagtcaccgtgacacctcctgatgggactagcgccc tggtggaatgcgagtgtggcggcacaaagatctccgagaccatcaacaagacaaaacagttcagccagtgcacaaaga aggagcagtgcagagcatatcggctgcagaacgataagtgggtgtataattctgacaaactgcccaaagcagcgggag ccaccttaaaaggaaaactgcatgtcccattcttgctggcagacggcaaatgcaccgtgcctctagcaccagaaccta tgataaccttcggtttcagatcagtgtcactgaaactgcaccctaagaatcccacatatctaatcacccgccaacttg ctgatgagcctcactacacgcacgagctcatatctgaaccagctgttaggaattttaccgtcaccgaaaaagggtggg agtttgtatggggaaaccacccgccgaaaaggttttgggcacaggaaacagcacccggaaatccacatgggctaccgc acgaggtgataactcattattaccacagataccctatgtccaccatcctgggtttgtcaatttgtgccgccattgcaa ccgtttccgttgcagcgtctacctggctgttttgcagatcaagagttgcgtgcctaactccttaccggctaacaccta acgctaggataccattttgtctggctgtgctttgctgcgcccgcactgcccgggccgagaccacctgggagtccttgg atcacctatggaacaataaccaacagatgttctggattcaattgctgatccctctggccgccttgatcgtagtgactc gcctgctcaggtgcgtgtgctgtgtcgtgcctttttttagtcatggccggcgccgcaggcgccggcgcctacgagcacg cgaccacgatgccgagccaagcgggaatctcgtataacactatagtcaacagagcaggctacgcaccactccctatca gcataacaccaacaaagatcaagctgatacctacagtgaacttggagtacgtcacctgccactacaaaacaggaatgg attcaccagccatcaaatgctgcggatctcaggaatgcactccaacttacaggcctgatgaacagtgcaaagtcttca caggggtttacccgttcatgtggggtggtgcatattgcttttgcgacactgagaacacccaagtcagcaaggcctacg taatgaaatctgacgactgccttgcggatcatgctgaagcatataaagcgcacacagcctcagtgcaggcgttcctca acatcacagtgggagaacactctattgtgactaccgtgtatgtgaatggagaaactcctgtgaatttcaatggggtca aaataactgcaggtccgctttccacagcttggacaccctttgatcgcaaaatcgtgcagtatgccggggagatctata attatgattttcctgagtatggggcaggacaaccaggagcatttggagatatacaatccagaacagtctcaagctctg atctgtatgccaataccaacctagtgctgcagagacccaaagcaggagcgatccacgtgccatacactcaggcacctt cgggttttgagcaatggaagaaagataaagctccatcattgaaatttaccgcccctttcggatgcgaaatatatacaa accccattcgcgccgaaaactgtgctgtagggtcaattccattagcctttgacattcccgacgccttgttcaccaggg tgtcagaaacaccgacactttcagcggccgaatgcactcttaacgagtgcgtgtattcttccgactttggtgggatcg ccacggtcaagtactcggccagcaagtcaggcaagtgcgcagtccatgtgccatcagggactgctaccctaaaagaag cagcagtcgagctaaccgagcaagggtcggcgactatccatttctcgaccgcaaatatccacccggagttcaggctcc aaatatgcacatcatatgttacgtgcaaaggtgattgtcacccccccgaaagaccatattgtgacacaccctcagtatc acgcccaaacatttacagccgcggtgtcaaaaaccgcgtggacgtggttaacatccctgctgggaggatcagccgtaa ttattataattggcttggtgctggctactattgtggccatgtacgtgctgaccaaccagaaacataattaaggatcta gatctgctgtgccttctagttgccagccatctgttgtttgcccctcccccgtgccttccttgaccctggaaggtgcca ctcccactgtcctttcctaataaaatgaggaaattgcatcgcattgtctgagtaggtgtcattctattctggggggtg gggtggggcaggacagcaagggggaggattgggaagacaatagcaggcatgctggggatgcggtgggctctatgggta cccaggtgctgaagaattgacccggttcctcctgggccagaaagaagcaggcacatccccttctctgtgacacaccct gtccacgcccctggttcttagttccagccccactcataggacactcatagctcaggagggctccgccttcaatcccac ccgctaaagtacttggagcggtctctccctccctcatcagcccaccaaaccaaacctagcctccaagagtgggaagaa attaaagcaagataggctattaagtgcagagggagagaaaatgcctccaacatgtgaggaagtaatgagagaaatcat agaattttaaggccatgatttaaggccatcatggcctaagcttgaaaggagataggatcaaagcttggcgtaatcatg gtcatagctgtttcctgtgtgaaattgttatccgctcacaattccacacaacatacgagccggaagcataaagtgtaa agcctggggtgcctaatgagtgagctaactcacattaattgcgttgcgctcactgcccgctttccagtcgggaaacct gtcgtgccagctgcattaatgaatcggccaacgcgcggggagaggcggtttgcgtattgggcgctcttccgcttcctc -continued gctcactgactcgctgcgctcggtcgttcggctgcggcgagcggtatcagctcactcaaaggcggtaatacggttatc cacagaatcaggggataacgcaggaaagaacatgtgagcaaaaggccagcaaaaggccaggaaccgtaaaaaggccgc gttgctggcgtttttccataggctccgcccccctgacgagcatcacaaaaatcgacgctcaagtcagaggtggcgaaa cccgacaggactataaagataccaggcgtttccccctggaagctccctcgtgcgctctcctgttccgaccctgccgct taccggatacctgtccgcctttctcccttcgggaagcgtggcgctttctcatagctcacgctgtaggtatctcagttc ggtgtaggtcgttcgctccaagctgggctgtgtgcacgaaccccccgttcagcccgaccgctgcgccttatccggtaa ctatcgtcttgagtccaacccggtaagacacgacttatcgccactggcagcagccactggtaacaggattagcagagc gaggtatgtaggcggtgctacagagttcttgaagtggtggcctaactacggctacactagaagaacagtatttggtat ctgcgctctgctgaagccagttaccttcggaaaaagagttggtagctcttgatccggcaaacaaaccaccgctggtag cggtggtttttttgtttgcaagcagcagattacgcgcagaaaaaaaggatctcaagaagatcctttgatcttttctac ggggtctgacgctcagtggaacgaaaactcacgttaagggattttggtcatgagattatcaaaaaggatcttcaccta gatccttttaaattaaaaatgaagttttaaatcaatctaaagtatatatgagtaaacttggtctgacagttaccaatg cttaatcagtgaggcacctatctcagcgatctgtctatttcgttcatccatagttgcctgactccccgtcgtgtagat aactacgatacgggagggcttaccatctggccccagtgctgcaatgataccgcgagaaccacgctcaccggctccaga tttatcagcaataaaccagccagccggaagggccgagcgcagaagtggtcctgcaactttatccgcctccatccagtc tattaattgttgccgggaagctagagtaagtagttcgccagttaatagtttgcgcaacgttgttgccattgctacagg catcgtggtgtcacgctcgtcgtttggtatggcttcattcagctccggttcccaacgatcaaggcgagttacatgatc ccccatgttgtgcaaaaaagcggttagctccttcggtcctccgatcgttgtcagaagtaagttggccgcagtgttatc actcatggttatggcagcactgcataattctcttactgtcatgccatccgtaagatgcttttctgtgactggtgagta ctcaaccaagtcattctgagaatagtgtatgcggcgaccgagttgctcttgcccggcgtcaatacgggataataccgc gccacatagcagaactttaaaagtgctcatcattggaaaacgttcttcggggcgaaaactctcaaggatcttaccgct gttgagatccagttcgatgtaacccactcgtgcacccaactgatcttcagcatcttttactttcaccagcgtttctgg gtgagcaaaaacaggaaggcaaaatgccgcaaaaaagggaataagggcgacacggaaatgttgaatactcatactctt cctttttcaatattattgaagcatttatcagggttattgtctcatgagcggatacatatttgaatgtatttagaaaaa taaacaaataggggttccgcgcacatttccccgaaaagtgccacctgacgtctaagaaaccattattatcatgacatt aacctataaaaataggcgtatcacgaggccctttcgggtcgcgcgtttcggtgatgacggtgaaaacctctgacacat gcagctcccggttgacggtcacagcttgtctgtaagcggatgccgggagcagacaagcccgtcagggcgcgtcagcggg tgttggcgggtgtcggggctggcttaactatgcggcatcagagcagattgtactgagagtgcaccataaaattgtaaa cgttaatattttgttaaaattcgcgttaaatttttgttaaatcagctcattttttaaccaataggccgaaatcggcaa aatcccttataaatcaaaagaatagcccgagatagggttgagtgttgttccagtttggaacaagagtccactattaaa gaacgtggactccaacgtcaaagggcgaaaaaccgtctatcagggcgatggcccactacgtgaaccatcacccaaatc aagttttttggggtcgaggtgccgtaaagcactaaatcggaaccctaaagggagcccccgatttagagcttgacgggg aaagccggcgaacgtggcgagaaaggaagggaagaaagcgaaaggagcgggcgctagggcgctggcaagtgtagcggt cacgctgcgcgtaaccaccacacccgccgcgcttaatgcgccgctacagggcgcgtactatggttgctttgacgtatg cggtgtgaaataccgcacagatgcgtaaggagaaaataccgcatcaggcgccattcgccattcaggctgcgcaactgt tgggaagggcgatcggtgcgggcctcttcgctattacgccagctggcgaaagggggatgtgctgcaaggcgattaagt tgggtaacgccagggttttcccagtcacgacgttgtaaaacgacggccagtgaattccatggtctcaacttttc Representative structure of plasmid vector that is used to express viral structural protein wherein a nucleotide sequence encoding at least one antigen is inserted in its E2 and E3 regions is shown in FIG. 2.

A nucleic acid molecule having at least 70%, 75%, 80%, 85%, 90%, 95% or 98% nucleotide sequence identity to the nucleic acid molecule having a nucleotide sequence represented by any one of SEQ ID Nos:57 and 59 and a nucleic acid molecule which may be a mutant where at most 10% of the amino acids are deleted, substituted, and/or added based on the nucleic acid molecule having a nucleotide sequence represented by any one of SEQ ID Nos.:57 and 59 are also provided by the present application.

The VLPs described as above may be prepared by stable cell line. The stable cell line can be prepared by using the above-described vectors and according to conventional procedures. For example, the following procedures may be employed to generate a stable cell line:

1. Transfect cells such as 293F cells are transfected with a VLP expression plasmid containing selection marker such as hygromycin B.

2. Incubate the transfected cells for one day

3. Culture the transfected cells in a selection medium containing such as Hygromycin at 150-200 ug/ml for 1-2 weeks.

4. Choose the cells that can grow and be split at least once in the selection medium.

5. Isolate a single cell and confirm the expression of the VLP in the supernatants by western blotting.

(3) Pharmaceutical Composition, Kit

In a third aspect, the present application provides a pharmaceutical composition and a kit comprising a pharmaceutical composition, wherein the pharmaceutical composition comprises (i) a virus like particle comprising a modified envelope protein E3 and/or (ii) a nucleic acid molecule consisting of a nucleotide sequence encoding a virus like particle comprising a modified envelope protein E3.

In one embodiment, the present application provides a pharmaceutical composition or a kit comprising a pharmaceutical composition, wherein the pharmaceutical composition comprises the Alphavirus or Flavivirus virus like particle (e.g. Chikungunya virus like particle or Venezuelan equine encephalitis virus like particle) as described above or the nucleic acid molecule as described above; and a pharmaceutically acceptable carrier. The amount of the Alphavirus or Flavivirus virus like particle and the amount of the nucleic acid molecule in the composition may be 0.00001-1 w/w % of the pharmaceutical composition.

Dosage amount of the particle provided by the present application (e.g. CHIKV VLP or VEEV VLP) may be 1-500 μg/day.

As described above, in one embodiment, the antigen contained in the virus like particle used for the pharmaceutical composition provided by the present application may be derived from *Plasmodium falciparum* circumsporozoite protein, PD-1, PD-L1, CTLA-4, IL-2, DISC1, HER2, BTLA, HVEM, PCSK9 or DPP-4.

The pharmaceutical composition may further comprise an adjuvant. Examples of adjuvants include, but are not limited to, Ribi solution (Sigma Adjuvant system, Sigma-Aldrich). The pharmaceutical composition provided by the present application may contain a buffering agent such as dibasic sodium phosphate hydrate, sodium dihydrogen phosphate and sodium chloride; and a preserving agent such as thimerosal. In one embodiment, the pharmaceutical composition is an aqueous solution containing 0.001-1 w/w % of a particle (e.g. CHIKV VLP or VEEV VLP) comprising a viral structural protein and an antigen (e.g. antigen derived from *Plasmodium falciparum* circumsporozoite protein, PD-1 or PD-L1), 1-10 w/w % of buffering agent, 0.01-1 w/w % of adjuvant and 0.00001-0.001 w/w % of preserving agent.

A skilled person can prepare the pharmaceutical composition using a conventional technique. For example, a particle (e.g. CHIKV VLP or VEEV VLP) comprising a viral structural protein and an antigen (e.g. antigen derived from *Plasmodium falciparum* circumsporozoite protein, PD-1, PD-L1, CTLA-4, IL-2, DISC1, HER2, BTLA, HVEM, PCSK9 or DPP-4) is mixed with a buffer solution having physiological pH (e.g. pH 5-9, such as pH7) to prepare the pharmaceutical composition.

In one embodiment, the pharmaceutical composition is a vaccine or an immunostimulant comprising a particle comprising a viral structural protein with a modified envelope protein E3. In one embodiment, the virus like particle comprises a viral structural protein and an antigen (e.g. antigen derived from *Plasmodium falciparum* circumsporozoite protein, PD-1, PD-L1, CTLA-4, IL-2, DISC1, HER2, BTLA, HVEM, PCSK9 or DPP-4). For example, the vaccine composition provided by the present application can be used for immunotherapy; treating or preventing cancer; treating or preventing infectious disease; or treating or preventing malaria.

In one embodiment, the pharmaceutical composition is a DNA vaccine comprising a nucleic acid molecule comprising a nucleotide sequence for expressing a particle which comprises a viral structural protein with a modified envelope protein E3. One embodiment, the virus like particle comprises a viral structural protein and an exogenous antigen (e.g. antigen derived from *Plasmodium falciparum* circumsporozoite protein, PD-1, PD-L1, CTLA-4, IL-2, DISC1, HER2, BTLA, HVEM, PCSK9 or DPP-4). In one embodiment, the DNA vaccine provided by the present application comprises CpG containing oligonucleotide.

The pharmaceutical composition provided in the third aspect of the present application can be administered one or more times. When the pharmaceutical composition provided in the third aspect of the present application is administered more than one time, different particles provided in the first aspect of the present application (e.g. CHIKV VLP or VEEV VLP) may be used for each of the administration. In one embodiment, combination of immunization using CHIKV VLP provided in the first aspect of the application and immunization using VEEV VLP provided in the first aspect of the application is employed. For example, CHIKV VLP provided in the first aspect of the present application may be used for the 1st immunization and VEEV VLP provided in the first aspect of the present application may be used for the 2nd immunization, or VEEV VLP provided in the first aspect of the present application may be used for the 1st immunization and CHIKV VLP provided in the first aspect of the present application may be used for the 2nd immunization.

A skilled person can determine timing of immunization using the composition or vaccine provided by the present application. For example, a 2nd immunization is performed 1, 2, 3, 4, 5, 6, 7, 8, 9 or 10 weeks after a 1st immunization.

In one embodiment, the present application provides a kit comprising (a) a pharmaceutical composition comprising a particle provided in the first aspect of the present application; and (b) another pharmaceutical composition comprising a particle provided in the first aspect of the present application, wherein the particle contained in (a) is a virus like particle which is different from the particle contained in (b). In this embodiment, the particle contained in (a) may be Chikungunya virus like particle and the particle contained in (b) may be Venezuelan equine encephalitis virus like particle.

In one embodiment, the present application provides a kit comprising (a) a pharmaceutical composition comprising a particle provided in the first aspect of the present application; and (b) another pharmaceutical composition comprising a particle provided in the first aspect of the present application, (c) one or more pharmaceutical composition, each of which comprises a particle provided in the first aspect of the present application, wherein (a) is used for priming immunization and (b) and (c) are used for boosting immunization; and the particle contained in (a) is a virus like particle which is different from the particle contained in (b); and the particle contained in (c) is different from the particle contained in (a) and (b), or the same as the particle contained in (a) or (b).

The respective pharmaceutical compositions contained in the above-described kit may be administered simultaneously, separately or sequentially.

The Alphavirus or Flavivirus virus like particle (e.g. Chikungunya virus or Venezuelan equine encephalitis virus) provided in the first aspect of the present application or the nucleic acid molecule provided by the second aspect of the application can be used for the pharmaceutical composition provided in the third aspect of the present application.

For example, Chikungunya or Venezuelan equine encephalitis virus like particle comprising or consisting of: one or more (e.g. 240) capsid of Chikungunya virus (CHIKV) or Venezuelan equine encephalitis virus (VEEV); one or more (e.g. 240) E1 of Chikungunya virus (CHIKV) or Venezuelan equine encephalitis virus (VEEV);

one or more (e.g. 240) E2 of Chikungunya virus (CHIKV) or Venezuelan equine encephalitis virus (VEEV); and one or more (e.g. 240) E3 of Chikungunya virus (CHIKV) or Venezuelan equine encephalitis virus (VEEV), wherein each of E2 is bound to each of E3, and an antigen is inserted into E3 of Chikungunya virus (CHIKV) or Venezuelan equine encephalitis virus (VEEV) may be used for preparing the composition or vaccine provided in the third aspect of the present application. The complex of E2 and E3 into which the antigen is inserted may consist of an amino acid sequence represented by any one of SEQ ID Nos.:46-49; the E1 may consist of an amino acid sequence represented by SEQ ID NO: 32 (or SEQ ID NO: 76); and the capsid may consist of an amino acid sequence represented by SEQ ID NO: 31 (or SEQ ID NO: 75); or the complex of E2 and E3 into which the antigen is inserted may consist of an amino acid sequence represented by any one of SEQ ID Nos.:50-53; the E1 may consist of an amino acid sequence represented by SEQ ID NO: 35; and the capsid may consist of an amino acid sequence represented by SEQ ID NO: 36.

(4) Method of Producing a Virus Like Particle

In a fourth aspect, the present application provides a method of producing a virus like particle comprising a modified envelope protein E3 comprising: culturing a cell which is transfected with a vector to express the virus like particle; and purifying the particle.

The virus like particle provided by the first aspect of the present application can be produced by the method provided by a fourth aspect of the present application.

In one embodiment, antigen may be an antigen derived from *Plasmodium falciparum* circumsporozoite protein, an antigen derived from PD-1, an antigen derived from PD-L1 or an antigen derived from CTLA-4, an antigen derived from IL-2, an antigen derived from DISC1, an antigen derived from HER2, an antigen derived from BTLA, an antigen derived from HVEM, an antigen derived from PCSK9 or an antigen derived from DPP-4.

Various host-vector systems may be used for expression of the virus like particle. Eukaryotic cells can be used for the method provided by the fourth aspect of the present application. Examples of eukaryotic cells include, but are not limited to, insect cells (e.g. sf9 cells, H5 cells), yeast cells (e.g. *S. cerevisiae*) and mammalian cells (e.g. CHO cells, human embryonic kidney (HEK) 293F cells). Vector used for the method provided by the fourth aspect of the present application comprises a nucleic acid molecule encoding the virus like particle to be expressed. Cells may be transfected with the vector using conventional methods (e.g. lipofection, electroporation). A skilled person can select culture medium or with DNA methyl transferase inhibitors and histone deacetylase inhibitors such as sodium butyrate, depending on cells used for the method provided by the fourth aspect of the present application. After the transfection, virus like particle can be produced in the cells and/or culture supernatant. Virus like particle may be recovered from the culture supernatant and purified using ultracentrifugation.

For example, cells are transfected with a vector contains the genes coding for CHIKV structural proteins capsid, 6K, E1, E2 and E3 wherein E3 is modified to contain a desired antigen. The cells transfected with the expression vector produce the proteins and the proteins spontaneously assembled to form the VLPs that can be recovered from the culture medium. The 6K protein acts as a signal sequence for transporting E1 protein to the endoplasmic reticulum, where it is processed by host signal peptidase and it is not assembled into virus particles.

(5) Method of Enhancing the Production of a Virus Like Particle

In a fifth aspect, the present application provides a method of enhancing the production of a virus like particle comprising a modified envelop protein E3. In one embodiment, the virus like particle comprises viral structural protein and at least one antigen, comprising (1) inserting the at least one antigen into an envelope protein E3 of the viral structural protein, and (2) isolating the virus like particle wherein at least one antigen is inserted into the envelope protein E3 of the viral structural protein.

At least one antigen may be inserted into a suitable position of E3. In one preferred embodiment, at least one antigen is inserted into furin cleavage site which is present in E3 of viral structural protein (e.g. CHIKV structural protein, VEEV structural protein) so that the virus like particle comprising antigen-inserted E3 can be expressed more efficiently when compared to expression of virus like particle comprising E2 into which at least one antigen is inserted.

For example, regarding Chikungunya viral structural protein, at least one antigen is inserted between residues H at 321-position and S at 326-position of SEQ ID NO: 1 or 2; between P at 320-position and S at 326-position of SEQ ID NO: 1 or 2; or between S at 319-position and S at 326-position of SEQ ID NO: 1 or 2.

For example, regarding Venezuelan equine encephalitis viral structural protein, at least one antigen is inserted between G at 330-position and S at 335-position of SEQ ID NO: 3; between P at 329-position and S at 335-position of SEQ ID NO: 3; or between C at 328-position and S at 335-position of SEQ ID NO: 3.

The step of inserting the at least one antigen into envelope protein E3 of the viral structural protein may be achieved by preparing a nucleic acid molecule comprising a nucleotide sequence encoding the virus like particle wherein at least one antigen is inserted into the envelope protein E3 of the viral structural protein; and allow the nucleic acid molecule to be expressed using cells such as insect cells (e.g. sf9 cells, H5 cells), yeast cells (e.g. *S. cerevisiae*) and mammalian cells (e.g. CHO cells, 293F cells).

The step of isolating the virus like particle wherein at least one antigen is inserted into the envelope protein E3 of the viral structural protein may be achieved by purifying the virus like particle using ultracentrifugation.

(6) Use of the Disclosed Virus Like Particle

In a sixth aspect, the present application provides use of (i) a virus like particle comprising a modified envelope protein E3 and/or (ii) a nucleic acid molecule consisting of a nucleotide sequence encoding a virus like particle comprising a modified envelope protein E3 for the manufacture of a pharmaceutical composition or a kit for treating or preventing cancer, neurological disease, infectious disease, malaria or lifestyle chronic disease; producing an antibody against the at least one antigen in a mammal; modulating an immune response; immunostimulation; inhibiting function of the at least one antigen; or presenting an antigen on macrophage.

The pharmaceutical composition may be administered to a mammal (e.g. human) intramuscularly (i.m.), intracutaneously (i.c.), subcutaneously (s.c.), intradermally (i.d.) or intraperitoneally (i.p.).

In one embodiment, the pharmaceutical composition is a vaccine, which can be applied to immunotherapy. In one embodiment, when an antigen derived from PD-1, PD-L1, CTLA-4, HER2, BTLA or HVEM is used for manufacturing the virus like particle, the virus like particle may be used for treating cancer or autoimmune disease. When the pharmaceutical composition is used for treating cancer or tumor, the composition may be administered intratumorally. In one embodiment, when an antigen derived from PD-1 or PD-L1 is used for manufacturing the virus like particle, the virus like particle may be used for treating or preventing an infectious disease. In one embodiment, when an antigen is derived from *Plasmodium falciparum* circumsporozoite protein, the virus like particle may be used for treating or preventing malaria. In one embodiment, when an antigen derived from DISC1 is used for manufacturing the virus like particle, the virus like particle may be used for treating or preventing a neurological disease. In one embodiment, when an antigen is derived from PCSK9 or DPP-4, the virus like particle may be used for treating or preventing a lifestyle chronic disease.

Examples of the cancer or tumor which may be treated include, but are not limited to, melanoma, renal cancer, prostate cancer, breast cancer, colon cancer and non-small cell lung cancer. Other examples of the cancer include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

Examples of infectious disease which may be treated include, but are not limited to, HIV, Influenza, Herpes, Giardia, Malaria, *Leishmania*, the pathogenic infection by the virus Hepatitis (A, B and C), herpes virus (e.g., VZV, HSV-I, HAV-6, HSV-II, and CMV, Epstein Barr virus), alphavirus, adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus Mucorales (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli*, Naegleriafowleri, *Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Examples of neurological disease which may be treated include, but are not limited to, Alzheimer disease, Parkinson's disease, epilepsy or Schizophrenia.

Examples of the lifestyle chronic disease which may be treated, but are not limited to, diabetes or hyperlipidemia.

When a pharmaceutical composition comprising a viral structural protein and an antigen (e.g. an antigen derived from *Plasmodium falciparum* circumsporozoite protein, an antigen derived from PD-1, an antigen derived from PD-L1, an antigen derived from CTLA-4, an antigen derived from IL-2, an antigen derived from DISC1, an antigen derived from HER2, an antigen derived from BTLA, an antigen derived from HVEM, an antigen derived from PCSK9 and an antigen derived from DPP-4) is administered to a mammal (e.g. human), an antibody against the antigen is produced in blood of the mammal. The produced antibody may modulate an immune response; show immunostimulating effects; or inhibit function of the antigen.

The produced antibody may be humanized using a conventional technique. Using the particle provided in a first aspect of the present application, monoclonal antibody or polyclonal antibody can be prepared. In one embodiment, the present application provides a method for producing an antibody comprising administering the particle provided in a first aspect of the present application to a non-human mammal and humanizing non-human mammal produced antibody.

As used herein, the term “antibody” refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, “human” antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

The present application will be described in detail with reference to the following examples, which, however, are not intended to limit the scope of the present application.

EXAMPLES

Example 1: Preparation of Venezuelan Equine Encephalitis Virus (VEEV)-Virus Like Particle (VLP) Comprising Malaria CSP Repeat Antigen Inserted into Envelope Protein E3 of the Viral Structural Protein The following polypeptides of malaria CSP protein were used for preparing a VEEV-VLP comprising malaria CSP repeat antigen. SGG is the N terminal linker and GGS is the C terminal linker for the antigen.

74 (6 repeat of NPNA amino acid sequence)
(SEQ ID NO: 56)
Sggnpnanpnanpnanpnanpnanpnaggs (SEQ ID NO: 60)
(Tccggaggaaacccgaatgccaatcccaacgcgaaccccaatgctaacc
caaatgccaacccaaacgccaaccccaacgctggtggatcc)

76 (14 repeat of NPNA amino acid sequence)
(SEQ ID NO: 61)
Sggnpnanpnanpnanpnanpnanpnanpnanpnanpnanpnanpnanpn
anpnanpnaggs (SEQ ID NO: 62)
(tccggaggcaaccccaacgccaaccctaatgccaatcccaacgctaatc
ccaatgctaaccctaacgcaaatccaaatgcaaaccccaatgccaaccca
aacgctaaccctaacgccaaccctaacgcaaacccaaacgccaatcctaa
tgctaacccaaatgcaaaccctaatgctggcggatcc)

78 (25 repeat of NPNA amino acid sequence)
(SEQ ID NO: 63)
Sggnpnanpnanpnanpnanpnanpnvdpnanpnanpnanpnanpnanpn
anpnanpnanpnanpnanpnanpnanpnanpnannanpnanpnanpnanp
naggs -continued (SEQ ID NO: 64)
(tccggaggaaacccgaatgccaatcccaacgcgaaccccaacgctaacc
ccaacgccaatccgaatgcaaacccgaacgttgacccaaacgccaacccg
aatgccaatcccaacgcgaaccccaatgctaacccaaatgccaacccaaa
cgccaaccccaacgctaatccaaacgccaaccctaacgccaatcccaacg
cgaatcctaacgctaatcccaacgcaaatcccaatgctaatccgaacgcg
aaccctaatgcaaaccccaacgccaacccgaacgctaacccgaacgctaa
tcccaacgccggtggatcc)

The respective polynucleotides were inserted between the codons encoding Ser at 518-position and Ser at 519-position of SEQ ID NO: 3 to construct a plasmid (hereinafter referred to as pVEEV-74.21, pVEEV-76.21 and pVEEV-78.21, respectively) for expressing VEEV-VLP where the respective antigen is inserted into E2 of Venezuelan equine encephalitis viral structural protein. Likewise, the respective polynucleotides were inserted between the codons encoding Gly at 330-position and Ser at 335-position of SEQ ID NO: 3 to construct a plasmid (hereinafter referred to as pVEEV-74.26, pVEEV-76.26 and pVEEV-78.26, respectively) for expressing VEEV-VLP where the respective antigen is inserted into E3 of Venezuelan equine encephalitis viral structural protein.

293F cells (Lifetechnology) were transfected with 180 μg of each of the plasmid (i.e. pVEEV-74.21, pVEEV-76.21, pVEEV-78.2, pVEEV-74.26, pVEEV-76.26 and pVEEV-78.26, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

Figure 3:
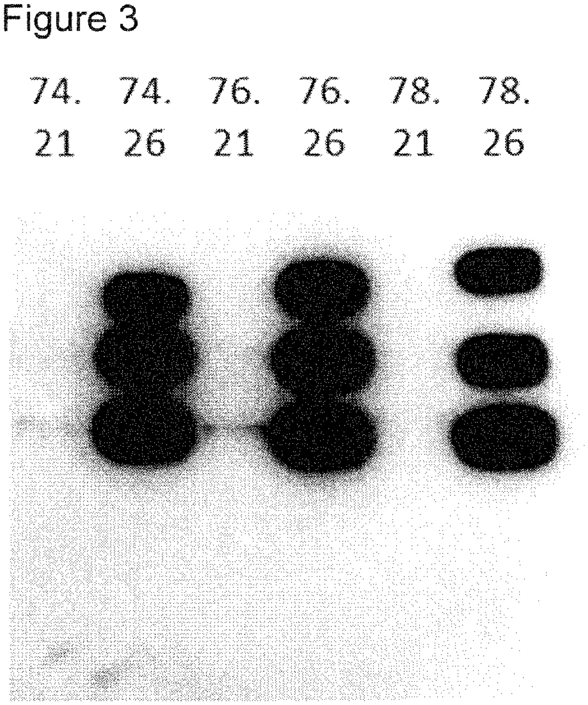
FIG. 3 shows results of western blotting. A CSP repeat sequence of NPNA (SEQ ID NO: 142), which is an antigen derived from *plasmodium falciparum* circumsporozoite protein, was inserted into E2 or E3 of virus like particle of Venezuelan equine encephalitis virus (VEEV) (strain TC-83). The antigen-inserted VEEV virus like particle expressed in 293F cells was confirmed by western blotting using mouse anti-VEEV antibody (1:1000).

The production of VLP comprising the CSP repeat antigen 74, 76 or 78 conjugated with VEEV structural polypeptide was confirmed by Western Blot using an anti-VEEV antibody (see FIG. 3). As seen in FIG. 3, antigen-inserted VLP was more efficiently produced when the antigen was inserted into E3 compared to when the antigen was inserted into E2.

Example 2: Preparation of Venezuelan Equine Encephalitis Virus (VEEV)-Virus Like Particle (VLP) Comprising Mouse Malaria CSP Repeat Antigen Inserted into Envelope Protein E3 of the Viral Structural Protein The following polypeptides of mouse malaria CSP protein was used for preparing a VEEV-VLP comprising mouse malaria CSP repeat antigen. SGG is the N terminal linker and GGS is the C terminal linker for the antigen.

261 (repeat of “qgpgap” (residues 4-9 of SEQ ID NO: 58))
(SEQ ID NO: 58)
SGG-qgpgapqgpgapqgpgapqgpgap-GGS -continued (SEQ ID NO: 65)
Tccggaggacagggacctggcgctcctcagggaccaggggcaccccaggg cccaggcgccccacaggagcctggqgcccctgggqgatcc The polynucleotides was inserted between the codons encoding Ser at 518-position and Ser at 519-position of SEQ ID NO: 3 to construct a plasmid (hereinafter referred to as pVEEV-261.25) for expressing VEEV-VLP where the antigen was inserted into E2 of Venezuelan equine encephalitis viral structural protein. Likewise, the polynucleotide coding for the peptide was inserted between the codons encoding Gly at 330-position and Ser at 335-position of SEQ ID NO: 3 to construct a plasmid (hereinafter referred to as pVEEV-261.66) for expressing VEEV-VLP where the antigen was inserted into E3 of Venezuelan equine encephalitis viral structural protein.

293F cells (Lifetechnology) were transfected with 180 g of each of the plasmid (i.e. pVEEV-261.25 and pVEEV-261.66, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising the CSP repeat antigen 261 conjugated with VEEV structural polypeptide was confirmed by Western Blot using an anti-VEEV antibody (see FIG. 4). As seen in FIG. 4, antigen-inserted VLP was more efficiently produced when the antigen was inserted into E3 compared to when the antigen was inserted into E2.

Example 3: Preparation of Venezuelan Equine Encephalitis Virus (VEEV)-Virus Like Particle (VLP) Comprising Malaria Antigen Inserted into Envelope Protein E3 of the Viral Structural Protein The following polypeptides derived from malaria protein were used for preparing a VEEV-VLP comprising malaria CSP repeat antigen. SGG is the N terminal linker (TCCGGAGGA in nuclear sequence) and GGS is the C terminal linker (GGAGGATCC in nuclear sequence) for the antigen.

74 (6 repeat of NPNA amino acid sequence)
(SEQ ID NO: 56)
sggnpnanpnanpnanpnanpnanpnaggs (SEQ ID NO: 60)
(tccggaggaaacccgaatgccaatcccaacgcgaaccccaatgctaacc caaatgccaacccaaacgccaaccccaacgctggtggatcc)

302R (antigen derived from pfs25)
(SEQ ID NO: 66)
SGG-cikidgnpvsyac-GGS 303R (antigen derived from pfs25)
(SEQ ID NO: 67)
tccggagggtgcatcaagatcgacggcaaccccgtgtcctacgcctgcgg gggatcc -continued (SEQ ID NO: 68)
SGG-cildtsnpvktgvc-GGS (SEQ ID NO: 69)
tccggaggctgcatcctggacaccagcaaccccgtgaaaaccggcgtgtg tggcggatcc The respective polynucleotides were inserted between the codons encoding Ser at 518-position and Ser at 519-position of SEQ ID NO: 3 to construct a plasmid (hereinafter referred to as pVEEV-74.21, pVEEV-302R.21 and pVEEV-303R.21, respectively) for expressing VEEV-VLP where the respective antigen is inserted into E2 of Venezuelan equine encephalitis viral structural protein. Likewise, the respective polynucleotides were inserted between the codons encoding Gly at 330-position and Ser at 335-position of SEQ ID NO: 3 to construct a plasmid (hereinafter referred to as pVEEV-74.66, pVEEV-302R.66 and pVEEV-303R.66, respectively) for expressing VEEV-VLP where the respective antigen is inserted into E3 of Venezuelan equine encephalitis viral structural protein.

293F cells (Lifetechnology) were transfected with 180 μg of each of the plasmid (i.e. pVEEV-74.21, pVEEV-302R.21, pVEEV-303R.2, pVEEV-74.66, pVEEV-302R.66 and pVEEV-303R.66, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising antigen 74, 302R or 303R conjugated with VEEV structural polypeptide was confirmed by Western Blot using an anti-VEEV antibody (see FIG. 5). As seen in FIG. 5, antigen-inserted VLP was more efficiently produced when the antigen was inserted into E3 compared to when the antigen was inserted into E2.

Example 4: Preparation of Chikungunya Virus (CHIKV)-Virus Like Particle Comprising a Viral Structural Protein and PD-1 Antigen or PD-1 Ligand Antigen The following polypeptides of PD-1 or PD-L1 were used for preparing a CHIKV-VLP comprising PD-1 antigen or PD-1 ligand antigen. SGG is the N terminal linker (TCCGGAGGA in nuclear sequence) and GGS is the C terminal linker (GGAGGATCC in nuclear sequence) for the antigen.

1. 299 (mousePD-L1 sequence): A sequence of a fragment of mousePD-L1 Domain3S attaching linker, which was used for an antigen:
Nuclear Sequence
(SEQ ID NO: 70)
tccggaggatgcatcatcagctacggcggagccgactacggaggatcc Amino Acid sequence
(SEQ ID NO: 71)
SGG-ciisyggadyC-GGS -continued 2. 274 (mouse PD-1 sequence): A sequence of a
fragment of mouse PD-1 domain2short attaching
linker, which was used for an antigen:
Nuclear Sequence (SEQ ID NO: 72)
tccggaggaggcgccatcagcctgcaccccaaggccaagatcgaggaatc tggaggatcc Amino Acid sequence (SEQ ID NO: 73)
SGG-gaislhpkakiees-GS The respective polynucleotides was inserted between the codons encoding Ser at 531-position and Asn at 532-position of SEQ ID NO: 2 to construct a plasmid (hereinafter referred to as pCHIKV-299.15 and pCHIKV-274.11, respectively) for expressing Chikungunya viral structural protein where the PD-1-derived peptide or the PD-L1-derived peptide is inserted into E2 of Chikungunya viral structural protein. Likewise, the respective polynucleotides were inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the PD-1-derived peptide or the PD-L1-derived peptide is inserted into E3 of Chikungunya viral structural protein.

293F cells (Lifetechnology) were transfected with 180 μg of each of the plasmid (i.e. pCHIKV-274.11, pCHIKV-299.15, pCHIKV-274.56 and pCHIKV-299.56, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising antigen 274 or 299 conjugated with CHIKV structural polypeptide was confirmed by Western Blot using an anti-CHIKV antibody (see FIG. 6). As seen in FIG. 6, antigen-inserted VLP was more efficiently produced when the antigen was inserted into E3 compared to when the antigen was inserted into E2.

Example 5: Preparation of Chikungunya Virus (CHIKV)-Virus Like Particle Comprising a Viral Structural Protein and Malaria Antigen The following polypeptides of malaria CSP protein was used for preparing a CHIKV-VLP comprising malaria CSP repeat antigen. SGG is the N terminal linker (TCCGGAGGA in nuclear sequence) and GGS is the C terminal linker (GGAGGATCC in nuclear sequence) for the antigen. CSP repeat antigen 74 (6 repeat of NPNA (SEQ ID NO: 142) amino acid sequence) sggnpnanpnanpnanpnanpnanpnaggs (SEQ ID NO: 56) (tccggaggaaacccgaatgccaatcccaacgcgaaccccaatgctaacccaaatgcca acccaaacgccaaccccaacgctggtggatcc) (SEQ ID NO: 60)

The polynucleotide was inserted between the codons encoding Ser at 531-position and Asn at 532-position of SEQ ID NO: 2 to construct a plasmid (hereinafter referred to as pCHIKV-74.11) for expressing Chikungunya viral structural protein where the malaria CSP repeat antigen is inserted into E2 of Chikungunya viral structural protein. Likewise, the malaria CSP repeat antigen was inserted between the codons encoding H at 321-position and S at 326-position of SEQ ID NO: 2 to construct a plasmid (hereinafter referred to as pCHIKV-74.16) for expressing Chikungunya viral structural protein where the malaria CSP repeat antigen is inserted into E3 of Chikungunya viral structural protein.

293F cells (Lifetechnology) were transfected with 180 μg of each of the plasmid (i.e. pCHIKV-74.11 and pCHIKV-74.16, respectively) using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising VLP74 conjugated with CHIKV structural polypeptide was confirmed by Western Blot using an anti-CHIKV antibody (see FIG. 7). As seen in FIG. 7, antigen-inserted VLP was more efficiently produced when the antigen was inserted into E3 compared to when the antigen was inserted into E2.

Example 6: Preparation of Chikungunya Virus (CHIKV)-Virus Like Particle Comprising a Viral Structural Protein and CTLA-4 Antigen The following polypeptides of CTLA-4 protein was used for preparing a CHIKV-VLP comprising CTLA-4 antigen. SGG is the N terminal linker (TCCGGAGGA in nuclear sequence) and GGS is the C terminal linker (GGAGGATCC in nuclear sequence) for the antigen.

mCTLA4_ver2

(SEQ ID NO: 74)
sggggkvelmypppytygmggggs (SEQ ID NO: 78)
tccggaggcggcggcaaggtggaactcatgtacccaccgccatactttgt gggcatgggcggcggcgqatcc mCTLA4_ver4

(SEQ ID NO: 79)
sggcattfteknt vgfldypfcggs (SEQ ID NO: 80)
tccggaggctgtgccacgacattcacagagaagaatacagtgggcttcct agattacccettctgcggcggatcc mCTLA4_ver5

(SEQ ID NO: 81)
sggattfteknt vgfldypfggs (SEQ ID NO: 82)
tccggaggcgccacgacattcacagagaagaatacagtgggcttcctaga ttacccettcggcggatcc The polynucleotide was inserted between the codons encoding H at 321-position and S at 326-position of SEQ ID NO: 2 to construct a plasmid for expressing Chikungunya viral structural protein where the mCTLA-4 antigen is inserted into E3 of Chikungunya viral structural protein.

293F cells (Lifetechnology) were transfected with 180 μg of each of the plasmid using PEI (GE Healthcare). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. When animals were immunized with virus like particles, the purified virus like particles were further concentrated using spin column (Molecular Weight-cutoff: 100 kDa) to prepare the virus like particles for the immunization.

The expression of VLP comprising each of mCTLA-4_ver2, 4 and 5 conjugated with CHIKV structural polypeptide was confirmed by Western Blot using an anti-CHIKV monkey sera.

Example 7 Preparation of Mature CHIKV VLP

CHIKV-P2 VLP expression plasmid that can express a CHIKV viral structural protein whose furin site RQRR (SEQ ID NO: 150) at the end of E3 region of CHIKV is replaced with SGGGS (SEQ ID NO: 151); CHIKV-Xa VLP expression plasmid that can express a CHIKV viral structural protein whose furin site RQRR (SEQ ID NO: 150) at the end of E3 region of CHIKV is replaced with Factor Xa recognition motif, IDGR and CHIKV-En VLP expression plasmid that can express a CHIKV viral structural protein whose furin site RQRR (SEQ ID NO: 150) at the end of E3 region of CHIKV is replaced with Enterokinase recognition motif, DDDDK (SEQ ID NO: 141) were used. The all three plasmid 10 ug were transfected into 293F cells and 4 days after the transfection, the supernatants were harvested. 20 ul of supernatants were treated with Water (Control), Factor Xa or Enterokinase for overnight. Then VLPs in the supernatants were measured by Western Blotting using serum against CHIKV. Results are shown in FIG. 8.

Immature VLPs were expressed in the supernatant of the cells transfected with the plasmids, CHIKV-P2, CHIKV-Xa and CHIKV-En. The immature VLP generated from the CHIKV-Xa-transfected cells were digested with Factor Xa. The immature VLP leased E3 and it became mature VLP form (Lane 5). The immature VLP generated from the CHIKV-En-transfected cells were digested with Enterokinase. The immature VLP leased E3 and it became mature VLP form (Lane 9).

Example 8 Preparation of Mature VEEV VLP

VEEV-P2 VLP expression plasmid that can express a VEEV viral structural protein whose furin site RQRR (SEQ ID NO: 150) at the end of E3 region of VEEV is replaced with SGGGS (SEQ ID NO: 151); VEEV-IDGR VLP expression plasmid that can express a VEEV viral structural protein whose furin site RQRR (SEQ ID NO: 150) at the end of E3 region of VEEV is replaced with Factor Xa recognition motif, IDGR (SEQ ID NO: 152); and VEEV-IEGR plasmid that can express a VEEV viral structural protein whose furin site RQRR (SEQ ID NO: 150) at the end of E3 region of VEEV is replaced with another Xa recognition motif, IEGR (SEQ ID NO: 153) were used. The all three plasmids 10 ug were transfected into 293F cells and 4 days after the transfection, the supernatants were harvested. 20 ul of supernatants were treated with Water (Control), Factor Xa for overnight. Then VLPs in the supernatants were measured by Western Blotting using serum against VEEV. Immature VLP were expressed in the supernatant of the cells transfected with the plasmids, VEEV-P2, VEEV-IDGR and VEEV-IEGR. The immature VLPs generated from the VEEV-IDGR and VEEV-IEGR-transfected cells were digested with Factor Xa. The result is shown in FIG. 9. The immature VLPs generated from the VEEV-IDGR and VEEV-IEGR-transfected cells leased E3 and they became the mature VLP forms (Lane 5 and 6).

Example 9: Preparation of Chikungunya Virus (CHIKV)-Virus Like Particle Comprising DISC1_451, 452 or 454 Inserted into Envelope Protein E3 of the Viral Structural Protein The following polypeptides of DISC1 protein were used for preparing a CHIKV-VLP comprising DISC1 antigen.

| Name | Amino acid sequence |
|---|---|
| DISC1_451 | SGGLLIQSLQLQEARGELSVEDERQMDDLEGGS (SEQ ID NO: 105) |
| DISC1_452 | SGGEARGELSVEDERQMDDLEGGS (SEQ ID NO: 106) |
| DISC1_454 | SGGEARGELSVEGGS (SEQ ID NO: 107) |
| **Name** | **DNA sequence** |
| DISC1_451 | tccggagggctgctgatccagtctctgcagctgcaggaagccagaggcgagctgagcgtggaagatgagcggcagatggacgacctggaagggggatcc (SEQ ID NO: 117) |
| DISC1_452 | tccggaggggaagccaaaggcgagagcgtggaagatgagcggcagatggacgacctggaagggggatcc (SEQ ID NO: 118) |
| DISC1_454 | tccggaggggaagccagaggcgagctgagagtqgaaggggggatcc (SEQ ID NO: 119) |

SGG is the N terminal linker (TCCGGAGGA in nuclear sequence) and GGS is the C terminal linker (GGAGGATCC in nuclear sequence) for the antigen.

The respective polynucleotides was inserted between the codons encoding Ser at 531-position and Asn at 532-position of SEQ ID NO: 2 as well as inserted between the codons encoding H at 321-position and S at 326-position of SEQ ID NO: 2 to construct a plasmid for expressing Chikungunya viral structural protein where the DISC1-derived peptide is inserted into both E2 and E3 of Chikungunya viral structural protein. The respective polynucleotides was inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the DISC1-derived peptide is inserted into E3 of Chikungunya viral structural protein.

The 293F cells were transfected with the indicated DISC1 expressing VLP. 4 days after transfection, the supernatants were harvested.

The expression of VLP comprising DISC1_451, _452 or _454 conjugated with CHIKV structural polypeptide was confirmed by Western Blot using an anti-CHIKV antibody (see FIG. 10). 1$^{st}$ antibody (1:1000 dilution) was anti-serum against Chikungunya and 2$^{nd}$ antibody (1:5000 dilution) was anti-mouse IgG-HRP antibody. As seen in FIG. 10, DISC1_451, _452 and _454-inserted VLPs were produced when the antigen was inserted into E3 and into both E2 and E3 (dual).

Example 10: Preparation of Chikungunya Virus (CHIKV)-Virus Like Particle Comprising IL-2 Inserted into Envelope Protein E3 of the Viral Structural Protein Human IL-2 mutant was prepared according to the method described in Levin et. al, Nature 484(7395): 529-533, 2012. Mouse IL-2 mutants are F54A (Mott H R et al. J. Mol. Biol. 247, 979-994, 1995) and D34K (Berndt et al. Biochemistry 33, 6571, 1994), the entire contents of those references are herein incorporated by reference.

The respective polynucleotides were inserted between the codons encoding H at 321-position and S at 326-position of SEQ ID NO: 2 to construct a plasmid (hereinafter referred to as pCHIKV-299.56 and pCHIKV-274.56, respectively) for expressing Chikungunya viral structural protein where the IL-2-derived peptide is inserted into E3 of Chikungunya viral structural protein. According to the same manner described in EXAMPLE 6, Chikungunya virus like particle comprising IL-2 were prepared and purified.

The expression of VLP comprising IL-2 conjugated with CHIKV structural polypeptide was confirmed by Western Blot using mouse anti CHIKV antibody (see FIGS. 11 and 12). As seen in FIGS. 11 and 12, Human IL-2 wild type, human IL-2 mutant, mouse IL-2 wild type and mouse IL-2 mutant-inserted VLPs were produced when those antigens were inserted into E3.

CHIKV viral structural proteins comprising IL-2 derived peptide in their envelope protein E3 provided as well as expression vectors expressing the viral structural proteins are SEQ ID NOs.: 83-92. Those sequences contains the 6K protein but the 6K protein acts as a signal sequence for transporting E1 protein to the endoplasmic reticulum, where it is processed by host signal peptidase and it is not assembled into virus particles.

Example 11: Protection of Mice Against Malaria (*Plasmodium yoelii*) by Intramuscle Injection of CHIKV VLP Comprising Mouse Malaria (*Plasmodium yoelii*) Inserted into Both Envelope Proteins E2 and E3 of the Viral Structural Protein Chikungunya VLP comprising Malaria *Plasmodium yoelii* CSP 4× repeat inserted into both envelop proteins E2 and E3 (261.261 CHIKV VLP) and Chikungunya VLP comprising Malaria *Plasmodium yoelii* CSP 14X repeat inserted into both envelop proteins E2 and E3 (264.264 CHIKV VLP) were prepared and purified in the similar manner as the previous Examples. Amino acid sequences and nucleotide sequences of the repeat antigens with linker used in this example are SEQ ID NOs.: 93-96. CHIKV viral structural proteins containing the antigens in both E2 and E3 and expression vectors for those viral structural proteins are SEQ ID NOs.: 97-100. Those sequences contains the 6K protein but the 6K protein acts as a signal sequence for transporting E1 protein to the endoplasmic reticulum, where it is processed by host signal peptidase and it is not assembled into virus particles.

The mice (n=10) were immunized with the 261.261 CHIKV VLP or 264.264 CHIKV VLP 2 times at week 0 and 3 (20 ug VLP per mouse) by intramuscle injection. VLPs were mixed with alhydrogel adjuvant before the injection. At week 5, the mice immunized with the 261.261 CHIKV VLP, 264.264 CHIKV VLP and CHIKV VLP with no inserted antigen (Control group) were challenged intravenously with 1000 dose of *P. yoelii* sporozoites.

Malaria infection was confirmed by PCR. Genomic DNA was purified from the mice blood day 14 after challenge. 18S malaria DNA was amplified by PCR. FIG. 13 shows results of the PCR, indicating that among 10 mice immunized with Control VLP, 9 mice were infected with malaria; among 10 mice immunized with Chikungunya VLP comprising Malaria CSP 4X repeat inserted into both envelop proteins E2 and E3 (261.261 VLP), 9 mice were not infected with malaria; and among 10 mice immunized with Chikungunya VLP comprising Malaria CSP 14X repeat inserted into both envelop proteins E2 and E3, 9 mice were not infected with malaria.

Example 12: Immunogenicity of Chikungunya Virus (CHIKV)-Virus Like Particles Comprising the Viral Structural Protein and Human Malaria CSP Repeat Epitope: 74.74 (E2 and E3 (Dual) Insertion), 74 (E2 Insertion) and 74 (E3 Insertion)

Chikungunya viral structural protein comprising Malaria CSP 6X repeat antigen (6 repeats of NPNA (SEQ ID NO: 142)) in its E2 or E3, as well as in both E2 and E3 were prepared in the similar manner as the previous examples. CHIKV viral structural protein comprising CSP 6X repeat antigen in both E2 and E3 is SEQ ID NOs: 101 and expression vector for the viral structural protein is SEQ ID NO: 102 (74.74.58). CHIKV VLPs comprising the CSP 6X repeat antigen were prepared and purified in the same manner as Example 6.

The mice (n=4 per group) were immunized with 10 ug of indicated VLPs. 10 days after immunization, the anti-CSP antibody titer in the serum of the immunized mice was measured by ELISA coated with recombinant CSP.

FIG. 14 shows that E3-inserted as well as E2- and E3-(dual) inserted VLP had higher titer than E2-inserted VLP.

Example 13: Preparation of Chikungunya Virus (CHIKV)-Virus Like Particle Comprising a Viral Structural Protein and hHER2 Antigen The following polypeptides derived from hHER2 protein were used for preparing a CHIKV-VLP comprising hHER2 antigen. SGG is the N terminal linker (TCCGGAGGA in nuclear sequence) and GGS is the C terminal linker (GGAGGATCC in nuclear sequence) for Ethe antigen.

| VLP | Amino acid sequence |
|---|---|
| 401 | SGGVTYNTDTFESMPGGS (SEQ ID NO: 108) |
| 403 | SGGYVNARHCLGGS (SEQ ID NO: 110) |
| 404 | SGGYVNARHGLGGS (SEQ ID NO: 111) |
| 405 | SGGKFPDEEGACQPCPIGGS (SEQ ID NO: 112) |
| 406 | SGGKFPDEEGACQPGGS (SEQ ID NO: 113) |
| 407 | SGGKDPPFCVGGS (SEQ ID NO: 114) |
| 408 | SGGYKDPPFCVAGGS (SEQ ID NO: 115) |
| 409 | SGGYKDPPFCVGGS (SEQ ID NO: 116) |

| VLP # | DNA sequence |
|---|---|
| 401 | aaaaaatccggaggcgtcacctacaacacagacacgtttgagtcc atgcccggcggatccaaa (SEQ ID NO: 120) |

-continued

| | |
|---|---|
| 403 | aaaaaatccggaggctatgtqaatgccaggcactgtttgggcgga tccaaa (SEQ ID NO: 121) |
| 404 | aaaaaatccggaggctatgtgaatgccaggcacggtttgggcgga tccaaa (SEQ ID NO: 122) |
| 405 | aaaaaatccggaggcaagtttccagatgaggaaggcgcataccag ccttgccccatcggcggatccaaa (SEQ ID NO: 123) |
| 406 | aaaaaatccggaggcaagtttccagatgaggagggcgcataccag cctggcggatccaca (SEQ ID NO: 124) |
| 407 | aaaaaatccggaggcaaggaccctcccttctgcgtgggcggatcc aaa (SEQ ID NO: 125) |
| 408 | aaaaaatccggaggctataaggaccctcccttctgcgtggcgcgc ggatccaaa (SEQ ID NO: 126) |
| 409 | aaaaaatccggaggctataaggaccctcccttctgcgtgggcgga tccaaa (SEQ ID NO: 127) |

The respective polynucleotides was inserted between the codons encoding Ser at 531-position and Asn at 532-position of SEQ ID NO: 2 to construct a plasmid for expressing Chikungunya viral structural protein where the hHER2-derived peptide is inserted into E2 of Chikungunya viral structural protein. Likewise, the respective polynucleotides were inserted between the codons encoding H at 321-position and S at 326-position of SEQ ID NO: 2 to construct a plasmid for expressing Chikungunya viral structural protein where the hHER2-derived peptide is inserted into E3 of Chikungunya viral structural protein.

According to the same manner described in EXAMPLE 6, the Chikungunya virus like particle comprising hHER2 was prepared and purified.

The expression of VLP comprising hHER2 conjugated with CHIKV structural polypeptide was confirmed by Western Blot using mouse anti CHIKV antibody (see FIG. 15). Among them, 401, 404, 406, and 409 were relatively high expression levels and because they code different epitopes.

Example 14: Immunogenicity

The mice (n=4 per group) were immunized with 10 ug of CHIKV VLP comprising hHER2 antigen #401 inserted into E2 or into both E2 and E3 (dual). The mice (n=10) were immunized with the VLP comprising the hHER2 antigen or CHIKV VLP comprising no antigen 2 times at week 0 and 3 (20 ug VLP per mouse) by intramuscle injection. VLPs were mixed with alhydrogel adjuvant before the injection.

2 weeks after $2^{nd}$ immunization (5 weeks after the $1^{st}$ immunization), the anti-hHER2 antibody titer in the serum of the immunized mice were measured by ELISA plate coated with recombinant hHER2.

FIG. 16 shows that CHIKV VLP comprising hHER2 antigen #401 in E2 or in both E2 and E3 (dual) generated antibody against hHER2 protein, and dual inserted VLP, i.e. antigen was inserted in both E2- and E3-, could provide higher titer than VLP whose antigen was inserted into E2.

Example 15: Preparation of Chikungunya Virus (CHIKV)-Virus Like Particle Comprising a Viral Structural Protein and hHER2 Antigen The following polypeptides derived from hHER2 protein (GENBANK number: NM_001005862) and derivatives were used for preparing a CHIKV-VLP comprising hHER2 antigen.

404 (hHer2 original):
sgg yvnarhgl ggs 404-1:
sggcgyvnarhglgcggs 409 (hHer2 original):
sgg ykdppfcv ggs 404-1:
sgg ykdppfgv ggs The amino acid sequences of “404,” “404-1,” “409” and “409-1” are shown in SEQ ID NOs. 128, 129, 130 and 131, respectively.

SGG is the N terminal linker and GGS is the C terminal linker for the antigen.

The respective polynucleotides were inserted between the codons encoding H at 321-position and S at 326-position of SEQ ID NO: 2 to construct a plasmid for expressing Chikungunya viral structural protein where the hHER2-derived peptide is inserted into E3 of Chikungunya viral structural protein.

The respective polynucleotides was inserted between the codons encoding Ser at 531-position and Asn at 532-position of SEQ ID NO: 2 to construct a plasmid for expressing Chikungunya viral structural protein where the hHER2-derived peptide is inserted into E2 of Chikungunya viral structural protein.

Likewise, the respective polynucleotides were inserted both E2 and E3 of chkungunya viral structural protein.

According to the same manner described in EXAMPLE 6, the Chikungunya virus like particle comprising hHER2 was prepared and purified. The expression of VLP comprising hHER2 that was inserted in E2, E3 or dual (both E2 and E3) of the CHIKV viral structural protein was confirmed by Western Blot using anti CHIKV antibody.

Example 16: Preparation of Chikungunya Virus (CHIKV)-Virus Like Particle Comprising a Viral Structural Protein and BTLA Antigen The polypeptide of hBTLA (383: SGGCKLNGTTCGGS (SEQ ID NO: 132), derived from GENBANK number: NM_001085357) was used for preparing a CHIKV-VLP comprising hBTLA antigen. SGG is the N terminal linker and GGS is the C terminal linker for the antigen.

The polynucleotide coding for the peptide was inserted between the codons encoding H at 321-position and S at 326-position of SEQ ID NO: 2 to construct a plasmid for expressing Chikungunya viral structural protein where the hBTLA-derived peptide is inserted into E3 of the Chikungunya viral structural protein.

According to the same manner described in EXAMPLE 6, the Chikungunya virus like particle comprising hBTLA antigen was prepared and purified.

Monoclonal antibody was prepared by a conventional procedure from mince immunized with thus obtained VLP. The property of the monoclonal antibody to bind the antigen was measured by ELISA coated with BTLA proteins. FIG. 17 shows that CHIKV VLP comprising BTLA antigen could generate monoclonal antibody that binds to both mouse BTLA (mBTLA) and human BTLA (hBTLA) proteins.

Example 17: Preparation of Chikungunya (CHIKV)-Virus Like Particle Comprising a Viral Structural Protein and HVEM Antigen The following of human HVEM peptides (hHVEM, derived from GENBANK number: NM_001297605) were used for preparing a CHIKV-VLP comprising hHVEM antigen.

354: (SEQ ID NO: 133)
SGGCVKEASGELTGTVCGGS

356: (SEQ ID NO: 134)
SGGCYRVKEASGELTGTVSEPCGGS

362: (SEQ ID NO: 135)
SGGCSRNSSRTENAVCGGS

372: (SEQ ID NO: 136)
SGGCQMSDPAMCLRSRNCGGS

SGG is the N terminal linker and GGS is the C terminal linker for the antigen. The polynucleotide coding for the peptide was inserted between the codons encoding H at 321-position and S at 326-position of SEQ ID NO: 2 to construct a plasmid for expressing Chikungunya viral structural protein where the hHVEM-derived peptide is inserted into E3 of Chikungunya viral structural protein.

According to the same manner described in EXAMPLE 6, the Chikungunya virus like particle comprising hHHVEM was prepared and purified. The expression of VLP comprising hHVEM conjugated with CHIKV structural polypeptide was confirmed (see FIG. 18).

Example 18: Expression of Immature CHIKV VLP from Stable Cell Line

The transfected cell line that expresses immature VLP obtained in EXAMPLE 8 was prepared.

1. 293F cells were transfected with an expression vector used in Example 8 that contains a selection marker such as hygromycin B.

2. The transfected cells were incubated for one day.

3. The transfected cells were cultured in a selection medium containing Hygromycin at 150-200 ug/ml for 1-2 weeks.

4. The cells that could grow and be split at least once in the selection medium were chosen.

5. A single cell was isolated and cloned. Then, the cells were confirmed to secrete the VLP in the supernatants by western blotting.

The cloned cells were cultured for 3 months in a medium comprising sodium butyrate, supernatant of the culture was obtained and the immature VLP in the supernatant was confirmed. Result is shown in FIG. 19. This data shows that the obtained cell line was stable and could continuously generate immature VLP for long term.

Example 19: Protection Against Tumor by PD-L1 VLP

PD-L1 VLP obtained according to Example 4 was used. The mice (n=10 per group) were intramuscully injected with 100 μl of PBS(-) (control group) or 50 μl of PD-L1 VLP (0.2 μg/μl) and 50 μl of alum adjuvant at week 0, 3, 6 and 9. At week 7, the amount of anti PD-L1 antibody in mice serum was determined. Results are shown in FIG. 20.

CT-26 mouse colon cancer cells ($1\times10^6$) suspended in PBS (100 μl) were injected subcutaneously into the right hind legs of the mice at week 8. The tumor sizes were measured at 12 days after the tumor innoculation. Results are shown in FIG. 21. PD-L1 VLP effectively suppressed growth of the tumor in the mice.

Example 20: Protection Against Tumor by PD-L1 VLP(2)

CT-26 mouse colon cancer cells ($1\times10^6$) suspended in PBS (100 μl) were injected subcutaneously into both the hind legs of the mice (Day 0). 50 μl of PD-L1 VLP (0.2 μg/μl) and 50 μl of almum adjuvant were injected intratumorally into the tumor in the right leg of the test mice (N=7). 50 μl of almum adjuvant and 50 μl of PBS were injected intratumorally into the tumor in the right leg of the control mice (N=6). The sizes of the tumor in the right (injected) and left (uninjected) legs were measured at 4, 7, 10, 14, 17, 20 and 24 days after tumor innoculation. Results are shown in FIG. 22. Pictures of the mice at day 24 are shown in FIG. 23.

At day 24, mice were sacrificed. Lymphocytes were isolated from the mouse spleen and analysed by flow cytometry using AH-1 tetramer and anti-CD8 antibody. AH-1 is a CT-26 specific antigen. Results are shown in FIGS. 24 and 25. As shown in those figures, significantly higher number of CT-26 specific CD8' cells were detected in the test animals than those in the control animals.

The amount of anti PD-L1 antibody in the test and control mice serum were also determined. As positive control, serum of the mice received im PD-L1 VLP injection in Example 19 was used. Results are shown in FIG. 26.

The intratumorally injected PD-L1 VLP effectively induced tumor specific cytotoxic T cells in tumor bearing mice. The intratumorally injected PD-L1 VLP also effectively induced anti PD-L1 antibody. Intratumoral injection of PD-L1 VLP effectively modulated the immune system of the animals and inhibited growth of the tumors not only those directly received the injection but also those distant from the injected site.

Example 21: Preparation of a Pharmaceutical Composition Comprising Chikungunya Virus (CHIKV) Like Particle Comprising a Viral Structural Protein and Malaria Antigen which is Inserted Both in Envelope Protein E2 and E3 of the Viral Structural Protein Chikungunya viral structural protein comprising Malaria CSP 14X repeat antigen 76 (14 repeats of NPNA (SEQ ID NO: 142)) in only E3 or in both E2 and E3 was expressed in 293F cells in the similar manner according to the previous Examples (CHIKV viral structural protein containing CSP 14X repeat antigen 76 in E2 and E3 is SEQ ID NO: 103 and expression vector for the viral structural protein is SEQ ID NO: 104). The Chikungunya virus like particle was prepared and purified in the similar manner as the previous Examples. The expression of VLP comprising the CSP repeat antigen 76 conjugated with CHIKV structural polypeptide was confirmed by Western Blot against CHIKV-VLP immunized monkey serum. See FIG. 27.

To prepare a pharmaceutical composition which is a vaccine composition, 80 μg of the prepared particles was mixed with 1 ml of Sucrose Phosphate Solution, pH 7.2, Endotoxin Free (Teknova, SP buffer).

Groups of BALB/c mice (n=4) were immunized intramuscularly three times at a 3 weeks' interval with 15 μg of thus obtained VLP, with or without Alhydrogel 2% adjuvant. The sera were collected 2 weeks after the third dose. The serum anti-CSP NANP (SEQ ID NO: 154) titer was measured by ELISA using $(NANP; SEQ ID NO: 154)_6$ peptide for coating. The results of this experiment are presented in FIG. 28. VLP containing CSP epitope NANP (SEQ ID NO: 154) stimulated the production of anti-CSP NANP (SEQ ID NO: 154) antibodies and the response was enhanced by the use of Alum.

What is claimed is:

1. A virus like particle comprising a viral structural protein which comprises a modified envelope protein E3, wherein at least one foreign antigen is inserted into said envelope protein E3.

2. The virus like particle according to claim 1, wherein the viral structural protein is an alphavirus or flavivirus structural protein.

3. The virus like particle according to claim 2, wherein the viral structural protein is a Chikungunya virus or Venezuelan equine encephalitis virus structural protein.

4. The virus like particle according to claim 3, wherein the viral structural protein is a viral structural protein of Chikungunya virus strain 37997 or strain OPY-1, or is a viral structural protein of Venezuelan equine encephalitis virus strain TC-83.

5. A virus like particle comprising a viral structural protein which comprises a modified envelope protein E3, wherein one or more amino acid residues are replaced, added and/or deleted at a furin cleavage site in the envelope protein E3.

6. The virus like particle according to claim 1, which comprises capsid, envelope protein E1, envelope protein E2 and envelope protein E3.

7. The virus like particle according to claim 1, wherein the at least one foreign antigen is further inserted into the envelope protein E2.

8. The virus like particle according to claim 1, wherein the at least one foreign antigen is an antigen from *Plasmodium falciparum*: circumsporozoite protein, PD-1, PD-L1, CTLA-4, DISCI, IL-2, HER2, BTLA or HVEM.

9. The virus like particle according to claim 8, wherein a peptide selected from the group consisting of (NPNA)n (n=4-30) (SEQ ID NO: 140) and SEQ ID NOs: 6-9 and 15-29 is inserted into the envelope E3 protein.

10. The virus like particle according to claim 8, wherein the at least one foreign antigen is a PD-L1 antigen.

11. A composition comprising:

(a) the virus like particle according to claim 5; and (b) a pharmaceutically acceptable carrier.

12. The virus like particle according to claim 5, wherein a furin cleavage site located in envelope protein E3 is altered or mutated to prevent the furin site from cleaving.

13. An isolated nucleic acid molecule comprising a nucleotide sequence encoding the virus like particle according to claim 1.

14. A vector comprising the nucleic acid molecule according to claim 13, wherein the vector optionally comprises an expression control sequence operably linked to the nucleic acid molecule.

15. An isolated nucleic acid molecule comprising a nucleotide sequence encoding the virus like particle according to claim 5.

16. A vector comprising the nucleic acid molecule according to claim 15, wherein the vector optionally comprises an expression control sequence operably linked to the nucleic acid molecule.

17. A cell line expressing a viral structural protein which comprises an alternation/mutation to the amino acid sequence at the furin site in the envelope protein E3 according to claim 5.

18. The cell line according to claim 17, wherein the cell line is a stable cell line.

19. The cell line according to claim 17, wherein the E3 is removed by a protease.

20. A method for treating cancer, which comprises administering the virus like particle according to claim 10 to a subject in need thereof.

* * * * *